US010774102B2

(12) United States Patent
Brimert et al.

(10) Patent No.: US 10,774,102 B2
(45) Date of Patent: *Sep. 15, 2020

(54) GALACTOSIDE INHIBITOR OF GALECTINS

(71) Applicant: Galecto Biotech AB, Copenhagen (DK)

(72) Inventors: Thomas Brimert, Blentarp (SE); Richard Johnsson, Lund (SE); Hakon Leffler, Lund (SE); Ulf Nilsson, Lund (SE); Fredrik Zetterberg, Askim (SE)

(73) Assignee: Galecto Biotech AB, Copenhagen (DK)

( * ) Notice: Subject to any disclaimer, the term of this patent is extended or adjusted under 35 U.S.C. 154(b) by 261 days.

This patent is subject to a terminal disclaimer.

(21) Appl. No.: 15/535,829

(22) PCT Filed: Jan. 28, 2016

(86) PCT No.: PCT/EP2016/051836
§ 371 (c)(1),
(2) Date: Jun. 14, 2017

(87) PCT Pub. No.: WO2016/120403
PCT Pub. Date: Aug. 4, 2016

(65) Prior Publication Data
US 2017/0349619 A1 Dec. 7, 2017

(30) Foreign Application Priority Data

Jan. 30, 2015 (EP) .................... 15153316
Oct. 30, 2015 (EP) .................... 15192291

(51) Int. Cl.
*C07H 17/02* (2006.01)
*C07H 19/056* (2006.01)
*C07H 15/203* (2006.01)
*C07H 13/10* (2006.01)
*C07H 13/08* (2006.01)
*C07H 15/26* (2006.01)
*C07H 15/207* (2006.01)

(52) U.S. Cl.
CPC .......... *C07H 15/203* (2013.01); *C07H 13/08* (2013.01); *C07H 13/10* (2013.01); *C07H 15/207* (2013.01); *C07H 15/26* (2013.01); *C07H 17/02* (2013.01); *C07H 19/056* (2013.01)

(58) Field of Classification Search
None
See application file for complete search history.

(56) References Cited

U.S. PATENT DOCUMENTS 10,526,360 B2 * 1/2020 Brimert .................. A61P 21/00

OTHER PUBLICATIONS

Rajput et al., Bioorganic and Medicinal Chemistry Letters, 2014, 24(15), pp. 3516-3520). (Year: 2014).*

Jenny Almkvist, et al., "Lipopolysaccharide-Induced Gelatinase Granule Mobilization Primes Neutrophils for Activation by Galectin-3 and Formylmethionyl-Leu-Phe", in Infection and Immunity, vol. 69, No. 2, Feb. 2001, pp. 832-837 (6 pgs.).
Samuel H. Barondes, et al., "Galectins", in The Journal of Biological Chemistry, vol. 269, No. 33, Aug. 19, 1994, pp. 20807-20810 (4 pgs.).
Sandra M. Blois, et al., "A pivotal role for galectin-1 in fetomaternal tolerance", in Nature Medicine, vol. 13, No. 12, Dec. 2007, pp. 1450-1457 (8 pgs.).
W-S. Chen, et al., "Targeting Galectin-1 and Galectin-3 Attenuates VEGF-A-induced Angiogenesis", in Molecular Biology Cell (suppl), Abstract, No. 2695, 2012, (1 pg.).
Ian Cumpstey, et al., "Synthesis of a phenyl thio-β-D-galactopyranoside library from 1,5-difluoro-2,4-dinitrobenzene: discovery of efficient and selective monosaccharide inhibitors of galectin-7", in Org. Biomol. Chem., vol. 3, 2005, pp. 1922-1932 (11 pgs.).
Ian Cumpstey, et al., "C2-Symmetrical thiodigalactoside bisbenzamido derivatives as high-affinity inhibitors of galectin-3: Efficient lectin inhibition through double arginine-arene interactions", in Angew. Chem. Int., Ed. 44, 2005, pp. 5110-5112 (3 pgs.).
Ian Cumpstey, et al., "Double Affinity Amplification of Galectin-Ligand Interactions through Arginine-Arene Interactions: Synthetic, Thermodynamic, and Computational Studies with Aromatic Diamido Thiodigalactosides", in Chem. Eur. J., vol. 14, 2008, pp. 4233-4245 (13 pgs.).
T. K. Dam, et al., "Effects of Clustered Epitopes in Multivalent Ligand-Receptor Interactions", in Biochemistry, vol. 47, 2008, pp. 8470-8476 (7 pgs.).
D. Delacour, et al., "Apical Sorting by Galectin-3-Dependent Glycoprotein Clustering", in Traffic, vol. 8, 2007, pp. 379-388 (10 pgs.).
T. Delaine, et al., "Galectin-Inhibitory Thiodigalactoside Ester Derivatives Have Antimigratory Effects in Cultured Lung and Prostate Cancer Cells", in J. Med. Chem., vol. 51, 2008, pp. 8109-8114 (6 pgs.).
N. Demotte, et al., "A Galectin-3 Ligand Corrects the Impaired Function of Human CD4 and CD8 Tumor-Infiltrating Lymphocytes and Favors Tumor Rejection in Mice", in Cancer Research, vol. 70, 2010, pp. 7476-7488 (14 pgs.).
I. Farkas, et al., "Synthesis of 1,2-trans-glycopyranosyl chlorides using the dichloromethyl methyl ether-boron trifluoride etherate reagent", in Carbohydrate Research, vol. 48, 1976, pp. 136-138 (3 pgs.).
O. B. Garner, et al., "Galectin-glycan lattices regulate cell-surface glycoprotein organization and signalling", in Biochemical Society Transactions, vol. 36, Part 6, 2008, pp. 1472-1477 (6 pgs.).
D. Giguère, et al., "Carbohydrate triazoles and isoxazoles as inhibitors of galectine-1 and -3", in Chem. Commun., 2006, pp. 2379-2381 (3 pgs.).

(Continued)

*Primary Examiner* — Traviss C McIntosh, III
(74) *Attorney, Agent, or Firm* — Maier & Maier, PLLC

(57) ABSTRACT

An embodiment of the present invention relates to a compound of the general formula. The compound of formula is suitable for use in a method for treating a disorder relating to the binding of a galectin, such as galectin-3 to a ligand in a mammal, such as a human. Furthermore an embodiment of the present invention concerns a method for treatment of a disorder relating to the binding of a galectin, such as galectin-3 to a ligand in a mammal, such as a human.

28 Claims, No Drawings

(56) References Cited

OTHER PUBLICATIONS

G. V. Glinsky, et al., "Inhibition of Human Breast Cancer Metastasis in Nude Mice by Synthetic Glycoamines", in Cancer Research, vol. 56, Dec. 1, 1996, pp. 5319-5324 (6 pgs.).
V. V. Glinsky, et al., "Synthetic Galectin-3 Inhibitor Increases Metastatic Cancer Cell Sensitivity to Taxol-Induced Apoptosis In Vitro and In Vivo", in Neoplasia, vol. 11, No. 9, Sep. 2009, pp. 901-909 (9 pgs.).
M. E. Huflejt et al., "Galectin-4 in normal tissues and cancer", in Glycoconjugate Journal 20, 2004, pp. 247-255 (9 pgs.).
L. Ingrassia, et al., "A Lactosylated Steroid Contributes in Vivo Therapeutic Benefits in Experimental Models of Mouse Lymphoma and Human Glioblastoma", in J. Med. Chem., vol. 49, 2006, pp. 1800-1807 (8 pgs.).
C. M. John, et al., "Truncated Galectin-3 Inhibits Tumor Growth and Metastasis in Orthotopic Nude Mouse Model of Human Breast Cancer", in Clinical Cancer Research, vol. 9, Jun. 2003, pp. 2374-2383 (10 pgs.).
T. Kouo, et al., "Galectin-3 Shapes Antitumor Immune Responses by Suppressing CD8 T Cells via LAG-3 and Inhibiting Expansion of Plasmacytoid Dendritic Cells", in Cancer Immunology Research, vol. 3, No. 4, Apr. 2015, pp. 412-423 (13 pgs.).
K. S. Lau, et al., "N-Glycans in cancer progression", in Glycobiology, vol. 18, No. 10, 2008, pp. 750-760 (11 pgs.).
K. S. Lau, et al., "Complex N-Glycan Number and Degree of Branching Cooperate to Regulate Cell Proliferation and Differentiation", in Cell 129, Apr. 6, 2007, pp. 123-134 (12 pgs.).
H. Leffler, et al., "Specificity of Binding of Three Soluble Rat Lung Lectins to Substituted and Unsubstituted Mammalian β-Galactosides", in The Journal of Biological Chemistry, vol. 261, No. 22, Aug. 5, 1986, pp. 10119-10126 (8 pgs.).
H. Leffler, "Galectins Structure and Function—A Synopsis", in Results and Problems in Cell Differentiation, vol. 33, 2001, pp. 57-83 (27 pgs.).
H. Leffler, et al., "Introduction to galectins", in Glycoconjugate Journal 19, 2004, pp. 433-440 (8 pgs.).
Lorenzo Chiariotti, et al., "Galectin genes: Regulation of expression", in Glycoconjugate Journal 19, 2004, pp. 441-449 (9 pgs.).
Chi-Iou Lin, et al., "Galectin-3 Targeted Therapy with a Small Molecule Inhibitor Activates Apoptosis and Enhances Both Chemosensitivity and Radiosensitivity in Papillary Thyroid Cancer", in Mol. Cancer Res., vol. 7, No. 10, Oct. 2009, pp. 1655-1662 (8 pgs.).
A. C. MacKinnon, et al., "Regulation of Alternative Macrophage Activation by Galectin-3", in The Journal of Immunology, vol. 180, 2008, pp. 2650-2658 (9 pgs.).
A. C. MacKinnon, et al., "Regulation of Transforming Growth Factor-β1-driven Lung Fibrosis by Galectin-3", in Am. J. Resp. Crit. Care Med., vol. 185, 2012, pp. 1-11 (11 pgs.).
S. M. Massa, et al., "L-29, an Endogenous Lectin, Binds to Glycoconjugate Ligands with Positive Cooperativity", in Biochemistry, vol. 32, 1993, pp. 260-267 (8 pgs.).
I. Melero, et al., "Evolving synergistic combinations of targeted immunotherapies to combat cancer", in Nature Reviews, vol. 15, Aug. 2015, pp. 457-472 (16 pgs.).
E. A. Partridge, et al., "Regulation of Cytokine Receptors by Golgi N-Glycan Processing and Endocytosis", in Science, vol. 306, Oct. 1, 2004, pp. 120-124 (6 pgs.).
M. J. Perone, et al., "Suppression of Autoimmune Diabetes by Soluble Galectin-1", in The Journal of Immunology, vol. 182, Sep. 15, 2017, pp. 2641-2653 (14 pgs.).
K. J. Pienta, et al., "Inhibition of Spontaneous Metastasis in a Rat Prostate Cancer Model by Oral Administration of Modified Citrus Pectin", in J. Natl. Cancer Inst., vol. 87, No. 5, Mar. 1, 1995, pp. 348-353 (6 pgs.).
Ramos-Soriano, J., et al., "Synthesis, Biological Evaluation, WAC and NMR Studies of S-Galactosides and Non-Carbohydrate Ligands of Cholera Toxin Based on Polyhydroxyalkylfuroate Moieties", in Chem. Eur. J., vol. 19, 2013, pp. 17989-18003 (15 pgs.).
Peter P. Ruvolo, "Galectin 3 as a guardian of the tumor microenvironment", in Biochimica et Biophysica Acta, Apr. 8, 2015, pp. 1-11: http://dx.doi.org/10.1016/j.bbamcr.2015.08.008 (11 pgs.).
Saegusa, J., et al., "Galectin-3 is critical for the development of the allergic inflammatory response in a mouse model of atopic dermatitis", in Am J Pathol, vol. 174, No. 3, Mar. 2009, pp. 922-931 (10 pgs.).
Salameh, B. A., et al., "3-(1,2,3-Triazol-1-yl)-1-thio-galactosides as small, efficient, and hydrolytically stable inhibitors of galectin-3", in Bioorg. Med. Chem. Lett., vol. 15, 2005, pp. 3344-3346 (3 pgs.).
Salameh, B.A., et al., "1H-1,2,3-Triazol-1-yl thiodigalactoside derivatives as high affinity galectin-3 inhibitors", in Bioorg Med Chem, vol. 18, 2010, pp. 5367-5378 (13 pgs.).
Salomonsson, E., et al., "Monovalent interactions of galectin-1", in Biochemistry, vol. 49, 2010, pp. 9518-9532 (15 pgs.).
Sörme, P., et al., "Low micromolar inhibitors of galectin-3 based on 3'-derivatization of N-acetyllactosamine", in ChemBioChem, vol. 3, 2002, pp. 183-189 (7 pgs.).
Sörme, P., et al., "Fluorescence polarization to study galectin-ligand interactions", in Meth. Enzymol., vol. 362, 2003a, pp. 504-512 (9 pgs.).
Sörme, P., et al., "Design and synthesis of galectin inhibitors", in Meth. Enzymol., vol. 363, 2003b, pp. 157-169 (13 pgs.).
Sörme, P., et al., "Fluorescence polarization as an analytical tool to evaluate galectin-ligand interactions", in Anal. Biochem., vol. 334, 2004, pp. 36-47 (12 pgs.).
Thijssen, V.L. J. L., et al., "Galectins in the tumor endothelium: opportunities for combined cancer therapy", in Blood, vol. 110, 2007, pp. 2819-2827 (10 pgs.).
Toscano, M.A., et al., "Differential glycosylation of TH1, TH2 and TH-17 effector cells selectively regulates susceptibility to cell death", in Nat Immunol, vol. 8, No. 8, Aug. 2007, pp. 825-834 (10 pgs.).
Tomohisa Ogawa, et al., "The speciation of conger eel galectins by rapid adaptive evolution", in Glycoconjugate Journal 19, 2004, pp. 451-458 (8 pgs.).
C. Fred Brewer, "Thermodynamic binding studies of galectin-1, -3 and -7", in Glycoconjugate Journal 19, 2004, pp. 459-465 (7 pgs.).
Ken Scott, et al., "Galectin-1: A bifunctional regulator of cellular proliferation", in Glycoconjugate Journal 19, 2004, pp. 467-477 (11 pgs.).
Hidenori Horie, et al., "Galectin-1 plays essential roles in adult mammalian nervous tissues. Roles of oxidized galectin-1", in Glycoconjugate Journal 19, 2004, pp. 479-489 (11 pgs.).
Michael S. Lipkowitz, et al., "Galectin 9 is the sugar-regulated urate transporter/channel UAT", in Glycoconjugate Journal 19, 2004, pp. 491-498 (8 pgs.).
Ronald J. Patterson, et al., "Understanding the biochemical activities of galectin-1 and galectin-3 in the nucleus", in Glycoconjugate Journal 19, 2004, pp. 499-506 (8 pgs.).
Daniel K. Hsu, et al., "Regulation of cellular homeostasis by galectins", in Glycoconjugate Journal 19, 2004, pp. 507-515 (9 pgs.).
Yehiel Zick, et al., "Role of galectin-8 as a modulator of cell adhesion and cell growth", in Glycoconjugate Journal 19, 2004, pp. 517-526 (10 pgs.).
Josiah Ochieng, et al., "Extracellular functions of galectin-3", in Glycoconjugate Journal 19, 2004, pp. 527-535 (9 pgs.).
Frèdèric van den Brûle, et al., "Expression of galectins in cancer: A critical review", in Glycoconjugate Journal 19, 2004, pp. 537-542 (6 pgs.).
Yukinori Takenaka, et al., "Galectin-3 and metastasis", in Glycoconjugate Journal 19, 2004, pp. 543-549 (7 pgs.).
Antonino Grassadonia, et al., "90K (Mac-2 BP) and galectins in tumor progression and metastasis", in Glycoconjugate Journal 19, 2004, pp. 551-556 (6 pgs.).
Nathalie Bidon-Wagner, et al., "Human galectin-8 isoforms and cancer", in Glycoconjugate Journal 19, 2004, pp. 557-563 (7 pgs.).
Gabriel A. Rabinovich, et al., "Shedding light on the immunomodulatory properties of galectins: Novel regulators of innate and adaptive immune responses", in Glycoconjugate Journal 19, 2004, pp. 565-573 (9 pgs.).

(56) References Cited

OTHER PUBLICATIONS

Jenny Almkvist, et al., "Galectins as inflammatory mediators", in Glycoconjugate Journal 19, 2004, pp. 575-581 (7 pgs.).

Sachiko Sato, et al., "Seeing strangers or announcing "danger": Galectin-3 in two models of innate immunity", in Glycoconjugate Journal 19, 2004, pp. 583-591 (9 pgs.).

Mitsuomi Hirashima, et al., "Galectin-9 in physiological and pathological conditions", in Glycoconjugate Journal 19, 2004, pp. 593-600 (8 pgs.).

Anna R. Young, et al., "Galectins in parasite infection and allergic inflammation", in Glycoconjugate Journal 19, 2004, pp. 601-606 (6 pgs.).

Karen E. Pace, et al., "Insect galectins: Roles in immunity and development", in Glycoconjugate Journal 19, 2004, pp. 607-614 (8 pgs.).

Diana J. Watt, et al., "The involvement of galectin-1 in skeletal muscle determination, differentiation and regeneration", in Glycoconjugate Journal 19, 2004, pp. 615-619 (5 pgs.).

R. Colin Hughes, "Galectins in kidney development", in Glycoconjugate Journal 19, 2004, pp. 621-629 (9 pgs.).

Office Action dated Sep. 19, 2019, in corresponding U.S. Appl. No. 16/539,078; 6 pages.

\* cited by examiner

GALACTOSIDE INHIBITOR OF GALECTINS

TECHNICAL FIELD

The present invention relates to novel compounds, the use of said compounds as medicament and for the manufacture of a medicament for the treatment of inflammation; fibrosis; scarring; keloid formation; aberrant scar formation; surgical adhesions; septic shock; cancers; autoimmune diseases; metabolic disorders; heart disease; heart failure; pathological angiogenesis; eye diseases; atherosclerosis; metabolic diseases; asthma and other interstitial lung diseases; and liver disorders in mammals. The invention also relates to pharmaceutical compositions comprising said novel compounds.

BACKGROUND ART

Galectins are proteins with a characteristic carbohydrate recognition domain (CRD) (Barondes et al., 1994; Leffler et al., 2004). This is a tightly folded β-sandwich of about 130 amino acids (about 15 kDa) with the two defining features 1) a 3-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004)

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Leffler et al., 2004). These were the first discovered galectins and are abundant in many tissues.

There are now over 3500 publications on galectins in PubMed, with most, as mentioned above, about galectins-1 (>900) and -3 (>1600). Strong evidence suggests roles for galectins in e.g. inflammation and cancer, and development recently reviewed in a special issue (Leffler (editor), 2004b).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004). They can also function in all these compartments; for galectin-3, solid evidence published in well respected journals support roles in RNA splicing in the nucleus, inhibition of apoptosis in the cytosol, and a variety of extracellular effects on cell signaling and adhesion (Leffler (editor), 2004b). Galectin-7 and -12 also act in the cytosol by enhancing apoptosis and regulating the cell cycle and differentiation in certain cells (Hsu and Liu in Leffler (editor), 2004b). Most galectins act also extracellularly by cross-linking glycoproteins (e.g. laminin, integrins, and IgE receptors) possibly forming supramolecular ordered arrays (Brewer et al., 2002) and may thereby modulate cell adhesion and induce intracellular signals. Related to this, recent years have seen the emergence of a molecular mechanism of these galectin functions involving a formation of microdomains (lattices) within membranes, (Dam et al., 2008; Garner et al., 2008) which in turn affects intracellular trafficking and cell surface presentation of glycoprotein receptors. (Delacour et al., 2007; Lau et al., 2007; Lau et al. 2008) This has been documented in cell culture, in null mutant mice, (Blois et al., 2007; Gedronneau et al., 2008; Thijssen et al., 2007; Toscano et al., 2007; Saegusa et al., 2009) and animals treated with galectin (Blois et al., 2007; Perone et al., 2009) or galectin inhibitors. (John et al., 2003; Pienta et al., 1995; Glinsky et al., 1996)

Potential Therapeutic Use of Galectin-3 Inhibitors

Galectin-3 has been implicated in diverse phenomena and, hence, inhibitors may have multiple uses. It is easy to perceive this as a lack of specificity or lack of scientific focus. Therefore, the analogy with aspirin and the cyclooxygenases (COX-1 and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation

A pro-inflammatory role of galectin-3 is indicated by its induction in cells at inflammatory sites, a variety of effects on immune cells (e.g. oxidative burst in neutrophils and chemotaxis in monocytes), and decrease of the inflammatory response, mainly in neutrophils and macrophages, in null mutant mice (in Leffler (editor), 2004b). Moreover, knockout mice of Mac-2BP, a galectin-3 ligand, have increased inflammatory responses (Trahey et al., 1999). Importantly, recent studies have identified galectin-3 as a key rate-limiting factor in macrophage M2 differentiation and myofibroblast activation, which influences the development of fibrosis (Mackinnon et al., 2008; Mackinnon et al., 2012).

Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of the TGF-β receptor (Partridge et al., 2004), which in turn regulates alternative macrophage differentiation into M2 macrophages and myofibroblast activation.

Hence, as galectin-3 is a good candidate for being an endogenous enhancer of TGF-β signaling and alternative macrophage differentiation and myofibroblast activation, galectin-3 inhibitors may be very useful in treating fibrosis and adverse tissue remodeling.

Treatment of Cancer

A large number of immunohistochemical studies show changed expression of certain galectins in cancer (van den Brule et. al. and Bidon et al. in Leffler (editor), 2004b) and for example galectin-3 is now an established histochemical marker of thyroid cancer. The direct evidence for a role of galectin-3 in cancer comes from mouse models, mainly by Raz et al, but also others (in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. Further, recent evidence have shown that galectin-3 plays a critical role in the tumor microenvironment—reviewed in Ruvolo, 2015. Galectin-3 is also believed to regulate the interaction between the tumor cells and immune cells, such as T-lymphocytes (T-cells), and inhibition of galectin-3 has been shown to restore T-cell activity (Demotte et al. 2010, Kouo et al. 2015, Menero et al. 2015). From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Lin et al., 2009), as well as in vivo (Glinsky et al., 2009).

Also galectin-1 is frequently over-expressed in low differentiated cancer cells, and galectin-9 or its relatives galectin-4 and galectin-8 may be induced in specific cancer types (Huflejt and Leffler. 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b). Therefore, the over-expression of these galectins in cancers might help the tumor to defend itself against the T-cell response raised by the host.

Null mutant mice for galectins-1 and -3 have been established many years ago (Poirier, 2002). These are healthy and reproduce apparently normally in animal house conditions. However, recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analyzed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Treatment of Angiogenesis

Vascular endothelial growth factors (VEGFs) signaling through VEGF receptor-2 (VEGFR-2) is the primary angiogenic pathway. Studies have been published demonstrating that both galectin-1 and galectin-3 are important modulators for VEGF/VEGFR-2 signaling pathway. It has also been published that a galectin inhibitor, TDX, is expected have efficacy against pathological angiogenesis. (Chen 2012)

Known Inhibitors

Natural Ligands

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or LacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

Cluster molecules having up to four lactose moieties showed a strong multivalency effect when binding to galectin-3, but not to galectin-1 and galectin-5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules.

Thiodigalactoside is known to be a synthetic and hydrolytically stable, yet polar inhibitor, approximately as efficient as N-acetyllactosamine (Leffler and Barondes, 1986). N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 µM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/13569 and US2007185041; WO/2005/113568, U.S. Pat. No. 7,638,623 B2) which lack O-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

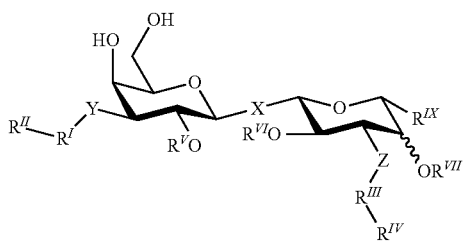

as described in WO/2005/113568, and

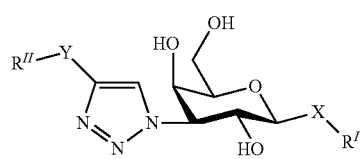

as described in WO/2005/113569, in which $R^1$ can be a D-galactose.

In recently published US20140099319 and WO2014067986 are disclosed a compound of formula

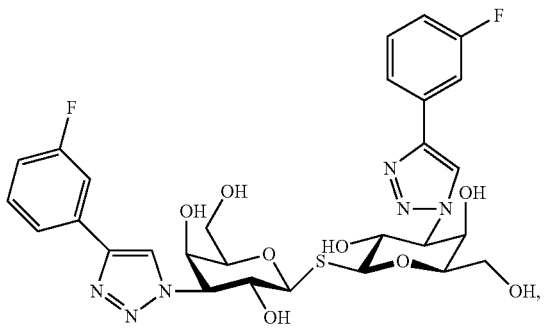

having fluorine (F) in the meta position on both the phenyl rings in relation to the triazole rings. This compound has been shown to be a promising drug candidate for lung fibrosis, and in particular is very selective on galectin-3 with high affinity.

In Bioorganic & Medicinal Chemistry 19 (2011) 3280-3287 "Inhibitory potential of chemical substitutions at bio-inspired sites of beta-D-galactopyranose on neoglycoprotein/cell surface binding of two classes of medically relevant lectins" are disclosed some beta-D-galactopyranosides with galectin-3 affinity in the same range or less lactose, which has a Kd of about 91 µM. There is no disclosure or mentioning of corresponding alpha-anomers having affinity towards galectin-3 better than lactose.

SUMMARY OF THE INVENTION

The compounds of the present invention are novel α-D-galactopyranose compounds that unexpectedly have shown very high affinity for galectin-3, and are considered novel potent drug candidates. Some of these compounds have very good PK properties for e.g. oral administration, such as low clearance and high bioavailability.

In broad aspect the present invention concerns a D-galactopyranose compound of formula (1)

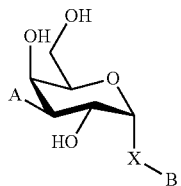

wherein
the pyranose ring is α-D-galactopyranose,
A is selected from

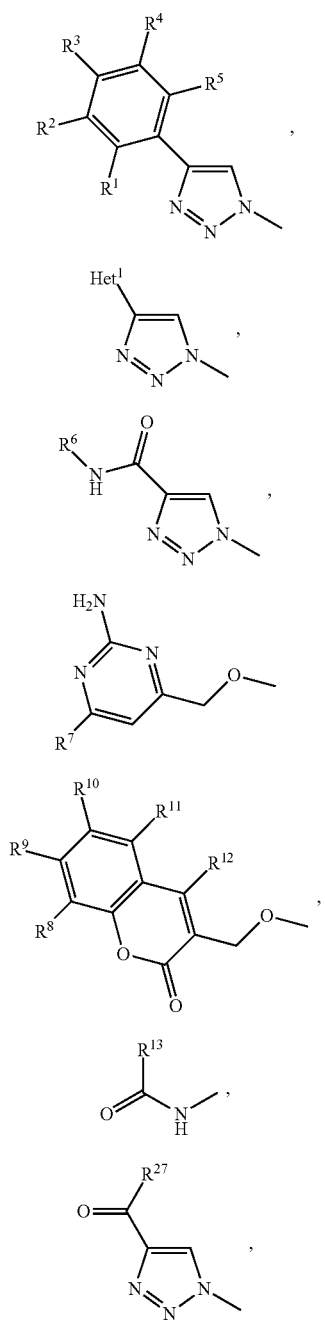

wherein Het¹ is selected from a five or six membered heteroaromatic ring, optionally substituted with a group selected from Br; F; Cl; CN; $NR^{19}R^{20}$, wherein $R^{19}$ and $R^{20}$ are independently selected from H, $C_{1-3}$ alkyl, cyclopropyl, iso-propyl, —C(=O)—$R^{21}$, wherein $R^{21}$ is selected from H and $C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; and $OC_{1-3}$ alkyl optionally substituted with a F;

wherein $R^1$-$R^5$ are independently selected from H, CN, $NH_2$, F, methyl optionally substituted with a fluorine (F), and $OCH_3$ optionally substituted with a F;

wherein $R^6$ is selected from $C_{1-6}$ alkyl optionally substituted with a halogen, branched $C_{3-6}$ alkyl and $C_{3-7}$ cycloalkyl;

wherein $R^7$ is selected from a five or six membered heteroaromatic ring, optionally substituted with a group selected from Br, F, Cl, methyl optionally substituted with a F, and $OCH_3$ optionally substituted with a F, and a phenyl optionally substituted with a group selected from Br, F, Cl, methyl optionally substituted with a F, and $OCH_3$ optionally substituted with a F;

wherein $R^8$-$R^{12}$ are independently selected from H, F, methyl optionally substituted with a fluorine (F), and $OCH_3$ optionally substituted with a F;

wherein $R^{13}$ is a five or six membered heteroaromatic ring optionally substituted with a group selected from H, OH, F, methyl optionally substituted with a fluorine (F), and $OCH_3$ optionally substituted with a F, or an aryl, such as phenyl or naphthyl, optionally substituted with a group selected from H, OH, F, methyl optionally substituted with a fluorine (F), and $OCH_3$ optionally substituted with a F;

X is selected from S, SO, $SO_2$, O, C=O, and $CR^7R^8$ wherein $R^7$ and $R^8$ are independently selected from hydrogen, OH, or halogen (e.g. F, Cl, Br);

wherein $R^{27}$ is selected from a $C_{1-6}$ alkyl, branched $C_{3-6}$ alkyl, $C_{1-6}$ alkoxy and branched $C_{3-6}$ alkoxy;

B is selected from a) a $C_{1-6}$ alkyl or branched $C_{3-6}$ alkyl substituted with a five or six membered heteroaromatic ring, optionally substituted with a substituent selected from CN, a halogen (e.g. Cl, F, Br, I), methyl optionally substituted with a F, $OCH_3$ optionally substituted with a F, $OCH_2CH_3$ optionally substituted with a F, OH, and $R_{14}$—CONH— wherein $R_{14}$ is selected from $C_{1-3}$ alkyl and cyclopropyl; or a $C_{1-6}$ alkyl substituted with a phenyl, optionally substituted with a substituent selected from CN, a halogen (e.g. Cl, F, Br, I), methyl optionally substituted with a F, $OCH_3$ optionally substituted with a F, $OCH_2CH_3$ optionally substituted with a F, OH, and $R_{15}$—CONH— wherein $R_{15}$ is selected from $C_{1-3}$ alkyl and cyclopropyl; b) an aryl, such as phenyl or naphthyl, optionally substituted with a group selected from a halogen (e.g. Cl, F, Br, I); CN; —COOH; —$CONR_{22}R_{23}$, wherein $R_{22}$ and $R_{23}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR_{28}R_{29}$, wherein $R_{28}$ and $R_{29}$ are independently selected from H, $C_{1-3}$ alkyl and isopropyl; OH; and $R_{16}$—CONH— wherein $R_{16}$ is selected from $C_{1-3}$ alkyl and cyclopropyl; c) a $C_{5-7}$ cycloalkyl, optionally substituted with a substituent selected from a halogen (e.g. Cl, F, Br, I), CN, methyl optionally substituted with a F, $OCH_3$ optionally substituted with a F, $OCH_2CH_3$ optionally substituted with a F, OH, and $R_{17}$—CONH— wherein $R_{17}$ is selected from $C_{1-3}$ alkyl and cyclopropyl; and d) a heterocycle, such as heteroaryl or heterocycloalkyl, optionally substituted with a group selected from a halogen (e.g. Cl, F, Br, I); CN; —COOH; —CONR$_{24}$R$_{25}$, wherein R$_{24}$ and R$_{25}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$_{30}$R$_{31}$, wherein R$_{30}$ and R$_{31}$ are independently selected from H, C$_{1-3}$ alkyl and isopropyl; OH; and R$_{18}$—CONH— wherein R$_{18}$ is selected from C$_{1-3}$ alkyl and cyclopropyl; e) a C$_{1-6}$ alkyl or branched C$_{3-6}$ alkyl; or a pharmaceutically acceptable salt or solvate thereof.

In a further aspect the present invention relates to a D-galactopyranose compound of formula (1)

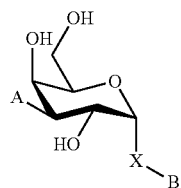
(1)

wherein
the pyranose ring is α-D-galactopyranose,
A is selected from

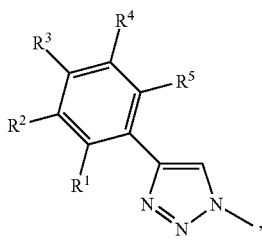
2

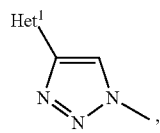
3

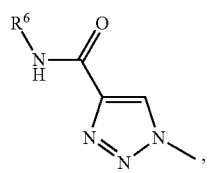
4

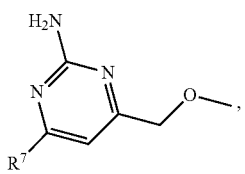
5

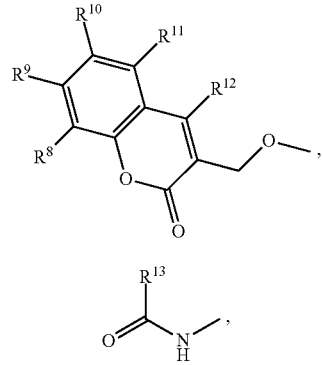
6

7 wherein Het$^1$ is selected from a five or six membered heteroaromatic ring, optionally substituted with a group selected from Br; F; Cl; CN; NR$^{19}$R$^{20}$, wherein R$^{19}$ and R$^{20}$ are independently selected from H, C$_{1-3}$ alkyl, cyclopropyl, iso-propyl, —C(=O)—R$^{21}$, wherein R$^{21}$ is selected from H and C$_{1-3}$ alkyl; C$_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; and OC$_{1-3}$ alkyl optionally substituted with a F;
wherein R$^1$-R$^5$ are independently selected from H, CN, NH$_2$, F, methyl optionally substituted with a fluorine (F), and OCH$_3$ optionally substituted with a F;
wherein R$^6$ is selected from C$_{1-6}$ alkyl, branched C$_{3-6}$ alkyl and C$_{3-7}$ cycloalkyl;
wherein R$^7$ is selected from a five or six membered heteroaromatic ring, optionally substituted with a group selected from Br, F, Cl, methyl optionally substituted with a F, and OCH$_3$ optionally substituted with a F, and a phenyl optionally substituted with a group selected from Br, F, Cl, methyl optionally substituted with a F, and OCH$_3$ optionally substituted with a F;
wherein R$^8$-R$^{12}$ are independently selected from H, F, methyl optionally substituted with a fluorine (F), and OCH$_3$ optionally substituted with a F;
wherein R$^{13}$ is a five or six membered heteroaromatic ring optionally substituted with a group selected from H, OH, F, methyl optionally substituted with a fluorine (F), and OCH$_3$ optionally substituted with a F, or an aryl, such as phenyl or naphthyl, optionally substituted with a group selected from H, OH, F, methyl optionally substituted with a fluorine (F), and OCH$_3$ optionally substituted with a F; X is selected from S, SO, SO$_2$, O, C=O, and CR$^7$R$^8$ wherein R$^7$ and R$^8$ are independently selected from hydrogen, OH, or halogen (e.g. F, Cl, Br); B is selected from a) a C$_{1-6}$ alkyl or branched C$_{3-6}$ alkyl substituted with a five or six membered heteroaromatic ring, optionally substituted with a substituent selected from CN, a halogen (e.g. Cl, F, Br, I), methyl optionally substituted with a F, OCH$_3$ optionally substituted with a F, OCH$_2$CH$_3$ optionally substituted with a F, OH, and R$^{14}$—CONH— wherein R$^{14}$ is selected from C$_{1-3}$ alkyl and cyclopropyl or a C$_{1-6}$ alkyl substituted with a phenyl, optionally substituted with a substituent selected from CN, a halogen (e.g. Cl, F, Br, I), methyl optionally substituted with a F, OCH$_3$ optionally substituted with a F, OCH$_2$CH$_3$ optionally substituted with a F, OH, and R$_{15}$—CONH— wherein R$^{15}$ is selected from C$_{1-3}$ alkyl and cyclopropyl; b) an aryl, such as phenyl or naphthyl, optionally substituted with a group selected from a halogen (e.g. Cl, F, Br, I); CN; —COOH;

—CONR²²R²³, wherein R²² and R²³ are independently selected from H, C₁₋₃ alkyl, cyclopropyl, and iso-propyl; C₁₋₃ alkyl, optionally substituted with a F; cyclopropyl, optionally substituted with a F; isopropyl, optionally substituted with a F; OC₁₋₃ alkyl, optionally substituted with a F; O-cyclopropyl, optionally substituted with a F; O-isopropyl, optionally substituted with a F; OH; and R¹⁶—CONH— wherein R¹⁶ is selected from C₁₋₃ alkyl and cyclopropyl; c) a C₅₋₇ cycloalkyl, optionally substituted with a substituent selected from a halogen (e.g. Cl, F, Br, I), CN, methyl optionally substituted with a F, OCH₃ optionally substituted with a F, OCH₂CH₃ optionally substituted with a F, OH, and R¹⁷—CONH— wherein R¹⁷ is selected from C₁₋₃ alkyl and cyclopropyl; and d) a heterocycle, such as heteroaryl or heterocycloalkyl, optionally substituted with a group selected from a halogen (e.g. Cl, F, Br, I), CN; —COOH; —CONR²⁴R²⁵, wherein R²⁴ and R²⁵ are independently selected from H, C₁₋₃ alkyl, cyclopropyl, and iso-propyl; C₁₋₃ alkyl, optionally substituted with a F; cyclopropyl, optionally substituted with a F; isopropyl, optionally substituted with a F; OC₁₋₃ alkyl, optionally substituted with a F; O-cyclopropyl, optionally substituted with a F; O-isopropyl, optionally substituted with a F; OH; and R¹⁸—CONH— wherein R¹⁸ is selected from C₁₋₃ alkyl and cyclopropyl; or a pharmaceutically acceptable salt or solvate thereof.

In a still further aspect the present invention relates to a D-galactopyranose compound of formula (1)

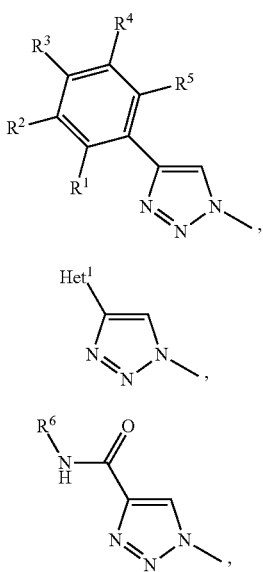

(1)

wherein
the pyranose ring is α-D-galactopyranose,
A is selected from

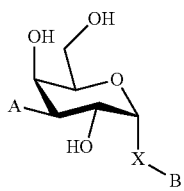

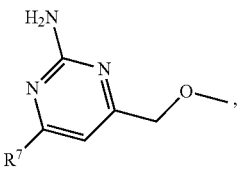

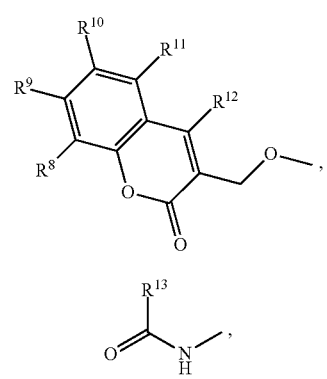

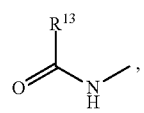

wherein Het¹ is selected from a five or six membered heteroaromatic ring, optionally substituted with a group selected from Br, F, Cl, methyl optionally substituted with a F, and OCH₃ optionally substituted with a F;

wherein R¹-R³ are independently selected from H, CN, NH₂, F, methyl optionally substituted with a F, and OCH₃ optionally substituted with a F;

wherein R⁶ is selected from C₁₋₆ alkyl, branched C₃₋₆ alkyl and C₃₋₇ cycloalkyl;

wherein R⁷ is selected from a five or six membered heteroaromatic ring, optionally substituted with a group selected from Br, F, Cl, methyl optionally substituted with a F, and OCH₃ optionally substituted with a F, and a phenyl optionally substituted with a group selected from Br, F, Cl, methyl optionally substituted with a F, and OCH₃ optionally substituted with a F;

wherein R⁸-R¹² are independently selected from H, F, methyl optionally substituted with a fluorine (F), and OCH₃ optionally substituted with a F;

wherein R¹³ is a five or six membered heteroaromatic ring optionally substituted with a group selected from H, OH, F, methyl optionally substituted with a fluorine (F), and OCH₃ optionally substituted with a F, or an aryl, such as phenyl or naphthyl, optionally substituted with a group selected from H, OH, F, methyl optionally substituted with a fluorine (F), and OCH₃ optionally substituted with a F; X is selected from S, SO, SO₂, O, C═O, and CR⁷R⁸ wherein R⁷ and R⁸ are independently selected from hydrogen, OH, or halogen (e.g. F, Cl, Br);

B is selected from a) a C₁₋₆ alkyl or branched C₃₋₆ alkyl substituted with a five or six membered heteroaromatic ring, optionally substituted with a substituent selected from CN, a halogen (e.g. Cl, F, Br, I), methyl optionally substituted with a F, OCH₃ optionally substituted with a F, OCH₂CH₃ optionally substituted with a F, OH, and R¹⁴—CONH— wherein R¹⁴ is selected from C₁₋₃ alkyl and cyclopropyl or a C₁₋₆ alkyl substituted with a phenyl, optionally substituted with a substituent selected from CN, a halogen (e.g. Cl, F, Br, I), methyl optionally substituted with a F, OCH₃ optionally substituted with a F, OCH₂CH₃ optionally substituted with a F, OH, and R₁₅—CONH— wherein R¹⁵ is selected from C₁₋₃alkyl and cyclopropyl; b) an aryl, such as phenyl or naphthyl, optionally substituted with a substituent selected from a halogen (e.g. Cl, F, Br, I), methyl optionally substituted with a F, $OCH_3$ optionally substituted with a F, $OCH_2CH_3$ optionally substituted with a F, OH, and $R^{16}$—CONH— wherein $R^{16}$ is selected from $C_{1-3}$ alkyl and cyclopropyl; c) a $C_{5-7}$ cycloalkyl, optionally substituted with a substituent selected from CN, a halogen (e.g. Cl, F, Br, I), methyl optionally substituted with a F, $OCH_3$ optionally substituted with a F, $OCH_2CH_3$ optionally substituted with a F, OH, and $R^{17}$—CONH— wherein $R^{17}$ is selected from $C_{1-3}$ alkyl and cyclopropyl; and d) a heterocycle, such as heteroaryl or heterocycloalkyl, optionally substituted with a substituent selected from a halogen (e.g. Cl, F, Br, I), methyl optionally substituted with a F, $OCH_3$ optionally substituted with a F, $OCH_2CH_3$ optionally substituted with a F, OH, and $R^{18}$—CONH— wherein $R^{18}$ is selected from $C_{1-3}$ alkyl and cyclopropyl; or a pharmaceutically acceptable salt or solvate thereof.

In an embodiment of the present invention A is selected from formula 2 wherein $R^1$-$R^5$ are independently selected from H, F, methyl optionally substituted with a fluorine (F), and $OCH_3$ optionally substituted with a F.

In another embodiment of the present invention A is selected from formula 2 wherein $R^1$ and $R^5$ are selected from H and $R^2$-$R^4$ are selected from F.

In a further embodiment of the present invention A is selected from formula 2 wherein $R^2$ and $R^3$ are F and $R^1$, $R^4$ and $R^5$ are H, or wherein $R^2$ and $R^4$ are F and $R^1$, $R^3$ and $R^5$ are H, or wherein $R^2$ is F and $R^1$, $R^3$-$R^5$ are H, or wherein $R^2$ and $R^4$ are F, $R^3$ is $OCH_3$, and $R^1$ and $R^5$ are H.

In a further embodiment of the present invention A is selected from formula 2 wherein $R^1$-$R^5$ are independently selected from H and F, provided that at least one of $R^1$-$R^5$ is F. Preferably from one to five, such as three or five, of $R^1$-$R^5$ are independently selected from F.

In a still further embodiment of the present invention A is selected from formula 3 wherein $Het^1$ is selected from a six membered heteroaromatic ring, optionally substituted with a group selected from Br, F, and Cl. Typically, $Het^1$ is selected from a pyridinyl substituted with a F, such as 3F.

In a further embodiment of the present invention A is selected from formula 4 wherein $R^6$ is selected from $C_{1-6}$ alkyl and branched $C_{3-6}$ alkyl. Typically, $R^6$ is $C_{1-6}$ alkyl, such as $CH_3$, $CH_2CH_3$, $CH_2CH_2CH_3$ and isopropyl, e.g. $CH_3$, or isopropyl.

In a further embodiment of the present invention A is selected from formula 4 wherein $R^6$ is selected from $C_{1-6}$ alkyl substituted with a halogen, such as one, two or three F, e.g. $CH_2CF_3$.

In a still further embodiment of the present invention A is selected from formula 5 wherein $R^7$ is selected from phenyl optionally substituted with a group selected from Br, F, Cl, methyl optionally substituted with a F, and $OCH_3$ optionally substituted with a F.

In a further embodiment of the present invention A is selected from formula 5 wherein $R^7$ is selected from phenyl substituted with a Cl.

In a still further embodiment of the present invention A is selected from formula 6 wherein $R^8$-$R^{12}$ are independently selected from H and F. Typically, $R^8$-$R^{12}$ are all H, or $R^{10}$-$R^{11}$ are F and $R^8$, $R^9$, and $R^{12}$ are H.

In a further embodiment of the present invention A is selected from formula 7 wherein $R^{13}$ is an aryl, such as phenyl or naphthyl, optionally substituted with a group selected from F. Typically, $R^{13}$ is phenyl, optionally substituted with one, two or three F.

In a further embodiment of the present invention A is selected from formula 8 wherein $R^{27}$ is selected from a $C_{1-6}$ alkyl, branched $C_{3-6}$ alkyl, $C_{1-6}$ alkoxy and branched $C_{3-6}$ alkoxy. Typically, $R^{27}$ is selected from a $C_{1-6}$ alkyl and $C_{1-6}$ alkoxy.

In a further embodiment of the present invention X is selected from S, SO, $SO_2$, and O. Preferably X is selected from S, SO, and $SO_2$. In a further embodiment X is selected from S and $SO_2$, such as S.

In a still further embodiment of the present invention B is selected from a $C_{1-6}$ alkyl substituted with a phenyl, optionally substituted with a group selected from Br, F, Cl, methyl optionally substituted with a F, and $OCH_3$ optionally substituted with a F.

In a further embodiment of the present invention B is selected from a $C_{1-6}$ alkyl substituted with a phenyl, such as benzyl or $CH_2$—$CH_2$-phenyl.

In a still further embodiment of the present invention B is selected from a $C_{1-6}$ alkyl substituted with a phenyl, said phenyl substituted with a group selected from Cl, such as benzyl substituted with one or two Cl, or —$CH_2$—$CH_2$-phenyl substituted with one Cl.

In a further embodiment of the present invention B is selected from a $C_{1-6}$ alkyl.

In a still further embodiment of the present invention B is selected from an aryl, such as phenyl or naphthyl, optionally substituted with one or more substituents selected from a halogen (e.g. Cl, F, Br, I), methyl optionally substituted with a F, $OCH_3$ optionally substituted with a F, $OCH_2CH_3$ optionally substituted with a F, OH, and $R^{16}$—CONH— wherein $R^{16}$ is selected from $C_{1-3}$ alkyl and cyclopropyl.

In a further embodiment of the present invention B is selected from an aryl, such as phenyl or naphthyl, optionally substituted with one or more substituents selected from I, COOH and $CONH_2$.

In a further embodiment of the present invention B is selected from an aryl, such as phenyl or naphthyl, optionally substituted with one or more substituents selected from $NR^{28}R^{29}$, wherein $R^{28}$ and $R^{29}$ are independently selected from H, $C_{1-3}$ alkyl and isopropyl.

In a still further embodiment of the present invention B is selected from an aryl, such as phenyl or naphthyl, optionally substituted with one or more substituents selected from CN.

In a further embodiment of the present invention B is selected from an unsubstituted phenyl.

In a still further embodiment of the present invention B is selected from an unsubstituted naphthyl.

In a further embodiment of the present invention B is selected from a phenyl substituted with one, two or three substituents selected from Cl, F, Br, CN, methyl, OH, CF3, $OCH_2CH_3$, $OCH_3$, $OCF_3$, $R^{16}$—CONH— wherein $R^{16}$ is selected from $C_{1-3}$ alkyl, such as methyl. Such as a phenyl substituted with two substituents selected from Cl, F, Br, CN. Such as a phenyl substituted with three substituents selected from Cl, F, and CN.

In a still further embodiment of the present invention B is selected from a phenyl substituted with one, two or three substituents selected from Cl, F, Br, I CN, methyl, OH, CF3, $OCH_2CH_3$, $OCH_3$, $OCF_3$, COOH, $CONH_2$, and $R^{16}$—CONH— wherein $R^{16}$ is selected from $C_{1-3}$alkyl, such as methyl. Such as a phenyl substituted with one substituent selected from I, COOH, and $CONH_2$.

In a further embodiment of the present invention B is selected from a heterocycle, such as heteroaryl or heterocycloalkyl, optionally substituted with one or more substituents selected from a halogen (e.g. Cl, F, Br, I); methyl optionally substituted with a F; $OCH_3$ optionally substituted with a F; OCH$_2$CH$_3$ optionally substituted with a F; CONH$_2$; OH; NR$^{30}$R$^{31}$, wherein R$^{30}$ and R$^{31}$ are independently selected from H, C$_{1-3}$ alkyl and isopropyl; and R$^{18}$—CONH— wherein R$^{18}$ is selected from C$_{1-3}$ alkyl and cyclopropyl.

In a still further embodiment of the present invention B is selected from a heterocycle, such as heteroaryl or heterocycloalkyl, optionally substituted with one or more substituents selected from a halogen (e.g. Cl, F, Br, I); methyl optionally substituted with a F; OCH$_3$ optionally substituted with a F; OCH$_2$CH$_3$ optionally substituted with a F; OH; and R$^{18}$—CONH— wherein R$^{18}$ is selected from C$_{1-3}$ alkyl and cyclopropyl.

In a further embodiment of the present invention B is selected from a heterocycle, such as heteroaryl or heterocycloalkyl, optionally substituted with one or more substituents selected from CONH$_2$; OH; Cl; Br; and CF$_3$.

In a still further embodiment of the present invention B is selected from a heterocycle, such as heteroaryl or heterocycloalkyl, optionally substituted with one or more substituents selected from CN.

In a further embodiment of the present invention B is selected from a heterocycle, such as heteroaryl or heterocycloalkyl, optionally substituted with one to three substituents selected from CONH$_2$; OH; CN; Cl; Br; and CF$_3$.

In a still further embodiment of the present invention B is selected from an unsubstituted pyridinyl.

In a further embodiment of the present invention B is selected from a pyridinyl substituted with one to three, such as two, substituents selected from Cl, Br, CF$_3$ and CN.

In a still further embodiment of the present invention B is selected from a pyridinyl substituted with one to three, such as one or two, substituents selected from CONH$_2$, and OH.

In a further embodiment of the present invention B is selected from a pyridinyl substituted with one to three, such as one, substituents selected from NR$^{30}$R$^{31}$, wherein R$^{30}$ and R$^{31}$ are independently selected from H, C$_{1-3}$ alkyl and isopropyl.

In a further embodiment of the present invention B is selected from a pyridazinyl substituted with one to three, such as two, substituents selected from Cl, OH, OCH$_3$, and CN.

In a still further embodiment of the present invention B is selected from a thiophenyl substituted with one to three, such as one, substituents selected from halogen, such as Cl.

In a further embodiment of the present invention B is selected from a C$_{5-7}$ cycloalkyl, optionally substituted with one or more substituents selected from a halogen (e.g. Cl, F, Br, I), methyl optionally substituted with a F, OCH$_3$ optionally substituted with a F, OCH$_2$CH$_3$ optionally substituted with a F, OH, and R$^{17}$—CONH— wherein R$^{17}$ is selected from C$_{1-3}$ alkyl and cyclopropyl.

In a still further embodiment of the present invention B is a cyclohexyl optionally substituted with one or more substituents selected from a halogen.

In a further embodiment of the present invention B is a cyclohexyl.

In a still further embodiment of the present invention B is a cyclohexyl substituted with one or two substituents selected from a halogen, such as 2F.

As mentioned above some of the compounds of the present invention have high galectin-3 affinity and very good PK properties, showing high oral bioavailability and are suitable for oral administration, and the data presented herein supports that at least the compounds of formula (1) of the present invention wherein A is selected from formula 2 wherein R$^1$-R$^5$ are independently selected from H, F, methyl optionally substituted with a F, and OCH$_3$ optionally substituted with a F, typically R$^1$-R$^5$ are selected from H, F, Br, and Cl, such as R$^2$-R$^4$ are selected from F, Br, and Cl, and R$^1$ and R$^5$ are H or R$^1$-R$^5$ are all selected from F, Br, and Cl; preferably, R$^1$-R$^5$ are selected from H and F, such as R$^2$-R$^4$ are selected from F, and R$^1$ and R$^5$ are H or R$^1$-R$^5$ are all selected from F; wherein X is selected from S and SO$_2$, and wherein B is selected from a phenyl substituted with one, two or three substituents selected from Cl, F, Br, methyl, OH, CN, CF3, OCH$_2$CH$_3$, OCH$_3$, OCF$_3$, R$^{16}$—CONH— wherein R$^{16}$ is selected from C$_{1-3}$ alkyl, such as methyl, typically B is phenyl substituted with 1-3 substituents selected from Cl, F, CN, and Br, such as Cl in meta or para position or both, F in ortho, meta or para position or all three, CN in meta position, or Br in meta or para position or both, or two or three selected from Cl, F, CN, and Br in ortho, meta and para position; or wherein B is selected from a pyridinyl and pyridazinyl substituted with one, two or three substituents selected from Cl, F, Br, OH, CN, CF$_3$, OCH$_2$CH$_3$, OCH$_3$, OCF$_3$, typically B is selected from a pyridinyl and pyridazinyl substituted in meta and para position with two substituents selected from Cl, Br, OH, CN, CF$_3$, OCH$_3$; have these very good PK properties and high galectin-3 affinity.

In a further embodiment of the present invention, the compound is selected from any one of examples 1-42:

3,4-Dimethylphenyl 3-deoxy-3-[4-(3,4,5-trifluorophenyl)-1H-1,2,3-triazol-1-yl]-1-thio-α-D-galactopyranoside, 3-Bromophenyl 3-deoxy-3-[4-(3,4,5-trifluorophenyl)-1H-1,2,3-triazol-1-yl]-1-thio-α-D-galactopyranoside, 3-Ethoxyphenyl 3-deoxy-3-[4-(3,4,5-trifluorophenyl)-1H-1,2,3-triazol-1-yl]-1-thio-α-D-galactopyranoside, 4-Pyridyl 3-deoxy-3-[4-(3,4,5-trifluorophenyl)-1H-1,2,3-triazol-1-yl]-1-thio-α-D-galactopyranoside, 2,4-Dichlorophenyl 3-deoxy-3-[4-(3,4,5-trifluorophenyl)-1H-1,2,3-triazol-1-yl]-1-thio-α-D-galactopyranoside, 4-Acetanilidyl 3-deoxy-3-[4-(3,4,5-trifluorophenyl)-1H-1,2,3-triazol-1-yl]-1-thio-α-D-galactopyranoside, 4-Methoxyphenyl 3-deoxy-3-[4-(3,4,5-trifluorophenyl)-1H-1,2,3-triazol-1-yl]-1-thio α-D-galactopyranoside, 2,3-Dichlorophenyl 3-deoxy-3-[4-(3,4,5-trifluorophenyl)-1H-1,2,3-triazol-1-yl]-1-thio-α-D-galactopyranoside, 3,4-Dichlorophenyl 3-deoxy-3-[4-(3,4,5-trifluorophenyl)-1H-1,2,3-triazol-1-yl]-1-thio-α-D-galactopyranoside, Benzyl 3-deoxy-1-thio-3-[4-(3,4,5-trifluorophenyl)-1H-1,2,3-triazol-1-yl]-1-thio-α-D-galactopyranoside, 3-Methoxyphenyl 3-deoxy-3-[4-(3,4,5-trifluorophenyl)-1H-1,2,3-triazol-1-yl]-1-thio-α-D-galactopyranoside, 2-Naphtyl 3-deoxy-3-[4-(3,4,5-trifluorophenyl)-1H-1,2,3-triazol-1-yl]-1-thio-α-D-galactopyranoside, 3-Methylphenyl 3-deoxy-3-[4-(3,4,5-trifluorophenyl)-1H-1,2,3-triazol-1-yl]-1-thio-α-D-galactopyranoside, 3-(Trifluoromethyl)phenyl 3-deoxy-3-[4-(3,4,5-trifluorophenyl)-1H-1,2,3-triazol-1-yl]-1-thio-α-D-galactopyranoside, 4-Bromophenyl 3-deoxy-3-[4-(3,4,5-trifluorophenyl)-1H-1,2,3-triazol-1-yl]-1-thio-α-D-galactopyranoside, 3,5-Dichlorophenyl 3-deoxy-3-[4-(3,4,5-trifluorophenyl)-1H-1,2,3-triazol-1-yl]-1-thio-α-D-galactopyranoside, 2,6-Dimethylphenyl 3-deoxy-3-[4-(3,4,5-trifluorophenyl)-1H-1,2,3-triazol-1-yl]-1-thio-α-D-galactopyranoside, 1-Naphthyl 3-deoxy-1-thio-3-[4-(3,4,5-trifluorophenyl)-1H-1,2,3-triazol-1-yl]-1-thio-α-D-galactopyranoside, 3-Chlorophenyl 3-deoxy-3-[4-(3,4,5-trifluorophenyl)-1H-1,2,3-triazol-1-yl]-1-thio-α-D-galactopyranoside, 3-(Trifluoromethoxy)phenyl 3-deoxy-3-[4-(3,4,5-trifluorophenyl)-1H-1,2,3-triazol-1-yl]-1-thio-α-D-galactopyranoside,
2-Pyridyl 3-deoxy-3-[4-(3,4,5-trifluorophenyl-1H-1,2,3-triazol-1-yl]-)-1-thio-α-D-galactopyranoside,
3,4-Dichlorophenyl 3-deoxy-3-[4-(3,4,5-trifluorophenyl)-1H-1,2,3-triazol-1-yl]-α-D-galactopyranoside,
4-Chlorophenyl 3-deoxy-3-[4-(3,4,5-trifluorophenyl)-1H-1,2,3-triazol-1-yl]-1-thio-α-D-galactopyranoside,
3,4-Dichlorophenyl 3-deoxy-3-[4-(3,4,5-trifluorophenyl)-1H-1,2,3-triazol-1-yl]-α-D-galactopyranosyl sulfoxide,
3,4-Dichlorophenyl 3-deoxy-3-[4-(3,4,5-trifluorophenyl)-1H-1,2,3-triazol-1-yl]-α-D-galactopyranosyl sulfone,
4-Chlorophenyl 3-deoxy-3-[4-(3,4,5-trifluorophenyl)-1H-1,2,3-triazol-1-yl]-α-D-galactopyranosyl sulfoxide,
Phenyl 3-deoxy-3-[4-(3,4,5-trifluorophenyl)-1H-1,2,3-triazol-1-yl]-1-thio-α-D-galactopyranoside,
3-Chloro-4-fluorophenyl 3-deoxy-3-[4-(3,4,5-trifluorophenyl)-1H-1,2,3-triazol-1-yl]-1-thio-α-D-galactopyranoside,
4-Tolyl 3-deoxy-3-[4-(3,4,5-trifluorophenyl)-1H-1,2,3-triazol-1-yl]-1-thio-α-D-galactopyranoside,
4-Fluorophenyl 3-deoxy-3-[4-(3,4,5-trifluorophenyl)-1H-1,2,3-triazol-1-yl]-1-thio-α-D-galactopyranoside,
4-Trifluoromethoxyphenyl 3-deoxy-3-[4-(3,4,5-trifluorophenyl)-1H-1,2,3-triazol-1-yl]-1-thio-α-D-galactopyranoside,
Phenyl 3-deoxy-3-[4-(3,4,5-trifluorophenyl)-1H-1,2,3-triazol-1-yl]-α-D-galactopyranoside,
3-Chlorophenyl 3-deoxy-3-[4-(3,4,5-trifluorophenyl)-1H-1,2,3-triazol-1-yl]-α-D-galactopyranoside,
4-Chlorophenyl 3-deoxy-3-[4-(3,4,5-trifluorophenyl)-1H-1,2,3-triazol-1-yl]-α-D-galactopyranoside,
Cyclohexyl 3-deoxy-3-[4-(3,4,5-trifluorophenyl)-1H-1,2,3-triazol-1-yl]-1-thio-α-D-galactopyranoside,
2,4,5-Trichlorophenyl 3-deoxy-3-[4-(3,4,5-trifluorophenyl)-1H-1,2,3-triazol-1-yl]-1-thio-α-D-galactopyranoside,
2,5-Dichlorophenyl 3-deoxy-3-[4-(3,4,5-trifluorophenyl)-1H-1,2,3-triazol-1-yl]-1-thio-α-D-galactopyranoside,
3-Hydroxy-phenyl 3-deoxy-3-[4-(3,4,5-trifluorophenyl)-1H-1,2,3-triazol-1-yl]-1-thio-α-D-galactopyranoside,
3-Bromophenyl 3-deoxy-3-[4-(3,4,5-trifluorophenyl)-1H-1,2,3-triazol-1-yl]-α-D-galactopyranosyl sulfoxide,
2-Phenethyl 3-deoxy-3-[4-(3,4,5-trifluorophenyl)-1H-1,2,3-triazol-1-yl]-1-thio-α-D-galactopyranoside,
3,4-Dichlorophenyl 3-O-[(2-amino-(4-chlorophenyl) pyrimidin-6-yl) methylene]-1-thio-α-D-galactopyranoside, and
3,4-Dichlorophenyl 3-deoxy-3-[4-(2,3,4,5,6-pentafluorophenyl)-1H-1,2,3-triazol-1-yl]-α-D-galactopyranosyl sulfoxide.

In a further embodiment of the present invention the compound is selected from any one of examples 43-55:
5-Chloropyridin-3-yl 3-deoxy-3-[4-(3,4,5-trifluorophenyl)-1H-1,2,3-triazol-1-yl]-1-thio-α-D-galactopyranoside,
5-Bromopyridin-3-yl 3-deoxy-3-[4-(3,4,5-trifluorophenyl)-1H-1,2,3-triazol-1-yl]-1-thio-α-D-galactopyranoside,
3-Chloro-5-cyanophenyl 3-deoxy-3-[4-(3,4,5-trifluorophenyl)-1H-1,2,3-triazol-1-yl]-1-thio-α-D-galactopyranoside,
3-Chloro-4-cyanophenyl 3-deoxy-3-[4-(3,4,5-trifluorophenyl)-1H-1,2,3-triazol-1-yl]-1-thio-α-D-galactopyranoside,
3-Chloro-6-fluoro-4-cyanophenyl 3-deoxy-3-[4-(3,4,5-trifluorophenyl)-1-H-1,2,3-triazol-1-yl]-1-thio-α-D-galactopyranoside,
3-Bromo-4-cyanophenyl 3-deoxy-3-[4-(3,4,5-trifluorophenyl)-1H-1,2,3-triazol-1-yl]-1-thio-α-D-galactopyranoside,
5-Bromo-6-trifluoromethyl-pyridin-3-yl 3-deoxy-3-[4-(3,4,5-trifluorophenyl)-1H-1,2,3-triazol-1-yl]-1-thio-α-D-galactopyranoside,
5-Chloro-6-cyano-pyridin-3-yl 3-deoxy-3-[4-(3,4,5-trifluorophenyl)-1H-1,2,3-triazol-1-yl]-1-thio-α-D-galactopyranoside,
5-Chloro-6-cyano-pyridazin-3-yl 3-deoxy-3-[4-(3,4,5-trifluorophenyl)-1H-1,2,3-triazol-1-yl]-1-thio-α-D-galactopyranoside,
3,4-Dichlorophenyl 3-deoxy-3-[4-(2,3,4,5,6-pentafluorophenyl)-1H-1,2,3-triazol-1-yl]-1-thio-α-D-galactopyranoside,
3,4-Dichlorophenyl 3-deoxy-3-[4-(2,3,4,5,6-pentafluorophenyl)-1H-1,2,3-triazol-1-yl]-α-D-galactopyranosyl sulfone,
5-Methoxy-6-cyano-pyridazin-3-yl 3-deoxy-3-[4-(3,4,5-trifluorophenyl)-1H-1,2,3-triazol-1-yl]-1-thio-α-D-galactopyranoside, and
5-Hydroxy-6-cyano-pyridazin-3-yl 3-deoxy-3-[4-(3,4,5-trifluorophenyl)-1H-1,2,3-triazol-1-yl]-1-thio-α-D-galactopyranoside, In a further embodiment of the present invention the compound is selected from any one of examples 56-106:
3-Chloro-2,4-difluorobenyl 3-deoxy-1-thio-3-[4-(3,4,5-trifluorophenyl)-1H-1,2,3-triazol-1-yl]-α-D-galactopyranoside,
3,4-Dichlorophenyl 3-deoxy-3-[4-(phenyl)-1H-1,2,3-triazol-1-yl]-1-thio-α-D-galactopyranoside,
3,5-Dichloro-4-fluorophenyl 3-deoxy-3-[4-(3,4,5-trifluorophenyl)-1H-1,2,3-triazol-1-yl]-1-thio-α-D-galactopyranoside,
3,4-Dichloro-6-fluorophenyl 3-deoxy-3-[4-(3,4,5-trifluorophenyl)-1H-1,2,3-triazol-1-yl]-1-thio-α-D-galactopyranoside,
3-Bromo-4-fluorophenyl 3-deoxy-3-[4-(3,4,5-trifluorophenyl)-1H-1,2,3-triazol-1-yl]-1-thio-α-D-galactopyranoside,
3-Chloro-4-(trifluoromethyl)phenyl 3-deoxy-1-thio-3-[4-(3,4,5-trifluorophenyl)-1H-1,2,3-triazol-1-yl]-α-D-galactopyranoside,
3,4,5-Trichlorophenyl 3-deoxy-1-thio-3-[4-(3,4,5-trifluorophenyl)-1H-1,2,3-triazol-1-yl]-α-D-galactopyranoside,
5-Chloro-2-fluorophenyl 3-deoxy-1-thio-3-[4-(3,4,5-trifluorophenyl)-1H-1,2,3-triazol-1-yl]-α-D-galactopyranoside,
5-Bromo-2-fluorophenyl 3-deoxy-1-thio-3-[4-(3,4,5-trifluorophenyl)-1H-1,2,3-triazol-1-yl]-α-D-galactopyranoside,
5-Chloro-2-methoxyphenyl 3-deoxy-1-thio-3-[4-(3,4,5-trifluorophenyl)-1H-1,2,3-triazol-1-yl]-α-D-galactopyranoside,
3-Iodophenyl 3-deoxy-1-thio-3-[4-(3,4,5-trifluorophenyl)-1H-1,2,3-triazol-1-yl]-α-D-galactopyranoside,
Picolinamide-5-yl 3-deoxy-3-[4-(3,4,5-trifluorophenyl)-1H-1,2,3-triazol-1-yl]-1-thio-α-D-galactopyranoside,
3-Cyanophenyl 3-deoxy-1-thio-3-[4-(3,4,5-trifluorophenyl)-1H-1,2,3-triazol-1-yl]-α-D-galactopyranoside,
2-Cyanopyridine-5-yl 3-deoxy-3-[4-(3,4,5-trifluorophenyl)-1H-1,2,3-triazol-1-yl]-1-thio-α-D-galactopyranoside,
4-Chloro-2-thienyl 3-deoxy-3-[4-(3,4,5-trifluorophenyl)-1H-1,2,3-triazol-1-yl]-1-thio-α-D-galactopyranoside,
3-Carboxyphenyl 3-deoxy-3-[4-(3,4,5-trifluorophenyl)-1H-1,2,3-triazol-1-yl]-1-thio-α-D-galactopyranoside,
Benzamide-3-yl 3-deoxy-3-[4-(3,4,5-trifluorophenyl)-1H-1,2,3-triazol-1-yl]-1-thio-α-D-galactopyranoside.

3,4-Dichlorophenyl 3-deoxy-3-[4-(3,4-difluorophenyl)-1H-1,2,3-triazol-1-yl]-1-thio-α-D-galactopyranoside,
3,4-Dichlorophenyl 3-deoxy-3-[4-(3,4-difluorophenyl)-1H-1,2,3-triazol-1-yl]-1-thio-α-D-galactopyranoside,
3,4-Dichlorophenyl 3-deoxy-3-[4-(3-fluorophenyl)-1H-1,2,3-triazol-1-yl]-1-thio-α-D-galactopyranoside,
3,3'-difluoro-cyklohexyl 3-deoxy-3-[4-(3,4,5-trifluorophenyl)-1H-1,2,3-triazol-1-yl]-1-thio-α-D-galactopyranoside,
n-Butyl 3-deoxy-3-[4-(3,4,5-trifluorophenyl)-1H-1,2,3-triazol-1-yl]-1-thio-α-D-galactopyranoside,
3,4-Dichlorophenyl 3-deoxy-3-[4-(3,5-difluoro-4-methoxyphenyl)-1H-1,2,3-triazol-1-yl]-1-thio-α-D-galactopyranoside,
2-Hydroxy-pyridin-4-yl 3-deoxy-3-[4-(3,4,5-trifluorophenyl)-1H-1,2,3-triazol-1-yl]-1-thio-α-D-galactopyranoside,
2-Chlorophenethyl 3-deoxy-3-[4-(3,4,5-trifluorophenyl)-1H-1,2,3-triazol-1-yl]-1-thio-α-D-galactopyranoside,
4-Chlorophenethyl 3-deoxy-3-[4-(3,4,5-trifluorophenyl)-1H-1,2,3-triazol-1-yl]-1-thio-α-D-galactopyranoside,
2-Chlorobenzyl 3-deoxy-1-thio-3-[4-(3,4,5-trifluorophenyl)-1H-1,2,3-triazol-1-yl]-α-D-galactopyranoside,
3,4-Dichlorobenzyl 3-deoxy-1-thio-3-[4-(3,4,5-trifluorophenyl)-1H-1,2,3-triazol-1-yl]-α-D-galactopyranoside,
3-Chlorophenethyl 3-deoxy-3-[4-(3,4,5-trifluorophenyl)-1H-1,2,3-triazol-1-yl]-1-thio-α-D-galactopyranoside,
4-Chlorobenzyl 3-deoxy-1-thio-3-[4-(3,4,5-trifluorophenyl)-1H-1,2,3-triazol-1-yl]-α-D-galactopyranoside,
Propyl 3-deoxy-3-[4-(3,4,5-trifluorophenyl)-1H-1,2,3-triazol-1-yl]-1-thio-α-D-galactopyranoside,
2-Aminopyridin-4-yl 3-deoxy-3-[4-(3,4,5-trifluorophenyl)-1H-1,2,3-triazol-1-yl]-1-thio-α-D-galactopyranoside,
5-dimethylamino-naphatlen-2-yl 3-deoxy-3-[4-(3,4,5-trifluorophenyl)-1H-1,2,3-triazol-1-yl]-1-thio-α-D-galactopyranoside,
Ethyl 3-deoxy-1-thio-3-[4-(3,4,5-trifluorophenyl)-1H-1,2,3-triazol-1-yl]-α-D-galactopyranoside,
S-5-Bromopyridin-3-yl 3-deoxy-3-[4-(3,4,5-trifluorophenyl)-1H-1,2,3-triazol-1-yl]-α-D-galactopyranosyl sulfoxide,
R-5-Bromopyridin-3-yl 3-deoxy-3-[4-(3,4,5-trifluorophenyl)-1H-1,2,3-triazol-1-yl]-α-D-galactopyranosyl sulfoxide.
5-Bromopyridin-3-yl 3-deoxy-3-[4-(3,4,5-trifluorophenyl)-1H-1,2,3-triazol-1-yl]-α-D-galactopyranosyl sulfone,
S-Chloropyridin-3-yl 3-deoxy-3-[4-(3,4,5-trifluorophenyl)-1H-1,2,3-triazol-1-yl]-α-D-galactopyranosyl sulfoxide,
R-Chloropyridin-3-yl 3-deoxy-3-[4-(3,4,5-trifluorophenyl)-1H-1,2,3-triazol-1-yl]-α-D-galactopyranosyl sulfoxide,
5-Dimethylamino-naphtalen-2-yl 3-deoxy-3-[4-(3,4,5-trifluorophenyl)-1H-1,2,3-triazol-1-yl]-α-D-galactopyranosyl sulfone,
3,4-dichlorophenyl-3-deoxy-3-(3,4,5-trifluorobenzamido)-1-thio-α-D-galactopyranoside,
3,4-Dichlorophenyl 3-deoxy-3-[4-(ethoxycarbonyl)-1H-1,2,3-triazol-1-yl]-1-thio-α-D-galactopyranoside,
3,4-Dichlorophenyl 3-deoxy-3-[4-(ethylaminocarbonyl)-1H-1,2,3-triazol-1-yl]-1-thio-α-D-galactopyranoside,
3,4-Dichlorophenyl 3-O-[(5,6-Difluoro-2-oxo-3-chromenyl)methyl]-1-thio-α-D-galactopyranoside,
5-Chloropyridin-3-yl 3-deoxy-3-[4-(3,4-difluorophenyl)-1H-1,2,3-triazol-1-yl]-1-thio-α-D-galactopyranoside,
5-Bromopyridin-3-yl 3-deoxy-3-[4-(3,4-difluorophenyl)-1H-1,2,3-triazol-1-yl]-1-thio-α-D-galactopyranoside,
3,4-Dichlorophenyl 3-deoxy-3-[4-(propyl-carbonyl)-1H-1,2,3-triazol-1-yl]-1-thio-α-D-galactopyranoside,
5-Chloro-6-trifluoromethyl-pyridine-3-yl 3-deoxy-3-[4-(3,4,5-trifluorophenyl)-1H-1,2,3-triazol-1-yl]-1-thio-α-D-galactopyranoside,
5-Chloro-2-trifluoromethyl-pyridine-3-yl 3-deoxy-3-[4-(3,4,5-trifluorophenyl)-1H-1,2,3-triazol-1-yl]-1-thio-α-D-galactopyranoside,
5-Chloro-6-cyano-pyridine-3-yl 3-deoxy-3-[4-(3,4-difluorophenyl)-1H-1,2,3-triazol-1-yl]-1-thio-α-D-galactopyranoside, and
3-Chloro-4-cyanophenyl 3-deoxy-3-[4-(3,4-difluorophenyl)-1H-1,2,3-triazol-1-yl]-1-thio-α-D-galactopyranoside.

In a further aspect the present invention relates to a compound of formula (1) for use as a medicine.

In a still further aspect the present invention relates to a pharmaceutical composition comprising the compound of any one of the previous claims and optionally a pharmaceutically acceptable additive, such as a carrier and/or excipient.

In a further aspect the present invention relates to a compound of formula (1) of the present invention for use in a method for treating a disorder relating to the binding of a galectin-3 to a ligand in a mammal, such as a human. In a further embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis.

In a still further aspect the present invention relates to a method for treatment of a disorder relating to the binding of a galectin-3 to a ligand in a mammal, such as a human, wherein a therapeutically effective amount of at least one compound of formula (1) of the present invention is administered to a mammal in need of said treatment. In a further embodiment of the present invention, the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis.

Another aspect of the present invention concerns combination therapy involving administering a compound of formula (1) of the present invention together with a therapeutically active compound different from the compound of formula (1) (interchangeable with "a different therapeutically active compound"). In one embodiment the present invention relates to a combination of a compound of formula (1) and a different therapeutically active compound for use in treatment of a disorder relating to the binding of a galectin-3 to a ligand in a mammal. Such disorders are disclosed below.

In an embodiment of the present invention, a therapeutically effective amount of at least one compound of formula (1) of the present invention is administered to a mammal in need thereof in combination with a different therapeutically active compound. In a further embodiment, said combination of a compound of formula (1) together with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis.

A non-limiting group of cancers given as examples of cancers that may be treated, managed and/or prevented by administration of a compound of formula (1) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In some aspects of the present invention, the administration of at least one compound of formula (1) of the present invention and at least one additional therapeutic agent demonstrate therapeutic synergy. In some aspects of the methods of the present invention, a measurement of response to treatment observed after administering both at least one compound of formula (1) of the present invention and the additional therapeutic agent is improved over the same measurement of response to treatment observed after administering either the at least one compound of formula (1) of the present invention or the additional therapeutic agent alone.

A further aspect of the present invention concerns combination therapy involving administering a compound of formula (1) of the present invention together with an anti-fibrotic compound different form the compound of formula (1) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, and PBI-4050.

A still further aspect of the present invention concerns combination therapy involving administering a compound of formula (1) in combination with a further conventional cancer treatment such as chemotherapy or radiotherapy, or treatment with immunostimulating substances, gene therapy, treatment with antibodies and treatment using dendritic cells, to a mammal in need thereof.

In an embodiment the compound of formula (1) is administered together with at least one additional therapeutic agent selected from an antineoplastic chemotherapy agent. In a further embodiment, the antineoplastic chemotherapeutic agent is selected from: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In some embodiments of the present invention the compound of formula (1) is administered together with at least one additional therapeutic agent selected from a checkpoint inhibitor. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITF, OX40, CD137, CD40, IDO, and TDO. These are known targets and some of these targets are described in Melero et al., Nature Reviews Cancer (2015).

In some embodiments of the present invention the compound of formula (1) is administered together with at least one additional therapeutic agent selected from an inhibitor of indoleamine-2,3-dioxygenase (IDO).

In some embodiments of the present invention the compound of formula (1) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (1) is administered together with at least one additional therapeutic agent selected from one or more inhibitors of the PD-1/PD-L pathway. In some embodiments, the one or more inhibitors of the PD-1/PD-L pathway are selected from one or more antibodies against PD-1, PD-L1, and/or PD-L2.

In a still further aspect the present invention relates to a process of preparing a compound of formula III or a pharmaceutically acceptable salt or solvate thereof comprising the step a1;

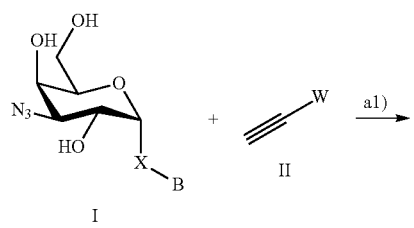

I

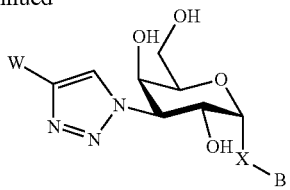

III

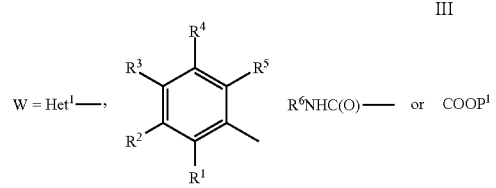

a1) Reacting the compound of formula I wherein X and B are as defined above under formula (1), with a compound of formula II in an inert solvent, such as DMF or acetonitrile, using a base, such as diisopropylethylamine, catalyzed by CuI to provide the compound of the formula III.

In a still further aspect the present invention relates to a process of preparing a compound of formula V or a pharmaceutically acceptable salt or solvate thereof comprising the step a2;

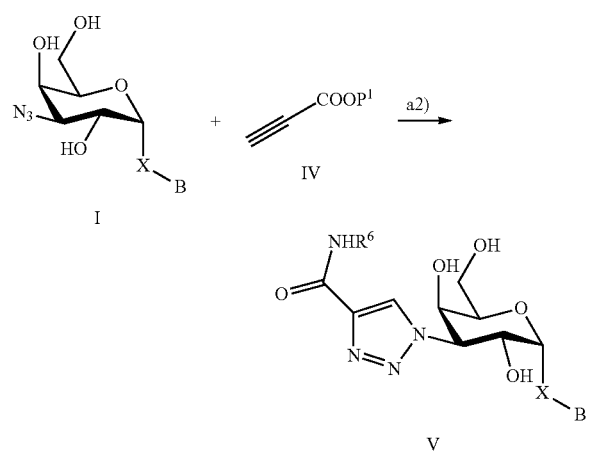

a2) reacting I with IV, wherein $P^1$ is selected from a $C_{1-5}$ alkyl group, in an inert solvent, such as DMF or acetonitrile, using a base, such as diisopropyletylamine, catalyzed by CuI to give a compound which upon treatment with a aliphatic base, such as $R^6$—$NH_2$ yields a compound of formula V.

In a still further aspect the present invention relates to a process of preparing a compound of formula VII and/or VIII or a pharmaceutically acceptable salt or solvate thereof comprising the step a3;

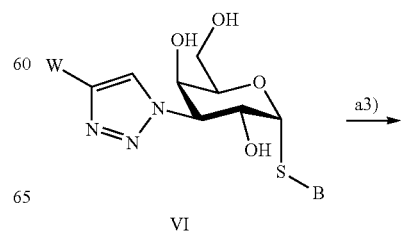

VI

-continued

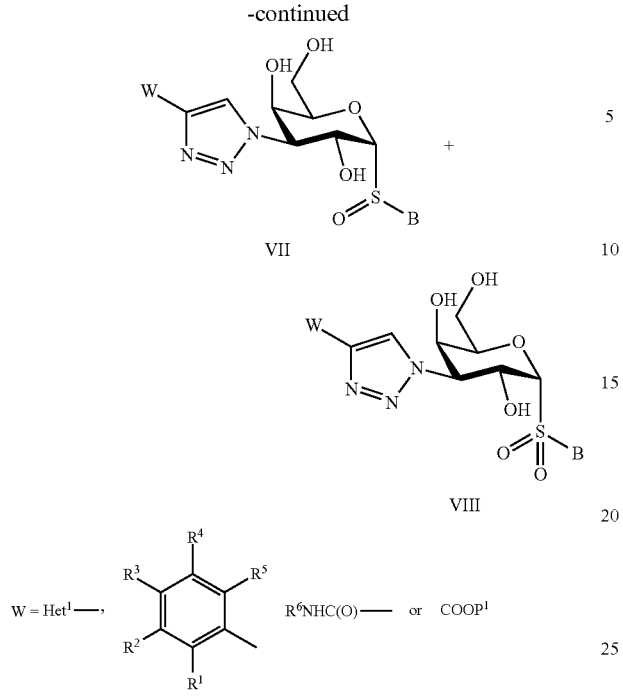

VII

VIII

W = Het¹—, R⁶NHC(O)— or COOP¹ a3) reacting a compound of formula VI with an oxidant such as hydrogen peroxide in a solvent such as acetic acid, alternatively 3-chloroperoxybenzoic acid in an inert solvent such as dichloromethane to give a compound of formula VII and/or VIII.

In a still further aspect the present invention relates to a process of preparing a compound of formula X wherein $R^7$ is as defined above under formula (1), or a pharmaceutically acceptable salt or solvate thereof comprising the step a4;

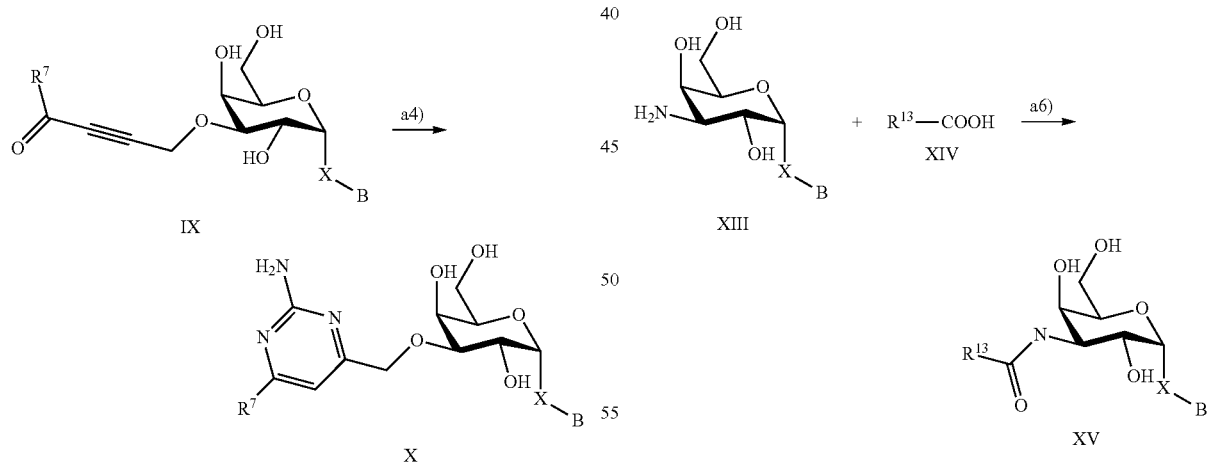

IX

X a4) Reacting a compound of the formula IX with guanidine hydrochloride in the presence of potassium carbonate in an inert solvent such as tetrahydrofuran, to give a compound of formula X.

In a still further aspect the present invention relates to a process of preparing a compound of formula XII or a pharmaceutically acceptable salt or solvate thereof comprising the step a5;

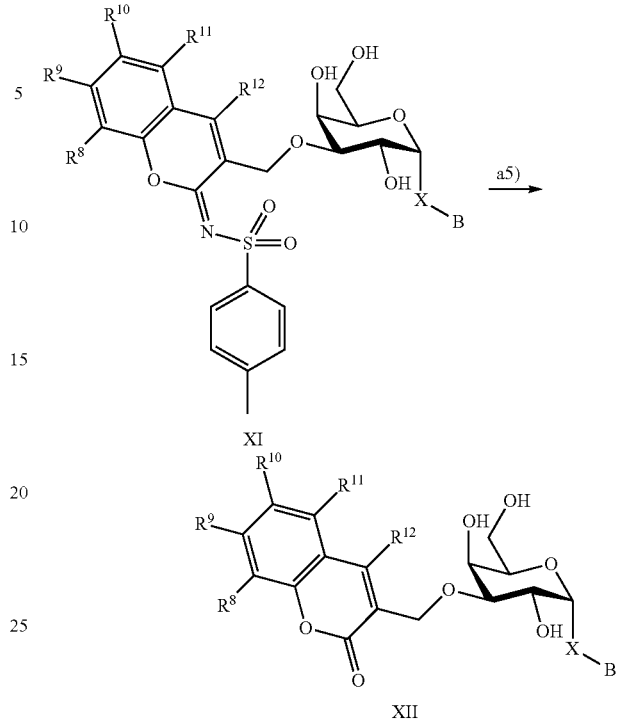

XI

XII a5) Reacting a compound of formula XI with a reagent such as sodium methoxide in methanol give a compound of formula XII.

In a still further aspect the present invention relates to a process of preparing a compound of formula XV or a pharmaceutically acceptable salt or solvate thereof comprising the steps a6;

XIII

XIV

XV a6) Reacting a compound of the formula XIII with a compound of the formula XIV using a reagents such as HATU in the presence of a base such as didisopropylethylamine (DIPEA) in an inert solvent such as DMF to give a compound of formula XV.

In a still further aspect the present invention relates to a process of preparing a compound of formula I wherein X is defined as oxygen or sulfur or a pharmaceutically acceptable salt or solvate thereof comprising the steps a7 and a8;

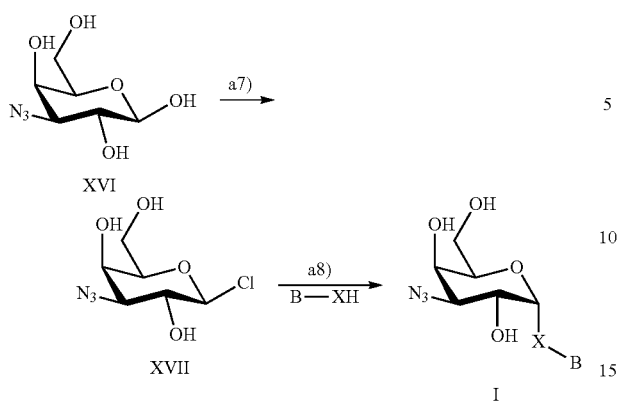

a7) Reacting a compound XVI with a chlorinating reagent such as dichloromethylmethylether or PCl$_5$ in the presence of a lewis acid such as BF$_3$Et$_2$O in an inert solvent as dichloromethane or chloroform to give a compound of formula XVII.

a8) Reacting a compound of the formula XVII with a nucleophile like B-XH, wherein X is defined as sulfur or oxygen, in the presence of a base like sodium hydride in an inert solvent such as DMF.

In a still further aspect the present invention relates to a process of preparing a compound of formula I wherein X is defined as CH$_2$ or a pharmaceutically acceptable salt or solvate thereof comprising the steps a9-a13;

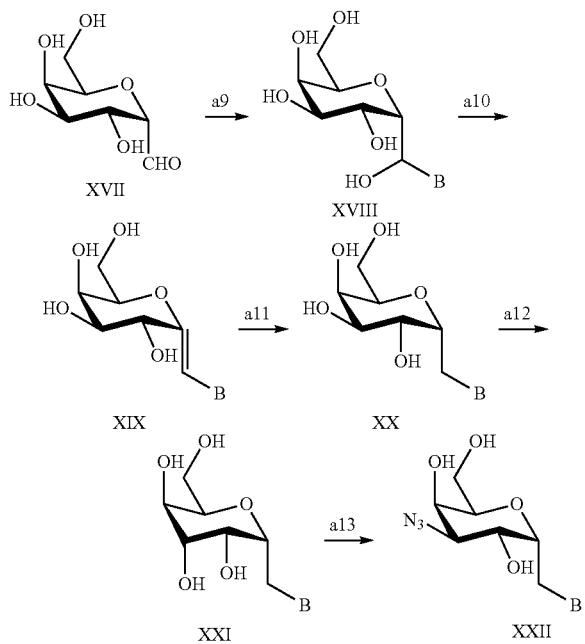

a9) A Compound XVII which can be prepared using the methods described in *Chem. Eur. J.* 2009, 15, 2861-2873 can be reacted with a nucleophile such as the Grignard reagent B-MgBr in an inert solvent such as ether to give a compound of formula XVIII.

a10) A compound of the formula XVIII could be transformed into a compound of the formula XIX using a reagent such as (ClCH$_2$O)$_2$ in the presence of a base such as pyridine.

a11) A compound of the formula XIX could be transformed to a compound of formula XX using hydrogen gas in the presence of a catalyst such as palladium on carbon in an inert solvent such as methanol.

a12) A compound of the formula XX could be selectively alkylated at the 3-hydroxy position by treatment of dibutyltinoxide followed by benzylbromide. The remaining hydroxy groups could then be protected using other protective groups which are stable under conditions for removing the benzyl, these include acetoxy, silyl and orthesters. The benzyl group is then selectively removed and the free hydroxy group in the 3 position is inverted using e.g. triflic anhydride in the presence of pyridine followed by Bu$_2$NNO$_2$ in an inert solvent such as DMF to give compound XXI a13) A compound of the formula XXI could be reacted with a reagent such as tosylchloride in the presence of a base such as pyridine to give a compound which could be reacted with sodium azide in an inert solvent such as DMF to give a compound of the formula XXII.

In a still further aspect the present invention relates to a process of preparing a compound of formula XXV wherein X is as defined above under formula (1), or a pharmaceutically acceptable salt or solvate thereof comprising the steps a14-16;

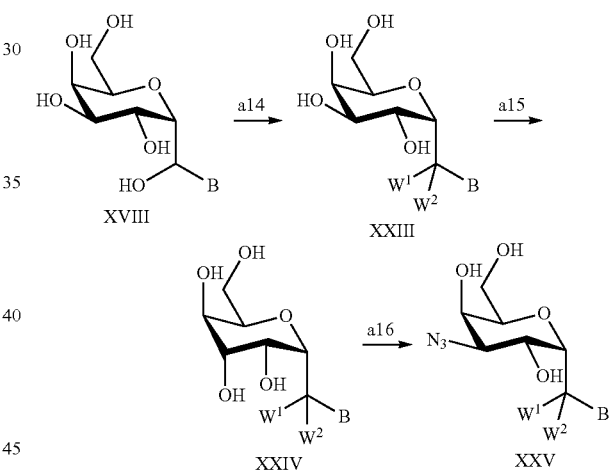

a14) A compound of the formula XVIII could be treated with a halide formation reagent such as DAST (fluorine), PCl$_5$ (chlorine), PBr$_5$ (Bromine) to give a compound XXIII wherein W$^1$ is the corresponding halide F, Cl or Br and W$^2$ is hydrogen.

Alternatively XVIII could be treated with an oxidising reagent such as PCC to give a compound XXIII where W$^1$ and W$^2$ together form a bond to oxygen. This compound could be treated with a halide formation reagent such as DAST (fluorine), PCl$_5$ (chlorine), PBr$_5$ (Bromine) to give a compound XXIII wherein W$_1$=W$^2$ is the corresponding halide F, Cl or Br.

a15) A compound of the formula XXIII could be selectively alkylated at the 3-hydroxy position by treatment of dibutyltinoxide followed by benzylbromide. The remaining hydroxy groups could then be protected using other protective groups which are stable under conditions for removing the benzyl, these include acetoxy, silyl and orthesters. The benzyl group is then selectively removed and the free hydroxy group in the 3 position is inverted using e.g. triflic anhydride in the presence of pyridine followed by Bu$_2$NNO$_2$ in an inert solvent such as DMF to give compound XXIV.

a16) A compound of the formula XXIV could be reacted with a reagent such as tosylchloride in the presence of a base such as pyridine to give a compound which could be reacted with sodium azide in an inert solvent such as DMF to give a compound of the formula XXV.

In a still further aspect the present invention relates to a process of preparing a compound of formula XI wherein R$^8$, R$^9$, R$^{10}$, R$^{11}$, R$^{12}$, X and B are defined as in formula (1) above, or a pharmaceutically acceptable salt or solvate thereof comprising the steps a17;

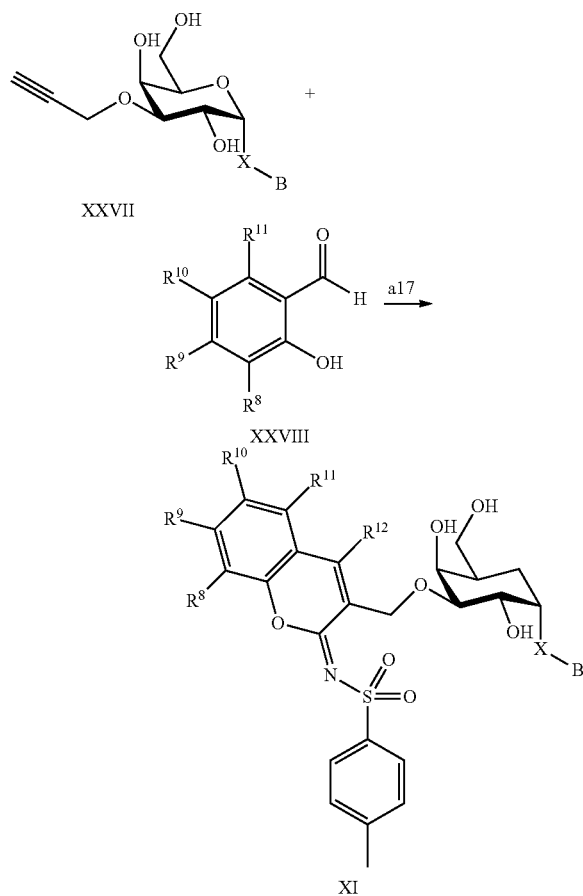

a17) A compound of the formula XXVII could be reacted with a compound of XXVII in the presence of toluenesulfoneazide, cupper iodide, triethyl amine in a solvent such as THF to give a compound of formula XI wherein R$^{12}$ is defined as H.

In a still further aspect the present invention relates to a process of preparing a compound of formula IX wherein R$^7$, X and B are defined as in formula (I) above, or a pharmaceutically acceptable salt or solvate thereof comprising the step a18;

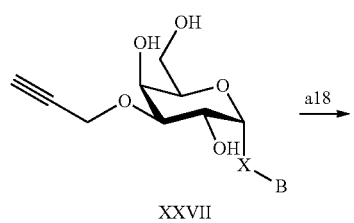

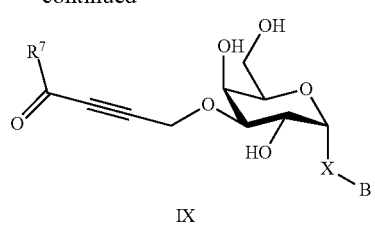

a18) A compound of formula XXVII could be reacted with a compound of formula R$^7$—COCl in the presence of CuI, PdCl$_2$(PPh$_3$)$_2$Cl$_2$ and triethylamine in an inert solvent such as THF to give a compound of formula IX.

In a still further aspect the present invention relates to a process of preparing a compound of formula XXVII, wherein X are defined as oxygen or sulfur and B is defined as above in formula (1), or a pharmaceutically acceptable salt or solvate thereof comprising the steps a19-a20;

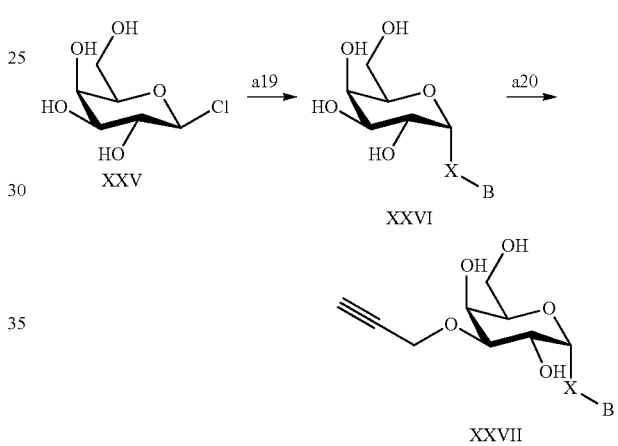

a19) Reacting a compound of the formula XXV, prepared in according to Farkas, I.; Szabó, I. F.; Bognár, R.; Anderle, D. *Carbohydr. Res.* 1976, 48, 136-138 or Ibatullin, F. M.; Selivanov, S. I., *Tetrahedron Letters* 2002, 43, 9577-9580, with a nucleophile such as B-XH, wherein X is defined as sulfur or oxygen, in the presence of a base like sodium hydride in an inert solvent such as DMF to give a compound of formula XXVI.

a20) Reacting a compound of the formula XXVI with dibutyltin oxide in an inert solvent such as methanol to give a compound which is further reacted with a 3-bromoprop-1-yne in the presence of tetrabutylammonium iodide in an inert solvent such as tetrahydrofuran to give a compound of formula XXVII.

In a still further aspect the present invention relates to a process of preparing a compound of formula II comprising the step a21:

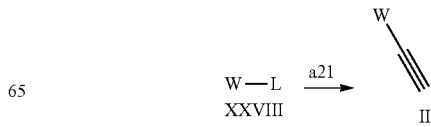

-continued

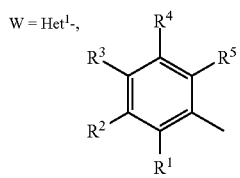

W = Het¹-, a21) Reacting a compound of formula XXVIII wherein P¹ is defined as a $C_{1-5}$ alkyl group, such as methyl and L is defined as a leaving group such as bromine, with trimethylsilane-acetylene using a palladium catalyst such as bis(triphenylphosphine)palladium-(II)-chloride, copper iodide and a base like diisopropylethylamine in an inert solvent, such as THF, to give a compound of formula II.

In a still further aspect the present invention relates to a process of preparing a compound of the formula XXIX comprising step a22)

a22)

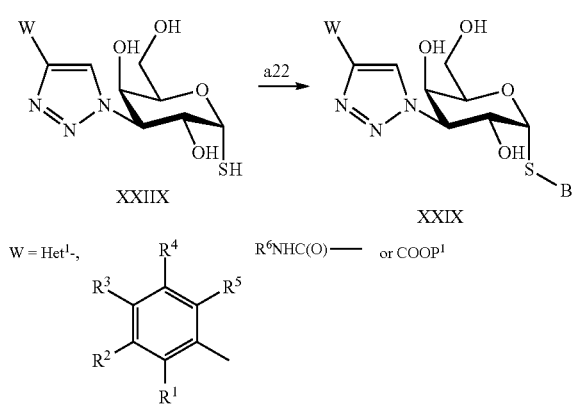

W = Het¹-,   R⁶NHC(O)— or COOP¹

Reacting a compound of the formula XXIIX with a compound of the formula B-L, wherein L is defined as a leaving group such as Chlorine, in an inert solvent as DMF using a base such as sodium hydride to give a compound of the formula XXIX.

In a still further aspect the present invention relates to a process of preparing a compound of the formula XXIIX comprising step a23-a25)

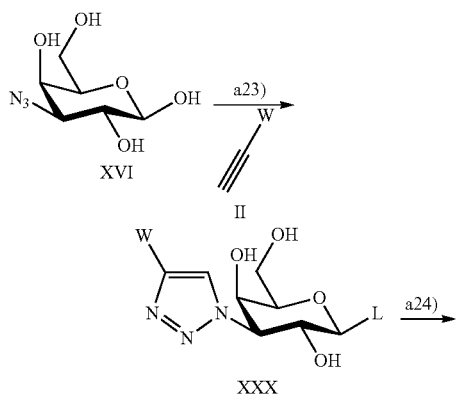

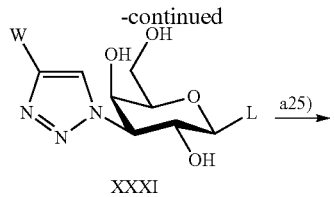

W = Het¹-,   R⁶NHC(O)— or COOP¹

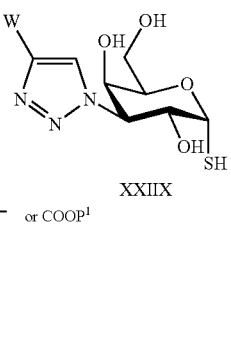

a23) Reacting the compound of formula XVI, with a compound of formula II in an inert solvent, such as DMF or acetonitrile, using a base, such as diisopropylethylamine, catalyzed by CuI to provide the compound of the formula XXX.

a24) Reacting a compound XXX with a chlorinating reagent such as dichloromethylmethylether or $PCl_5$ in the presence of a lewis acid such as $BF_3Et_2O$ in an inert solvent as dichloromethane or chloroform to give a compound of formula XXXI.

a25) Reacting a compound of formula XXXI with a sulfurus nucleophile such as thioacetate followed by deprotection using a base such as sodium methoxide, to give XXIIX.

In a still further aspect the present invention relates to a process of preparing a compound of the formula XXXV comprising step a26-a28

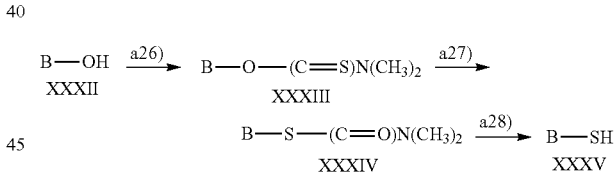

a26) Reacting a compound of the formula XXXII with an activated thioamide such as dimethylcarbamoyl chloride using a base such as sodium hydride in an inert solvent such as DMF to give a compound of formula XXXIII.

a27) Heating a compound of the formula XXXIII at elevated temperatures to form compound XXXIV.

a28) Reacting a compound of formula XXXIV with a base such as potassium hydroxide to give a compound of the formula XXXV.

In a still further aspect the present invention relates to a process of preparing a compound of the formula XXXV comprising step a29-a30

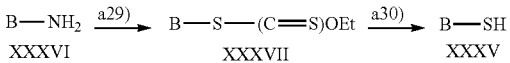

a29) A compound of the formula XXXVI could upon treatment with sodium nitrite form the corresponding diazocompound. This compound could be further reacted with a sulfurus source such as potassium Ethyl xantogenate to form the compound XXXVII.

a30) Reacting a compound of formula XXXVII with a base such as potassium hydroxide to give a compound of formula XXXV.

In a still further aspect the present invention relates to a process of preparing a compound of the formula XLI comprising step a31-a34

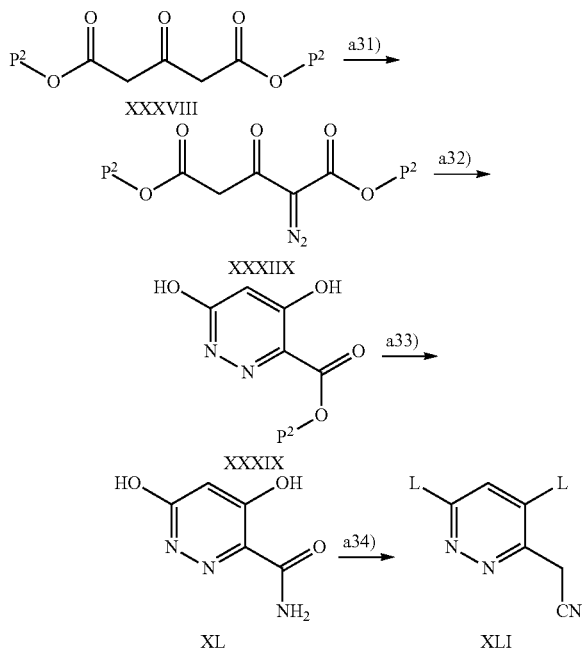

a31) Reacting a compound of formula XXXVIII wherein P² is defined an C_{1-6} alkyl with a diazotizing agent such as N-(4-azidosulfonylphenyl)acetamide in an inert solvent such as acetonitrile, optionally in the prescence of a base such as triethyl amine to give XXXIIX.

a32) Reacting a Compound of the formula XXXIIX with triphenylphosphine, followed by subsequent reaction with acetic acid to give a compound of formula XXXIX.

a33) Reacting a compound of the formula XXXIX with a solution of ammonia in an alcohol such as methanol to give compound XL.

a34) Reacting a compound of formula XL with a reagent such a POCl₃ or POBr₃ to give a compound of the formula XLI, wherein L is defined as a halide such as chlorine or bromine.

In a still further aspect the present invention relates to a process of preparing a compound of the formula XLIV comprising step a35-a36

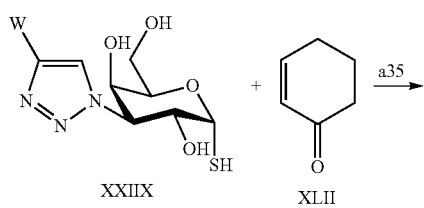

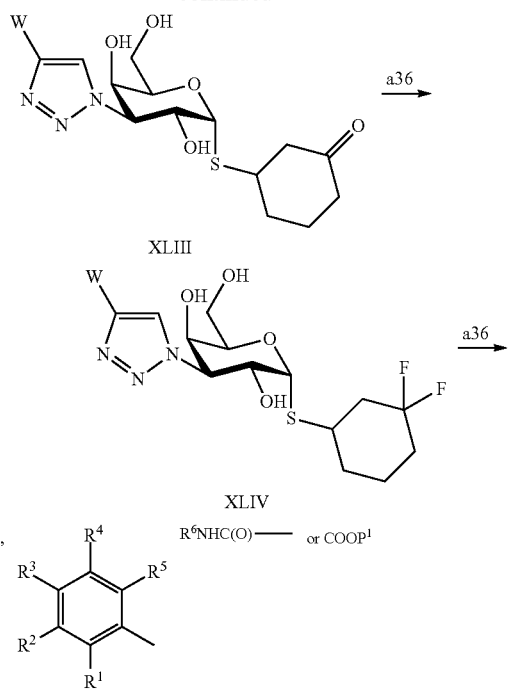

a35) Reacting a compound of the formula XXIIX alfabeta unsaturated ketone such as XLII, a so-called conjugate addition, to form a compound of the formula XLIII, in an inert solvent such as DCM using a base such as diethylamine.

a36) Reacting a compound of the formula XLIII to form a compound of the formula XLIV, using a fluorination reagents such as DAST in an insert solvent such as DCM.

In a still further aspect the present invention relates to a process of preparing a compound of the formula XLVI comprising step a37

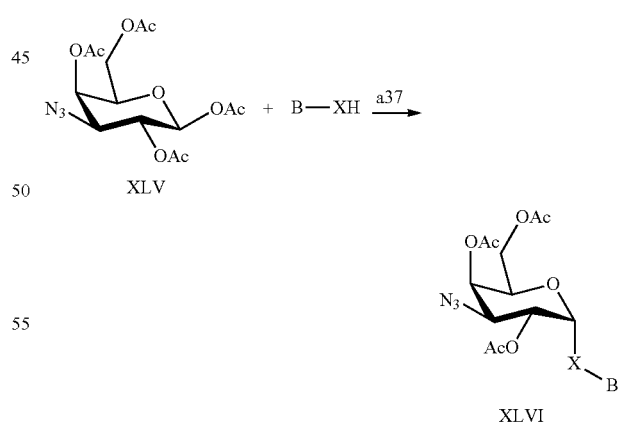

a37) Reacting a compound of formula XLV to form a compound of formula XLVI, using a lewis acid such as BF₃.OEt₂ in an inert solvent such as CHCl₃.

In a still further aspect the present invention relates to a process of preparing a compound of the formula XLVIII comprising step a38

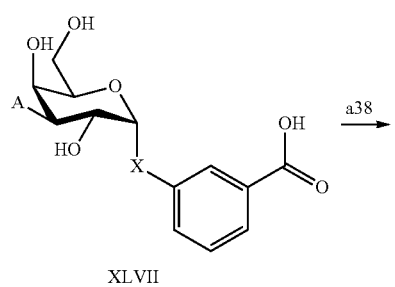

XLVII

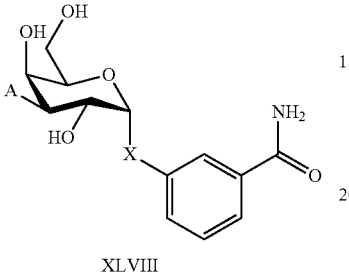

XLVIII a38) Reacting a compound of formula XLVII with ammonium chloride to form a compound of formula XLVIII, using a reagent such as HATU, a base such as TEA in an inert solvent such as DMF.

In a still further aspect the present invention relates to a process of preparing a compound of the formula XLIX comprising step a39

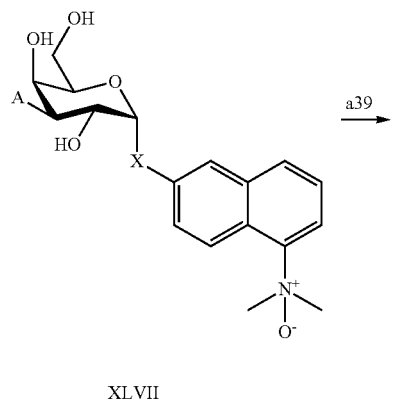

XLVII

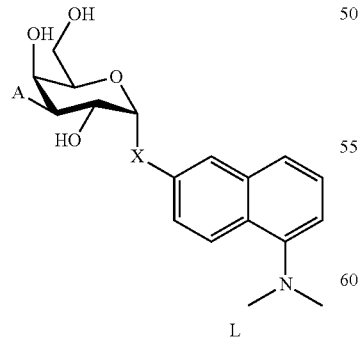

L a39) Reacting a compound of formula XLIX with hydrogen gas to form a compound of formula L, using a reagent such as Pd/C in an inert solvent such as methanol.

In a still further aspect the present invention relates to a process of preparing a compound of the formula LIII comprising steps a40-a41

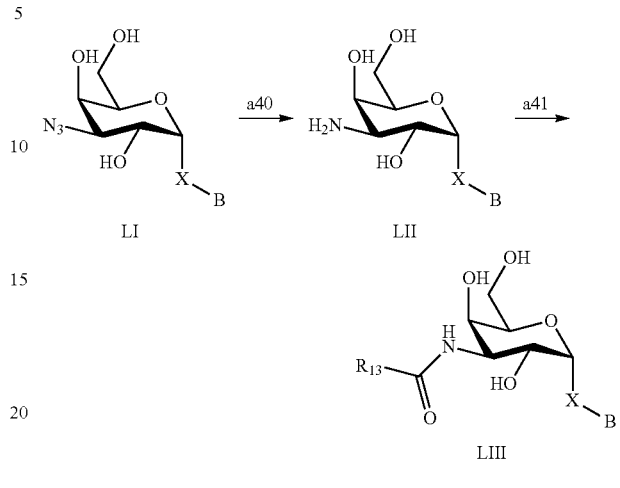

a40) Reacting a compound of formula LI with hydrogen gas to form a compound of formula LII, using a reagent such as Pd/C in an inert solvent such as methanol. Optionally with the addition of DCM. An alternative approach would be to react LI with triphenylphosphine to form LII in an inert solvent such as DCM.

a41) Reacting a compound of formula LII with a compound of the formula $R^{13}$—COOH to give a compound of formula LIII, using a coupling reagent such as HATU in an inert solvent such as DMF. Optionally with the addition of an organic base such as diisopropylethylamine.

In a still further aspect the present invention relates to a process of preparing a compound of the formula LVII comprising step a42-a44

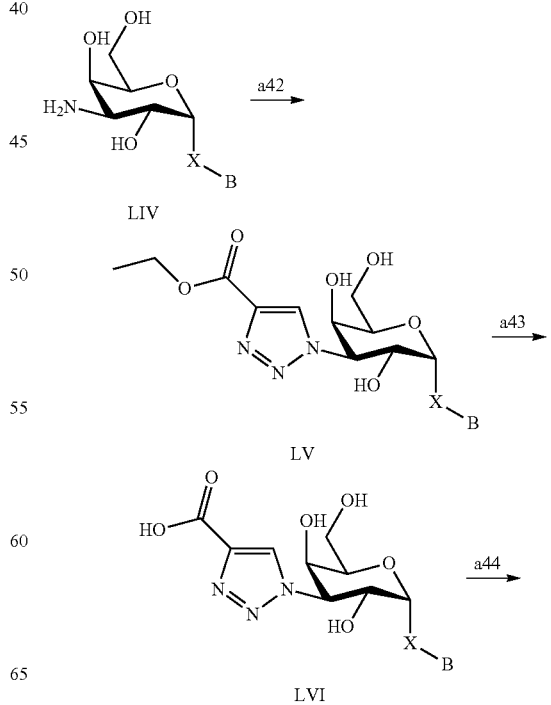

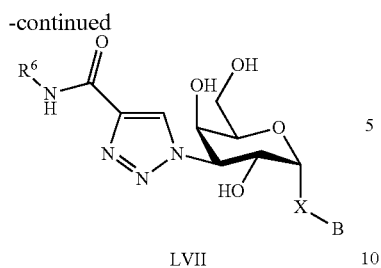

LVII

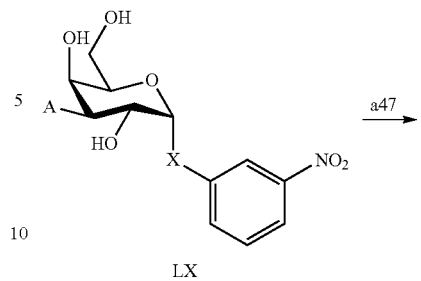

LX a42) Reacting a compound of the formula LIV with ethyl propiolate to give a compound of formula LV using CuI in an inert solvent such as DMF or acetonitrile, using a base, such as diisopropylethylamine.

a43) Reacting a compound of formula LV with a base such as potassium hydroxide to give a compound of formula LVI.

a44) Reacting a compound of formula LVI with a compound of formula $R^6$—$NH_2$ Using a coupling reagent such as HATU in an inert solvent such as DMF. Optionally in the presence of an organic base such as diisopropylethyl amine.

In a still further aspect the present invention relates to a process of preparing a compound of the formula LIX comprising step a45-a47

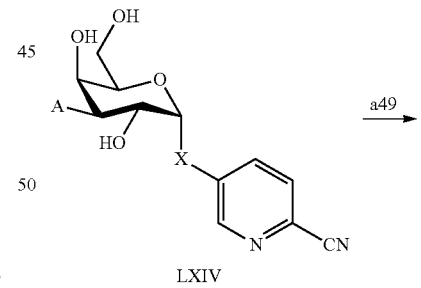

LXI a47) Reacting a compound of the formula LX with a reducing agent such as $SnCl_2$, in an inert solvent such as EtOAc to give a compound of formula LXI.

In a still further aspect the present invention relates to a process of preparing a compound of the formula LXIII comprising step a48

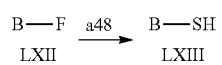

a48) Reacting a compound of the formula LXII with $Na_2S.10H_2O$ in the presence of a base such as NaOH in an inert solvent such as DMF to give a compound of formula LXIII.

In a still further aspect the present invention relates to a process of preparing a compound of the formula LXV comprising step a49

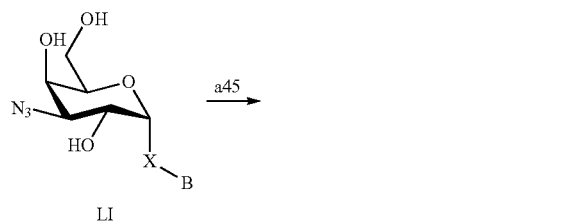

LI

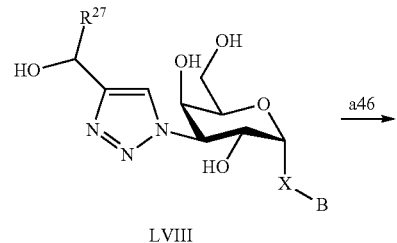

LVIII

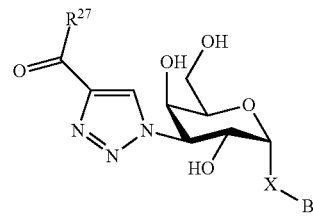

LIX a45) Reacting a compound of formula LI with a compound of formula $R^{27}$—CHOH—CC—H to give a compound of formula LVIII, using CuI in an inert solvent such as DMF or acetonitrile, using a base, such as diisopropylethylamine.

a46) Reacting a compound of formula LVIII with an oxidizing reagent such as Dess-Martin periodinane in an inert solvent such as DCM to give a compound of formula LIX.

In a still further aspect the present invention relates to a process of preparing a compound of the formula LXI comprising step a47.

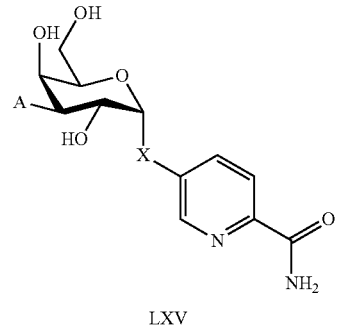

LXV a49) Reacting a compound of the formula LXIV with triethylamine in an in methanol and water to give a compound of formula LXV.

In a still further aspect the present invention relates to a process of preparing a compound of the formula LXVII comprising step a50

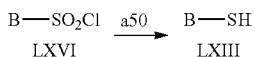

a50) Reacting a compound of formula LXVI with a reducing agent such as triphenylphosphine in an inert solvent such as toluene to give a compound of formula LXIII In a still further aspect the present invention relates to a process of preparing a compound of the formula LXVII comprising step a51

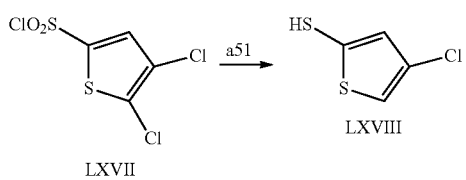 [SMILES: O=S(=O)(Cl)c1cc(Cl)c(Cl)s1 ; Sc1cc(Cl)cs1]

a51) Reacting a compound of formula LXVII with a reducing agent such as triphenylphosphine in an inert solvent such as toluene to give a compound of formula LXVIII In a still further aspect the present invention relates to a process of preparing a compound of the formula LXX comprising step a52

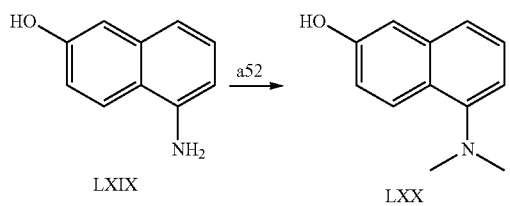

a52) Reacting a compound of formula LXIX with methyl iodide using a base such as potassium carbonate in an inert solvent such as acetone to give a compound of formula LXX.

In a still further aspect the present invention relates to a process of preparing a compound of the formula XXXVI comprising step a53.

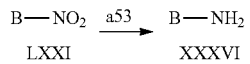

a53) Reacting a compound of formula LXXI with a reducing agent such as Fe, in the presence of ammonium chloride in a solvent mixture of ethenaol and water to give a compound of formula XXXVI.

In a still further aspect the present invention relates to a process of preparing a compound of the formula LXXIV comprising step a54-a55

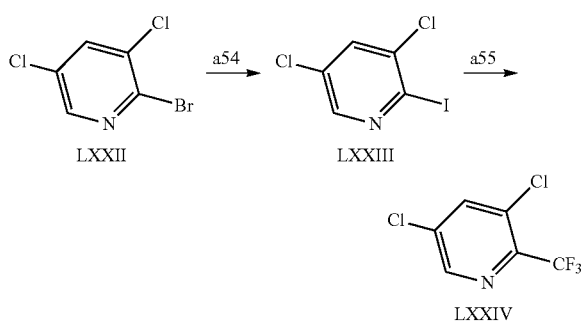

a54) Reacting a compound of formula XXII with sodium iodide, in the presence of trimethylsilyl chloride in an inert solvent such as acetonitrile to give a compound of formula LXXIII.

a55) Reacting a compound of formula LXXII with trimethyl (trifluoromethyl)silane in a solvent such as NMP the presence of a preheated mixture of CuI and potassium fluoride to give a compound of formula LXXIV.

DETAILED DESCRIPTION OF THE INVENTION

The present compounds of formula (1) differ from prior art compounds in particular in that the pyranose ring is α-D-galactopyranose. It is important to emphasize that alpha and beta anomers are very different isomers and it is by no means considered to be obvious to the skilled person to expect same or similar activity of both anomers. Consequently alpha and beta anomers do not in general posses the same activity, and this is common knowledge to the skilled person. In general the compounds of formula (1) are >10 fold better with respect to galectin-3 affinity compared to the corresponding beta-anomers.

In a broad aspect the present invention relates to a D-galactopyranose compound of formula (1)

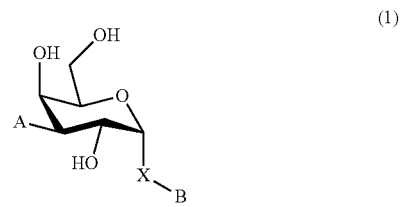

(1)

wherein
the pyranose ring is α-D-galactopyranose,
A is selected from

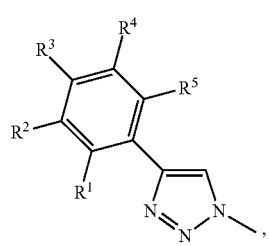

2

-continued

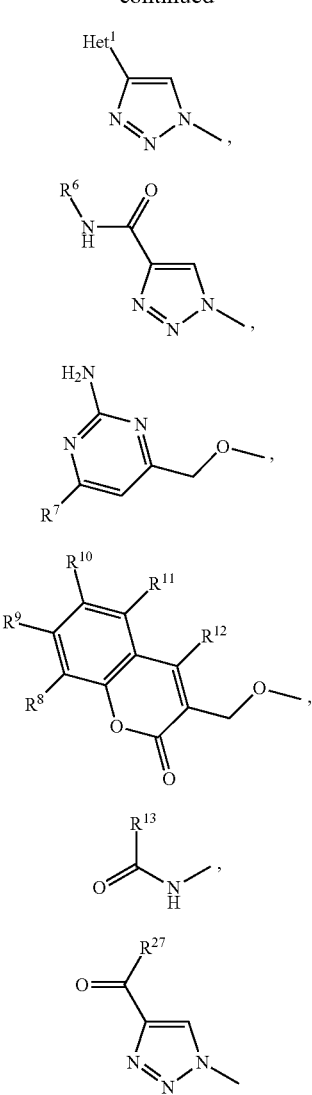

wherein Het¹ is selected from a five or six membered heteroaromatic ring, optionally substituted with a group selected from Br; F; Cl; CN; $NR^{19}R^{20}$, wherein $R^{19}$ and $R^{20}$ are independently selected from H, $C_{1-3}$ alkyl, cyclopropyl, iso-propyl, —C(=O)—$R^{21}$, wherein $R^{21}$ is selected from H and $C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; and $OC_{1-3}$ alkyl optionally substituted with a F;

wherein $R^1$-$R^5$ are independently selected from H, CN, $NH_2$, F, methyl optionally substituted with a fluorine (F), and $OCH_3$ optionally substituted with a F;

wherein $R^6$ is selected from $C_1$, alkyl optionally substituted with a halogen, branched C3 alkyl and $C_{3-7}$ cycloalkyl;

wherein $R^7$ is selected from a five or six membered heteroaromatic ring, optionally substituted with a group selected from Br, F, Cl, methyl optionally substituted with a F, and $OCH_3$ optionally substituted with a F, and a phenyl optionally substituted with a group selected from Br, Cl, methyl optionally substituted with a F, and $OCH_3$ optionally substituted with a F;

wherein $R^8$-$R^{12}$ are independently selected from H, F, methyl optionally substituted with a fluorine (F), and $OCH_3$ optionally substituted with a F;

wherein $R^{13}$ is a five or six membered heteroaromatic ring optionally substituted with a group selected from H, OH, F, methyl optionally substituted with a fluorine (F), and $OCH_3$ optionally substituted with a F, or an aryl, such as phenyl or naphthyl, optionally substituted with a group selected from H, OH, F, methyl optionally substituted with a fluorine (F), and $OCH_3$ optionally substituted with a F;

X is selected from S, SO, $SO_2$, O, C=O, and $CR^7R^8$ wherein $R^7$ and $R^8$ are independently selected from hydrogen, OH, or halogen (e.g. F, Cl, Br);

wherein $R^{27}$ is selected from a $C_{1-6}$ alkyl, branched $C_{3-6}$ alkyl, $C_{1-6}$ alkoxy and branched $C_{3-6}$ alkoxy;

B is selected from a) a $C_{1-6}$ alkyl or branched $C_{3-6}$ alkyl substituted with a five or six membered heteroaromatic ring, optionally substituted with a substituent selected from CN, a halogen (e.g. Cl, F, Br, I), methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl; or a $C_{1-6}$ alkyl substituted with a phenyl, optionally substituted with a substituent selected from CN, a halogen (e.g. Cl, F, Br, I), methyl optionally substituted with a F. $OCH_3$ optionally substituted with a F, $OCH_2CH_3$ optionally substituted with a F, OH, and $R^{15}$—CONH— wherein $R^{15}$ is selected from $C_{1-3}$ alkyl and cyclopropyl; b) an aryl, such as phenyl or naphthyl, optionally substituted with a group selected from a halogen (e.g. Cl, F, Br, I); CN; —COOH; —$CONR^{22}R^{23}$, wherein $R^{22}$ and $R^{23}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{28}R^{29}$, wherein $R^{28}$ and $R^{29}$ are independently selected from H, $C_{1-3}$ alkyl and isopropyl; OH; and $R^{16}$—CONH— wherein $R^{16}$ is selected from $C_{1-3}$ alkyl and cyclopropyl; c) a $C_{5-7}$ cycloalkyl, optionally substituted with a substituent selected from a halogen (e.g. Cl, F, Br, I), CN, methyl optionally substituted with a F, $OCH_3$ optionally substituted with a F, $OCH_2CH_3$ optionally substituted with a F, OH, and $R^1$—CONH— wherein $R^{17}$ is selected from $C_{1-3}$ alkyl and cyclopropyl; and d) a heterocycle, such as heteroaryl or heterocycloalkyl, optionally substituted with a group selected from a halogen (e.g. Cl, F, Br, I); CN; —COOH; —$CONR^{24}R^{25}$, wherein $R^{24}$ and $R^{25}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{30}R^{31}$, wherein $R^{30}$ and $R^{31}$ are independently selected from H, $C_{1-3}$ alkyl and isopropyl; OH; and $R^{18}$—CONH— wherein $R^{18}$ is selected from $C_{1-3}$ alkyl and cyclopropyl; e) a $C_{1-6}$ alkyl or branched $C_{3-6}$ alkyl; or a pharmaceutically acceptable salt or solvate thereof.

In one particular embodiment the compounds of formula (1) are 15-80 fold better with respect to galectin-3 affinity compared to the corresponding beta-anomers, wherein A is selected from formula (2) wherein $R^1$-$R^5$ are independently selected from H and F, provided that at least one of $R^1$-$R^5$ is F, typically 2 or 3F;

X is selected from S, SO or SO$_2$; and

B is selected from i) phenyl substituted with one, two or three groups selected from halogen; CN; —COOH; —CONR$^{22}$R$^{23}$, wherein R$^{22}$ and R$^{23}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{28}$R$^{29}$, wherein R$^{28}$ and R$^{29}$ are independently selected from H, C$_{1-3}$ alkyl and isopropyl; OH; and R$^{16}$—CONH— wherein R$^{16}$ is selected from C$_{1-3}$ alkyl and cyclopropyl; provided that the 3-position relative to X is substituted with one atom selected from Cl, Br and I;

ii) pyridin substituted with one, two or three groups selected from halogen; CN; —COOH; —CONR$^{22}$R$^{23}$, wherein R$^{22}$ and R$^{23}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{28}$R$^{29}$, wherein R$^{28}$ and R$^{29}$ are independently selected from H, C$_{1-3}$ alkyl and isopropyl; OH; and R$^{16}$—CONH— wherein R$^{16}$ is selected from C$_{1-3}$ alkyl and cyclopropyl; provided that the 3-position relative to X is substituted with one atom selected from Cl, Br and I;

iii) pyridazin substituted with one, two or three groups selected from halogen; CN; —COOH; —CONR$^{22}$R$^{23}$, wherein R$^{22}$ and R$^{23}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{28}$R$^{29}$, wherein R$^{28}$ and R$^{29}$ are independently selected from H, C$_{1-3}$ alkyl and isopropyl; OH; and R$^{16}$—CONH— wherein R$^{16}$ is selected from C$_{1-3}$ alkyl and cyclopropyl; provided that the 3-position relative to X is substituted with one atom selected from Cl, Br and I.

In an embodiment A is selected from formula (2) wherein R$^1$-R$^5$ are independently selected from H, CN, NH$_2$, F, methyl optionally substituted with a fluorine (F), and OCH$_3$ optionally substituted with a F. In a further embodiment R$^1$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment R$^1$ is selected from H and F. In a further embodiment R$^2$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment R$^2$ is selected from F. In a further embodiment R$^3$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment R$^3$ is selected from H, OCH$_3$ and F. In a further embodiment R$^4$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment R$^4$ is selected from H and F. In a further embodiment R$^5$ is selected from H, CN, NH$_2$, F, methyl optionally substituted with a fluorine (F), and OCH$_3$ optionally substituted with a F, such as H, CN, NH$_2$, F, methyl, CF$_3$, OCH$_3$ and OCF$_3$. In a further embodiment R$^5$ is selected from H and F.

In another embodiment A is selected from formula (3) wherein Het$^1$ is selected from a five or six membered heteroaromatic ring, optionally substituted with a group selected from Br; F; Cl; CN; NR$^{19}$R$^{20}$, wherein R$^{19}$ and R$^{20}$ are independently selected from H, C$_{1-3}$ alkyl, cyclopropyl, iso-propyl, —C(=O)—R$^{21}$, wherein R$^{21}$ is selected from H and C$_{1-3}$ alkyl; methyl optionally substituted with a F; and OCH$_3$ optionally substituted with a F. In a further embodiment A is selected from formula (3) wherein Het$_1$ is selected from a five or six membered heteroaromatic ring, optionally substituted with a group selected from Br, F, Cl, methyl optionally substituted with a F, and OCH$_3$ optionally substituted with a F. In a further embodiment Het$^1$ is selected from a five membered heteroaromatic ring. In a further embodiment Het$^1$ is selected from a five membered heteroaromatic ring substituted with a group selected from Br, F, Cl, methyl, CF$_3$, OCH$_3$ and OCF$_3$.

In a further embodiment Het$^1$ is selected from a six membered heteroaromatic ring.

In a further embodiment Het$^1$ is selected from a six membered heteroaromatic ring substituted with a group selected from Br, F, Cl, methyl, CF$_3$, OCH$_3$ and OCF$_3$. In a further embodiment Het$^1$ is selected from a six membered heteroaromatic ring substituted with a group selected from Br, F, and Cl.

In a further embodiment Het$^1$ is selected from pyridinyl, pyrimidinyl, pyrazinyl, pyridazyl, oxazoyl, thiazoyl, thiadiazoly, oxadiazoyl, thiophenyl, and imidazolyl optionally substituted with a group selected from Br, F, Cl, methyl, CF$_3$, OCH$_3$ and OCF$_3$. In a further embodiment Het$^1$ is selected from pyridinyl substituted with a group selected from Br, F, and Cl. In a further embodiment Het$^1$ is selected from pyridinyl substituted with a group selected from F, such as one, two or three F, typically 3F.

In a further embodiment A is selected from formula (4) wherein R$^6$ is selected from C$_{1-6}$ alkyl, branched C$_{3-6}$ alkyl and C$_{3-7}$ cycloalkyl. In an embodiment R$^6$ is a C$_{1-6}$ alkyl, such as methyl or ethyl. In another embodiment R$^6$ is a cyclopropyl, cyclopentyl or cyclohexyl.

In a further embodiment A is selected from formula (4) wherein R$^6$ is selected from C$_{1-6}$ alkyl substituted with a halogen. In a further embodiment R$^6$ is a C$_{1-3}$ alkyl substituted with one, two or three halogens, such as one, two or three F, e.g. CH$_2$CF$_3$.

In a further embodiment A is selected from formula (5) wherein R$^7$ is selected from a five or six membered heteroaromatic ring, optionally substituted with a group selected from Br, F, Cl, methyl optionally substituted with a F, and OCH$_3$ optionally substituted with a F, and a phenyl optionally substituted with a group selected from Br, F, Cl, methyl optionally substituted with a F, and OCH$_3$ optionally substituted with a F. In a further embodiment R$^7$ is selected from a five membered heteroaromatic ring. In a further embodiment R$^7$ is selected from a five membered heteroaromatic ring substituted with a group selected from Br, F, Cl, methyl, CF$_3$, OCF$_3$ and OCH$_3$. In a further embodiment R$^7$ is selected from a six membered heteroaromatic ring. In a further embodiment R$^7$ is selected from a six membered heteroaromatic ring substituted with a group selected from Br, F, Cl, methyl, CF$_3$, OCF$_3$ and OCH$_3$, such as 1, 2 or 3 selected from Br, F, Cl, methyl, CF$_3$, OCF$_3$ and OCH$_3$. In a further embodiment R$^7$ is selected from a phenyl. In a further embodiment R$^7$ is selected from a phenyl substituted with a group selected from Br, F, Cl, methyl, CF$_3$, OCF$_3$ and OCH$_3$, such as 1, 2 or 3 selected from Br, F, Cl, methyl, CF$_3$, OCF$_3$ and OCH$_3$. In a further embodiment R$^7$ is selected from a phenyl substituted with a group selected from Cl.

In a further embodiment A is selected from formula (6) wherein $R^8$-$R^{12}$ are independently selected from H, F, methyl optionally substituted with a fluorine (F), and $OCH_3$ optionally substituted with a F. In a further embodiment $R^1$-$R^{12}$ are independently selected from H and F. In a further embodiment $R^8$-$R^{12}$ are H. In a further embodiment $R^8$-$R^{12}$ are independently selected from H and F, provided that at least two of $R^8$-$R^{12}$ are F. In a further embodiment $R^{10}$-$R^{11}$ are F and $R^8$, $R^9$ and $R^{12}$ are H. In a further embodiment $R^8$ is selected from H, F, methyl optionally substituted with a fluorine (F), and $OCH_3$ optionally substituted with a F, such as H, F, methyl, $CF_3$, $OCF_3$ and $OCH_3$. In a further embodiment $R^9$ is selected from H, F, methyl optionally substituted with a fluorine (F), and $OCH_3$ optionally substituted with a F, such as H, F, methyl, $CF_3$, $OCF_3$ and $OCH_3$. In a further embodiment $R^{10}$ is selected from H, F, methyl optionally substituted with a fluorine (F), and $OCH_3$ optionally substituted with a F, such as H, F, methyl, $CF_3$, $OCF_3$ and $OCH_3$. In a further embodiment $R^{11}$ is selected from H, F, methyl optionally substituted with a fluorine (F), and $OCH_3$ optionally substituted with a F, such as H, F, methyl, $CF_3$, $OCF_3$ and $OCH_3$. In a further embodiment $R^{12}$ is selected from H, F, methyl optionally substituted with a fluorine (F), and $OCH_3$ optionally substituted with a F, such as H, F, methyl, $CF_3$, $OCF_3$ and $OCH_3$, typically H or methyl.

In a further embodiment A is selected from formula (7) wherein $R^{13}$ is a five or six membered heteroaromatic ring optionally substituted with a group selected from H, OH, F, methyl optionally substituted with a fluorine (F), and $OCH_3$ optionally substituted with a F, or an aryl, such as phenyl or naphthyl, optionally substituted with a group selected from H, OH, F, methyl optionally substituted with a fluorine (F), and $OCH_3$ optionally substituted with a F. In an embodiment $R^{13}$ is a five membered heteroaromatic ring. In another embodiment $R^{13}$ is a five membered heteroaromatic ring substituted with a group selected from H, OH, F, methyl, $CF_3$, $OCF_3$ and $OCH_3$, such as 1, 2 or 3 selected from OH, F, methyl, $CF_3$, $OCF_3$ and $OCH_3$. In an embodiment $R^{13}$ is a six membered heteroaromatic ring. In an embodiment $R^{13}$ is a six membered heteroaromatic ring substituted with a group selected from H, OH, F, methyl, $CF_3$, $OCF_3$ and $OCH_3$, such as 1, 2 or 3 selected from OH, F, methyl, $CF_3$, $OCF_3$ and $OCH_3$. In a further embodiment $R^{13}$ is a phenyl or naphthyl. In a further embodiment $R^{13}$ is a phenyl substituted with a group selected from H, OH, F, $CF_3$, $OCF_3$ and $OCH_3$, such as 1, 2 or 3 selected from OH, F, methyl, $CF_3$, $OCF_3$ and $OCH_3$. In a further embodiment $R^{13}$ is a phenyl substituted with a group selected from F, such as one, two or three F. In a further embodiment $R^{13}$ is a naphthyl substituted with a group selected from H, OH, F, $CF_3$, $OCF_3$ and $OCH_3$, such as 1, 2 or 3 selected from OH, F, methyl, $CF_3$, $OCF_3$ and $OCH_3$.

In a further embodiment A is selected from formula (8) wherein $R^{27}$ is selected from a $C_{1-6}$ alkyl, branched $C_{3-6}$ alkyl, $C_{1-6}$ alkoxy and branched $C_{3-6}$ alkoxy. In a further embodiment $R^{27}$ is selected from a $C_{1-6}$ alkyl, such as $C_{1-4}$ alkyl, e.g. methyl, ethyl, propyl. In a further embodiment $R^{27}$ is selected from a $C_{1-6}$ alkoxy, such as $C_{1-4}$ alkoxy, e.g. methoxy, ethoxy, propoxy.

In a still further embodiment X is selected from S, SO, $SO_2$, O, C=O, and $CR^7R^8$ wherein $R^7$ and $R^8$ are independently selected from hydrogen, OH, or halogen (e.g. F, Cl, Br). In a further embodiment X is selected from S. In a further embodiment X is selected from SO. In a further embodiment X is selected from $SO_2$. In a further embodiment X is selected from O. In a further embodiment X is selected from C=O. In a further embodiment X is selected from $CR^7R^8$ wherein $R^7$ and $R^8$ are independently selected from hydrogen, OH, F, Cl, and Br, such as $CH_2$, CHF, CHCl, CHBr, CHOH, $CF_2$, $CCl_2$ and $CBr_2$.

In a still further embodiment B is selected from a $C_{1-6}$ alkyl or branched $C_{3-6}$ alkyl substituted with a five or six membered heteroaromatic ring, optionally substituted with a substituent selected from a halogen (e.g. Cl, F, Br, I), CN, methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl. In a further embodiment B is selected from a $C_{1-6}$ alkyl substituted with a five membered heteroaromatic ring. In a further embodiment B is selected from a branched $C_{3-6}$ alkyl substituted with a five membered heteroaromatic ring. In a further embodiment B is selected from a $C_{1-6}$ alkyl substituted with a five membered heteroaromatic ring substituted with a substituent selected from CN, Cl, F, Br, I, methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl. In a further embodiment B is selected from a $C_{1-6}$ alkyl substituted with a five membered heteroaromatic ring substituted with a substituent selected from CN, Cl, F, Br, I, methyl, $CF_3$, $OCH_3$, $OCF_3$, $OCH_2CH_3$, $OCF_2CF_3$, OH, and $R^{14}$—CONH— wherein $R^{14}$ is selected from methyl. In a further embodiment B is selected from a branched $C_{3-6}$ alkyl substituted with a five membered heteroaromatic ring substituted with a substituent selected from CN, Cl, F, Br, I, methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl. In a further embodiment B is selected from a branched $C_{3-6}$ alkyl substituted with a five membered heteroaromatic ring substituted with a substituent, such as 1, 2 or 3, selected from CN, Cl, F, Br, I, methyl, $CF_3$, $OCH_3$, $OCF_3$, $OCH_2CH_3$, $OCF_2CF_3$, OH, and $R^{14}$—CONH— wherein $R^{14}$ is selected from methyl. In a further embodiment B is selected from a $C_{1-6}$ alkyl substituted with a phenyl, such as benzyl or $CH_2CH_2$-phenyl. In a further embodiment B is selected from a $C_{1-6}$ alkyl substituted with a phenyl substituted with a substituent, such as 1, 2 or 3, selected from CN, Cl, F, Br, I, methyl, $CF_3$, $OCH_3$, $OCF_3$, $OCH_2CH_3$, $OCF_2CF_3$, OH, and $R^{15}$—CONH— wherein $R^{15}$ is selected from methyl. In a further embodiment B is selected from a $C_{1-6}$ alkyl substituted with a phenyl substituted with a group selected from Cl, F, Br, methyl, $CF_3$, $OCH_3$, $OCF_3$, such as benzyl substituted with one or two Cl, or $CH_2CH_2$-phenyl substituted with one Cl. In a still further embodiment B is selected from a phenyl. In a further embodiment B is selected from a naphthyl. In a further embodiment B is selected from a naphthyl substituted with a group selected from $NR^{28}R^{29}$, wherein $R^{28}$ and $R^{29}$ are independently selected from H and $C_{1-3}$ alkyl. In a further embodiment B is selected from a naphthyl substituted with a group selected from $NR^{28}R^{29}$, wherein $R^{28}$ and $R^{29}$ are independently selected from H and $CH_3$. In a further embodiment B is selected from a naphthyl substituted with a group selected from $NR^{28}R^{29}$, wherein $R^{28}$ and $R^{29}$ selected from $CH_3$. In a further embodiment B is selected from a phenyl substituted with a group, such as 1, 2 or 3, selected from Cl, F, Br, I, methyl, $CF_3$, $OCH_3$, $OCF_3$, $OCH_2CH_3$, $OCF_2CF_3$, OH, and $R^{16}$—CONH— wherein $R^{16}$ is selected from methyl. In a still further embodiment B is selected from a phenyl substituted with a group, such as 1, 2 or 3, selected from Cl, F, Br, I, CN, methyl, $CF_3$, $OCH_3$, $OCF_3$, $OCH_2CH_3$, $OCF_2CF_3$, OH, and $R^{16}$—CONH— wherein $R^{16}$ is selected from methyl. In a further embodiment B is selected from a phenyl substituted with a group, such as 1, 2 or 3, selected from COOH and $CONH_2$. In a still further embodiment B is selected from a naphthyl substituted with a group, such as 1, 2 or 3, selected from Cl, F, Br, I, methyl, $CF_3$, $OCH_3$, $OCF_3$, $OCH_2CH_3$, $OCF_2CF_3$, OH, and $R^{16}$—CONH— wherein $R^{16}$ is selected from methyl. In a further embodiment B is selected from a naphthyl. In a still further embodiment B is selected from a naphthyl substituted with a $NR^{28}R^{29}$, wherein $R^{28}$ and $R^{29}$ are independently selected from H, $C_{1-3}$ alkyl and isopropyl, such as naphthyl substituted with a $N(CH_3)_2$.

In a further embodiment B is selected from a $C_{5-7}$ cycloalkyl, such as cyclopentyl or cyclohexyl. In a further embodiment B is selected from cyclohexyl. In a still further embodiment B is selected from a $C_{5-7}$ cycloalkyl, such as cyclohexyl, substituted with a group, such as 1, 2 or 3, selected from CN, Cl, F, Br, I, methyl, $CF_3$, $OCH_3$, $OCF_3$, $OCH_2CH_3$, $OCF_2CF_3$, OH, and $R^{17}$—CONH— wherein $R^{17}$ is selected from methyl. In a still further embodiment B is selected from a cyclohexyl, substituted with a halogen, such as one or two halogens, typically F.

In a further embodiment of the present invention B is selected from a $C_{1-4}$ alkyl. Typically, B is selected from ethyl, propyl and butyl.

In a still further embodiment B is selected from a heterocycle, such as heteroaryl or heterocycloalkyl. In a still further embodiment B is selected from a heteroaryl substituted with a group, such as 1, 2 or 3, selected from Cl, F, Br, I, methyl $CF_3$, $OCH_3$, $OCF_3$, $OCH_2CH_3$, $OCF_2CF_3$, OH, and $R^{18}$—CONH— wherein $R^{18}$ is selected from methyl. In a further embodiment B is selected from a heteroaryl substituted with a group, such as 1, 2 or 3, selected from Cl, F, Br, I, CN, methyl, $CF_3$, $OCH_3$, $OCF_3$, $OCH_2CH_3$, $OCF_2CF_3$, OH, and $R^{18}$—CONH— wherein $R^{18}$ is selected from methyl. In a still further embodiment B is selected from a heterocycloalkyl substituted with a group, such as 1, 2 or 3, selected from Cl, F, Br, I, methyl $CF_3$, $OCH_3$, $OCF_3$, $OCH_2CH_3$, $OCF_2CF_3$, OH, and $R^{18}$—CONH— wherein $R^{18}$ is selected from methyl. In a further embodiment B is selected from a heteroaryl substituted with a group, such as 1, 2 or 3, selected from $NR^{30}R^{31}$, wherein $R^{30}$ and $R^{31}$ are independently selected from H, $C_{1-3}$ alkyl and isopropyl. Typically, B is selected from a pyridinyl substituted with a group, such as 1, 2 or 3, selected from $NH_2$, such as one $NH_2$. In another embodiment B is selected from a thiophenyl substituted with a halogen, such as one Cl. In a further embodiment B is selected from a pyridazinyl. In a further embodiment B is selected from a pyridazinyl substituted with one, two or three, substituents selected from $OCH_3$, CN, OH and Cl.

In a further aspect the present invention relates to a compound of formula (1) of the present invention for use as a medicine.

In a still further aspect the present invention relates to a pharmaceutical composition comprising a compound of formula (1) of the present invention and optionally a pharmaceutically acceptable additive, such as a carrier and/or excipient.

In a further aspect the present invention relates to a compound of formula (1) of the present invention for use in a method for treating a disorder relating to the binding of a galectin-3 to a ligand in a mammal, such as a human. In an embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis. A non-limiting group of cancers given as examples of cancers that may be treated, managed and/or prevented by administration of a compound of formula (1) include: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer. Each of these disorders is considered a single embodiment and may be made the subject of a claim specifically to such disease or disorder.

In a still further aspect the present invention relates to a method for treatment of a disorder relating to the binding of a galectin-3 to a ligand in a mammal, such as a human, wherein a therapeutically effective amount of at least one compound of formula (1) of the present invention is administered to a mammal in need of said treatment. In an embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock;

cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis. Each of these disorders are considered a single embodiment and may be made the subject of a claim specifically to such disease or disorder.

The skilled person will understand that it may be necessary to adjust or change the order of steps in the processes a1 to a55, and such change of order is encompassed by the aspects of the process as described above in the reaction schemes and accompanying description of the process steps.

Furthermore the skilled person will understand that the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g. t-butyldimethylsilyl, t-butyldipheylsilyl or trimethylsilyl), AcO (acetoxy), TBS (t-butyldimethylsilyl), TMS (trimethylsilyl), PMB (p-methoxybensyl), and tetrahydropyranyl. Suitable protecting groups for carboxylic acid include $(C_{1-6})$-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)NH$_2$, TIPS.

The protection and deprotection of functional groups may take place before or after any reaction in the above mentioned processes.

Furthermore the skilled person will appreciate, that, in order to obtain compounds of the invention in an alternative, and on some occasions more convenient manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound (1) is on free form. "On free form" as used herein means a compound of formula (1), either an acid form or base form, or as a neutral compound, depending on the substitutents. The free form does not have any acid salt or base salt in addition. In one embodiment the free form is an anhydrate. In another embodiment the free form is a solvate, such as a hydrate.

In a further embodiment the compound (1) is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "$C_{1-x}$ alkyl" as used herein means an alkyl group containing 1-x carbon atoms, e.g. $C_{1-5}$ or $C_{1-6}$, such as methyl, ethyl, propyl, butyl, pentyl or hexyl.

The term "branched $C_{3-6}$ alkyl" as used herein means a branched alkyl group containing 3-6 carbon atoms, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "$C_{5-7}$ cycloalkyl" as used herein means a cyclic alkyl group containing 5-7 carbon atoms, such as cyclopentyl, cyclohexyl, or cycloheptyl.

The term "Oxo" as used herein means an oxygen atom with double bonds, also indicated as =O.

The term "CN" as used herein means a nitril.

The term "a five or six membered heteroaromatic ring" as used herein means one five membered heteroaromatic ring or one six membered heteroaromatic ring. The five membered heteroaromatic ring contains 5 ring atoms of which one to four are heteroatoms selected from N, O, and S. The six membered heteroaromatic ring contains 6 ring atoms of which one to five are heteroatoms selected from N, O and S. Examples include thiophene, furan, pyran, pyrrole, imidazole, pyrazole, isothiazole, isooxazole, pyridine, pyrazine, pyrimidine and pyridazine. When such heteroaromatic rings are substituents they are termed thiophenyl, furanyl, pyranyl, pyrrolyl, imidazolyl, pyrazolyl, isothiazolyl, isooxazolyl, pyridinyl, pyrazinyl, pyrimidinyl and pyridazinyl. Also included are oxazoyl, thiazoyl, thiadiazoly, oxadiazoyl, and pyridonyl.

The term "a heterocycle, such as heteroaryl or heterocycloalkyl" as used herein means a heterocycle consisting of one or more 3-7 membered ring systems containing one or more heteroatoms and wherein such ring systems may optionally be aromatic. The term "a heteroaryl" as used herein means a mono or bicyclic aromatic ringsystem containing one or more heteroatoms, such as 1-10, e.g. 1-6, selected from O, S, and N, including but not limited to oxazolyl, oxadiazolyl, thiophenyl, thiadiazolyl, thiazolyl, pyridyl, pyrimidinyl, pyridonyl, pyrimidonyl, quinolinyl, azaquionolyl, isoquinolinyl, azaisoquinolyl, quinazolinyl, azaquinazolinyl, bensozazoyl, azabensoxazoyl, bensothiazoyl, or azabensothiazoyl. The term "a heterocycloalkyl" as used herein means a mono or bicyclic 3-7 membered alifatic heterocycle containing one or more heteroatoms, such as 1-7, e.g. 1-5, selected from O, S, and N, including but not limited to piperidinyl, tetrahydropyranyl, tetrahydrothipyranyl, or piperidonyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person skilled within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compounds as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context). This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Procedures

| Example | Name | structure | Galectin-3 Kd (μM) |
|---|---|---|---|
| 1 | 3,4-Dimethylphenyl 3-deoxy-3-[4-(3,4,5-trifluorophenyl)-1H-1,2,3-triazol-1-yl]-1-thio-α-D-galactopyranoside | 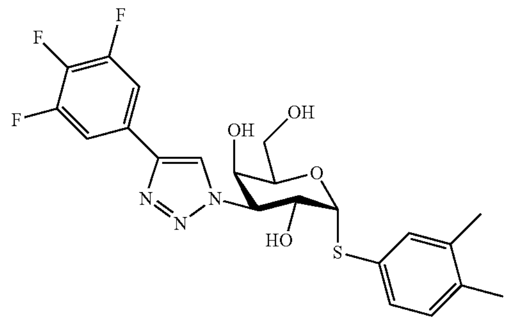 | 0.150 |
| 2 | 3-Bromophenyl 3-deoxy-3-[4-(3,4,5-trifluorophenyl)-1H-1,2,3-triazol-1-yl]-1-thio-α-D-galactopyranoside | 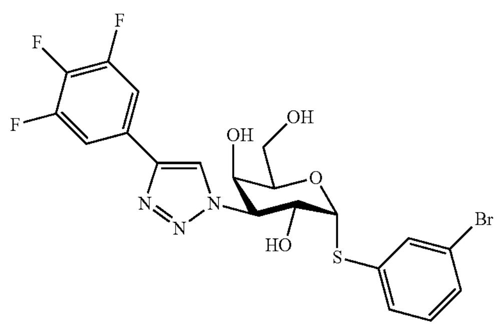 | 0.037 |
| 3 | 3-Ethoxyphenyl 3-deoxy-3-[4-(3,4,5-trifluorophenyl)-1H-1,2,3-triazol-1-yl]-1-thio-α-D-galactopyranoside | 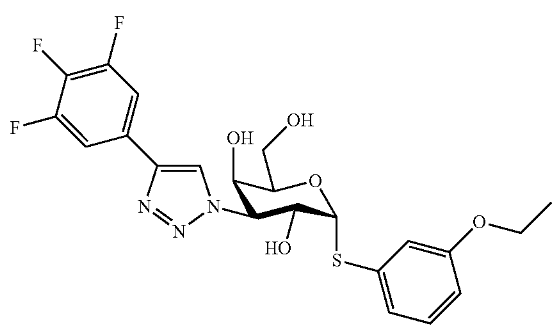 | 0.420 |
| 4 | 3-Pyridyl 3-deoxy-3-[4-(3,4,5-trifluorophenyl)-1H-1,2,3-triazol-1-yl]-1-thio-α-D-galactopyranoside | 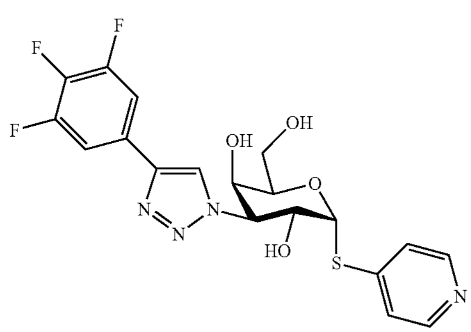 | 0.190 |

-continued

| Example | Name | structure | Galectin-3 Kd (μM) |
|---|---|---|---|
| 5 | 2,4-Dichlorophenyl 3-deoxy-3-[4-(3,4,5-trifluorophenyl)-1H-1,2,3-triazol-1-yl]-1-thio-α-D-galactopyranoside | 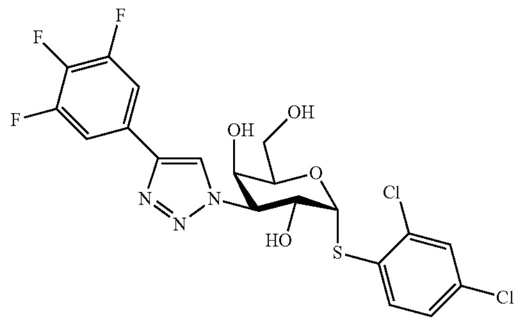 | 0.650 |
| 6 | 4-Acetanilidyl 3-deoxy-3-[4-(3,4,5-trifluorophenyl)-1H-1,2,3-triazol-1-yl]-1-thio-α-D-galactopyranoside | 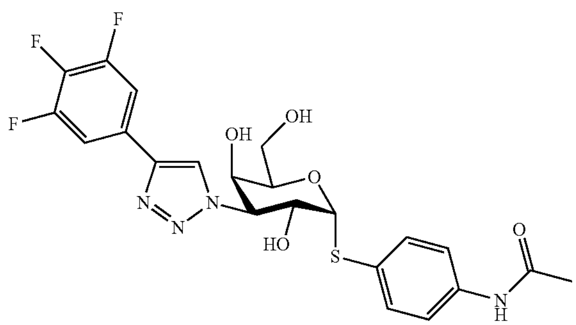 | 0.313 |
| 7 | 4-Methoxyphenyl 3-deoxy-3-[4-(3,4,5-trifluorophenyl)-1H-1,2,3-triazol-1-yl]-1-thio-α-D-galactopyranoside | 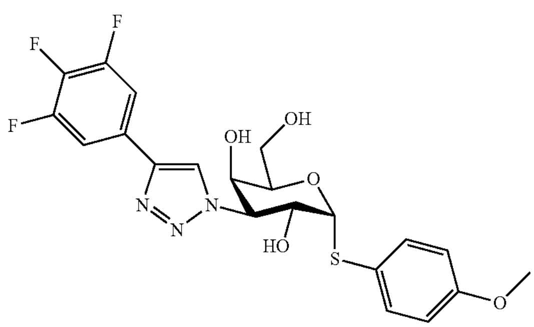 | 0.410 |
| 8 | 2,3-Dichlorophenyl 3-deoxy-3-[4-(3,4,5-trifluorophenyl)-1H-1,2,3-triazol-1-yl]-1-thio-α-D-galactopyranoside | 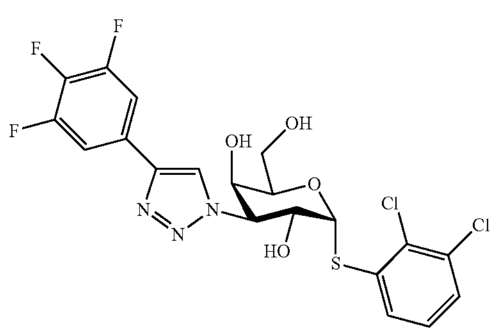 | 0.530 |

-continued

| Example | Name | structure | Galectin-3 Kd (μM) |
|---|---|---|---|
| 9 | 3,4-Dichlorophenyl 3-deoxy-3-[4-(3,4,5-trifluorophenyl)-1H-1,2,3-triazol-1-yl]-1-thio-α-D-galactopyranoside | 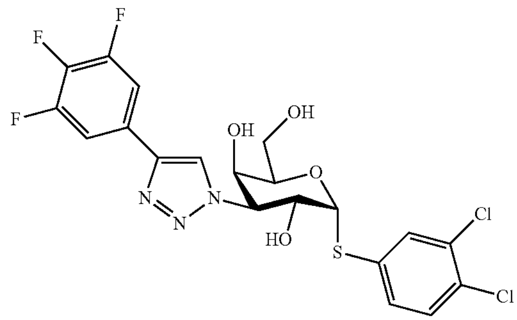 | 0.017 |
| 10 | Benzyl 3-deoxy-1-thio-3-[4[(3,4,5-trifluorophenyl)-1H-1,2,3-triazol-1-yl]-1-thio-α-D-galactopyranoside | 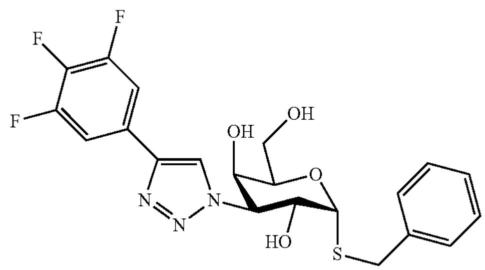 | 1.130 |
| 11 | 3-Methoxyphenyl 3-deoxy-3-[4-(3,4,5-trifluorophenyl)-1H-1,2,3-triazol-1-yl]-1-thio-α-D-galactopyranoside | 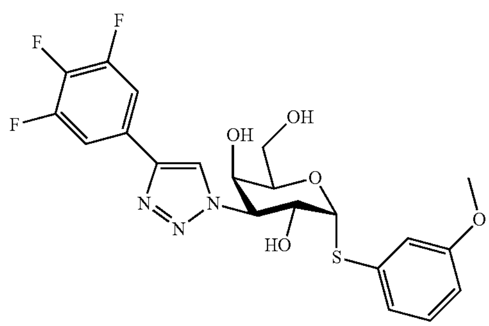 | 0.270 |
| 12 | 2-Naphtyl 3-deoxy-3-[4-(3,4,5-trifluorophenyl)-1H-1,2,3-triazol-1-yl]-1-thio-α-D-galactopyranoside | 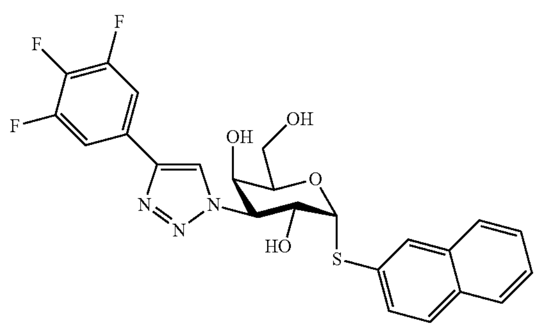 | 0.180 |
| 13 | 3-Methylphenyl 3-deoxy-3-[4-(3,4,5-trifluorophenyl)-1H-1,2,3-triazol-1-yl]-1-thio-α-D-galactopyranoside | 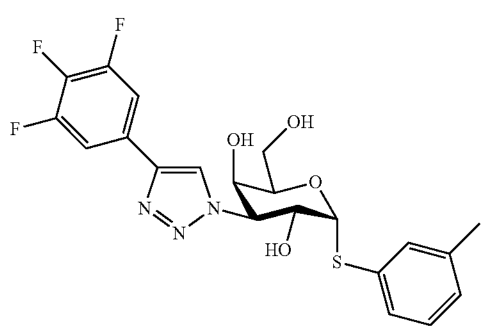 | 0.240 |

-continued

| Example | Name | structure | Galectin-3 Kd (μM) |
|---|---|---|---|
| 14 | 3-(Trifluoromethyl)phenyl 3-deoxy-3-[4-(3,4,5-trifluorophenyl)-1H-1,2,3-triazol-1-yl]-1-thio-α-D-galactopyranoside | 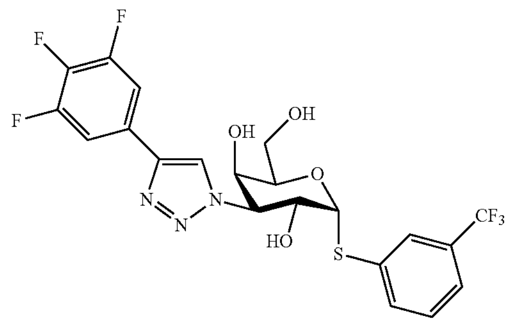 | 0.130 |
| 15 | 4-Bromophenyl 3-deoxy-3-[4-(3,4,5-trifluorophenyl)-1H-1,2,3-triazol-1-yl]-1-thio-α-D-galactopyranoside | 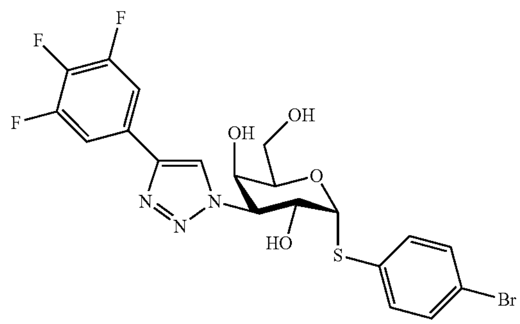 | 0.520 |
| 16 | 3,5-Dichlorophenyl 3-deoxy-3-[4-(3,4,5-trifluorophenyl)-1H-1,2,3-triazol-1-yl]-1-thio-α-D-galactopyranoside | 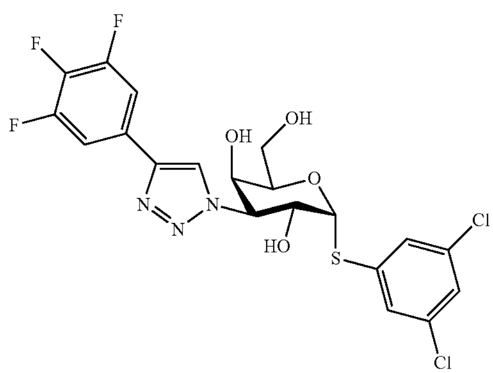 | 0.080 |
| 17 | 2,6-Dimethylphenyl 3-deoxy-3-[4-(3,4,5-trifluorophenyl)-1H-1,2,3-triazol-1-yl]-1-thio-α-D-galactopyranoside | 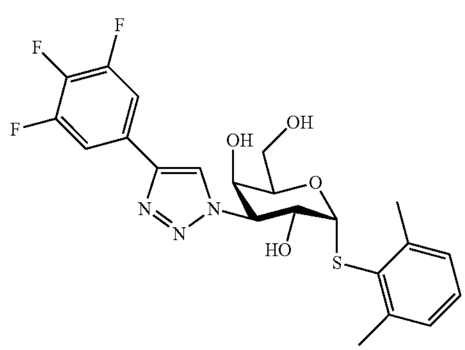 | 1.580 |

-continued

| Example | Name | structure | Galectin-3 Kd (μM) |
|---|---|---|---|
| 18 | 1-Naphthyl 3-deoxy-1-thio-3-[4-(3,4,5-trifluorophenyl)-1H-1,2,3-triazol-1-yl]-1-thio-α-D-galactopyranoside | 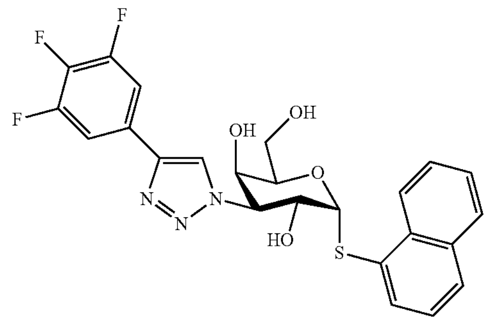 | 0.960 |
| 19 | 3-Chlorophenyl 3-deoxy-3-[4-(3,4,5-trifluorophenyl)-1H-1,2,3-triazol-1-yl]-1-thio-α-D-galactopyranoside | 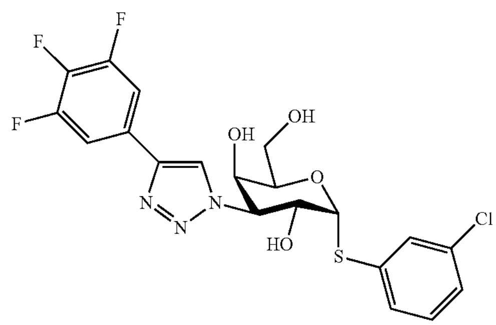 | 0.049 |
| 20 | 3-(Trifluoromethoxy)phenyl 3-deoxy-3-[4-(3,4,5-trifluorophenyl)-1H-1,2,3-triazol-1-yl]-1-thio-α-D-galactopyranoside | 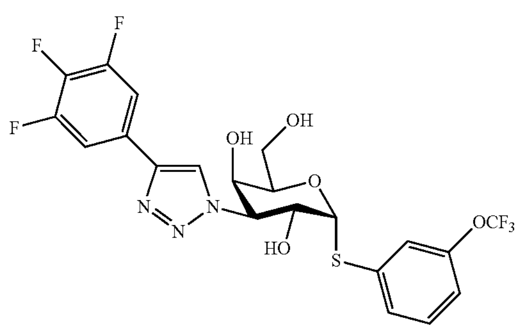 | 0.500 |
| 21 | 2-Pyridyl 3-deoxy-3-[4-(3,4,5-trifluorophenyl-1H-1,2,3-triazol-1-yl]-)-1-thio-α-D-galactopyranoside | 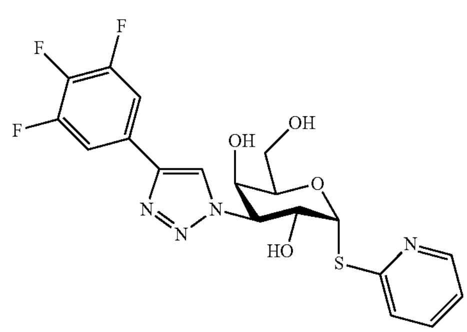 | 0.510 |

-continued

| Example | Name | structure | Galectin-3 Kd (µM) |
|---|---|---|---|
| 22 | 3,4-Dichlorophenyl 3-deoxy-3-[4-(3,4,5-trifluorophenyl)-1H-1,2,3-triazol-1-yl]-α-D-galactopyranoside | 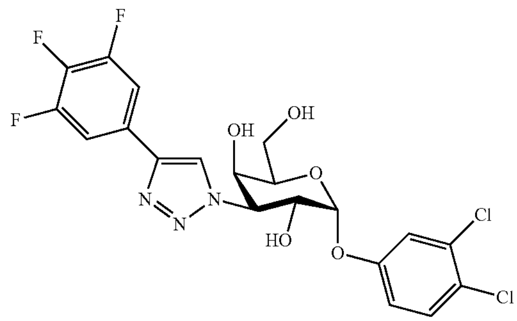 | 0.49 |
| 23 | 4-Chlorophenyl 3-deoxy-3-[4-(3,4,5-trifluorophenyl)-1H-1,2,3-triazol-1-yl]-1-thio-α-D-galactopyranoside | 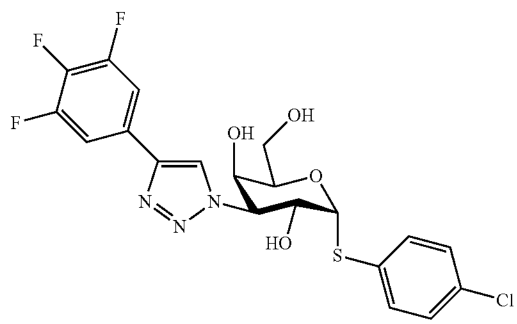 | 0.200 |
| 24 | 3,4-Dichlorophenyl 3-deoxy-3-[4-(3,4,5-trifluorophenyl)-1H-1,2,3-triazol-1-yl]-α-D-galactopyranosyl sulfoxide | 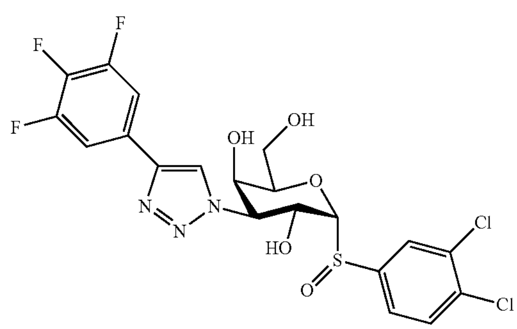 | 0.010 |
| 25 | 3,4-Dichlorophenyl 3-deoxy-3-[4-(3,4,5-trifluorophenyl)-1H-1,2,3-triazol-1-yl]-α-D-galactopyranosyl sulfone | 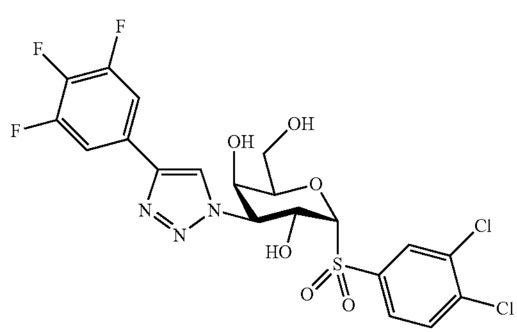 | 0.062 |

| Example | Name | structure | Galectin-3 Kd (μM) |
|---|---|---|---|
| 26 | 4-Chlorophenyl 3-deoxy-3-[4-(3,4,5-trifluorophenyl)-1H-1,2,3-triazol-1-yl]-α-D-galactopyranosyl sulfoxide | 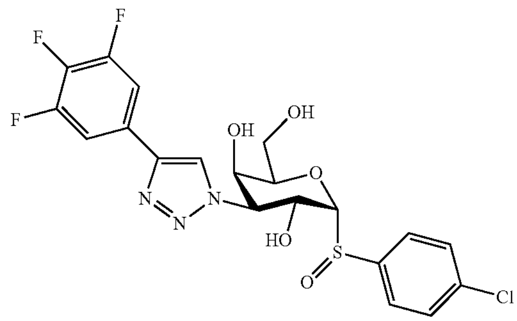 | 0.770 |
| 27 | Phenyl 3-deoxy-3-[4-(3,4,5-trifluorophenyl)-1H-1,2,3-triazol-1-yl]-1-thio-α-D-galactopyranoside | 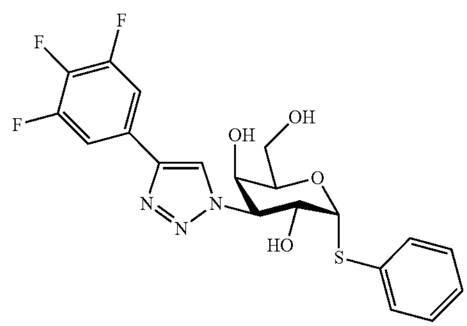 | 0.400 |
| 28 | 4-Chloro-4-fluorophenyl 3-deoxy-3-[4-(3,4,5-trifluorophenyl)-1H-1,2,3-triazol-1-yl]-1-thio-α-D-galactopyranoside | 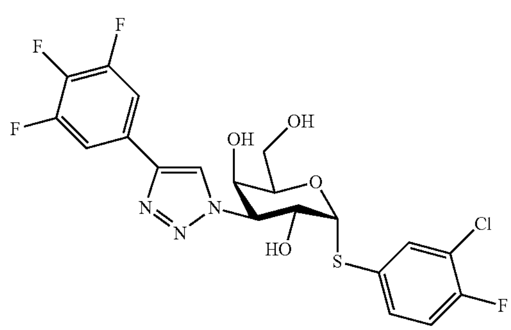 | 0.048 |
| 29 | 4-Tolyl 3-deoxy-3-[4-(3,4,5-trifluorophenyl)-1H-1,2,3-triazol-1-yl]-1-thio-α-D-galactopyranoside | 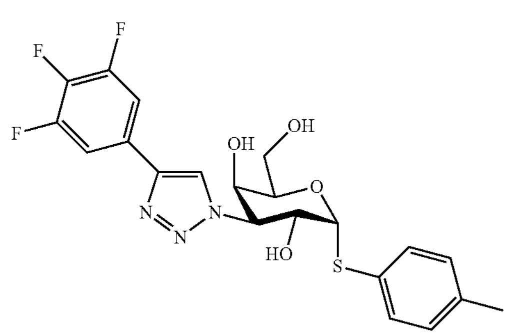 | 0.460 |

-continued

| Example | Name | structure | Galectin-3 Kd (μM) |
|---|---|---|---|
| 30 | 4-Fluorophenyl 3-deoxy-3-[4-(3,4,5-trifluorophenyl)-1H-1,2,3-triazol-1-yl]-1-thio-α-D-galactopyranoside | 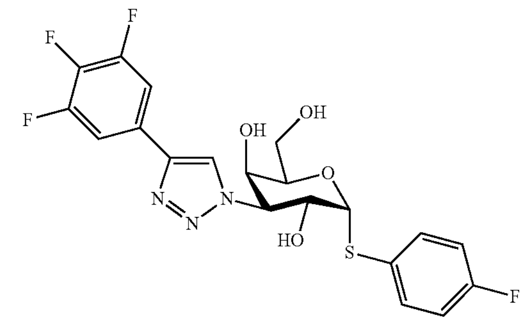 | 0.270 |
| 31 | 4-Trifluoromethoxyphenyl 3-deoxy-3-[4-(3,4,5-trifluorophenyl)-1H-1,2,3-triazol-1-yl]-1-thio-α-D-galactopyranoside | 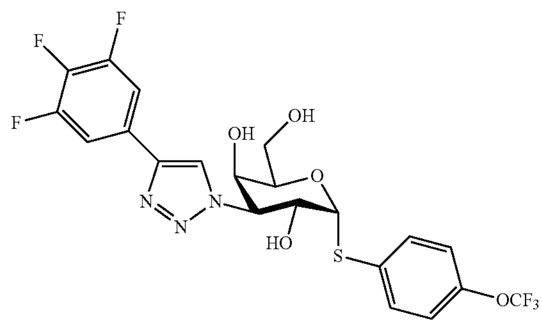 | 0.280 |
| 32 | Phenyl 3-deoxy-3-[4-(3,4,5-trifluorophenyl)-1H-1,2,3-triazol-1-yl]-α-D-galactopyranoside | 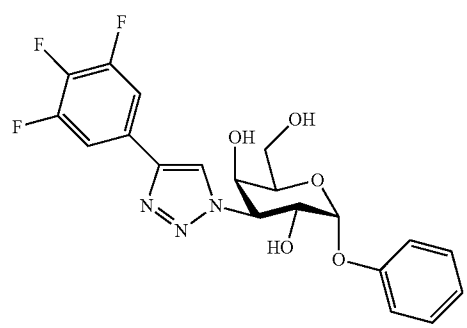 | 1.000 |
| 33 | 3-Chlorophenyl 3-deoxy-3-[4-(3,4,5-trifluorophenyl)-1H-1,2,3-triazol-1-yl]-α-D-galactopyranoside | 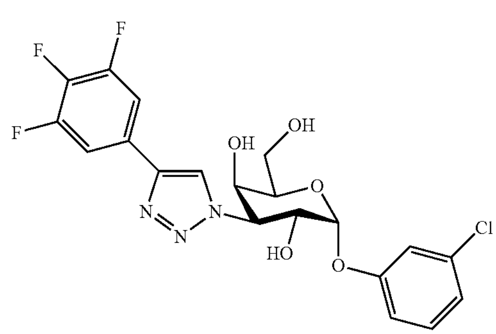 | 0.250 |

-continued

| Example | Name | structure | Galectin-3 Kd (µM) |
|---|---|---|---|
| 34 | 4-Chlorophenyl 3-deoxy-3-[4-(3,4,5-trifluorophenyl)-1H-1,2,3-triazol-1-yl]-α-D-galactopyranoside | 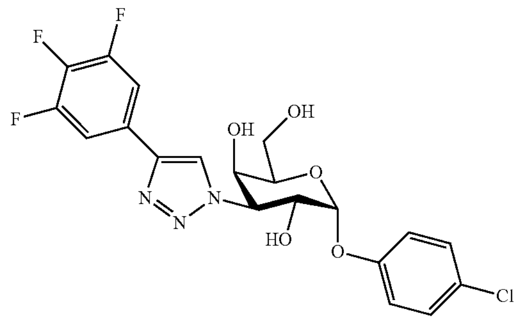 | 0.570 |
| 35 | Cyclohexyl 3-deoxy-3-[4-(3,4,5-trifluorophenyl)-1H-1,2,3-triazol-1-yl]-1-thio-α-D-galactopyranoside | 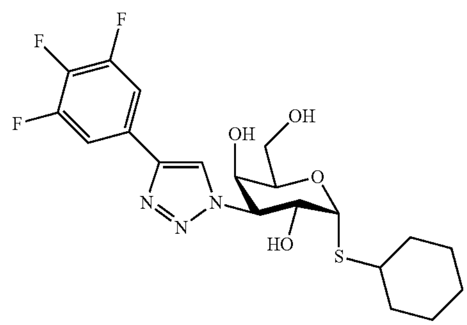 | 0.440 |
| 36 | 2,4,5-Trichlorophenyl 3-deoxy-3-[4-(3,4,5-trifluorophenyl)-1H-1,2,3-triazol-1-yl]-1-thio-α-D-galactopyranoside | 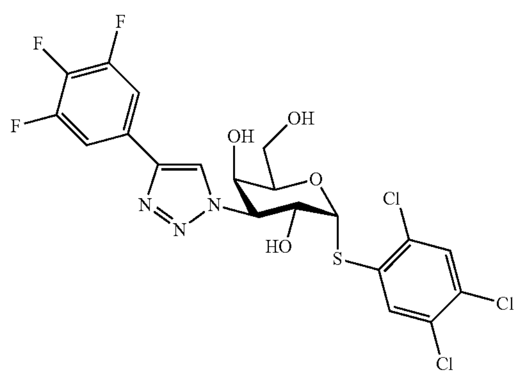 | 0.060 |
| 37 | 2,5-Dichlorophenyl 3-deoxy-3-[4-(3,4,5-trifluorophenyl)-1H-1,2,3-triazol-1-yl]-1-thio-α-D-galactopyranoside | 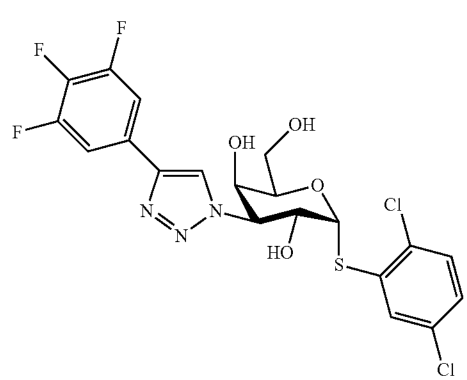 | 0.084 |

-continued

| Example | Name | structure | Galectin-3 Kd (μM) |
|---|---|---|---|
| 38 | 3-Hydroxy-phenyl 3-deoxy-3-[4-(3,4,5-trifluorophenyl)-1H-1,2,3-triazol-1-yl]-1-thio-α-D-galactopyranoside | 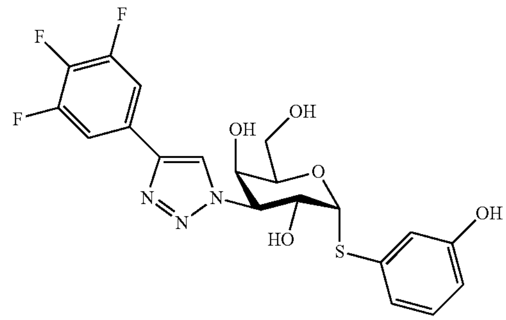 | 0.490 |
| 39 | 3-Bromophenyl 3-deoxy-3-[4-(3,4,5-trifluorophenyl)-1H-1,2,3-triazol-1-yl]-α-D-galactopyranosyl sulfoxide | 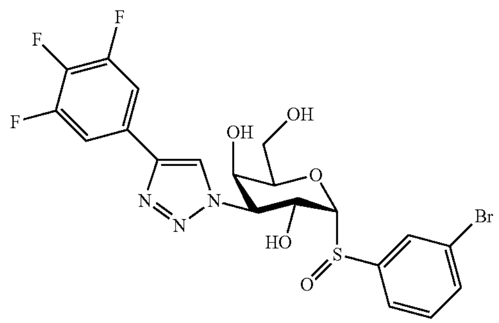 | 0.023 |
| 40 | 2-Phenetyl 3-deoxy-3-[4-(3,4,5-trifluorophenyl)-1H-1,2,3-triazol-1-yl]-1-thio-α-D-galactopyranoside | 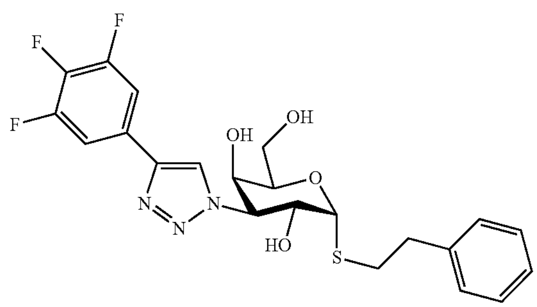 | 0.480 |
| 41 | 3,4-Dichlorophenyl 3-O-[(2-amino-(4-chlorophenyl) pyrimidin-6-yl) methylene]-1-thio-α-D-galactopyranoside | 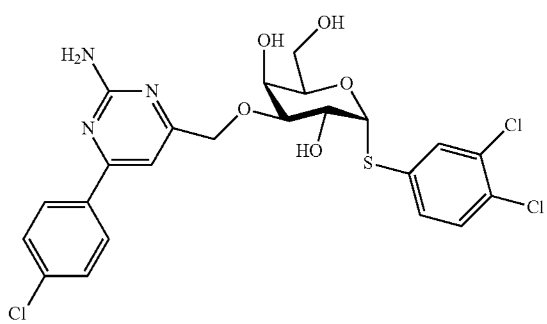 | 1.300 |
| 42 | 3,4-Dichlorophenyl 3-deoxy-3-[4-(2,3,4,5,6-pentafluorophenyl)-1H-1,2,3-triazol-1-yl]-α-D-galactopyranosyl sulfoxide | 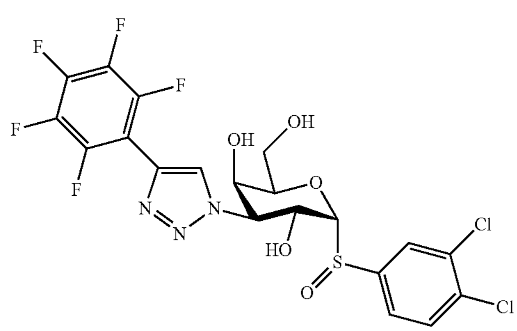 | 0.002 |

| Example | Name | structure | Galectin-3 Kd (μM) |
|---|---|---|---|
| 43 | 5-Chloropyridin-3-yl 3-deoxy-3-[4-(3,4,5-trifluorophenyl)-1H-1,2,3-triazol-1-yl]-1-thio-α-D-galactopyranoside | 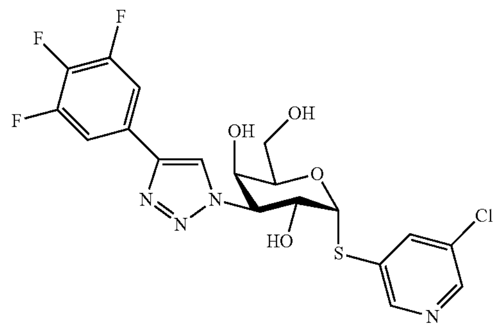 | 0.035 |
| 44 | 5-Bromopyridin-3-yl 3-deoxy-3-[4-(3,4,5-trifluorophenyl)-1H-1,2,3-triazol-1-yl]-1-thio-α-D-galactopyranoside | 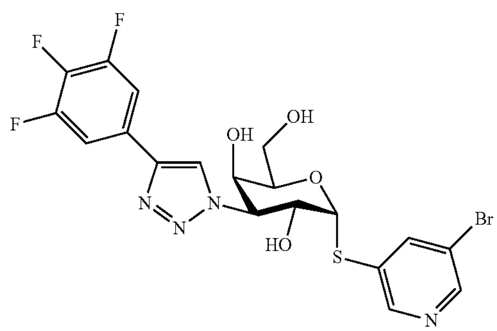 | 0.023 |
| 45 | 5-Chloro-5-cyanophenyl 3-deoxy-3-[4-(3,4,5-trifluorophenyl)-1H-1,2,3-triazol-1-yl]-1-thio-α-D-galactopyranoside | 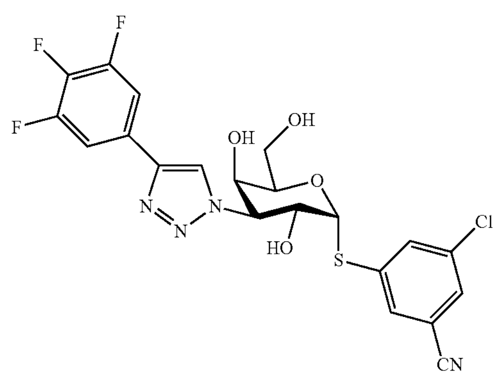 | 0.041 |
| 46 | 3-Chloro-4-cyanophenyl 3-deoxy-3-[4-(3,4,5-trifluorophenyl)-1H-1,2,3-triazol-1-yl]-1-thio-α-D-galactopyranoside | 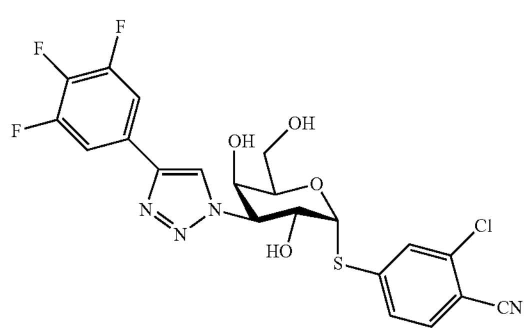 | 0.031 |

-continued

| Example | Name | structure | Galectin-3 Kd (μM) |
|---|---|---|---|
| 47 | 5-Chloro-6-fluoro-4-cyanophenyl 3-deoxy-3-[4-(3,4,5-trifluorophenyl)-1H-1,2,3-triazol-1-yl]-1-thio-α-D-galactopyranoside | 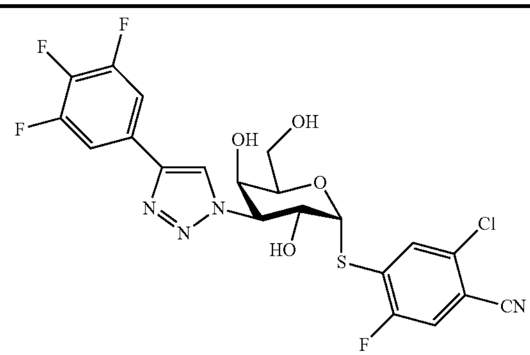 | 0.029 |
| 48 | 3-Bromo-4-cyanophenyl 3-deoxy-3-[4-(3,4,5-trifluorophenyl)-1H-1,2,3-triazol-1-yl]-1-thio-α-D-galactopyranoside | 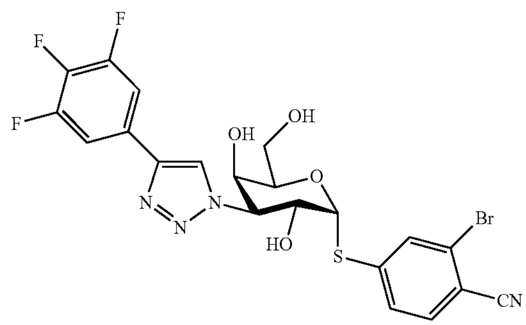 | 0.043 |
| 49 | 5-Bromo-6-trifluoromethyl-pyridin-3-yl 3-deoxy-3-[4-(3,4,5-trifluorophenyl)-1H-1,2,3-triazol-1-yl]-1-thio-α-D-galactopyranoside | 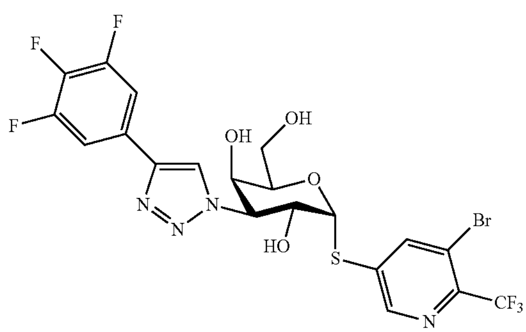 | 0.023 |
| 50 | 5-Chloro-6-cyano-pyridin-3-yl 3-deoxy-3-[4-(3,4,5-trifluorophenyl)-1H-1,2,3-triazol-1-yl]-1-thio-α-D-galactopyranoside | 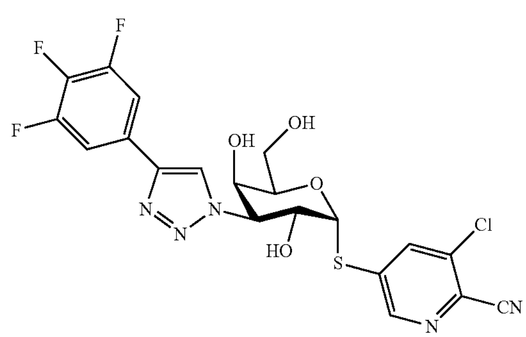 | 0.039 |

| Example | Name | structure | Galectin-3 Kd (μM) |
|---|---|---|---|
| 51 | 5-Chloro-6-cyano-pyridazin-3-yl 3-deoxy-3-[4-(3,4,5-trifluorophenyl)-1H-1,2,3-triazol-1-yl]-1-thio-α-D-galactopyranoside | 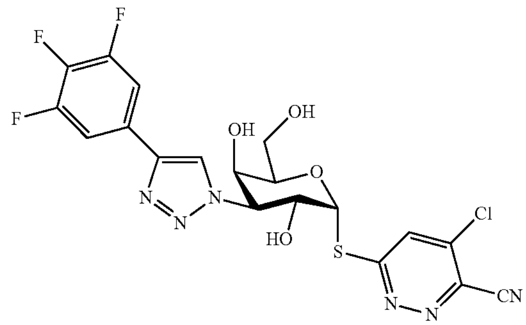 | 0.054 |
| 52 | 3,4-Dichlorophenyl 3-deoxy-3-[4-(2,3,4,5,6-pentafluorophenyl)-1H-1,2,3-triazol-1-yl]-1-thio-α-D-galactopyranoside | 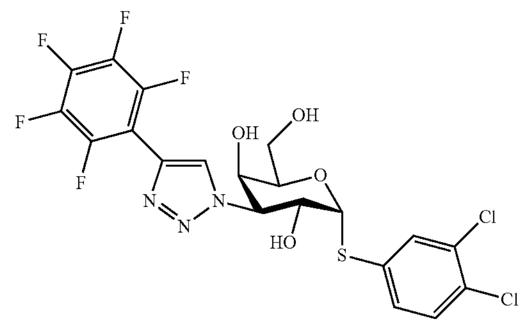 | 0.037 |
| 53 | 3,4-Dichlorophenyl 3-deoxy-3-[4-(2,3,4,5,6-pentafluorophenyl)-1H-1,2,3-triazol-1-yl]-α-D-galactopyranosyl sulfone | 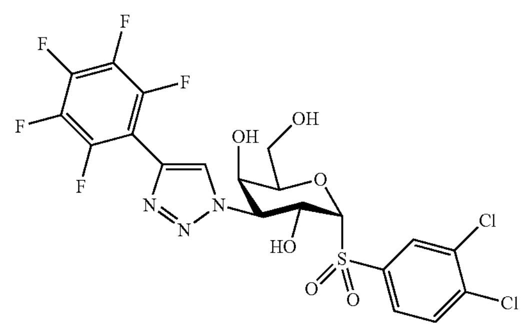 | 0.013 |
| 54 | 5-Methoxy-6-cyano-pyridazin-3-yl 3-deoxy-3-[4-(3,4,5-trifluorophenyl)-1H-1,2,3-triazol-1-yl]-1-thio-α-D-galactopyranoside | 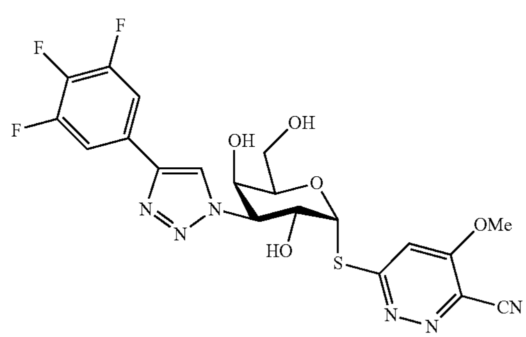 | 0.25 |

-continued

| Example | Name | structure | Galectin-3 Kd (μM) |
|---|---|---|---|
| 55 | 5-Hydroxy-6-cyano-pyridazin-3-yl 3-deoxy-3-[4-(3,4,5-trifluorophenyl)-1H-1,2,3-triazol-1-yl]-1-thio-α-D-galactopyranoside | 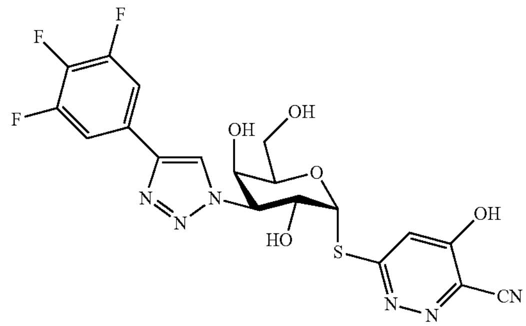 | 0.94 |
| 56 | 3-Chloro-2,4 difluorophenyl 3-deoxy-1-thio-3-[4-(3,4,5-trifluorophenyl)-1H-1,2,3-triazol-1-yl]-α-D-galactopyranoside | 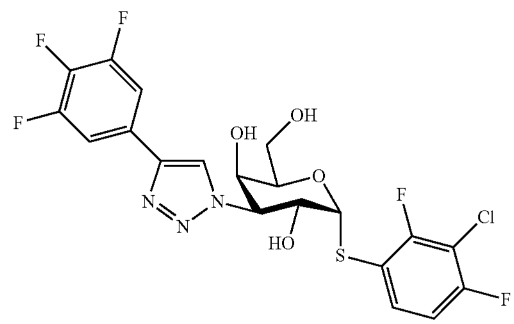 | 0.15 |
| 57 | 3,4-Dichlorophenyl 3-deoxy-3-[4-(phenyl)-1H-1,2,3-triazol-1-yl]-1-thio-α-D-galactopyranoside | 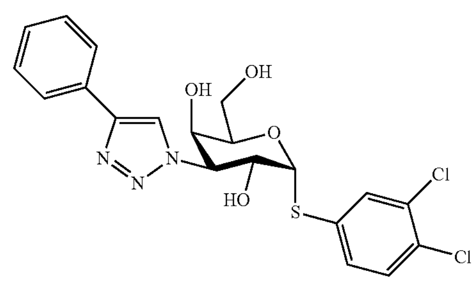 | 1.45 |
| 58 | 3,4-Dichloro-4-fluorophenyl 3-deoxy-3-[4-(3,4,5-trifluorophenyl)-1H-1,2,3-triazol-1-yl]-1-thio-α-D-galactopyranoside | 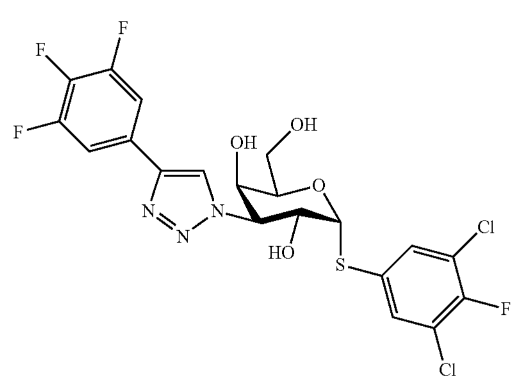 | 0.018 |

-continued

| Example | Name | structure | Galectin-3 Kd (μM) |
|---|---|---|---|
| 59 | 3,4-Dichloro-6-fluorophenyl 3-deoxy-3-[4-(3,4,5-trifluorophenyl)-1H-1,2,3-triazol-1-yl]-1-thio-α-D-galactopyranoside | 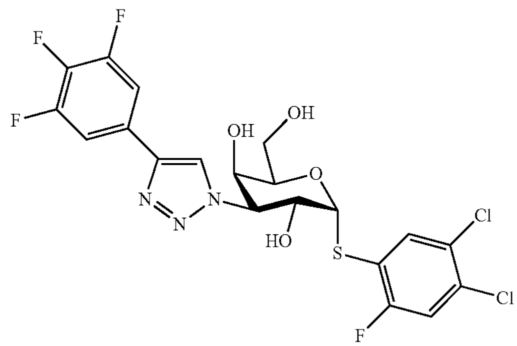 | 0.027 |
| 60 | 5-Bromo-4-fluorophenyl 3-deoxy-3-[4-(3,4,5-trifluorophenyl)-1H-1,2,3-triazol-1-yl]-1-thio-α-D-galactopyranoside | 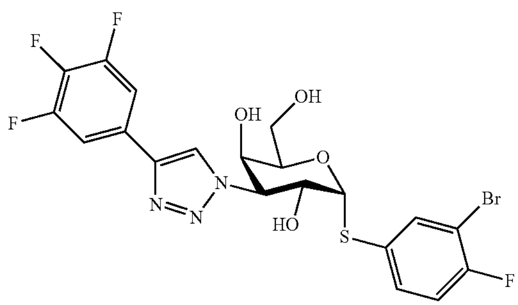 | 0.024 |
| 61 | 3-Chloro-4-(trifluoromethyl)phenyl 3-deoxy-1-thio-3-[4-(3,4,5-trifluorophenyl)-1H-1,2,3-triazol-1-yl]-α-D-galactopyranoside | 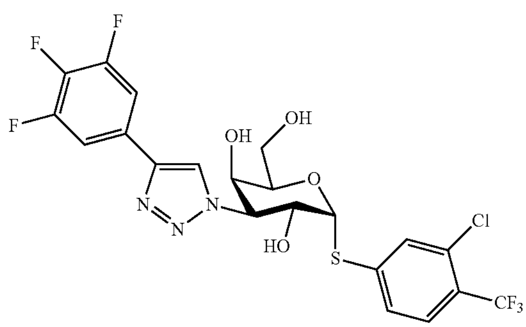 | 0.031 |
| 62 | 3,4,5-Trichlorophenyl 3-deoxy-1-thio-3-[4-(3,4,5-trifluorophenyl)-1H-1,2,3-triazol-1-yl]-α-D-galactopyranoside | 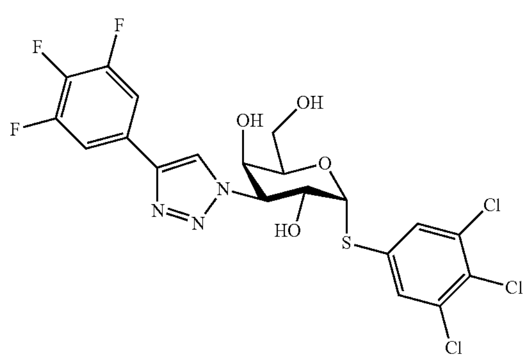 | 0.034 |

-continued

| Example | Name | structure | Galectin-3 Kd (μM) |
|---|---|---|---|
| 63 | 6-Chloro-2-fluorophenyl 3-deoxy-1-thio-3-[4-(3,4,5-trifluorophenyl)-1H-1,2,3-triazol-1-yl]-α-D-galactopyranoside | 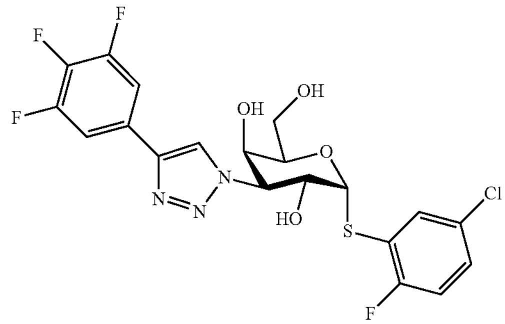 | 0.046 |
| 64 | 5-Bromo-2-fluorophenyl 3-deoxy-1-thio-3-[4-(3,4,5-trifluorophenyl)-1H-1,2,3-triazol-1-yl]-α-D-galactopyranoside | 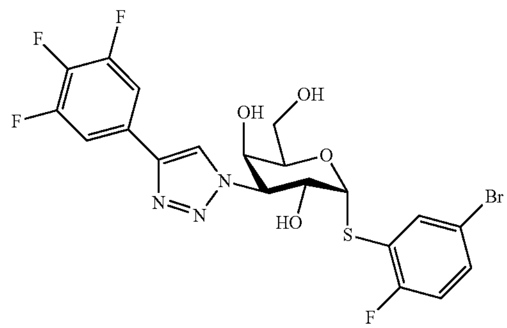 | 0.047 |
| 65 | 5-Chloro-2-methoxyphenyl 3-deoxy-1-thio-3-[4-(3,4,5-trifluorophenyl)-1H-1,2,3-triazol-1-yl]-α-D-galactopyranoside | 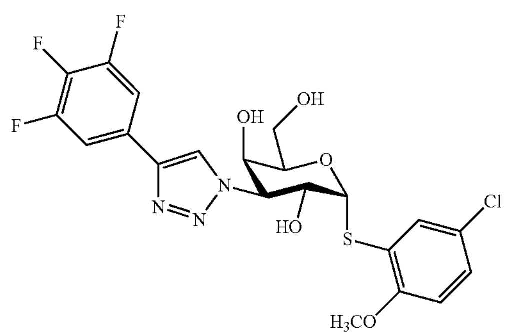 | 0.084 |
| 66 | 3-Iodophenyl 3-deoxy-1-thio-3-[4-(3,4,5-trifluorophenyl)-1H-1,2,3-triazol-1-yl]-α-D-galactopyranoside | 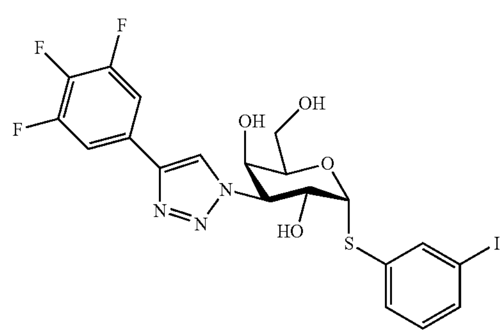 | 0.090 |

| Example | Name | structure | Galectin-3 Kd (μM) |
|---|---|---|---|
| 67 | Picolinamide-5-yl 3-deoxy-3-[4-(3,4,5-trifluorophenyl)-1H-1,2,3-triazol-1-yl]-1-thio-α-D-galactopyranoside | 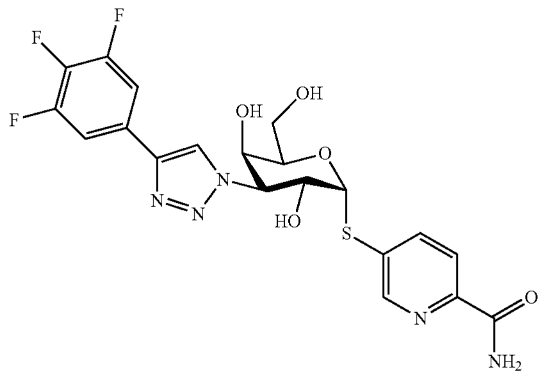 | 0.180 |
| 68 | 3-Cyanophenyl 3-deoxy-1-thio-3-[4-(3,4,5-trifluorophenyl)-1H-1,2,3-triazol-1-yl]-α-D-galactopyranoside | 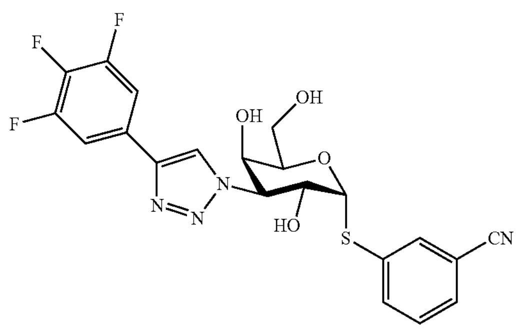 | 0.192 |
| 69 | 2-Cyanopyridine-5-yl 3-deoxy-3-[4-(3,4,5-trifluorophenyl)-1H-1,2,3-triazol-1-yl]-1-thio-α-D-galactopyranoside | 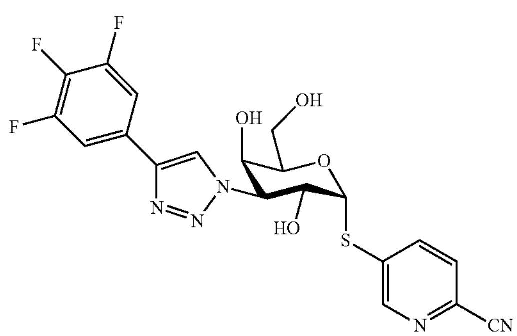 | 0.26 |
| 70 | 4-Chloro-2-thienyl 3-deoxy-3-[4-(3,4,5-trifluorophenyl)-1H-1,2,3-triazol-1-yl]-1-thio-α-D-galactopyranoside | 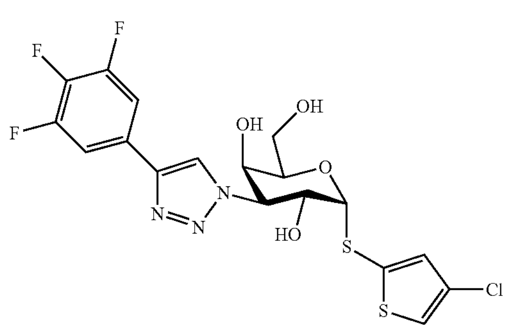 | 0.33 |

-continued

| Example | Name | structure | Galectin-3 Kd (μM) |
|---|---|---|---|
| 71 | 3-Carboxyphenyl 3-deoxy-3-[4-(3,4,5-trifluorophenyl)-1H-1,2,3-triazol-1-yl]-1-thio-α-D-galactopyranoside | 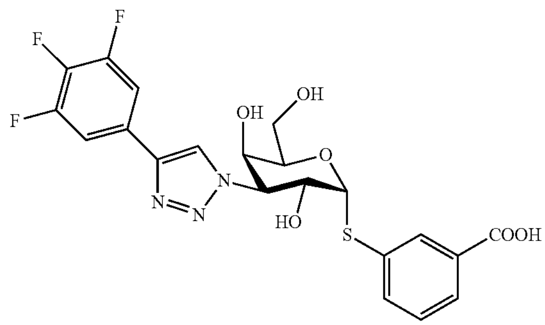 | 0.35 |
| 72 | Benzamide-3-yl 3-deoxy-3-[4-(3,4,5-trifluorophenyl)-1H-1,2,3-triazol-1-yl]-1-thio-α-D-galactopyranoside | 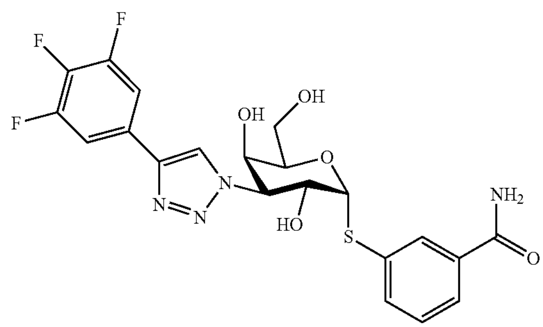 | 0.38 |
| 73 | 3,4-Dichlorophenyl 3-deoxy-3-[4-(3,4-difluorophenyl)-1H-1,2,3-triazol-1-yl]-1-thio-α-D-galactopyranoside | 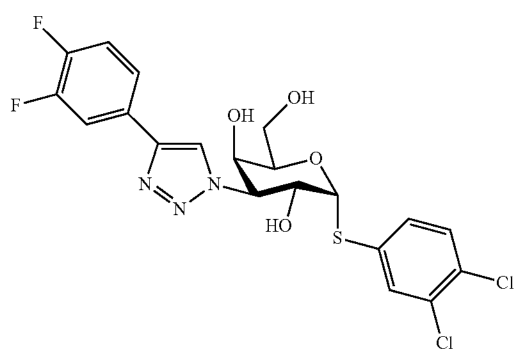 | 0.11 |
| 74 | 3,4-Dichlorophenyl 3-deoxy-3-[4-(3,4-difluorophenyl)-1H-1,2,3-triazol-1-yl]-1-thio-α-D-galactopyranoside | 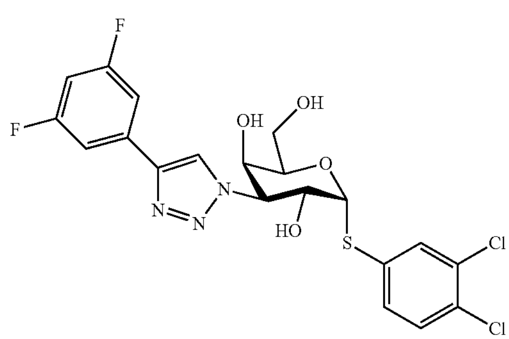 | 0.11 |

| Example | Name | structure | Galectin-3 Kd (μM) |
|---|---|---|---|
| 75 | 3,4-Dichlorophenyl 3-deoxy-3-[4-(3-fluorophenyl)-1H-1,2,3-triazol-1-yl]-1-thio-α-D-galactopyranoside | 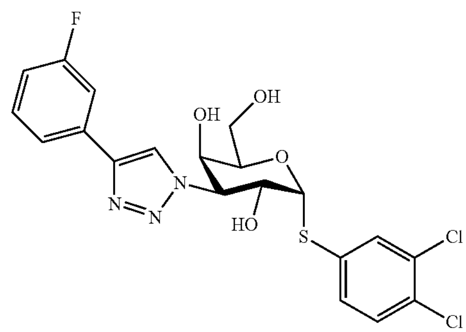 | 0.14 |
| 76 | 3,3'-difluoro-cyklohexyl 3-deoxy-3-[4-(3,4,5-trifluorophenyl)-1H-1,2,3-triazol-1-yl]-1-thio-α-D-galactopyranoside | 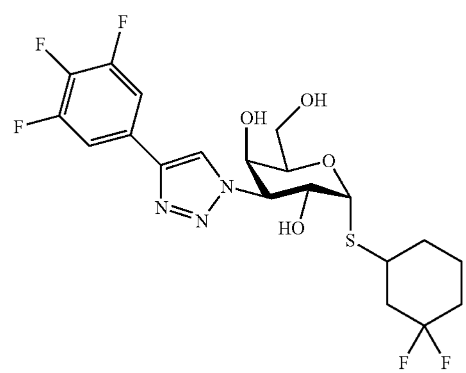 | 0.24 |
| 77 | n-Butyl 3-deoxy-3-[4-(3,4,5-trifluorophenyl)-1H-1,2,3-triazol-1-yl]-1-thio-α-D-galactopyranoside | 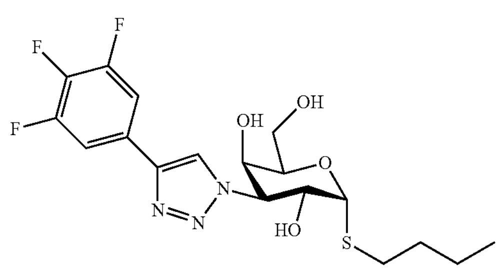 | 0.45 |
| 78 | 3,4-Dichlorophenyl 3-deoxy-3-[4-(3,5-difluoro-4-methoxyphenyl)-1H-1,2,3-triazol-1-yl]-1-thio-α-D-galactopyranoside | 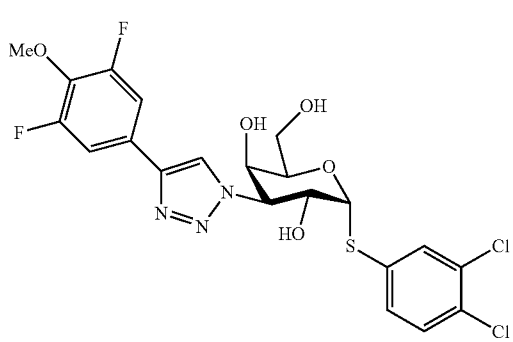 | 0.47 |

-continued

| Example | Name | structure | Galectin-3 Kd (μM) |
|---|---|---|---|
| 79 | 5-Hydroxy-pyridin-4-yl 3-deoxy-3-[4-(3,4,5-trifluorophenyl)-1H-1,2,3-triazol-1-yl]-1-thio-α-D-galactopyranoside | 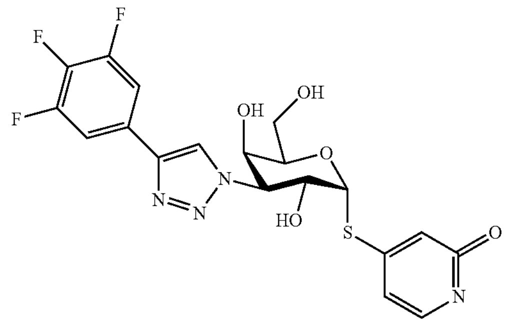 | 0.51 |
| 80 | 2-Chlorophenetyl 3-deoxy-3-[4-(3,4,5-trifluorophenyl)-1H-1,2,3-triazol-1-yl]-1-thio-α-D-galactopyranoside | 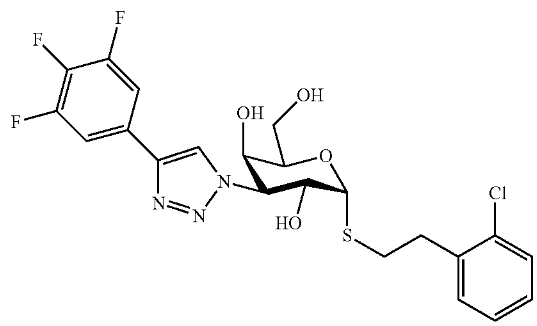 | 0.75 |
| 81 | 4-Chlorophenetyl 3-deoxy-3-[4-(3,4,5-trifluorophenyl)-1H-1,2,3-triazol-1-yl]-1-thio-α-D-galactopyranoside | 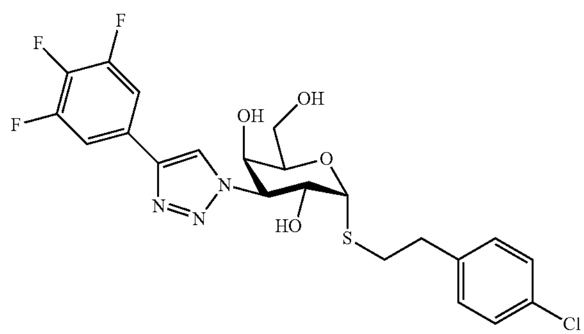 | 0.76 |
| 82 | 4-Chlorobenzyl 3-deoxy-1-thio-3-[4-(3,4,5-trifluorophenyl)-1H-1,2,3-triazol-1-yl]-α-D-galactopyranoside | 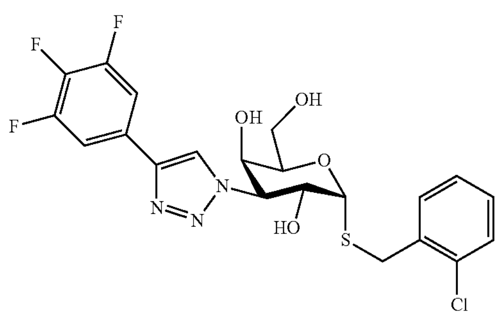 | 0.77 |
| 83 | 3,4-Dichlorobenzyl 3-deoxy-1-thio-3-[4-(3,4,5-trifluorophenyl)-1H-1,2,3-triazol-1-yl]-α-D-galactopyranoside | 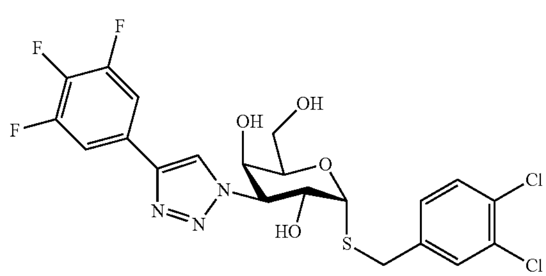 | 0.79 |

-continued

| Example | Name | structure | Galectin-3 Kd (μM) |
|---|---|---|---|
| 84 | 3-Chlorophenetyl 3-deoxy-3-[4-(3,4,5-trifluorophenyl)-1H-1,2,3-triazol-1-yl]-1-thio-α-D-galactopyranoside | 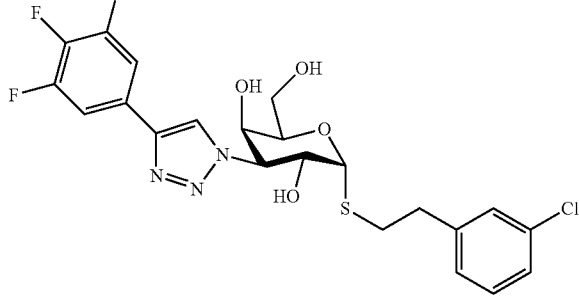 | 0.82 |
| 85 | 4-Chlorobenzyl 3-deoxy-1-thio-3-[4-(3,4,5-trifluorophenyl)-1H-1,2,3-triazol-1-yl]-α-D-galactopyranoside | 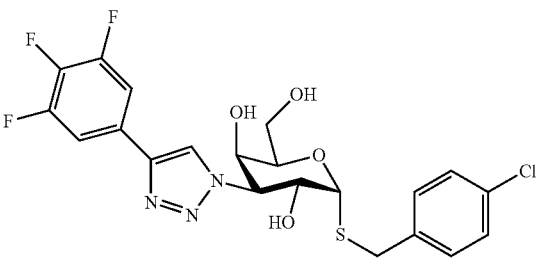 | 0.95 |
| 86 | Propyl 3-deoxy-3-[4-(3,4,5-trifluorophenyl)-1H-1,2,3-triazol-1-yl]-1-thio-α-D-galactopyranoside | 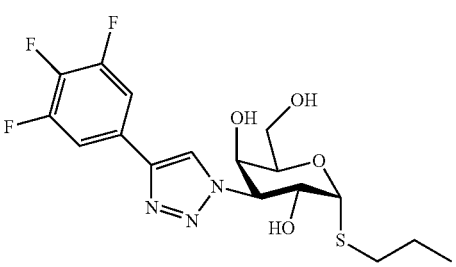 | 0.98 |
| 87 | 2-Aminopyridin-4-yl 3-deoxy-3-[4-(3,4,5-trifluorophenyl)-1H-1,2,3-triazol-1-yl]-1-thio-α-D-galactopyranoside | 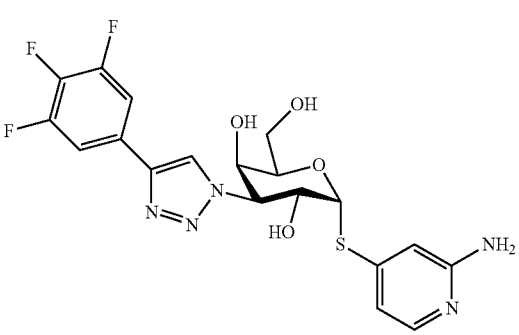 | 0.99 |
| 88 | 5-dimethylamino-naphatlen-2-yl 3-deoxy-3-[4-(3,4,5-trifluorophenyl)-1H-1,2,3-triazol-1-yl]-1-thio-α-D-galactopyranoside | 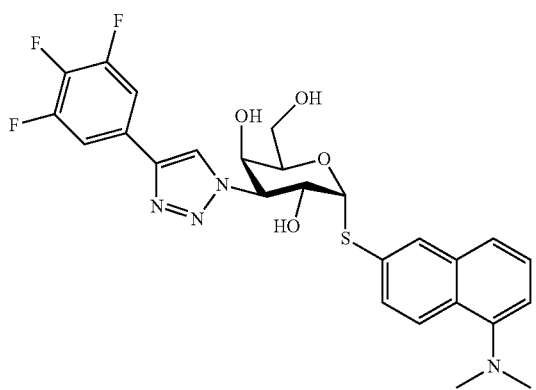 | 1.06 |

-continued

| Example | Name | structure | Galectin-3 Kd (μM) |
|---|---|---|---|
| 89 | Ethyl 3-deoxy-1-thio-3-[4-(3,4,5-trifluorophenyl)-1H-1,2,3-triazol-1-yl]-α-D-galactopyranoside | 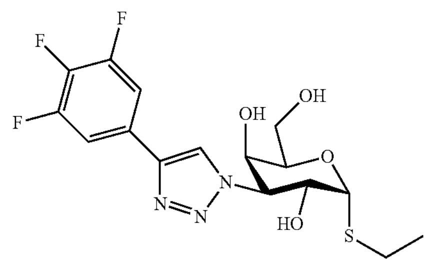 | 1.1 |
| 90 | 5-Bromopyridin-3-yl 3-deoxy-3-[4-(3,4,5-trifluorophenyl)-1H-1,2,3-triazol-1-yl]-α-D-galactopyranosyl sulfoxide, isomer 1 | isomer 1 | 0.028 |
| 91 | 5-Bromopyridin-3-yl 3-deoxy-3-[4-(3,4,5-trifluorophenyl)-1H-1,2,3-triazol-1-yl]-α-D-galactopyranosyl sulfoxide, isomer 2 | isomer 2 | 0.130 |
| 92 | 5-Bromopyridin-3-yl 3-deoxy-3-[4-(3,4,5-trifluorophenyl)-1H-1,2,3-triazol-1-yl]-α-D-galactopyranosyl sulfone | 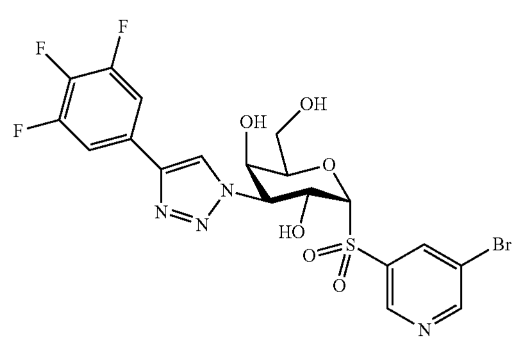 | 0.031 |

-continued

| Example | Name | structure | Galectin-3 Kd (μM) |
|---|---|---|---|
| 93 | 5-Chloropyridin-3-yl 3-deoxy-3-[4-(3,4,5-trifluorophenyl)-1H-1,2,3-triazol-1-yl]-α-D-galactopyranosyl sulfoxide, isomer 1 | isomer 1 | 0.106 |
| 94 | 5-Chloropyridin-3-yl 3-deoxy-3-[4-(3,4,5-trifluorophenyl)-1H-1,2,3-triazol-1-yl]-α-D-galactopyranosyl sulfoxide, isomer 2 | isomer 2 | 0.041 |
| 95 | 5-Dimethylamino-naphtalen-2-yl 3-deoxy-3-[4-(3,4,5-trifluorophenyl)-1H-1,2,3-triazol-1-yl]-α-D-galactopyranosyl sulfone | 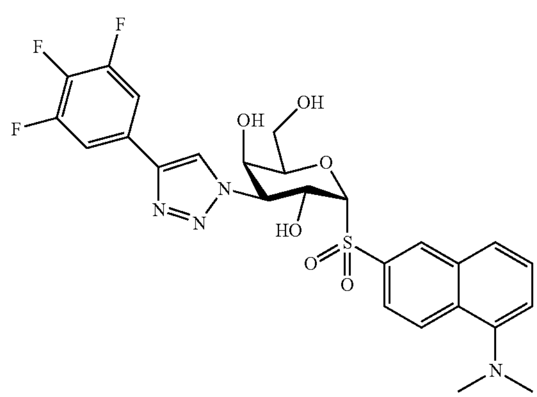 | 0.96 |
| 96 | 3,4-dichlorophenyl 3-deoxy-3-(3,4,5-trifluorobenzamido)-1-thio-α-D-galactopyranoside | 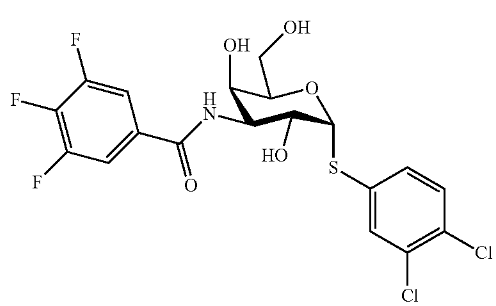 | 3.5 |

| Example | Name | structure | Galectin-3 Kd (μM) |
|---|---|---|---|
| 97 | 3,4-Dichlorophenyl 3-deoxy-3-[4-(ethoxycarbonyl)-1H-1,2,3-triazol-1-yl]-1-thio-α-D-galactopyranoside | 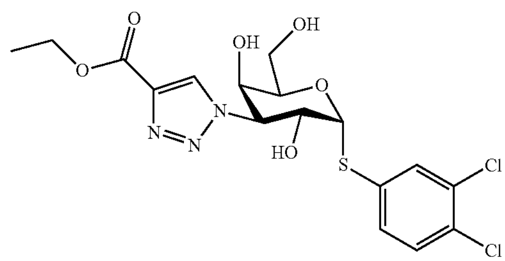 | 3.5 |
| 98 | 3,4-Dichlorophenyl 3-deoxy-3-[4-(ethylaminocarbonyl)-1H-1,2,3-triazol-1-yl]-1-thio-α-D-galactopyranoside | 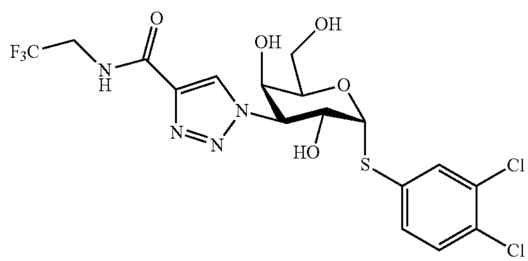 | 0.56 |
| 99 | 3,4-Dichlorophenyl 3-O-[(5,6-Difluoro-2-oxo-3-chromenyl)methyl]-1-thio-α-D-galactopyranoside | 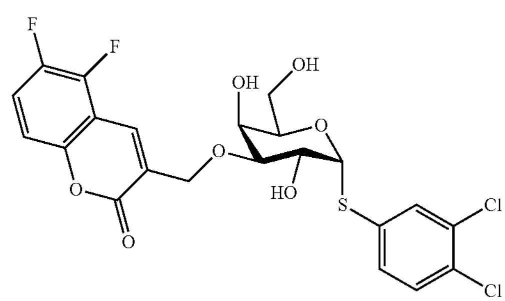 | 0.92 |
| 100 | 5-Chloropyridin-3-yl 3-deoxy-3-[4-(3,4-difluorophenyl)-1H-1,2,3-triazol-1-yl]-1-thio-α-D-galactopyranoside | 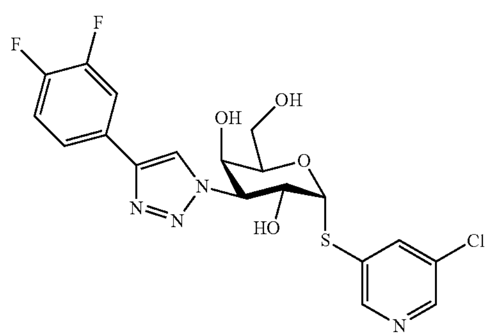 | 0.100 |
| 101 | 5-Bromopyridin 3-yl 3-deoxy-3-[4-(3,4-difluorophenyl)-1H-1,2,3-triazol-1-yl]-1-thio-α-D-galactopyranoside | 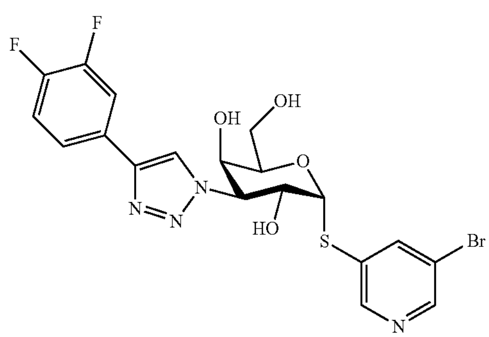 | 0.047 |

-continued

| Example | Name | structure | Galectin-3 Kd (μM) |
|---|---|---|---|
| 102 | 3,4-Dichlorophenyl 3-deoxy-3-[4-(propyl-carbonyl)-1H-1,2,3-triazol-1-yl]-1-thio-α-D-galactopyranoside | 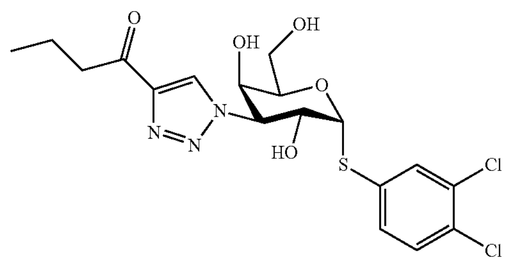 | 1.01 |
| 103 | 5-Chloro-6-trifluoromethyl-pyridine-3-yl 3-deoxy-3-[4-(3,4,5-trifluorophenyl)-1H-1,2,3-triazol-1-yl]-1-thio-α-D-galactopyranoside | 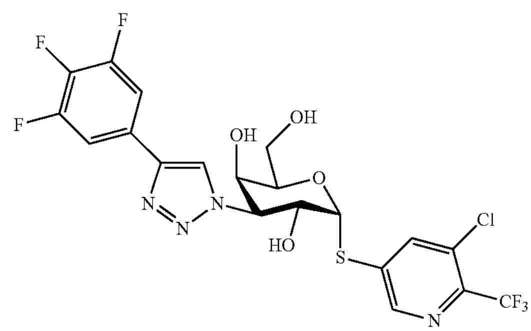 | 0.026 |
| 104 | 5-Chloro-2-trifluoromethyl-pyridine-3-yl 3-deoxy-3-[4-(3,4,5-trifluorophenyl)-1H-1,2,3-triazol-1-yl]-1-thio-α-D-galactopyranoside | 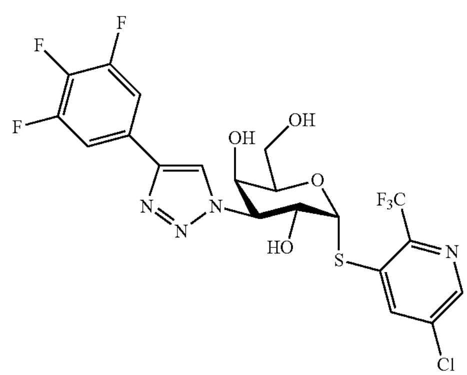 | 0.093 |
| 105 | 5-Chloro-6-cyano-pyridine-3-yl 3-deoxy-3-[4-(3,4-difluorophenyl)-1H-1,2,3-triazol-1-yl]-1-thio-α-D-galactopyranoside | 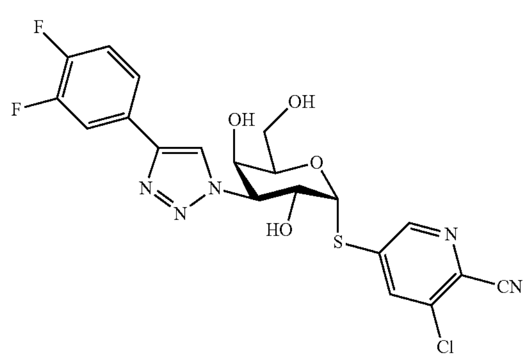 | 0.074 |

| Example | Name | structure | Galectin-3 Kd (µM) |
|---|---|---|---|
| 106 | 3-Chloro-4-cyanophenyl 3-deoxy-3-[4-(3,4-difluorophenyl)-1H-1,2,3-triazol-1-yl]-1-thio-α-D-galactopyranoside | 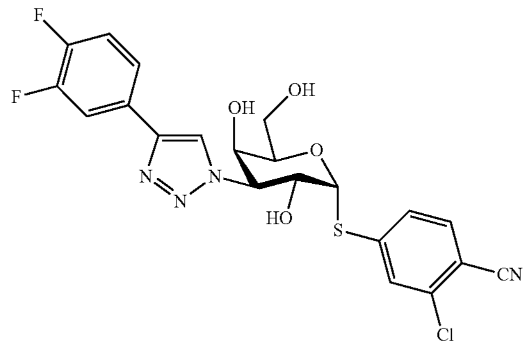 | 0.083 |

Evaluation of Kd Values

The affinity of Example 1-106 for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47, (Sörme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al., 2010). The assay was also adapted to be able to measure the high affinity of compounds for galectin-3 by using the below probe constructed to have high affinity for galectin-3 which made it possible to use a low concentration of galectin-3 (50 nM). 100 nM albumin was included as a carrier to prevent protein loss at such low concentration of galectin.

exemplified by Example 9 3,4-Dichlorophenyl 3-deoxy-3-[4-(3,4,5-trifluorophenyl)-1H-1,2,3-triazol-1-yl]-1-thio-α-D-galactopyranoside in the table below.

| | Clearance (CL) (ml/min/kg) | Halflife (t½) (h) | Bioavailability (F) (%) | Cmax p.o. Dose 10 mg/kg (µM) |
|---|---|---|---|---|
| Example 9 | 1.2 | 4.5 | 75 | 16 |

Synthesis of Examples and Intermediates

General Procedures

Nuclear Magnetic Resonance (NMR) spectra were recorded on a 400 MHz Varian or a 500 MHz Bruker AVANCE III 500 instrument, at 25° C. Chemical shifts are reported in ppm (δ) using the residual solvent as internal standard. Peak multiplicities are expressed as follow: s,

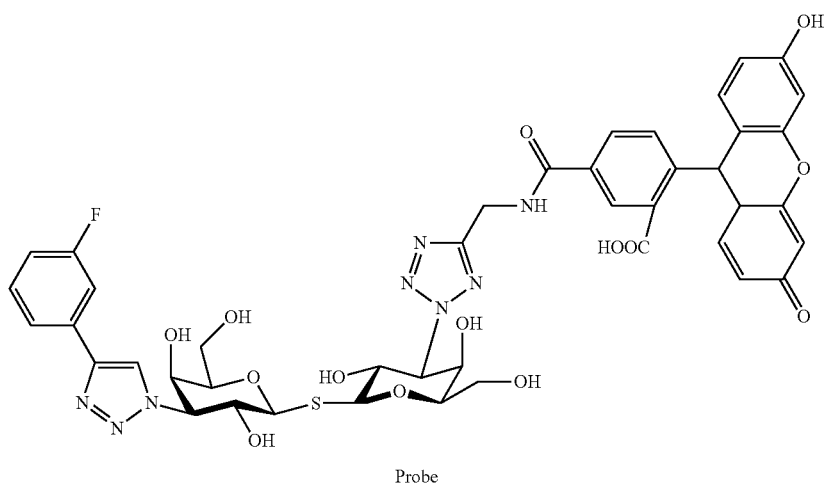

Probe

PK Experiments

Good in vitro PK properties were observed for some of the compounds of Formula 1 which translated into high oral bioavailability, low clearance, good halflife and high Cmax at 10 mg/kg in pharmacokinetic studies in mice. This is singlet; d, doublet; dd, doublet of doublets; t, triplet; dt, doublet of triplet; q, quartet; m, multiplet; br s, broad singlet.

LC-MS were acquired on an Agilent 1100 or Agilent 1200 HPLC coupled with an Agilent MSD mass spectrometer operating in ES (+) ionization mode. Columns: Waters symmetry 2.1×30 mm C18, Chromolith RP-18 2×50 mm or XBridge C18 (4.6×50 mm, 3.5 μm) or SunFire C18 (4.6×50 mm, 3.5 μm). Solvent A water+0.1% TFA and solvent B Acetonitrile+0.1% TFA. Wavelength: 254 nM Preparative HPLC was performed on a Gilson system. A) Flow: 10 ml/min Column: kromasil 100-5-C18 column. Wavelength: 254 nM. Solvent A water+0.1% TFA and solvent B Acetonitrile+0.1% TFA. B) on a Gilson 215. Flow: 25 ml/min Column: XBrige prep C18 10 μm OBD (19×250 mm) column. Wavelength: 254 nM. Solvent A water (10 mM Ammonium hydrogen carbonate) and solvent B Acetonitrile.

Flash chromatography was performed on a Biotage SP1 automated system, using Biotage Snap KP-Sil 25 g or 50 g cartridges.

The following abbreviations are used
EtOAc: Ethylacetate
DIEA: N,N-Diisopropylethylamine
PE: petroleum ether
NEt₃: Triethylamine
DMF: N,N-dimethylformamide
BF₃.OEt₂: Borontrifuoride etherate
ESI-MS: Electrospray ionization mass spectrometry
Calcd: Calculated
TFA: trifluoroacetic acid
Rt: Room temperature
UV: Ultraviolet
PMA: polymolybdenic acid
DAST: Diethylaminosulfur trifluoride
TBDMS: tert-Butyldimethylsilyl
TBAF: tetrabutylammonium Fluoride
MTBE: tert-butyl methyl ether
HATU: 1-[Bis(dimethylamino)methylene]-1H-1,2,3-triazolo[4,5-b]pyridinium 3-oxid hexafluorophosphate Example 1

3,4-Dimethylphenyl 3-deoxy-3-[4-(3,4,5-triflooro-phenyl)-1H-1,2,3-triazol-1-yl]-α-1-thio-D-galacto-pyranoside

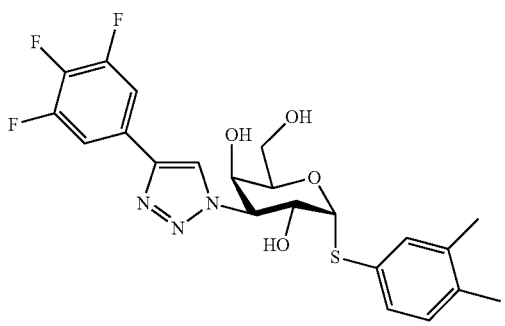

3,4-Dimethyl-phenyl 2,4,6-tri-O-acetyl-3-azido-3-deoxy-1-thio-α-D-galactopyranoside, i1, (46 mg, 0.10 mmol) was dissolved in anhydrous acetonitrile (3 mL) and stirred at rt under N₂. CuI (20 mg, 0.11 mmol) was added and after five minutes 3,4,5-trifluorophenylacetylene (0.028 mL, 0.21 mmol) was added. After another five minutes DIEA (0.018 mL, 0.10 mmol) was added and the mixture was stirred at rt for eighteen hours. The mixture was filtered through a short silica column, eluting with EtOAc and concentrated down. The residue was dissolved in methanolic NaOMe (20 mL, 0.05 M) and stirred at rt. After four hours acetic acid (2 mL) was added and the mixture was concentrated down. The crude product was purified by preparative HPLC and lyophilized to give 28 mg (57%) of 3,4-dimethylphenyl 3-deoxy-1-thio-3-[4-(3,4,5-trifluorophenyl)-1H-1,2,3-triazol-1-yl]-α-D-galactopyranoside. ¹H NMR (400 MHz, Methanol-d₄) δ 8.53 (s, 1H), 7.70-7.61 (m, 2H), 7.40 (s, 1H), 7.33 (d, J=7.7 Hz, 1H), 7.10 (d, J=7.7 Hz, 1H), 5.66 (d, J=5.3 Hz, 1H), 4.98 (dd, J=11.4, 2.7 Hz, 1H), 4.88 (dd, J=11.6, 5.3 Hz, 1H), 4.59 (t, J 6.1 Hz, 1H), 4.20 (s, 1H), 3.71 (qd, J=11.4, 6.2 Hz, 2H), 2.26 (s, 6H). ESI-MS n/z calcd for [C₂₂H₂₃F₃N₃O₄S]⁺ (M+H)⁺: 482.1; found: 482.1.

Example 2-16 were made from their corresponding intermediate i2-i16 using a similar procedure as Example 1.

Example 2

3-Bromophenyl 3-deoxy-3-[4-(3,4,5-trifluorophe-nyl)-1H-1,2,3-triazol-1-yl]-1-thio-α-D-galactopyra-noside

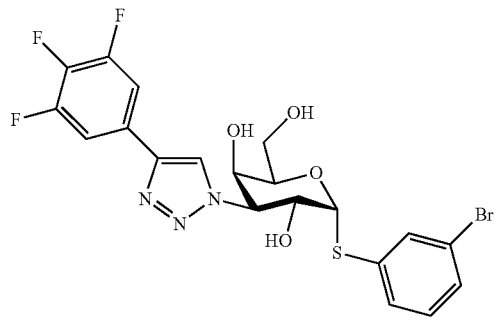

Yield 53%. ¹H NMR (400 MHz, Methanol-d₄) δ 8.54 (s, 1H), 7.80 (s, 1H), 7.71-7.55 (m, 3H), 7.45 (d, J=8.5 Hz, 1H), 7.25 (t, J=7.9 Hz, 1H), 5.83 (d, J=5.1 Hz, 1H), 4.98 (dd, J=11.5, 2.6 Hz, 1H), 4.91 (dd, J=11.4, 5.2 Hz, 1H), 4.51 (t, J=6.1 Hz, 1H), 4.21 (d, J=1.6 Hz, 1H), 3.72 (qd, J=11.4, 6.2 Hz, 2H). ESI-MS m/z calcd for [C₂₀H₁₈BrF₃N₃O₄S]⁺ (M+H)⁺: 532.0; found: 531.9.

Example 3

3-Ethoxyphenyl 3-deoxy-3-[4-(3,4,5-trifluorophe-nyl)-1H-1,2,3-triazol-1-yl]-1-thio-α-D-galactopyra-noside

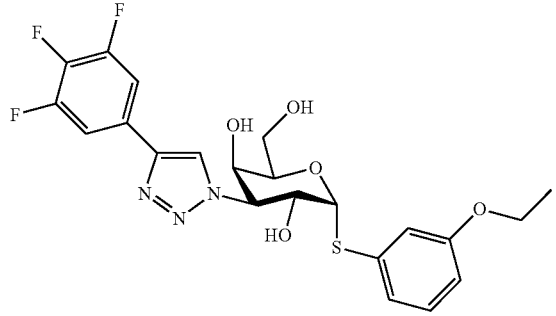

Yield 78%. $^1$H NMR (400 MHz, Methanol-d$_4$) δ 8.54 (s, 1H), 7.71-7.60 (m, 2H), 7.27-7.12 (m, 3H), 6.84 (d, J=7.9 Hz, 1H), 5.78 (d, J=5.2 Hz, 1H), 4.97 (dd, J=11.5, 2.7 Hz, 1H), 4.89 (dd, J=11.5, 5.3 Hz, 1H), 4.56 (t, J=6.1 Hz, 1H), 4.21 (d, J=1.7 Hz, 1H), 4.05 (q, J=7.0 Hz, 2H), 3.72 (qd, J=11.3, 6.2 Hz, 2H), 1.39 (t, J=7.0 Hz, 3H). ESI-MS m/calcd for [C$_{22}$H$_{23}$F$_3$N$_3$O$_5$S]$^+$ (M+H)$^+$: 498.1; found: 498.0.

Example 4

4-Pyridyl 3-deoxy-1-thio-3-[4-(3,4,5-trifluorophenyl)-1H-1,2,3-triazol-1-yl]-1-thio-α-D-galactopyranoside

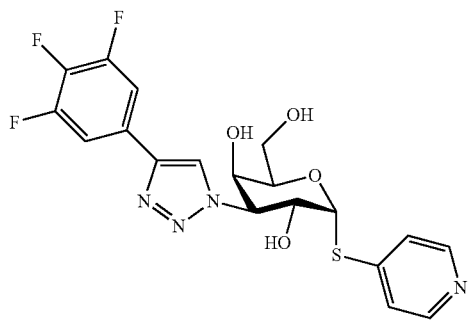

Yield 73%. $^1$H NMR (400 MHz, Methanol-d$_4$) δ 8.58 (s, 1H), 8.52 (d, J=6.8 Hz, 2H), 8.07 (d, J=6.8 Hz, 2H), 7.71-7.58 (m, 2H), 6.49 (bs, 1H), 5.06 (d, J=1.4 Hz, 2H), 4.25 (t, J=6.0 Hz, 1H), 4.20 (s, 1H), 3.72 (dd, J=5.9, 2.5 Hz, 2H). ESI-MS m/z calcd for [C$_{19}$H$_{18}$F$_3$N$_4$O$_4$S]$^+$ (M+H)$^+$: 455.1; found: 455.0.

Example 5

2,4-Dichlorophenyl 3-deoxy-3-[4-(3,4,5-trifluorophenyl)-1H-1,2,3-triazol-1-yl]-1-thio-α-D-galactopyranoside

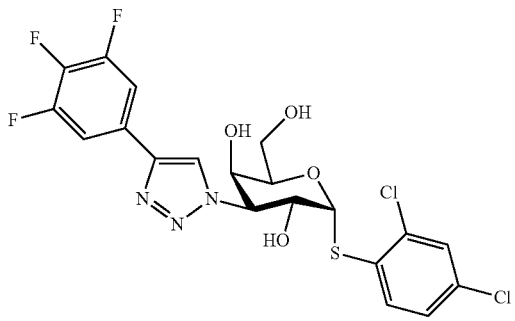

Yield 58%. $^1$H NMR (400 MHz, Methanol-d$_4$) δ 8.55 (s, 1H), 7.77 (d, J=8.5 Hz, 1H), 7.69-7.59 (m, 2H), 7.51 (d, J=2.1 Hz, 1H), 7.32 (dd, J=8.5, 2.1 Hz, 1H), 5.99 (d, J=5.3 Hz, 1H), 5.07 (dd, J=11.4, 2.7 Hz, 1H), 4.96 (dd, J=11.4, 5.4 Hz, 1H), 4.44 (t, J=6.2 Hz, 1H), 4.22 (d, J=1.7 Hz, 1H), 3.70 (dd, J=11.4, 5.9 Hz, 1H), 3.61 (dd, J=11.4, 6.4 Hz, 1H). ESI-MS m/z calcd for [C$_{20}$H$_{17}$Cl$_2$F$_3$N$_3$O$_4$S]$^+$ (M+H)$^+$: 522.0; found: 522.0.

Example 6

4-Acetanilidyl 3-deoxy-3-[4-(3,4,5-trifluorophenyl)-1H-1,2,3-triazol-1-yl]-1-thio-α-D-galactopyranoside

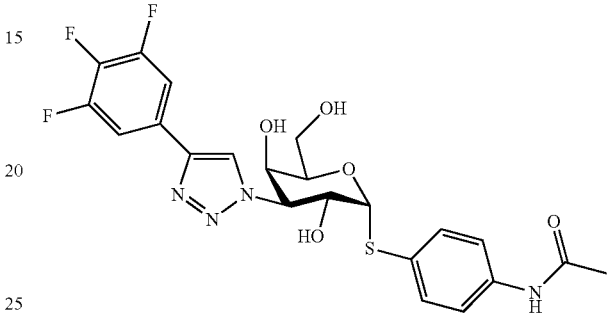

Yield 36%. $^1$H NMR (400 MHz, Methanol-d$_4$) δ 8.53 (s, 1H), 7.64 (dd, J=8.6, 6.8 Hz, 2H), 7.58-7.51 (m, 4H), 5.69 (d, J=5.2 Hz, 1H), 4.98 (dd, J=11.4, 2.7 Hz, 1H), 4.88 (dd, J=11.5, 5.3 Hz, 1H), 4.58 (t, J=6.1 Hz, 1H), 4.21 (d, J=2.0 Hz, 1H), 3.72 (qd, J=11.4, 6.2 Hz, 2H), 2.13 (s, 3H). ESI-MS m/z calcd for [C$_{22}$H$_{22}$F$_3$N$_4$O$_5$S]$^+$ (M+H)$^+$: 511.1; found: 511.0.

Example 7

4-Methoxyphenyl 3-deoxy-3-[4-(3,4,5-trifluorophenyl)-1H-1,2,3-triazol-1-yl]-1-thio-α-D-galactopyranoside

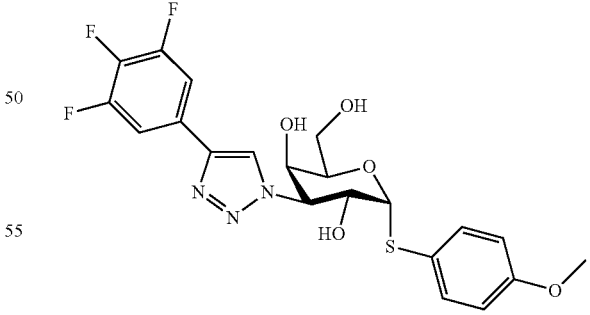

Yield 49%. $^1$H NMR (400 MHz, Methanol-d$_4$) δ 8.53 (s, 1H), 7.70-7.60 (m, 2H), 7.54 (d, J=8.6 Hz, 2H), 6.91 (d, J=8.7 Hz, 2H), 5.59 (d, J=5.3 Hz, 1H), 4.98 (dd, J=11.4, 2.8 Hz, 1H), 4.88 (d, J=5.4 Hz, 1H), 4.61 (t, J=6.1 Hz, 1H), 4.21 (d, J=1.9 Hz, 1H), 3.80 (s, 3H), 3.72 (qd, J=11.3, 6.1 Hz, 2H). ESI-MS m/z calcd for [C$_{21}$H$_{21}$F$_3$N$_3$O$_5$S]$^+$: (M+H)$^+$: 484.1; found: 484.0.

Example 8

2,3-Dichlorophenyl 3-deoxy-3-[4-(3,4,5-trifluorophenyl)-1H-1,2,3-triazol-1-yl]-1-thio-α-D-galactopyranoside

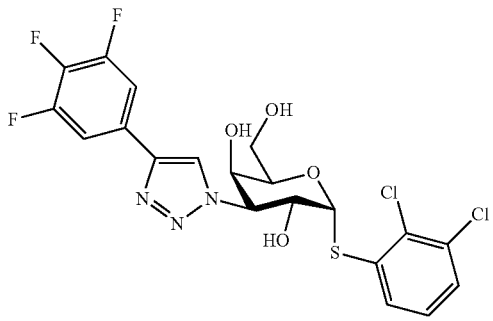

Yield 33%. $^1$H NMR (400 MHz, Methanol-d$_4$) δ 8.55 (s, 1H), 7.75 (d, J=8.0 Hz, 1H), 7.65 (dd, J=8.4, 6.9 Hz, 2H), 7.43 (d, J=8.0 Hz, 1H), 7.28 (t, J=8.0 Hz, 1H), 6.05 (d, J=5.4 Hz, 1H), 5.08 (dd, J=11.4, 2.7 Hz, 1H), 4.98 (dd, J=11.4, 5.3 Hz, 1H), 4.43 (t, J=6.2 Hz, 1H), 4.22 (d, J=2.2 Hz, 1H), 3.70 (dd, J=11.4, 6.0 Hz, 1H), 3.61 (dd, J=11.4, 6.3 Hz, 1H). ESI-MS m/z calcd for $[C_{20}H_{17}Cl_2F_3N_3O_4S]^+$ (M+H)$^+$: 522.0; found: 522.0.

Example 9

3,4-Dichlorophenyl 3-deoxy-3-[4-(3,4,5-triflorophenyl)-1H-1,2,3-triazol-1-yl]-1-thio-α-D-galactopyranoside

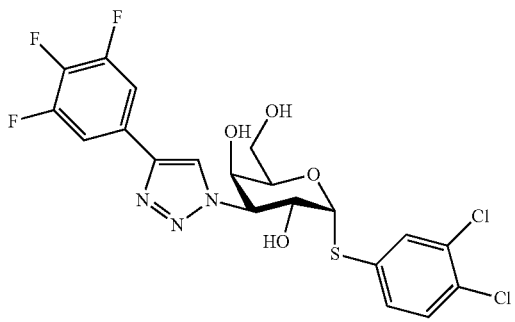

Yield 77%. $^1$H NMR (400 MHz, Chloroform-d) δ 8.13 (s, 1H), 7.66 (d, J=2.1 Hz, 1H), 7.48-7.35 (m, 4H), 5.86 (d, J=5.3 Hz, 1H), 4.91 (dd, J=11.0, 5.3 Hz, 1H), 4.73 (dd, J=11.0, 2.5 Hz, 1H), 4.63 (s, 1H), 4.46 (t, J=4.0 Hz, 1H), 4.14-4.00 (m, 2H). ESI-MS m/z calcd for $[C_{20}H_{16}Cl_2F_3N_3O_4S]^+$ (M+H)$^+$: 522.0; found: 521.9.

Example 10

Benzyl 3-deoxy-1-thio-3-[4-(3,4,5-trifloorophenyl)-1H-1,2,3-triazol-1-yl]-1-thio-α-D-galactopyranoside

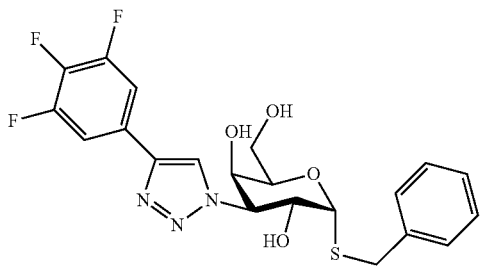

Yield 74%. $^1$H NMR (400 MHz, Chloroform-d) δ 7.95 (s, 1H), 7.31-7.09 (m, 7H), 5.45 (d, J=5.1 Hz, 1H), 4.66 (dd, J=11.0, 5.2 Hz, 1H), 4.59 (dd, J=11.0, 2.5 Hz, 1H), 4.42 (d, J=2.3 Hz, 1H), 4.24 (t, J=4.4 Hz, 1H), 3.86-3.73 (m, 4H). ESI-MS m/z calcd for $[C_{21}H_{20}F_3N_3O_4S]^+$ (M+H)$^+$: 468.1; found: 468.0.

Example 11

3-Methoxyphenyl 3-deoxy-3-[4-(3,4,5-trifluorophenyl)-1H-1,2,3-triazol-1-yl]-1-thio-α-D-galactopyranoside

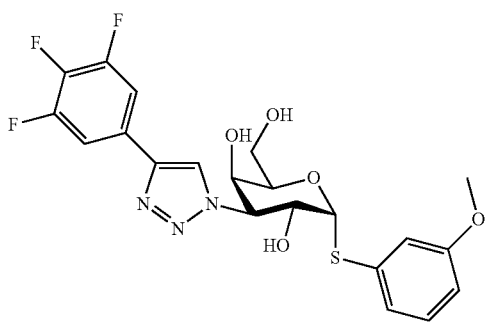

Yield 69%. $^1$H NMR (400 MHz, Chloroform-d) δ 8.12 (s, 1H), 7.39 (dd, J=8.1, 6.3 Hz, 2H), 7.30-7.23 (m, 1H), 7.16-7.07 (m, 2H), 6.92-6.84 (m, 1H), 5.87 (d, J=5.2 Hz, 1H), 4.86 (dd, J=11.1, 5.3 Hz, 1H), 4.73 (dd, J=11.2, 2.4 Hz, 1H), 4.61 (d, J=2.5 Hz, 1H), 4.51 (d, J=4.0 Hz, 11H), 4.11-3.98 (m, 2H), 3.82 (s, 3H). ESI-MS m/z calcd for $[C_{21}H_{20}F_3N_3O_5S]^+$ (M+H)$^+$: 484.1; found: 484.1.

Example 12

2-Naphtyl 3-deoxy-3-[4-(3,4,5-trifluorophenyl)-1H-1,2,3-triazol-1-yl]-1-thio-α-D-galactopyranoside

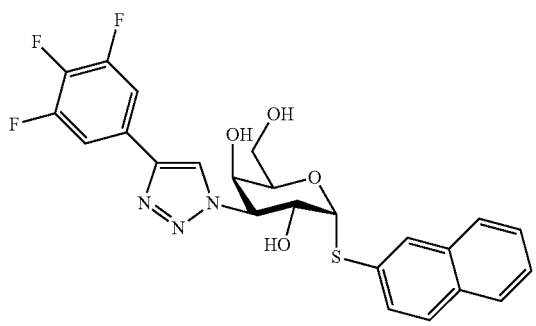

Yield 56%. $^1$H NMR (400 MHz, Chloroform-d) δ 8.16 (s, 1H), 8.07 (s, 1H), 7.88-7.78 (m, 3H), 7.60 (d, J=8.6 Hz, 1H), 7.57-7.50 (m, 2H), 7.47 (d, J=7.1 Hz, 2H), 5.96 (d, J=5.2 Hz, 1H), 4.90 (dd, J=11.2, 5.2 Hz, 1H), 4.79 (d, J=11.3 Hz, 1H), 4.65 (s, 1H), 4.58 (s, 1H), 4.14-4.01 (m, 2H). ESI-MS m/z calcd for $[C_{24}H_{20}F_3N_3O_4S]^+$ (M+H)$^+$: 504.1; found: 504.0.

Example 13

3-Methylphenyl 3-deoxy-3-[4-(3,4,5-trifluorophenyl)-1H-1,2,3-triazol-1-yl]-1-thio-α-D-galactopyranoside

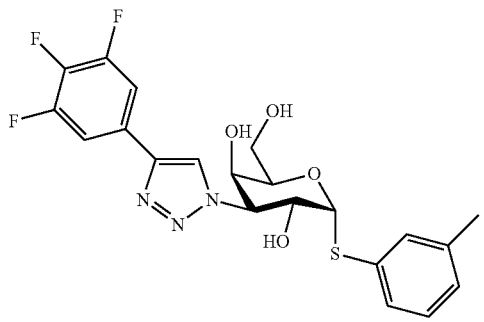

Yield 58%. $^1$H NMR (400 MHz, Chloroform-d) δ 8.11 (s, 1H), 7.43-7.31 (m, 4H), 7.24 (d, J=7.6 Hz, 1H), 7.16 (d, J=7.6 Hz, 11H), 5.83 (d, J=5.1 Hz, 1H), 4.90-4.81 (m, 1H), 4.72 (dd, J=11.1, 2.4 Hz, 1H), 4.61 (d, J=1.9 Hz, 1H), 4.51 (t, J=4.2 Hz, 1H), 4.08-4.01 (m, 2H), 2.36 (s, 3H). ESI-MS m/z calcd for $[C_{21}H_{20}F_3N_3O_4S]^+$ (M+H)$^+$: 468.1; found: 468.0.

Example 14

3-(Trifluoromethyl)phenyl 3-deoxy-3-[4-(3,4,5-trifluorophenyl)-1H-1,2,3-triazol-1-yl]-1-thio-α-D-galactopyranoside

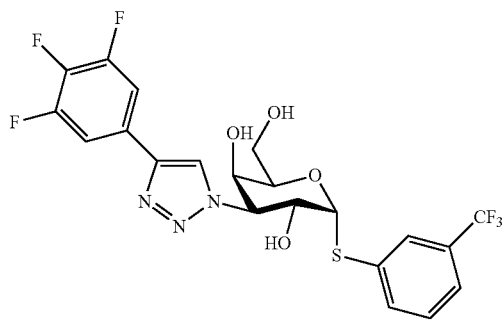

Yield 65%. $^1$H NMR (400 MHz, Methanol-d$_4$) δ 8.55 (d, J=2.2 Hz, 1H), 7.92-7.84 (m, 2H), 7.64 (ddd, J=9.0, 6.6, 2.4 Hz, 2H), 7.59 (d, J=8.2 Hz, 1H), 7.53 (td, J=7.7, 2.2 Hz, 1H), 5.88 (dd, J=5.3, 2.3 Hz, 1H), 5.01 (dt, J=11.6, 2.6 Hz, 1H), 4.98-4.89 (m, 1H), 4.58-4.50 (m, 1H), 4.23 (s, 1H), 3.72 (dddd, J=26.3, 9.2, 6.2, 3.3 Hz, 2H). ESI-MS m/z calcd for $[C_{21}H_{17}F_6N_3O_4S]^+$ (M+H)$^+$: 522.1; found: 522.0.

Example 15

4-Bromophenyl 3-deoxy-3-[4-(3,4,5-trifluorophenyl)-1H-1,2,3-triazol-1-yl]-1-thio-α-D-galactopyranoside

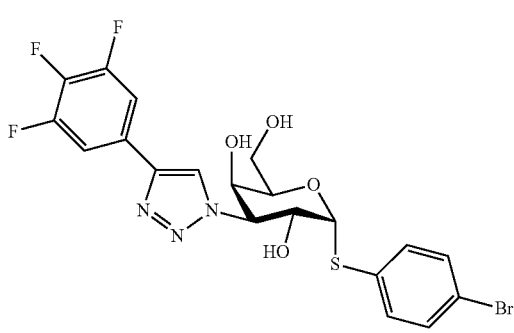

Yield 0.2%. $^1$H NMR (400 MHz, Chloroform-d) δ 8.14 (s, 1H), 7.54-7.39 (m, 6H), 5.83 (d, J=5.3 Hz, 1H), 4.88 (dd, J=11.0, 5.2 Hz, 1H), 4.73 (dd, J=11.0, 2.5 Hz, 1H), 4.63 (s, 1H), 4.49 (d, J=4.1 Hz, 1H), 4.13-3.99 (m, 2H). ESI-MS m/z calcd for $[C20H17BrF3N3O4S]^+$ (M+H)$^+$: 532.0; found: 532.0.

Example 16

3,5-Dichlorophenyl 3-deoxy-3-[4-(3,4,5-trifluorophenyl)-1H-1,2,3-triazol-1-yl]-1-thio α-D-galactopyranoside

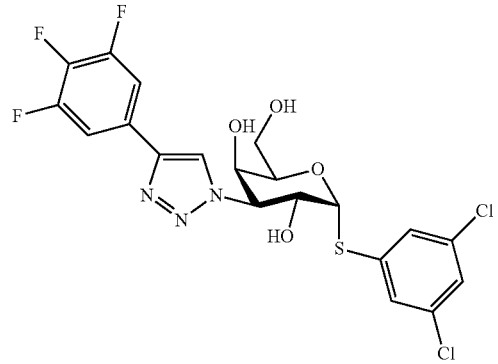

Yield 14%. $^1$H NMR (400 MHz, Chloroform-d) δ 8.09 (s, 1H), 7.37 (d, J=1.7 Hz, 2H), 7.32-7.20 (m, 3H), 5.85 (d, J=5.2 Hz, 1H), 4.90 (dd, J=11.2, 5.2 Hz, 1H), 4.70 (d, J=11.2 Hz, 1H), 4.56 (s, 1H), 4.40 (s, 1H), 4.03-3.97 (m, 2H). ESI-MS m/z calcd for $[C20H16Cl2F3N3O4S]^+$ (M+H)$^+$: 522.0; found: 521.9.

Example 17

2,6-Dimethylphenyl 3-deoxy-3-[4-(3,4,5-trifluorophenyl)-1H-1,2,3-triazol-1-yl]-1-thio-α-D-galactopyranoside

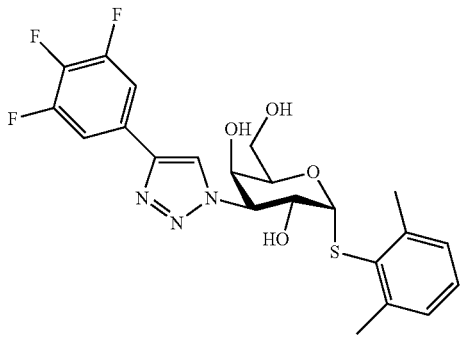

2,4,6-tri-O-acetyl-3-azido-1-chloro-3-deoxy-p-D-galactopyranoside (123 mg, 0.35 mmol) dissolved in anhydrous DMF (1 mL) and Cs$_2$CO$_3$ (184 mg, 0.56 mmol) was added. After five minutes 2,6-dimethylbenzenethiol (0.052 mL, 0.39 mmol) was added and the mixture was heated to 50° C. After two hours the reaction was allowed to cool to rt and MeCN (2 mL) was added followed by CuI (34 mg, 0.18 mmol). After five minutes 3,4,5-trifluorophenylacetylene (0.095 mL, 0.71 mmol) was added and after an additional five minutes DIEA (0.092 mL, 0.53 mmol) was added and the mixture was stirred at rt for eighteen hours. The mixture was filtered through a short silica column, eluting with EtOAc and concentrated down. The residue was dissolved in methanolic NaOMe (10 mL, 0.05 M) and stirred at rt After four hours acetic acid (2 mL) was added and the mixture was concentrated down. The crude product was purified by preparative HPLC and lyophilized to give 24 mg (11%) of 2,6-dimethylphenyl 3-deoxy-1-thio-3-[4-(3,4,5-trifluorophenyl)-1H-1,2,3-triazol-1-yl]-α-D-galactopyranoside. $^1$H NMR (400 MHz, Methanol-d$_4$) δ 8.53 (s, 1H), 7.84-7.58 (m, 2H), 7.14 (bs, 3H), 5.36 (d, J=5.3 Hz, 1H), 5.03 (dd, J=11.6, 2.6 Hz, 1H), 4.83-4.76 (m, 1H), 4.56 (t, J=6.2 Hz, H), 4.24 (d, J=1.4 Hz, 1H), 3.78-3.57 (m, 2H), 2.60 (s, 6H). ESI-MS m/z calcd for [C$_{22}$H$_{23}$F$_3$N$_3$O$_4$S]$^+$ (M+H)$^+$: 482.1; found: 482.1.

Example 18-21 were made from their corresponding thiol using a similar procedure as Example 17;

Example 18

1-Naphthyl 3-deoxy-1-thio-3-[4-(3,4,5-trifluorophenyl)-1H-1,2,3-triazol-1-yl]-1-thio-α-D-galactopyranoside

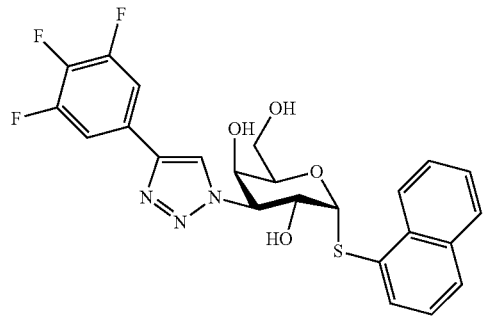

Yield 17%. $^1$H NMR (400 MHz, Methanol-d$_4$) δ 8.63-8.58 (m 1H), 8.56 (s, 1H), 7.99-7.82 (m, 3H), 7.76-7.50 (m, 4H), 7.47 (t, J=7.7 Hz, 1H), 5.73 (d, J=5.3 Hz, 1H), 5.13 (dd, J=11.5, 2.8 Hz, 1H), 4.93 (dd, J=11.5, 5.4 Hz, 1H), 4.69 (t, J=6.2 Hz, 1H), 4.27 (d, J=2.0 Hz, 1H), 3.76-3.69 (m, 1H), 3.63 (dd, J=11.3, 6.3 Hz, 1H). ESI-MS m/z calcd for [C$_{24}$H$_{21}$F$_3$N$_3$O$_4$S]$^+$ (M+H)$^+$: 504.1, found: 504.0.

Example 19

3-Chlorophenyl 3-deoxy-3-[4-(3,4,5-trifluorophenyl)-1H-1,2,3-triazol-1-yl]-1-thio-α-D-galactopyranoside

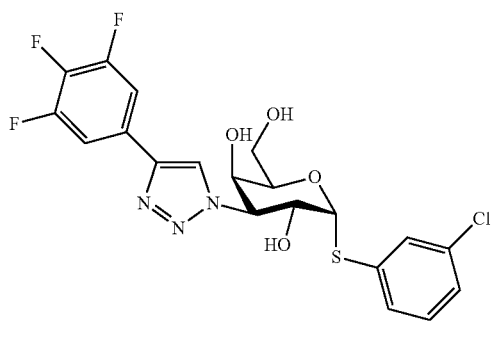

Yield 25%. $^1$H NMR (400 MHz, Chloroform-d) δ 8.10 (s, 1H), 7.52 (d, J=1.9 Hz, 1H), 7.40 (dt, J=7.2, 1.7 Hz, 1H), 7.35-7.22 (m, 4H), 5.85 (d, J=5.2 Hz, 1H), 4.90 (dd, J=11.1, 5.3 Hz, 1H), 4.73 (dd, J=11.1, 2.5 Hz, 1H), 4.59 (d, J=2.5 Hz, 1H), 4.46 (t, J=4.3 Hz, 1H), 4.06-3.90 (m, 2H). ESI-MS m/z calcd for [C$_{20}$H$_7$ClF$_3$N$_3$O$_4$S]$^+$ (M+H)$^+$: 488.1; found: 488.0.

Example 20

3-(Trifluoromethoxy)phenyl 3-deoxy-3-[4-(3,4,5-trifluorophenyl)-1H-1,2,3-triazol-1-yl]-1-thio-α-D-galactopyranoside

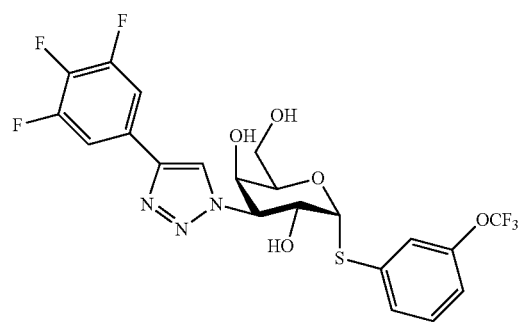

Yield 4%. $^1$H NMR (400 MHz, Chloroform-d) δ 8.15 (s, 1H), 7.55-7.36 (m, 5H), 7.21 (d, J=8.7 Hz, 1H), 5.92 (d, J=5.3 Hz, 1H), 4.91 (dd, J=11.0, 5.1 Hz, 1H), 4.75 (q, J=14.4, 14.0 Hz, 1H), 4.64 (s, 1H), 4.50-4.45 (m, 1H), 4.14-4.00 (m, 2H). ESI-MS m/z calcd for [C$_{21}$H$_7$F$_6$N$_3$O$_5$S]$^+$ (M+H)$^+$: 538.1; found: 538.1.

Example 21

2-Pyridyl 3-deoxy-3-[4-(3,4,5-trifluorophenyl-1H-1,2,3-triazol-1-yl]-)-1-thio-α-D-galactopyranoside

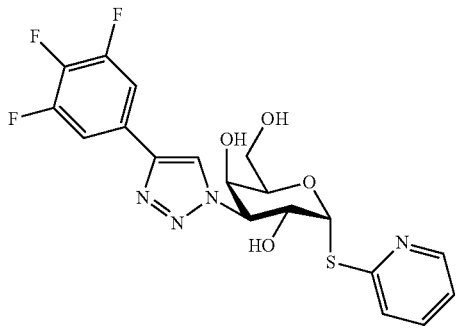

Yield 4%. ¹H NMR (400 MHz, Methanol-d₄) δ 8.57 (s, 1H), 8.50 (d, J=5.3 Hz, 1H), 7.90 (dd, J=8.9, 7.1 Hz, 1H), 7.78 (d, J=7.7 Hz, 1H), 7.66 (t, J=7.6 Hz, 2H), 7.38 (t, J=7.4 Hz, 1H), 6.50 (s, 1H), 5.01 (t, J=1.9 Hz, 2H), 4.35 (t, J=6.2 Hz, 1H), 4.20 (s, 1H), 3.75-3.62 (m, 2H). ESI-MS m/z calcd for $[C_{19}H_{17}F3N_4O_4S]^+$ (M+H)⁺: 455.1; found: 455.0.

Examples 22-23 were made from their corresponding intermediate i22-i23 using a similar procedure as Example 1;

Example 22

1-O-(3,4-Dichlorophenyl) 3-deoxy-3-[4-(3,4,5-trifluorophenyl)-1H-1,2,3-triazol-1-yl]-α-D-galactopyranoside

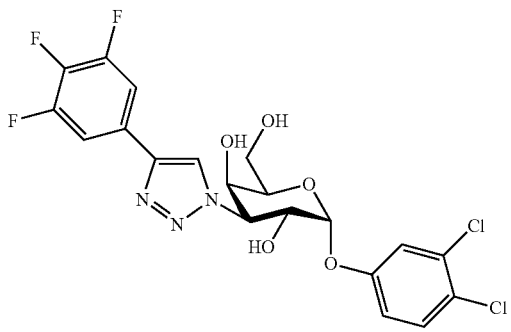

Yield 42%. ¹H NMR (400 MHz, Methanol-d₄) δ 8.59 (s, 1H), 7.78-7.58 (m, 2H), 7.53-7.40 (m, 2H), 7.21 (dd, J=8.9, 2.7 Hz, 1H), 5.69 (d, J=3.6 Hz, 1H), 5.27 (dd, J=11.4, 2.8 Hz, 1H), 4.69 (dd, J=11.4, 3.6 Hz, 1H), 4.21 (d, J=2.0 Hz, 1H), 4.11 (t, J=6.1 Hz, 1H), 3.72 (d, J=6.1 Hz, 2H). ESI-MS m/z calcd for $[C_{20}H_{17}Cl_2F_3N_3O_5]^+$ (M+H)⁺: 506.0; found: 506.0.

Example 23

4-Chlorophenyl 3-deoxy-3-[4-(3,4,5-trifluorophenyl)-1H-1,2,3-triazol-1-yl]-1-thio-α-D-galactopyranoside

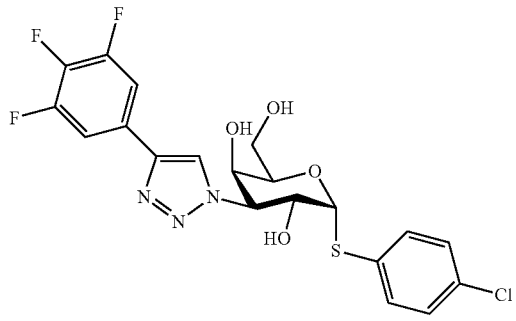

Yield 31%. ¹H NMR (400 MHz, Chloroform-d) δ 8.12 (s, 1H), 7.49 (d, J=8.5 Hz, 2H), 7.41 (t, J=7.6 Hz, 2H), 7.34 (d, J=8.4 Hz, 2H), 7.27 (d, J=0.7 Hz, 2H), 5.82 (d, J=5.2 Hz, 1H), 4.88 (dd, J=11.1, 5.2 Hz, 1H), 4.73 (dd, J=11.1, 2.3 Hz, 1H), 4.62 (s, 1H), 4.48 (t, J=4.4 Hz, 1H), 4.11-3.97 (m, 2H). ESI-MS m/z calcd for $[C_{20}H_{17}ClF_3N_3O_4S]^+$ (M+H)⁺: 488.1; found: 488.0.

From the purification of the title compound, in addition product 4-chlorophenyl 2,4,6-tri-O-acetyl-3-deoxy-1-thio-3-[4-(3,4,5-trifluorophenyl)-1H-1,2,3-triazol-1-yl]-α-D-galactopyranoside was isolated (yield 6%).

Example 24

3,4-Dichlorophenyl 3-deoxy-3-[4-(3,4,5-trifluorophenyl)-1H-1,2,3-triazol-yl]-α-D-galactopyranosyl sulfoxide

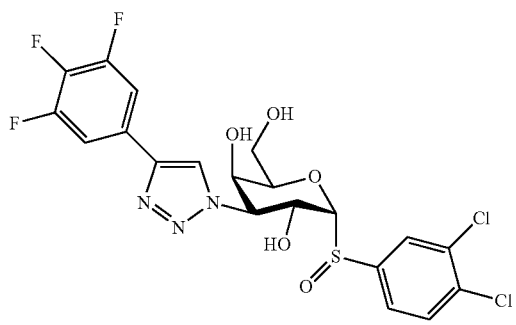

3,4-Dichlorophenyl 3-deoxy-1-thio-3-[4-3,4,5-trifluorophenyl)-1H-1,2,3-triazol-1-yl]-α-D-galactopyranoside (30 mg, 0.06 mmol) was dissolved in acetic acid (4 ml). Aqueous 27% hydrogen peroxide solution (0.20 ml) was added. The mixture was heated to 45° C. After 2 h the mixture was diluted with water (2 ml) and purified on HPLC column. The title compound was isolated as lyophilized white powder (20 mg, 65%).

¹H NMR (400 MHz, Chloroform-d) δ 8.14 (s, 1H), 7.86 (d, J=1.9 Hz, 1H), 7.71 (d, J=8.3 Hz, 1H), 7.62-7.55 (m, 1H), 7.44 (dd, J=8.0, 6.4 Hz, 2H), 5.32 (d, J=10.9 Hz, 1H), 5.08 (d, J=4.7 Hz, 1H), 5.03-4.95 (m, 1H), 4.91 (s, 1H), 4.52 (t, J=4.9 Hz, 1H), 4.10 (dd, J=12.1, 5.4 Hz, 1H), 4.02 (dd, J=12.0, 4.4 Hz, 1H). ESI-MS m/z calcd for $[C_{20}H_{16}Cl_2F_3N_3O_5S]^+$ (M+H)$^+$: 538.0; found: 537.9.

Example 25

3,4-Dichlorophenyl 3-deoxy-3-[4-(3,4,5-trifluorophenyl)-1H-1,2,3-triazol-1-yl]-α-D-galactopyranosyl sulfone

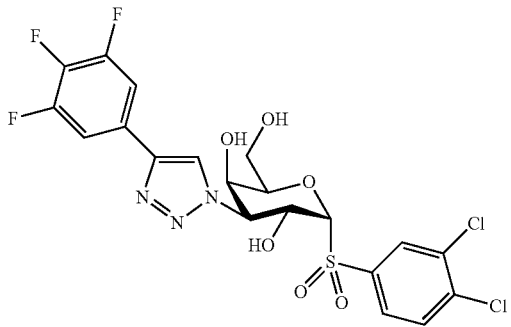

From the purification described for Example 24 was also isolated the title compound (1 mg, 3%).

$^1$H NMR (400 MHz, Methanol-d$_4$) δ 8.54 (s, 1H), 8.16 (d, J=2.0 Hz, 1H), 7.92 (dd, J=8.5, 2.0 Hz, 1H), 7.80 (d, J=8.5 Hz, 1H), 7.65 (dd, J=8.5, 6.7 Hz, 2H), 5.74 (dd, J=11.5, 2.7 Hz, 1H), 5.34 (d, J=6.4 Hz, 1H), 5.13 (dd, J=11.5, 6.4 Hz, 1H), 4.52 (t, J=6.1 Hz, 1H), 4.28 (d, J=2.6 Hz, 1H), 3.60 (qd, J=11.6, 5.9 Hz, 2H). ESI-MS m/z calcd for $[C_{20}H_{16}Cl_2F_3N_3O_6S]^+$ (M+H)$^+$: 554.0; found: 554.0.

Example 26

4-Chlorophenyl 3-deoxy-3-[4-(3,4,5-trifluorophenyl)-1H-1,2,3-triazol-1-yl]-α-D-galactopyranosyl sulfoxide

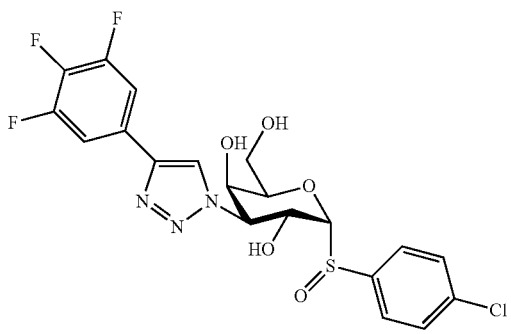

4-Chlorophenyl 2,4,6-tri-O-acetyl-3-deoxy-1-thio-3-[4-(3,4,5-trifluorophenyl)-1H-1,2,3-triazol-1-yl]-α-D-galactopyranoside (10 mg, 0.02 mmol) was dissolved in acetic acid (3 ml). Hydrogen peroxide (100 μl) was added. The mixture was stirred at 45° C. 1 h and then diluted with water and freezedried. The residue was dissolved in MeOH (10 ml) and 1M sodium methoxide in methanol (1 ml) was added. After one night at rt the mixture was concentrated in vacuo and the residue purified by HPLC. The product was isolated after freezedrying as a white fluffy powder (3 mg, 37%).

$^1$H NMR (400 MHz, Methanol-d$_4$) δ 8.54 (s, 1H), 7.91-7.81 (m, 2H), 7.69-7.59 (m, 4H), 5.52 (dd, J=11.4, 2.8 Hz, 1H), 5.13 (dd, J=11.3, 5.6 Hz, 1H), 4.92 (d, J=5.5 Hz, 1H), 4.26 (d, J=2.8 Hz, H), 4.08 (t, J=6.1 Hz, 1H), 3.53 (dd, J=11.4, 5.8 Hz, 1H), 3.41 (dd, J=11.4, 6.4 Hz, 1H). ESI-MS m/z calcd for $[C_{20}H_{17}ClF_3N_3O_5S]^+$ (M+H)$^+$: 504.1; found: 504.0.

Example 27

Phenyl 3-deoxy-3-[4-(3,4,5-trifluorophenyl)-1H-1,2,3-triazol-1-yl]-1-thio-α-D-galactopyranoside

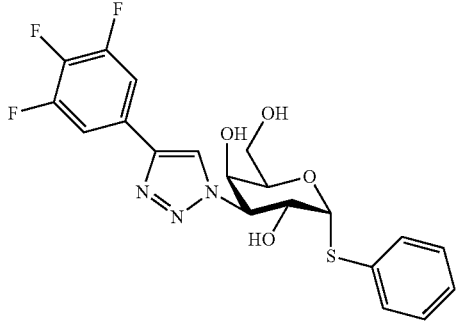

To a solution of phenyl 2,4,6-tri-O-acetyl-3-azido-3-deoxy-1-thio-α-D-galactopyranoside (160 mg, α-anomer:β-anomer=100:8, 0.38 mmol) in DMF (3 mL) were added trimethyl-[2-(3,4,5-trifluorophenyl)ethynyl]silane (4) (170 mg, 0.74 mmol), copper(I) iodide (20 mg, 0.11 mmol) and triethylamine (0.26 mL, 1.85 mmol). The mixture was stirred at 100° C. for 1 h. Water (10 mL) was added and the mixture was filtrated. The filtrate was diluted by DCM (40 mL), washed with brine. The organic layers were dried over anhydrous Na$_2$SO$_4$ and concentrated in vacuo. The residue was dissolved in methanolic NaOMe (8 mL, pH=9-10) and stirred at r.t for 2 h. Neutralization with H$^+$ resin, filtered and concentrated to afford a syrup. The crude product was purified by prep-HPLC and then chiral-HPLC to afford the α-anomer product 40 mg as a white solid.

Chiral-HPLC conditions: instrument: SFC-80 (Thar, Waters), column: IC 20*250 mm, 5 um (Decial), column temperature: 35° C., mobile phase: CO$_2$/Methanol(0.1% NH$_4$OH)=65/35, flow rate: 80 g/min, back pressure: 100 bar, detection wavelength: 214 nm, cycle time: 4.2 min, sample solution: 60 mg dissolved in 15 mL methanol, injection volume: 5.0 mL.

$^1$H NMR (500 MHz, Methanol-d$_4$) δ 8.57 (s, 1H), 7.67 (d, J=6.5 Hz, 1H), 7.65 (d, J=7.0 Hz, 1H), 7.63-7.61 (m, 2H), 7.36-7.30 (m, 3H), 5.77 (d, J=5.5 Hz, 1H), 5.00 (dd, J=11.5, 2.5 Hz, 1H), 4.91 (d, J=5.0 Hz, 1H), 4.57 (t, J=6.5 Hz, 1H), 4.21 (d, J=1.5 Hz, 1H), 3.74 (dd, J=11.5, 6.0 Hz, 1H), 3.67 (dd, J=11.5, 6.5 Hz, 1H). ESI-MS m/z calcd for $[C_{20}H_{19}F_3N_3O_4S]^+$ (M+H)$^+$: 454.1; found: 454.0.

Example 28

3-Chloro-4-fluorophenyl 3-deoxy-3-[4-(3,4,5-trifluorophenyl)-1H-1,2,3-triazol-1-yl]-1-thio-α-D-galactopyranoside

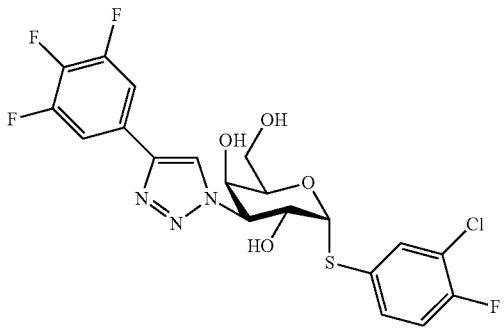

To a solution of 3-chloro-4-fluorophenyl 2,4,6-tri-O-acetyl-3-azido-3-deoxy-1-thio-α-D-galactopyranoside (210 mg, 0.44 mmol) in DMF (3 mL) were added trimethyl-[2-(3,4,5-trifluorophenyl)ethynyl]silane (200 mg, 0.88 mmol), copper(I) iodide (30 mg, 0.13 mmol) and triethylamine (0.30 mL, 2.2 mmol). The mixture was stirred at 100° C. for 1 h. Water (10 mL) was added and the mixture was filtrated. The filtrate was diluted with DCM (40 mL), washed with brine. The organic layers were dried over anhydrous $Na_2SO_4$ and concentrated in vacuo. The residue was dissolved in methanolic NaOMe (8 mL, pH=9-10) and stirred at r.t for 2 h. Neutralization with $H^+$ resin, filtered and concentrated to afford a syrup. The crude product was purified by prep-HPLC to afford the α-anomer product 120 mg as a white solid.

$^1$H NMR (500 MHz, Methanol-$d_4$) δ 8.57 (s, 1H), 7.80 (dd, J=7.5, 2.5 Hz, 1H), 7.68 (dd, J=9.0, 6.5 Hz, 2H), 7.60 (m, 1H), 7.25 (t, J=9.0 Hz, 1H), 5.78 (d, J=5.5 Hz, 1H), 5.00 (dd, J=11.5, 3.0 Hz, 1H), 4.93 (t, J=5.5 Hz, 1H), 4.55 (t, J=6.0 Hz, 1H), 4.22 (d, J=1.5 Hz, 1H), 3.78-3.70 (m, 2H). ESI-MS m/z calcd for $[C_{20}H_{17}ClF_4N_3O_4S]^+$ $(M+H)^+$: 506.1; found: 506.0.

Example 29

4-Tolyl 3-deoxy-3-[4-(3,4,5-trifluorophenyl)-1H-1,2,3-triazol-1-yl]-1-thio-α-D-galactopyranoside

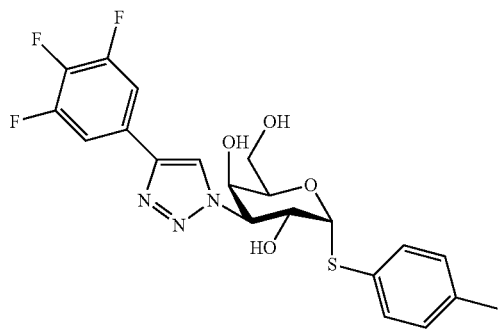

To a solution of 4-tolyl-2,4,6-tri-O-acetyl-3-deoxy-1-thio-3-[4-(3,4,5-trifluorophenyl)-1H-1,2,3-triazol-1-yl]-α-D-galactopyranoside (85 mg, 0.14 mmol) in MeOH (5 mL), methoxysodium solution (30%, 7.7 mg, 0.04 mmol) was added and the solution was stirred at room temperature for 1 h. TLC (silica gel, PE:EtOAc=1:1) analysis indicated the total consumption of the starting material. After completion, the Dowex 50W×8 hydrogen form (100-200 mesh) exchange resin was added (pH=7) and the mixture was filtered. The filtrate was concentrated and purified by prep-HPLC, lyophilized to afford product 14 mg as a white solid.

$^1$H NMR (500 MHz, DMSO-$d_6$) δ 8.79 (s, 1H), 7.87-7.83 (m, 2H), 7.45 (d, J=8.0 Hz, 2H), 7.17 (d, J=8.0 Hz, 2H), 5.77 (brs, 1H), 5.67 (d, J=5.5 Hz, 1H), 5.50 (brs, 1H), 4.79 (dd, J=11.5 Hz, 3.0 Hz, 1H), 4.73-4.70 (m, 2H), 4.34 (t, J=6.0 Hz, 1H), 4.03 (s, 1H), 3.54 (brs, 1H), 3.42-3.38 (m, 1H), 2.30 (s, 3H). ESI-MS m/z calcd for $[C_{21}H_{20}F_3N_3O_4S]^+$ $(M+H)]^+$: 468.1; found: 468.1.

Example 30

4-Fluorophenyl 3-deoxy-3-[4-(3,4,5-trifluorophenyl)-1H-1,2,3-triazol-1-yl]-1-thio-α-D-galactopyranoside

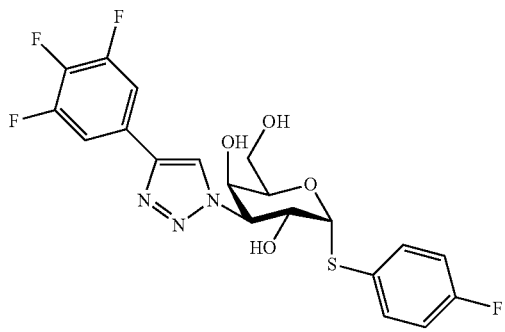

To a solution of 4-fluorophenyl-2,4,6-tri-O-acetyl-3-deoxy-1-thio-3-[4-(3,4,5-trifluorophenyl)-1H-1,2,3-triazol-1-yl]-α-D-galactopyranoside (150 mg, 0.25 mmol) in MeOH (5 mL). Sodium methoxide solution (30%, 9 mg, 0.05 mmol) was added and the solution was stirred at room temperature for 1 h. TLC (silica gel, PE:EtOAc=3:1, UV, PMA) analysis indicated the total consumption of the starting material. The Dowex 50W×8 hydrogen form (100-200 mesh) exchange resin was added (pH=7) and the mixture was filtered. Removal of solvent gave a residue. The crude was purified by flash column chromatography (silica gel, DCM:MeOH=20:1) to afford product 58 mg as a white solid.

$^1$H NMR (500 MHz, DMSO-$d_6$) δ 8.80 (s, 1H), 7.86-7.83 (m, 2H), 7.63-7.60 (m, 2H), 7.23-7.19 (m, 2H), 5.83 (s, 1H), 5.71 (d, J=5.0 Hz, 1H), 5.51 (d, J=6.0 Hz, 1H), 4.80 (dd, J=11.5 Hz, 2.5 Hz, 1H), 4.75-4.71 (m, 2H), 4.33 (t, J=6.0 Hz, 1H), 4.04 (s, 1H), 3.57-3.52 (m, 1H), 3.43-3.39 (m, 1H). ESI-MS m/z calcd for $[C_{20}H_7F_4N_3O_4S]^+$ $(M+H)^+$: 472.1; found: 472.0.

Example 31

4-Trifluoromethoxyphenyl 3-deoxy-3-[4-(3,4,5-trifluorophenyl)-1H-1,2,3-triazol-1-yl]-1-thio-α-D-galactopyranoside

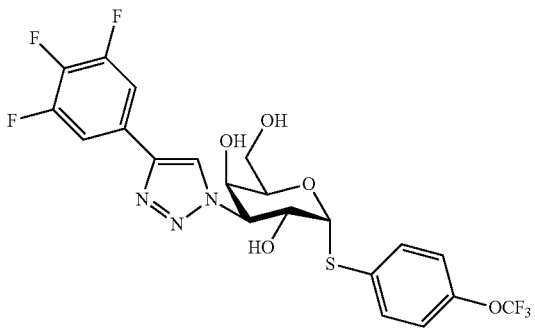

To a solution of 4-trifluoromethoxy (2,4,6-tri-O-acetyl-3-azido-3-deoxy-1-thio-α-D-galactopyranoside (150 mg, 0.23 mmol) in MeOH (5 mL), methoxysodium solution (30%, 8 mg, 0.05 mmol) was added and the solution was stirred at room temperature for another 1 h. TLC (silica gel, PE:EtOAc=3:1, UV, PMA) analysis indicated the total consumption of the starting material. The Dowex 50W×8 hydrogen form (100-200 mesh) exchange resin was added (pH=7) and mixture was filtered. Removal of solvent gave a residue. The residue was purified by flash column chromatography (silica gel, DCM:MeOH=20:1) to afford product 44 mg as a white solid.

$^1$H NMR (500 MHz, DMSO-d$_6$) δ 8.67 (s, 1H), 7.73-7.69 (m, 2H), 7.54 (d, J=9.0 Hz, 2H), 7.21 (d, J=8.0 Hz, 2H), 5.71 (dd, J=8.5 Hz, 4.5 Hz, 2H), 5.38 (d, J=6.0 Hz, 1H), 4.67 (dd, J=11.5 Hz, 2.5 Hz, 1H), 4.62-4.60 (m, 2H), 4.15 (t, J=6.5 Hz, 1H), 3.90 (dd, J=6.0 Hz, 2.5 Hz, 1H), 3.43-3.38 (m, 1H), 3.25-3.30 (m, 11H). ESI-MS m/z calcd for [C$_{21}$H$_{17}$F$_6$N$_3$O$_5$S]$^+$ (M+H)$^+$: 538.1; found: 538.1.

Examples 32-38 were made using a similar procedure as Example 1 from the corresponding intermediate i32-i38

Example 32

Phenyl 3-deoxy-3-[4-(3,4,5-trifluorophenyl)-1H-1,2,3-triazol-1-yl]-α-D-galactopyranoside

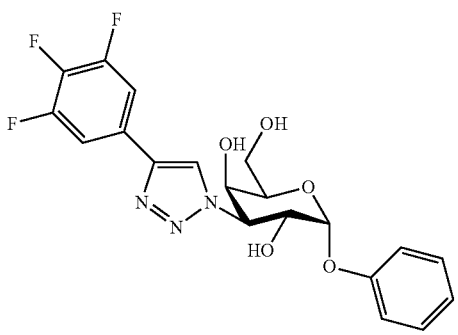

Yield 70%. $^1$H NMR (400 MHz, Methanol-d) δ 8.59 (s, 1H), 7.66 (dd, J=8.6, 6.8 Hz, 2H), 7.32 (t, J=7.9 Hz, 2H), 7.24 (d, J=7.9 Hz, 2H), 7.05 (t, J=7.2 Hz, 1H), 5.67 (d, J=3.6 Hz, 1H), 5.31 (dd, J=11.4, 2.8 Hz, 1H), 4.68 (dd, J=11.4, 3.6 Hz, 1H), 4.23 (d, J=2.4 Hz, 1H), 4.18 (t, J=6.2 Hz, 1H), 3.72 (dd, J=6.1, 3.4 Hz, 2H). ESI-MS m/z calcd for [C$_{20}$H$_{19}$F$_3$N$_3$O$_5$]$^+$ (M+H)$^+$: 438.1; found: 438.1.

Example 33

3-Chlorophenyl 3-deoxy-3-[4-(3,4,5-trifluorophenyl)-1H-1,2,3-triazol-1-yl]-α-D-galactopyranoside

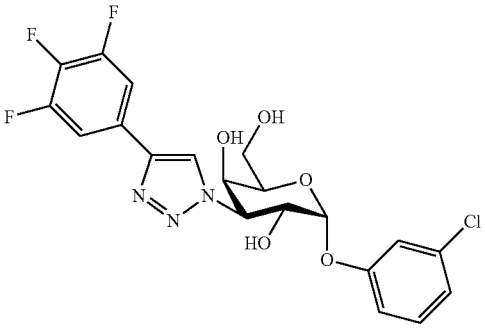

Yield 75%. $^1$H NMR (400 MHz, Methanol-d$_4$) δ 8.59 (s, 1H), 7.70-7.63 (m, 2H), 7.34-7.27 (m, 2H), 7.20 (d, J=8.5 Hz, 1H), 7.07 (d, J=7.2 Hz, 1H), 5.69 (d, J=3.6 Hz, 1H), 5.29 (dd, J=11.5, 2.8 Hz, 1H), 4.69 (dd, J=11.4, 3.6 Hz, 1H), 4.23-4.20 (m, 1H), 4.14 (t, J=6.1 Hz, 1H), 3.72 (d, J=6.0 Hz, 2H). ESI-MS m/z calcd for [C$_{20}$H$_{18}$ClF$_3$N$_3$O$_5$]$^+$ (M+H)$^+$: 472.1; found: 472.0.

Example 34

3-Chlorophenyl 3-deoxy-3-[4-(3,4,5-trifluorophenyl)-1H-1,2,3-triazol-1-yl]-α-D-galactopyranoside

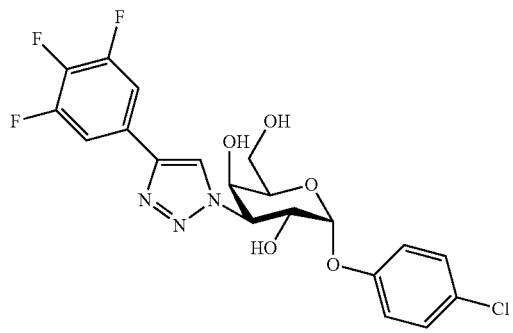

Yield 60%. $^1$H NMR (400 MHz, Methanol-d$_4$) δ 8.59 (s, 1H), 7.69-7.62 (m, 2H), 7.31 (d, J=9.0 Hz, 2H), 7.23 (d, J=9.0 Hz, 2H), 5.65 (d, J=3.4 Hz, 1H), 5.29 (dd, J=11.4, 2.6 Hz, 1H), 4.68 (dd, J=11.4, 3.5 Hz, 1H), 4.22 (d, J=1.3 Hz, 1H), 4.14 (t, J=6.0 Hz, 1H), 3.72 (d, J=6.1 Hz, 2H). ESI-MS m/z calcd for [C$_{20}$H$_{18}$ClF$_3$N$_3$O$_5$]$^+$ (M+H)$^+$: 472.1; found: 472.0.

Example 35

Cyclohexyl 3-deoxy-3-[4-(3,4,5-trifluorophenyl)-1H-1,2,3-triazol-1-yl]-1-thio-α-D-galactopyranoside

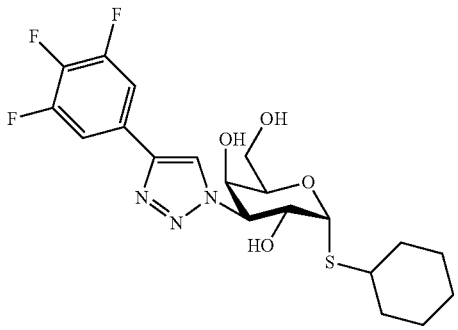

Yield 99%. $^1$H NMR (400 MHz, Methanol-$d_4$) δ 8.50 (s, 1H), 7.67-7.60 (m, 2H), 5.65 (d, J=5.4 Hz, 1H), 4.91 (dd, J=11.4, 2.8 Hz, 1H), 4.79 (dd, J=11.4, 5.4 Hz, 1H), 4.43 (t, J=6.1 Hz, 1H), 4.13 (s, 1H), 3.73 (d, J=6.0 Hz, 2H), 2.96 (t, J=10.0 Hz, 1H), 2.16-1.26 (m, 10H). ESI-MS m/z calcd for $[C_{20}H_{25}F_3N_3O_4S]^+$ (M+H)$^+$: 460.2; found: 460.0.

Example 36

2,4,5-Trichlorophenyl 3-deoxy-3-[4-(3,4,5-trifluorophenyl)-1H-1,2,3-triazol-1-yl]-1-thio-α-D-galactopyranoside

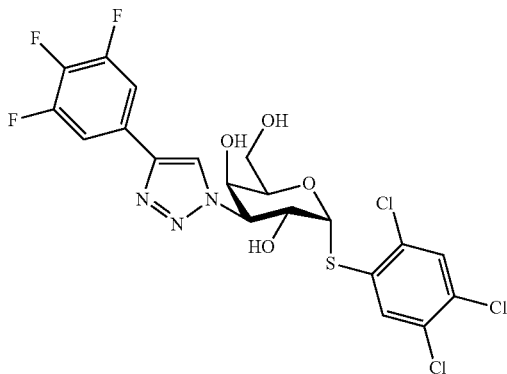

Yield 65%. $^1$H NMR (400 MHz, Methanol-$d_4$) δ 8.55 (s, 1H), 7.96 (s, 1H), 7.70-7.61 (m, 3H), 6.03 (d, J=5.3 Hz, 1H), 5.06 (dd, J=11.4, 2.3 Hz, 1H), 4.98 (dd, J=11.4, 5.3 Hz, 1H), 4.40 (t, J=6.0 Hz, 1H), 4.22 (s, 1H), 3.71 (dd, J=11.3, 5.7 Hz, 1H), 3.64 (dd, J=11.4, 6.5 Hz, 1H). ESI-MS m/z calcd for $[C_{20}H_{16}Cl_3F_3N_3O_4S]^+$ (M+H)$^+$: 556.0; found: 555.9.

Example 37

2,5-Dichlorophenyl 3-deoxy-3-[4-(3,4,5-trifluorophenyl)-1H-1,2,3-triazol-1-yl]-1-thio-α-D-galactopyranoside

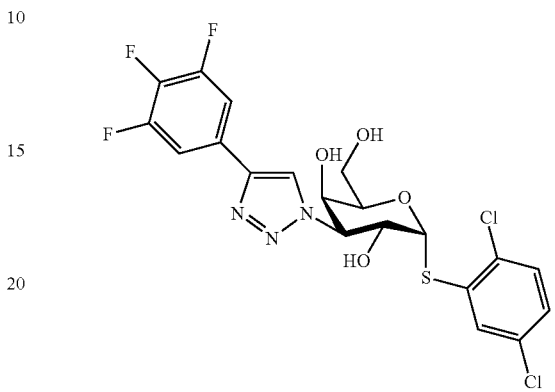

Yield 32%. $^1$H NMR (400 MHz, Methanol-d4) δ 8.55 (s, 1H), 7.81 (q, J=1.7 Hz, 1H), 7.69-7.60 (m, 2H), 7.42 (dt, J=8.5, 1.5 Hz, 1H), 7.25 (ddt, J=8.7, 2.8, 1.5 Hz, 1H), 6.03 (d, J=5.3 Hz, 1H), 5.11-5.02 (m, 1H), 4.98 (ddt, J=11.5, 5.4, 1.5 Hz, 1H), 4.47-4.39 (m, 1H), 4.23 (q, J=1.5 Hz, 1H), 3.73 (ddt, J=11.4, 6.1, 1.5 Hz, 1H), 3.63 (ddt, J=11.3, 6.4, 1.5 Hz, 1H). ESI-MS m/z calcd for $[C_{20}H_{17}Cl_2F_3N_3O_4S]^+$ (M+H)$^+$: 522.0; found: 522.1.

Example 38

3-Hydroxy-phenyl 3-deoxy-3-[4-(3,4,5-trifluorophenyl)-1H-1,2,3-triazol-1-yl]-1-thio-α-D-galactopyranoside

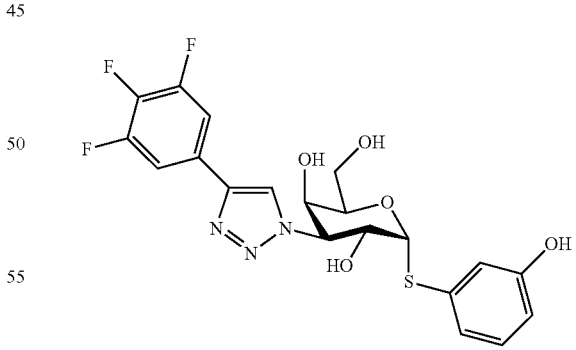

Yield 14%. $^1$H NMR (400 MHz, Methanol-d4) δ 8.53 (s, 1H), 7.65 (dd, J=8.6, 6.6 Hz, 2H), 7.14 (t, J=7.9 Hz, 1H), 7.09-7.02 (m, 2H), 6.71 (dt, J=7.9, 1.6 Hz, 1H), 5.78 (d, J=5.2 Hz, 1H), 4.97 (dd, J=11.5, 2.7 Hz, 1H), 4.94-4.87 (m, 1H), 4.54 (t, J=6.3 Hz, 1H), 4.21 (d, J=2.7 Hz, 1H), 3.73 (qd, J=11.3, 6.1 Hz, 2H). ESI-MS m/z calcd for $[C_{20}H_{18}F_3N_3O_5S]+$ (M+H)$^+$: 470.1; found: 470.2.

Example 39

3-Bromophenyl 3-deoxy-3-[4-(3,4,5-trifluorophenyl)-1H-1,2,3-triazol-1-yl]-α-D-galactopyranosyl sulfoxide

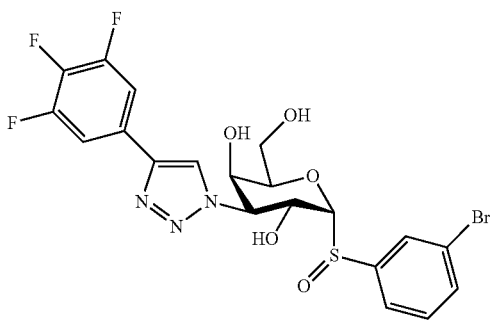

3-Bromophenyl 3-deoxy-3-[4-(3,4,5-trifluorophenyl)-1H-1,2,3-triazol-1-yl]-1-thio-α-D-galactopyranoside (12 mg, 0.023 mmol) was dissolved in CH$_2$Cl$_2$ (3 mL) and stirred at rt. mCPBA (6.4 mg, 0.027 mmol) dissolved in CH$_2$Cl$_2$ (0.355 mL) was added. After 3 h the mixture was filter through a short silica column, eluting with EtOAc, and concentrated down. Purified on preparative HPLC and lyophilized to give 11 mg (89%) of the sulfoxide.

$^1$H NMR (400 MHz, Methanol-d$_4$) δ 8.54 (s, 1H), 8.03 (s, 1H), 7.78 (dd, J=21.7, 7.9 Hz, 2H), 7.70-7.61 (m, 2H), 7.52 (t, J=7.9 Hz, 1H), 5.55 (dd, J=11.2, 2.7 Hz, 1H), 5.13 (dd, J=11.3, 5.6 Hz, 1H), 4.94 (d, J=5.7 Hz, 1H), 4.28 (s, 1H), 4.16 (t, J=6.1 Hz, 1H), 3.55 (dd, J=11.4, 5.8 Hz, 1H), 3.46 (dd, J=11.5, 6.4 Hz, 1H). ESI-MS m/z calcd for [C$_{20}$H$_{18}$BrF$_3$N$_3$O$_5$S]$^+$ (M+H)$^+$: 548.0; found: 548.0.

Example 40

2-Phenethyl 3-deoxy-3-[4-(3,4,5-trifluorophenyl)-1H-1,2,3-triazol-1-yl]-1-thio-α-D-galactopyranoside

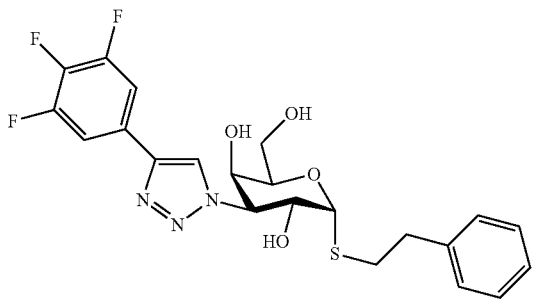

To a solution of 2-phenethyl 2,4,6-tri-O-acetyl-3-azido-3-deoxy-1-thio-α-D-galactopyranoside (80 mg, 0.18 mmol) in DMF (3 mL) were added trimethyl-[2-(3,4,5-trifluorophenyl)ethynyl]silane (80 mg, 0.35 mmol), copper(I) iodide (10 mg, 0.05 mmol) and triethylamine (0.12 mL, 0.89 mmol). The mixture was stirred at 100° C. for 1 h. Water (10 mL) was added and the mixture was filtrated through celite. The filtrate was diluted by CH$_2$Cl$_2$ (40 mL), washed with sat. NaCl solution. The organic layers were dried over anhydrous Na$_2$SO$_4$ and concentrated in vacuo. The residue was dissolved in methanolic NaOMe (8 mL, pH=9-10) and stirred at 15° C. for 2 h. Neutralization with H$^+$ resin, filtered and concentrated to a syrup. The crude product was purified by prep-HPLC to afford 2-phenethyl 3-(4-(3,4,5-trifluorophenyl)-1H-1,2,3-triazole)-3-deoxy-1-thio-α-D-galactopyranoside 35 mg as a white solid.

$^1$H NMR (500 MHz, Methanol-d$_4$) δ 8.50 (s, 1H), 7.64 (d, J=7.0 Hz, 1H), 7.62 (d, J=6.5 Hz, 1H), 7.28-7.26 (m, 4H), 7.20-7.18 (m, 1H), 5.62 (d, J=5.5 Hz, 1H), 4.94 (dd, J=11.0, 2.5 Hz, 1H), 4.83 (dd, J=11.5, 5.5 Hz, 1H), 4.40 (t, J=6.0 Hz, 1H), 4.30 (d, J=2.5 Hz, 1H), 3.77-3.75 (m, 2H), 2.99-2.95 (m, 3H), 2.89-2.87 (m, 1H). ESI-MS m/z calcd for [C$_{22}$H$_{23}$F$_3$N$_3$O$_4$S]$^+$ (M+H)$^+$: 482.1; found: 482.0.

Example 41

3,4-Dichlorophenyl 3-O-[(2-amino-(4-chlorophenyl)pyrimidin-6-yl) methylene]-1-thio-α-D-galactopyranoside

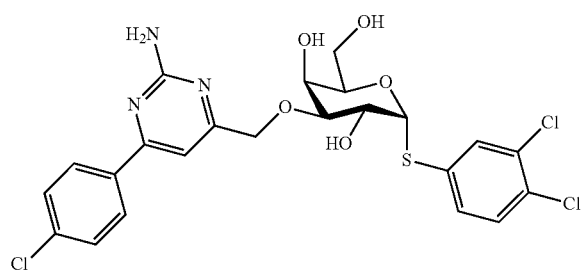

To a solution of 3,4-dichlorophenyl 2,4,6-tri-O-acetyl-3-O-[(4-chlorophenyl)-4-oxobut-2-ynyl]-1-thio-α-D-galactopyranoside (140 mg, 0.22 mmol) in tetrahydrofuran (10 mL) was added guanidine hydrochloride (52 mg, 0.54 mmol) and K$_2$CO$_3$ (90 mg, 0.65 mmol). The reaction vessel was purged 3 times with nitrogen. Then the mixture was heated to reflux with stirring for 20 h. The reaction mixture was concentrated by rotovapor. Dilute with MeOH (10 mL), concentrated by rotovapor. The residue was dilute with MeOH (5 mL), filtered and the filtrate was purified by prep-HPLC to yield 3,4-dichlorophenyl-3-O-[(2-amino-(4-chlorophenyl)pyrimidin-6-yl) methylene]-1-thio-α-D-galactopyranoside 22 mg (18.1%) as a white solid.

$^1$H NMR (500 MHz, Methanol-d$_4$) δ 8.13 (d, J=8.6 Hz, 2H), 7.76 (d, J=2.0 Hz, 1H), 7.56-7.42 (m, 5H), 5.74 (d, J=5.6 Hz, 1H), 4.65-4.75 (dd, 2H), 4.42-4.48 (m, 1H), 4.33-4.22 (m, 2H), 3.76 (dd, J=15.0, 6.1 Hz, 2H), 3.65 (dd, J=10.1, 3.0 Hz, 1H). ESI-MS m/z calcd for [C$_{23}$H$_{23}$Cl$_3$N$_3$O$_5$S]$^+$ [M+H]$^+$: 558.1; found: 558.1.

Synthesis of Intermediates i1-i41 i1) 3,4-Dimethylphenyl 2,4,6-tri-O-acetyl-3-azido-3-deoxy-1-thio-α-D-galactopyranoside

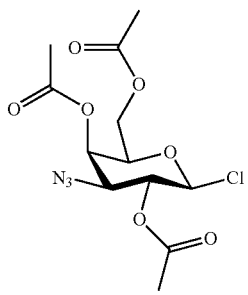

2,4,6-tri-O-acetyl-3-azido-1-chloro-3-deoxy-β-D-galactopyranoside was synthesized from 1,2,4,6-tetra-O-acetyl-3-azido-3-deoxy-β-D-galactopyranoside according to a known literature procedure (Farkas et al, 1976). However, the product was used without purification in the next step.

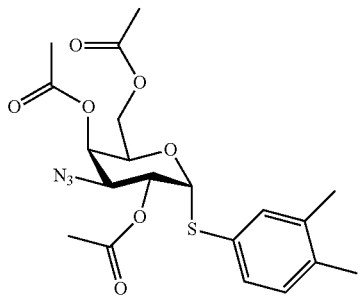

Synthesized according to a known literature procedure (Ramos-Soriano et al, 2013). 3,4-Dimethylbenzenethiol (0.056 mL, 0.42 mmol) was dissolved in anhydrous DMF (1 mL) and stirred at it. NaH (21 mg, 57-63%, 0.55 mmol) was added and the mixture was stirred at rt for one hour and then added to 3-azido-3-deoxy-3-D-galactopyranoside chloride (73 mg, 0.21 mmol) dissolved in anhydrous DMF (1 mL) and the mixture was stirred at 55° C. for one hour and then at rt for 18 hours. The reaction mixture was diluted with EtOAc and washed four times with brine, the combined water phase was extracted once with EtOAc and the combined organic phase was dried ($Na_2SO_4$) and concentrated. The residue was purified by flash chromatography, 7-75% EtOAc in petroleum ether to give 46 mg (49%) of 3,4-dimethylphenyl 2,4,6-tri-O-acetyl-3-azido-3-deoxy-1-thio-α-D-galactopyranoside as an amorphous white solid. $^1$H NMR (400 MHz, Chloroform-d) δ 7.31-7.22 (m, 2H), 7.11 (d, J=7.8 Hz, 1H), 5.93 (d, J=5.5 Hz, 1H), 5.52 (d, J=2.9 Hz, 1H), 5.31 (dd, J=10.9, 5.5 Hz, 1H), 4.75 (t, J=6.4 Hz, 1H), 4.15 (dd, J=11.5, 5.6 Hz, 1H), 4.11-3.98 (m, 2H), 2.28 (s, 6H), 2.23 (s, 3H), 2.20 (s, 3H), 2.04 (s, 3H). ESI-MS m/z calcd for $[C_{20}H_{25}N_3O_7SNa]^+$ (M+Na)$^+$: 474.1; found: 474.0.

Intermediate i2-i9 i11-i16 were made using a similar procedure as i1 using the corresponding arylthiol.

i2) 3-Bromophenyl 2,4,6-tri-O-acetyl-3-azido-3-deoxy-1-thio-α-D-galactopyranoside

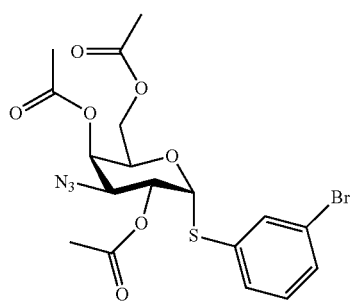

Yield 31%. $^1$H NMR (400 MHz, Chloroform-d) δ 7.52 (s, 1H), 7.35-7.24 (m, 2H), 7.08 (t, J=7.9 Hz, 1H), 5.90 (d, J=5.5 Hz, 1H), 5.38 (d, J=3.1 Hz, H), 5.19 (dd, J=10.9, 5.5 Hz, 1H), 4.58-4.49 (m, 1H), 4.03 (dd, J=11.6, 5.0 Hz, 1H), 3.97-3.81 (m, 2H), 2.08 (d, J=8.3 Hz, 6H), 1.90 (s, 3H). ESI-MS m/z calcd for $[C_{18}H_{20}BrN_3O_7SNa]^+$ (M+Na)$^+$: 524.0; found: 524.0.

i3) 3-Ethoxyphenyl 2,4,6-tri-O-acetyl-3-azido-3-deoxy-1-thio-α-D-galactopyranoside

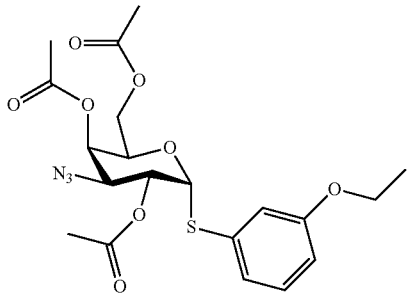

Yield 29%. $^1$H NMR (400 MHz, Chloroform-d) δ 7.36-7.22 (m, 1H), 7.08 (d, J=6.7 Hz, 2H), 6.91-6.84 (m, 1H), 6.05 (d, J=5.5 Hz, 1H), 5.54 (d, J=3.0 Hz, 1H), 5.35 (dd, J=11.0, 5.5 Hz, 1H), 4.74 (t, J=6.3 Hz, 1H), 4.19 (dd, J=11.5, 5.3 Hz, 1H), 4.13-3.99 (m, 4H), 2.25 (s, 3H), 2.23 (s, 3H), 2.05 (s, 3H), 1.47 (t, J=7.0 Hz, 3H). ESI-MS m/z calcd for $[C_{20}H_{25}N_3O_8SNa]^+$ (M+Na)$^+$: 490.1; found: 490.0.

i4) 4-Pyridyl 2,4,6-tri-O-acetyl-3-azido-3-deoxy-1-thio-α-D-galactopyranoside

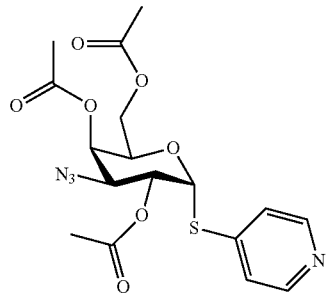

Yield 29%. $^1$H NMR (400 MHz, Chloroform-d) δ 8.41 (d, J=6.1 Hz, 2H), 7.31-7.24 (m, 2H), 6.20 (d, J=5.6 Hz, 1H), 5.43 (d, J=3.1 Hz, 1H), 5.29 (dd, J=11.0, 5.6 Hz, 1H), 4.54-4.41 (m, 1H), 4.08 (dd, J=11.6, 5.0 Hz, 1H), 4.00-3.87 (m, 2H), 2.13 (s, 3H), 2.12 (s, 3H), 1.82 (s, 3H). ESI-MS m/z calcd for $[C_{17}H_{21}N_4O_7S]^+$ (M+H)$^+$: 425.1; found: 425.0.

i5) 2,4-Dichlorophenyl 2,4,6-tri-O-acetyl-3-azido-3-deoxy-1-thio-α-D-galactopyranoside

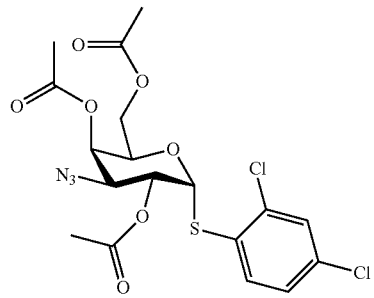

Yield 39%. $^1$H NMR (400 MHz, Chloroform-d) δ 7.57-7.45 (m, 2H), 7.26 (dd, J=8.4, 2.0 Hz, 1H), 6.07 (d, J=5.5 Hz, 1H), 5.53 (d, J=2.3 Hz, 1H), 5.35 (dd, J=11.0, 5.5 Hz, 1H), 4.65 (t, J=6.2 Hz, 1H), 4.21-3.96 (m, 3H), 2.24 (s, 3H), 2.20 (s, 3H), 2.01 (s, 3H). ESI-MS m/z calcd for [C$_{18}$H$_{19}$Cl$_2$N$_3$O$_7$SNa]$^+$ (M+Na)$^+$: 514.0; found: 514.0.

i6) 4-Acetanilidyl 2,4,6-tri-O-acetyl-3-azido-3-deoxy-1-thio-α-D-galactopyranoside

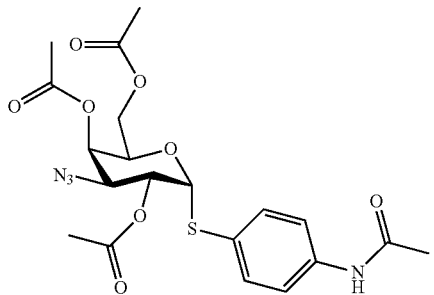

Yield 56%. $^1$H NMR (400 MHz, Chloroform-d) δ 7.51-7.38 (m, 4H), 5.86 (d, J=5.5 Hz, 1H), 5.47 (d, J=2.4 Hz, 1H), 5.25 (dd, J=10.9, 5.5 Hz, 1H), 4.69 (t, J=6.3 Hz, 11H), 4.15-4.06 (m, 1H), 4.04-3.93 (m, 2H), 2.19 (s, 3H), 2.17 (s, 31H), 2.15 (s, 3H), 2.02 (s, 3H). ESI-MS m/z calcd for [C$_{20}$H$_{24}$N$_4$O$_8$SNa]$^+$ (M+Na)$^+$: 503.1; found: 503.1.

i7) 4-Methoxyphenyl 2,4,6-tri-O-acetyl-3-azido-3-deoxy-1-thio-α-D-galactopyranoside

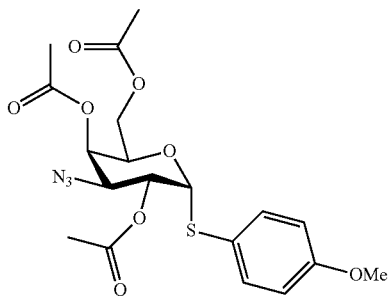

Yield 52%. $^1$H NMR (400 MHz, Chloroform-d) δ 7.28 (d, J=8.6 Hz, 2H), 6.74 (d, J=8.7 Hz, 2H), 5.68 (d, J=5.5 Hz, 1H), 5.37 (d, J=2.6 Hz, 1H), 5.14 (dd, J=10.9, 5.5 Hz, 1H), 4.61 (t, J=6.3 Hz, 1H), 4.00 (dd, J=11.5, 5.5 Hz, 1H), 3.95-3.83 (m, 2H), 3.69 (s, 3H), 2.09 (s, 3H), 2.04 (s, 3H), 1.92 (s, 3H). ESI-MS m/z calcd for [C$_{19}$H$_{23}$N$_3$O$_8$SNa]$^+$ (M+Na)$^+$: 476.1; found: 476.0.

i8) 2,3-Dichlorophenyl 2,4,6-tri-O-acetyl-3-azido-3-deoxy-1-thio-α-D-galactopyranoside

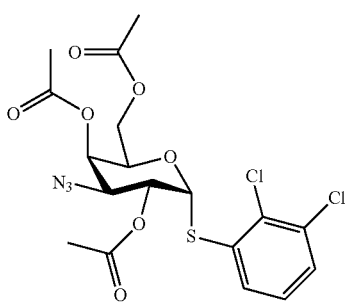

Yield 29%. $^1$H NMR (400 MHz, Chloroform-d) δ 7.28 (dd, J=7.9, 1.2 Hz, 1H), 7.20 (dd, J=8.0, 1.3 Hz, 1H), 6.98 (t, J=8.0 Hz, 1H), 5.91 (d, J=5.6 Hz, 1H), 5.31 (d, J=3.2 Hz, 1H), 5.14 (dd, J=11.0, 5.6 Hz, 1H), 4.42 (t, J=6.3 Hz, 1H), 3.97-3.75 (m, 3H), 2.01 (s, 3H), 1.98 (s, 3H), 1.76 (s, 3H). ESI-MS m/z calcd for [C$_{18}$H$_{19}$Cl$_2$N$_3$O$_7$SNa]$^+$ (M+Na)$^+$: 514.0; found; 513.9.

i9) 3,4-Dichlorophenyl 2,4,6-tri-O-acetyl-3-azido-3-deoxy-1-thio-α-D galactopyranoside

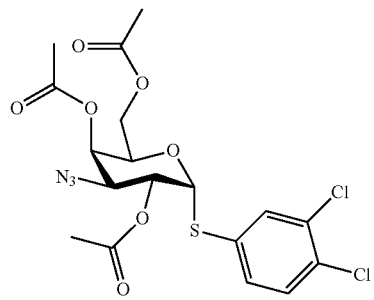

Yield 57%. ESI-MS m/z calcd for [C$_{18}$H$_{19}$Cl$_2$N$_3$O$_7$SNa]$^+$ (M+Na)$^+$: 514.0; found: 513.9.

i11) 3-Methoxyphenyl 2,4,6-tri-O-acetyl-3-azido-3-deoxy-1-thio-α-D-galactopyranoside

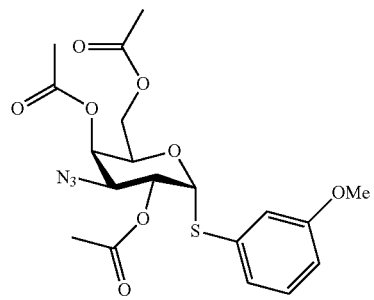

Yield 22%. ESI-MS m/z calcd for [C$_{14}$H$_{23}$N$_3$NaO$_8$S]$^+$ (M+Na)$^+$: 476.1; found: 476.0.

i12) 2-Naphtyl 2,4,6-tri-O-acetyl-3-azido-3-deoxy-1-thio-α-D-galactopyranoside

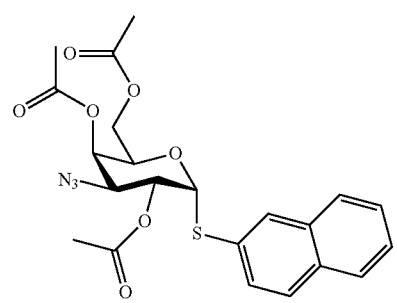

Yield 22%. ESI-MS m/z calcd for [C$_{22}$H$_{23}$N$_3$NaO$_7$S]$^+$ (M+Na)$^+$: 496.1; found: 496.1.

i13) 3-Methylphenyl 2,4,6-tri-O-acetyl-3-azido-3-deoxy-1-thio-α-D-galactopyranoside

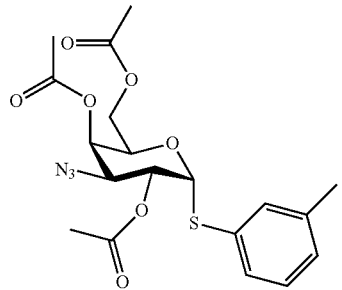

Yield 46%. ESI-MS m/z calcd for $[C_{19}H_{23}N_3NaO_7S]^+$ (M+Na)$^+$: 460.1, found: 460.1.

i14) 3-Trifluoromethylphenyl 2,4,6-tri-O-acetyl-3-azido-3-deoxy-1-thio-α-D-galactopyranoside

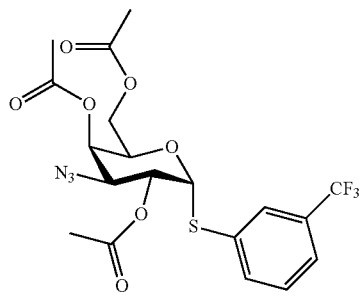

Yield 19%. ESI-MS m/z calcd for $[C_{19}H_{20}F_3N_3NaO_7S]^+$ (M+Na)$^+$: 514.1. found: 514.1.

i15) 4-Bromophenyl 2,4,6-tri-O-acetyl-3-azido-3-deoxy-1-thio-α-D-galactopyranoside

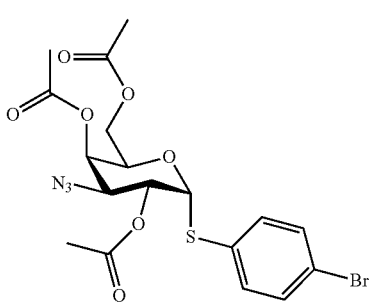

Yield 19%. ESI-MS m/z calcd for $[C_{18}H_{20}BrN_3NaO_7S]^+$ (M+Na)$^+$: 524.0; found: 524.1.

i16) 3,5-Dichlorophenyl 2,4,6-tri-O-acetyl-3-azido-3-deoxy-1-thio-α-D-galactopyranoside

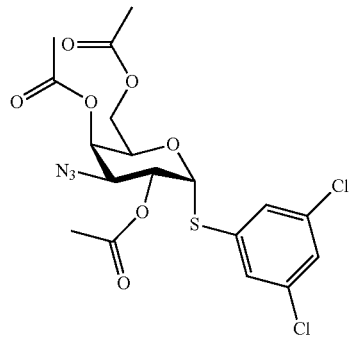

Yield 15%. ESI-MS m/z calcd for $[C_{18}H_{23}Cl_2N_4O_7S]^+$ (M+NH$_4$)$^+$: 509.1; found: 509.1.

i22) 3,4-Dichlorophenyl 2,4,6-tri-O-acetyl-3-azido-3-deoxy-α-D-galactopyranoside

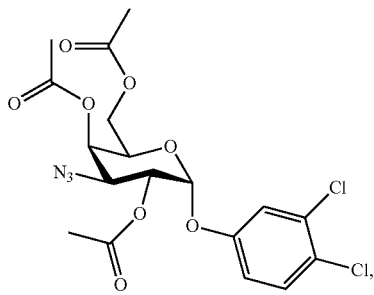

1,2,4,6-tetra-O-acetyl-3-azido-3-deoxy-β-D-galactopyranoside (155 mg, 0.42 mmol) was dissolved in 1,2-dichloroethane (5 mL) and 3,4-dichlorophenol (131 mg, 0.80 mmol) was added followed by BF$_3$.OEt$_2$ (0.155 mL, 1.26 mmol). The mixture was heated to 60° C. and after eighteen hours 3,4-dichlorophenol (138 mg, 0.85 mmol) and BF$_3$.OEt$_2$ (0.155 mL, 1.26 mmol) was added. After an additional 72 h the mixture was allowed to cool to rt and NEt$_3$ (2 mL) was added and the mixture was concentrated down. The residue was purified by flash chromatography, 6-75% EtOAc in petroleum ether to give 95 mg (48%) of 2,3-dichlorophenyl 2,4,6-tri-O-acetyl-3-azido-3-deoxy-α-D-galactopyranoside as an amorphous white solid. $^1$H NMR (400 MHz, Chloroform-d) δ 7.28 (d, J=8.9 Hz, 1H), 7.15 (d, J=2.8 Hz, 1H), 6.84 (dd, J=8.9, 2.8 Hz, 1H), 5.62 (d, J=3.5 Hz, 1H), 5.41 (d, J=3.0 Hz, 1H), 5.11 (dd, J=10.9, 3.5 Hz, 1H), 4.13 (dd, J=10.8, 3.5 Hz, 2H), 4.03 (dd, J=11.5, 5.2 Hz, 1H), 3.93 (dd, J=11.4, 7.6 Hz, 1H), 2.10 (s, 3H), 2.07 (s, 3H), 1.90 (s, 3H).). ESI-MS m/z calcd for $[C_{18}H_{19}Cl_2N_3O_8Na]^+$ (M+Na)$^+$: 498.0; found: 498.0.

Intermediate i10, i23 were made using a similar procedure as i22 using the corresponding arylthiol.

i10) Benzyl 2,4,6-tri-O-acetyl-3-azido-3-deoxy-1-thio-α-D-galactopyranoside

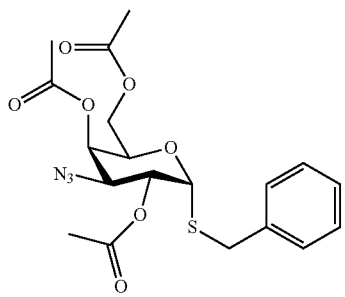

Yield 20%. ESI-MS m/z calcd for $[C_{19}H_{23}N_3O_7SNa]^+$ $(M+Na)^+$: 460.1. found: 460.1.

i23) 4-Chlorophenyl 2,4,6-tri-O-acetyl-3-azido-3-deoxy-1-thio-α-D-galactopyranoside

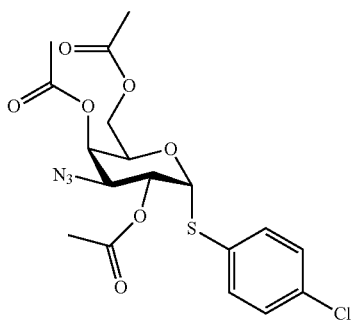

Yield 34%. $^1$H NMR (400 MHz, Chloroform-d) δ 7.43-7.30 (m, 2H), 7.30-7.21 (m, 2H), 5.91 (d, J=5.5 Hz, 1H), 5.45 (d, J=2.7 Hz, 1H), 5.25 (ddd, J=11.0, 5.5, 1.3 Hz, 1H), 4.61 (t, J=6.0 Hz, 1H), 4.08 (ddd, J=11.5, 5.2, 1.4 Hz, 1H), 4.03-3.90 (m, 2H), 2.16 (s, 3H), 2.13 (s, 3H), 1.96 (s, 3H). ESI-MS m/z calcd for [C18H20ClN3O7SNa]$^+$ (M+Na)$^+$: 480.1; found: 480.0.

i27) phenyl 2,4,6-tri-O-acetyl-3-azido-3-deoxy-1-thio-α-D-galactopyranoside 2,4,6-tri-O-acetyl-3-azido-1-chloro-3-deoxy-p-D-galactopyranoside

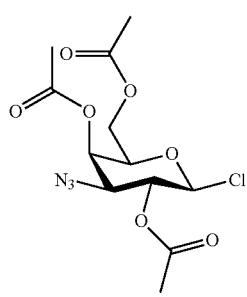

To a stirred suspension of 1,2,4,6-tetra-O-acetyl-3-azido-3-deoxy-3-D-galactopyranoside (1.0 g, 2.68 mmol) and PCl$_5$ (610 mg, 2.93 mmol) in dry DCM (10 mL), BF$_3$.Et$_2$O (15 μL) was added. After stirring for 20 min, TLC analysis showed complete disappearance of the starting material. The reaction mixture was diluted with DCM (50 mL) and then washed with ice-cold water, sat. ice-cold NaHCO$_3$ solution (2×30 mL), and again ice-cold water successively, dried over anhydrous Na$_2$SO$_4$ and evaporated under reduced pressure to afford the crude product 2,4,6-tri-O-acetyl-3-azido-1-chloro-3-deoxy-P-D-galactopyranoside 850 mg as a white solid.

$^1$H NMR (500 MHz, CDCl$_3$) δ 5.48 (dd, J=3.0, 1.0 Hz, 1H), 5.34 (dd, J=10.0, 9.0 Hz, 1H), 5.24 (d, J=8.5 Hz, 1H), 4.18 (dd, J=11.0, 5.5 Hz, 1H), 4.10 (dd, J=11.5, 6.5 Hz, 1H), 3.98 (m, 1H), 3.60 (dd, J=10.0, 3.5 Hz, 1H), 2.20 (s, 3H), 2.17 (s, 3H), 2.07 (s, 3H). ESI-MS m/z calcd for $[C_{12}H_{21}N_4O_8]^+$ (M−Cl+OH+NH$_4$)$^+$: 349.1; found: 349.1.

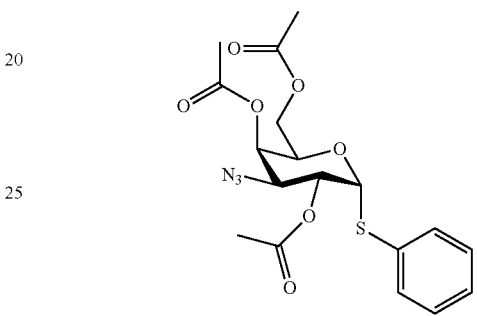

To a stirred solution of benzenethiol (190 mg, 1.72 mmol) in dry DMF (4 mL) was added NaH (60 mg, 60% in mineral oil, 1.67 mmol) at 0° C. The mixture was stirred at r.t for 30 min. Then 2,4,6-tri-O-acetyl-3-azido-1-chloro-3-deoxy-β-D-galactopyranoside (200 mg, 0.57 mmol) was added. The mixture was stirred at 50° C. for 10 h and then overnight at r.t. The solvent was removed and the resulting crude was diluted with DCM and washed with water and brine. The organic layer was dried over anhydrous Na$_2$SO$_4$, filtered and evaporated. The crude product was purified by chromatography column (PE:EtOAc=2:1) to afford the product mixture 160 mg as white solid. [α-anomer:β-anomer=100:8].

$^1$H NMR (α-anomer, 500 MHz, CDCl$_3$) δ 7.46-7.44 (m, 2H), 7.33-7.29 (m, 3H), 5.97 (d, J=6.0 Hz, 1H), 5.48 (d, J=2.0 Hz, 1H), 5.28 (dd, J=11.0, 5.5 Hz, 1H), 4.69 (t, J=6.5 Hz, 1H), 4.11 (dd, J=11.0, 6.5 Hz, 1H), 4.03-3.97 (m, 2H), 2.19 (s, 3H), 2.16 (s, 3H), 1.97 (s, 3H). ESI-MS m/z calcd for $[C_{18}H_{25}N_4O_7S]^+$ (M+NH$_4$)$^+$: 441.1; found: 441.1.

i28) 3-chloro-4-fluorophenyl 2,4,6-tri-O-acetyl-3-azido-3-deoxy-1-thio-α-D-galactopyranoside

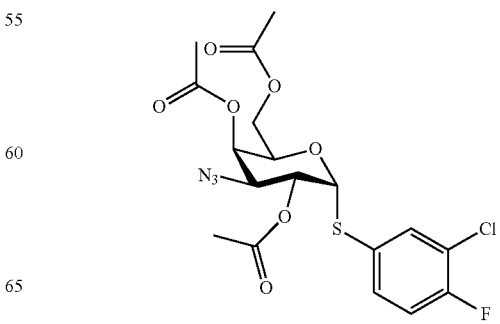

To a stirred solution of 3-chloro-4-fluoro-benzenethiol (280 mg, 1.72 mmol) in dry DMF (4 mL) was added NaH (60 mg, 60% in mineral oil, 1.67 mmol) at 0° C. The mixture was stirred at r.t for 30 min. Then 2,4,6-tri-O-acetyl-3-azido-1-chloro-3-deoxy-β-D-galactopyranoside (200 mg, 0.57 mmol) was added. The mixture was stirred at 50° C. for 10 h and then overnight at r.t. Then, the solvent was removed and the resulting crude was diluted with DCM and washed with water and brine. The organic layer was dried over anhydrous $Na_2SO_4$, filtered and evaporated. The crude product was purified by chromatography column (PE:EtOAc=3:1) to afford the α-anomer product 210 mg as a white solid.

$^1$H NMR (500 MHz, $CDCl_3$) δ 7.54 (dd, J=6.5, 2.0 Hz, 1H), 7.33 (m, 1H), 7.10 (t, J=9.0 Hz, 1H), 5.90 (d, J=5.5 Hz, 1H), 5.48 (d, J=2.0 Hz, 1H), 5.26 (dd, J=11.5, 5.5 Hz, 1H), 4.64 (t, J=6.0 Hz, 1H), 4.12 (dd, J=12.0, 5.0 Hz, 1H), 4.02 (dd, J=12.0, 8.0 Hz, 1H), 3.93 (dd, J=11.0, 3.5 Hz, 1H), 2.20 (s, 3H), 2.16 (s, 3H), 2.03 (s, 3H). ESI-MS m/z calcd for $[C_{18}H_{23}ClFN_4O_7S]^+$ $(M+NH_4)^+$: 493.1; found: 493.0.

i29) 4-tolyl-2,4,6-tri-O-acetyl-3-deoxy-1-thio-3-[4-(3,4,5-trifluorophenyl)-1H-1,2,3-triazol-1-yl]-α-D-galactopyranoside 4-tolyl 2,4,6-tri-O-acetyl-3-azido-3-deoxy-1-thio-α-D-galactopyranoside

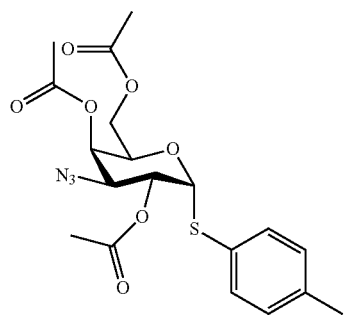

To a solution of 1,2,4,6-tetra-O-acetyl-3-azido-3-deoxy-3-D-galactopyranoside (200 mg, 0.54 mmol) in 1,2-dichloroethane (10 mL) were added boron trifluoride etherate (0.4 mL, 3.2 mmol), 3 A molecular sieve, 4-methylbenzenethiol (144 mg, 1.1 mmol) and the solution was stirred at 60° C. for 17 h. TLC (silica gel, PE:EtOAc=3:1, UV, PMA) analysis indicated the total consumption of the starting material. The mixture was filtered and the filtrate was poured on sat. $NaHCO_3$ (20 mL) and DCM (50 mL). The organic phase was washed with water (20 mL) and brine (20 mL), dried over anhydrous sodium sulphate. Removal of solvent gave a residue and the residue was purified by flash column chromatography (silica gel, PE:EtOAc=3:1) to give 4-tolyl 2,4,6-tri-O-acetyl-3-azido-3-deoxy-1-thio-α-D-galactopyranoside 70 mg and as a side product the corresponding β-isomer 59 mg as white solid.

$^1$H NMR (α-isomer, 500 MHz, $CDCl_3$) δ 7.34 (d, J=8.5 Hz, 2H), 7.12 (d, J=7.5 Hz, 2H), 5.88 (d, J=5.5 Hz, 1H), 5.47 (d, J=2.5 Hz, 1H), 5.26 (dd, J=6.0, 5.5 Hz, 1H), 4.70 (t, J=6.0 Hz, 1H), 4.10 (dd, J=11.5 Hz, 5.0 Hz, 1H), 4.02-3.96 (m, 2H), 2.33 (s, 3H), 2.19 (s, 3H), 2.15 (s, 3H), 2.00 (s, 3H). ESI-MS m/z calcd for $[C_{19}H_{23}N_3O_7S]^+$ $(M+NH_4)^+$: 455.1; found: 455.1.

4-tolyl-2,4,6-tri-O-acetyl-3-deoxy-1-thio-3-[4-(3,4,5-trifluorophenyl)-1H-1,2,3-triazol-1-yl]-α-D-galactopyranoside

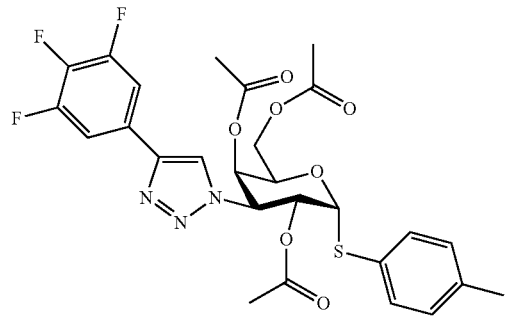

To a solution of 4-tolyl-2,4,6-tri-O-acetyl-3-azido-3-deoxy-1-thio-α-D-galactopyranoside (70 mg, 0.16 mmol) in dry DMF (5 mL) were added N,N-diethylethanamine (0.11 mL, 0.8 mmol), copper(I) iodide (9.1 mg, 0.05 mmol), trimethyl-[2-(3,4,5 trifluorophenyl) ethynyl]silane (73 mg, 0.32 mmol) and the solution was stirred at 100° C. for 1 h. The reaction mixture was poured on water (50 mL) and filtered. The aqueous phase was extracted with ethyl acetate (2×50 mL), the combined organic phases were washed with water (4×50 mL) and brine (100 mL), dried over anhydrous sodium sulphate. Removal of solvent to gave a residue, which was purified by flash column chromatography (silica gel, PE:EtOAc=3:1) to afford the title compound 85 mg as a white solid.

$^1$H NMR (500 MHz, $CDCl_3$) δ 7.77 (s, 1H), 7.44 (t, J=7.0 Hz, 2H), 7.38 (d, J=7.5 Hz, 2H), 7.16 (d, J=8.0 Hz, 2H), 6.07-6.03 (m, 2H), 5.60 (dd, J=3.5 Hz, 1.0 Hz, 1H), 5.27-5.23 (m, 1H), 4.93 (t, 6.5 Hz, 1H), 4.14 (dd, J=11.5 Hz, 6.0 Hz, 1H), 4.06 (dd, J=11.5 Hz, 7.50 Hz, 1H), 2.35 (s, 3H), 2.05 (s, 3H), 2.00 (s, 3H), 1.97 (s, 3H). ESI-MS nm/z calcd for $[C_{27}H_{26}F_3N_3O_7S]^+$ $(M+H)^+$: 594.1; found: 594.2.

i30) 4-fluorophenyl-2,4,6-tri-O-acetyl-3-deoxy-1-thio-3-[4-(3,4,5-trifluorophenyl)-1H-1,2,3-triazol-1-yl]-α-D-galactopyranoside 4-fluorophenyl (2,4,6-tri-O-acetyl-3-azido-3-deoxy-1-thio-α-D-galactopyranoside

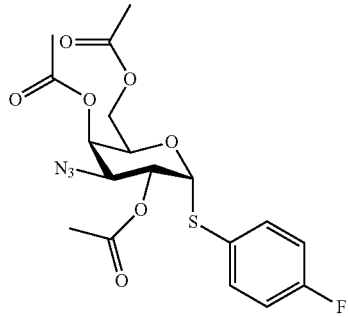

To a solution of 2,4,6-tri-O-acetyl-3-azido-1-chloro-3-deoxy-β-D-galactopyranoside (200 mg, 0.57 mmol) in dry DMF (5 mL) were added 4-fluorobenzenethiol (219 mg, 1.7 mmol), sodium hydride (60% in mineral oil, 68 mg, 1.7 mmol). The solution was stirred at 50° C. for 17 h. TLC (silica gel, PE:EtOAc-3:1, UV, PMA) analysis indicated the total consumption of the starting material, the reaction mixture was poured on water (50 mL) and EtOAc (50 mL). The organic phase was washed with water (2×50 mL), brine (50 mL), dried over anhydrous sodium sulphate. Removal of solvent gave a residue, which was purified by flash column chromatography (silica gel, PE:EtOAc=3:1) to give 4-fluorophenyl (2,4,6-tri-O-acetyl-3-azido-3-deoxy-1-thio-α-D-galactopyranoside 156 mg as a white solid.

$^1$H NMR (500 MHz, CDCl$_3$) δ 7.46-7.43 (m, 2H), 7.04-7.00 (m, 2H), 5.87 (d, J=5.0 Hz, 1H), 5.48 (d, J=2.5 Hz, 1H), 5.25 (dd, J=11.5 Hz, 5.5 Hz, 1H), 4.67 (t, J 6.0 Hz, 1H), 4.10 (dd, J=11.0 Hz, 5.5 Hz, 1H), 4.03-3.95 (m, 2H), 2.20 (s, 3H), 2.16 (s, 3H), 2.01 (s, 3H). ESI-MS m/z calcd for [C$_{18}$H$_{20}$FN$_3$O$_7$S]$^+$ (M+NH$_4$)$^+$: 459.1; found: 459.0.

4-fluorophenyl-2,4,6-tri-O-acetyl-3-deoxy-1-thio-3-[4-(3,4,5-trifluorophenyl)-1H-1,2,3-triazol-1-yl]-α-D-galactopyranoside

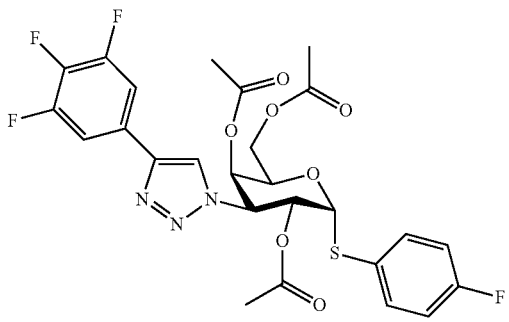

To a solution of 4-fluorophenyl (2,4,6-tri-O-acetyl-3-azido-3-deoxy-1-thio-α-D-galactopyranoside 156 mg in DMF (10 mL) were added triethylamine (179 mg, 1.8 mmol), copper(I) iodide (20 mg, 0.11 mmol), trimethyl-[2-(3,4,5-trifluorophenyl)ethynyl]silane (161 mg, 0.71 mmol). The solution was stirred at 100° C. for 1 h under N$_2$. TLC (silica gel, PE:EtOAc=3:1, UV, PMA) analysis indicated the total consumption of the starting material. Water (50 mL) and EtOAc (50 mL) were added. The mixture was filtered and the filtrate was extracted with ethyl acetate (2×50 mL), the combined organic phases were washed with water (100 mL) and brine (100 mL), dried over anhydrous sodium sulphate. Removal of solvent gave a residue. The crude was purified by flash column chromatography (silica gel, PE:EtOAc=3:1) to afford product 150 mg as a white solid.

$^1$H NMR (500 MHz, CDCl$_3$) δ 7.77 (m, 1H), 7.51-7.42 (m, 4H), 7.07-7.04 (m, 2H), 6.07-6.02 (m, 2H), 5.60 (dd, J=2.5 Hz, J=1.0 Hz, 1H), 5.22 (dd, J=10.5 Hz, 3.0 Hz, 1H), 4.90 (t, J=7.0 Hz, 1H), 4.15-4.05 (m, 2H), 2.06 (s, 3H), 2.02 (s, 3H), 2.00 (s, 3H). ESI-MS m/z calcd for [C$_{26}$H$_{23}$F$_4$N$_3$O$_7$S]$^+$ (M+H)$^+$: 598.1; found: 598.0.

i31) 4-trifluoromethoxyphenyl-2,4,6-tri-O-acetyl-3-deoxy-1-thio-3-[4-(3,4,5-trifluorophenyl)-1H-1,2,3-triazol-1-yl]-α-D-galactopyranoside trifluoromethoxyphenyl (2,4,6-tri-O-acetyl-3-azido-3-deoxy-1-thio-α-D-galactopyranoside

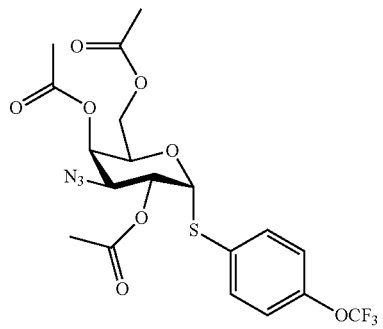

To a solution of 2,4,6-tri-O-acetyl-3-azido-1-chloro-3-deoxy-β-D-galactopyranoside (200 mg, 0.57 mmol) in dry DMF (5 mL) were added 4-(trifluoromethoxy) benzenethiol (333 mg, 1.7 mmol), sodium hydride (60% in mineral oil, 68 mg, 1.7 mmol), the solution was stirred at 50° C. for 17 h. TLC (silica gel, PE:EtOAc=3:1, UV, PMA) analysis indicated the total consumption of the starting material. The reaction mixture was poured on water (50 mL) and EtOAc (50 mL). The organic phase was washed with water (2×50 mL), brine (50 mL), dried over anhydrous sodium sulphate. Removal of solvent gave a residue, which was purified by flash column chromatography (silica gel, PE:EtOAc=3:1) to give 4-trifluoromethoxyphenyl (2,4,6-tri-O-acetyl-3-azido-3-deoxy-1-thio-α-D-galactopyranoside 117 mg as a white solid.

$^1$H NMR (500 MHz, CDCl$_3$) δ 7.50-7.47 (m, 2H), 7.17-7.16 (m, 2H), 5.97 (d, J=6.0 Hz, 1H), 5.48 (d, J=2.0 Hz, 1H), 5.28 (dd, J=11.5, 6.0 Hz, 1H), 4.65 (t, J=6.5 Hz, 1H), 4.13-4.10 (m, 1H), 4.03-3.95 (m, 2H), 2.19 (s, 3H), 2.17 (s, 3H), 1.97 (s, 3H). ESI-MS m/z calcd for [C$_{19}$H$_{20}$F$_3$N$_3$O$_8$S]$^+$ (M+NH$_4$)$^+$: 525.1; found: 525.0.

4-trifluoromethoxyphenyl 2,4,6-tri-O-acetyl-3-deoxy-1-thio-3-[4-(3,4,5-trifluorophenyl)-1H-1,2,3-triazol-1-yl]-α-D-galactopyranoside

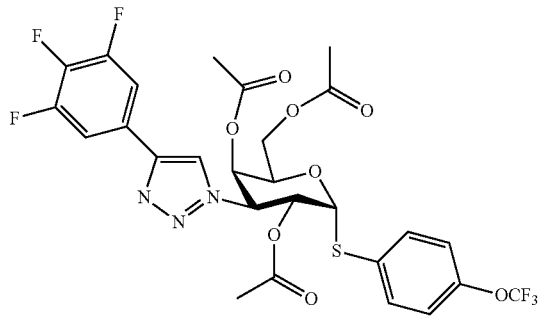

To a solution of 4-trifluoromethoxyphenyl (2,4,6-tri-O-acetyl-3-azido-3-deoxy-1-thio-α-D-galactopyranoside (117 mg, 0.23 mmol) in DMF (10 mL) were added N,N-diethylethanamine (117 mg, 1.1 mmol), copper(I) iodide (13 mg, 0.07 mmol), trimethyl-[2-(3,4,5-trifluorophenyl)ethynyl]silane (105 mg, 0.46 mmol). The solution was stirred at 100° C. for 1 h under $N_2$. TLC (silica gel, PE:EtOAc=3:1, UV, PMA) analysis indicated the total consumption of the starting material. Water (50 mL) and EtOAc (50 mL) were added. The mixture was filtered and the filtrate was extracted with ethyl acetate (2×50 mL). The combined organic phases were washed with water (100 mL) and brine (100 mL), dried over anhydrous sodium sulphate. Removal of solvent gave a residue. The crude was purified by flash column chromatography (silica gel, PE:EtOAc=3:1) to afford 4-trifluoromethoxyphenyl 2,4,6-tri-O-acetyl-3-deoxy-1-thio-3-[4-(3,4,5-trifluorophenyl)-1H-1,2,3-triazol-1-yl]-α-D-galactopyranoside 150 mg as a white solid.

$^1$H NMR (500 MHz, CDCl$_3$) δ 7.77 (s, 1H), 7.55-7.52 (m, 2H), 7.45-7.42 (m, 2H), 7.20 (d, J=8.0 Hz, 2H), 6.13 (d, J=6.0 Hz, 1H), 6.08 (dd, J=11.5 Hz, 5.5 Hz, 1H), 5.61 (d, J=2.5 Hz, 1H), 5.23 (dd, J=11.5 Hz, 3.0 Hz, 1H), 4.88 (t, J=6.5 Hz, H), 4.17-4.06 (m, 2H), 2.06 (s, 3H), 1.98 (s, 3H), 1.97 (s, 3H). ESI-MS m/z calcd for $[C_{27}H_{23}F_6N_3O_8S]^+$ (M+H)$^+$: 664.1; found: 664.0.

Example i32-i34 were made using a similar procedure as i22 from the corresponding nucleophile i32) Phenyl 2,4,6-tri-O-acetyl-3-azido-3-deoxy-α-D-galactopyranoside

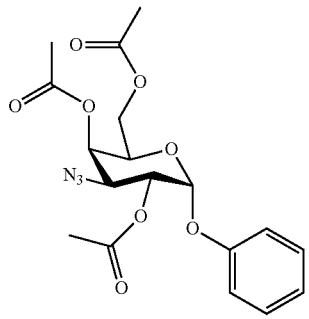

Yield 37%. $^1$H NMR (400 MHz, Chloroform-d) δ 7.32 (t, J=8.0 Hz, 2H), 7.10-7.06 (m, 3H), 5.77 (d, J=3.5 Hz, 1H), 5.51 (d, J=2.9 Hz, 1H), 5.22 (dd, J=10.9, 3.5 Hz, 1H), 4.36-4.25 (m, 2H), 4.14 (dd, J=11.4, 5.7 Hz, 11H), 4.01 (dd, J=11.4, 7.2 Hz, 1H), 2.19 (s, 3H), 2.16 (s, 3H), 1.95 (s, 3H). ESI-MS m/z calcd for $[C_{18}H_{21}N_3O_8Na]^+$ (M+Na)$^+$: 430.1; found: 430.0.

i33) 3-Chlorophenyl 2,4,6-tri-O-acetyl-3-azido-3-deoxy-α-D-galactopyranoside

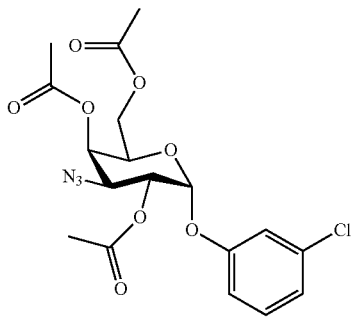

Yield 27%. $^1$H NMR (400 MHz, Chloroform-d) δ 7.31-7.23 (m, 1H), 7.22-7.14 (m, 1H), 7.10 (d, J=8.0 Hz, 1H), 6.99 (dd, J=8.3, 1.4 Hz, 1H), 5.77 (d, J=3.4 Hz, 1H), 5.56-5.50 (m, 1H), 5.24 (dd, J=10.9, 3.5 Hz, 1H), 4.32-4.25 (m, 2H), 4.16 (dd, J=11.4, 5.3 Hz, 1H), 4.06 (dd, J=11.4, 7.6 Hz, 1H) 2.22 (s, 3H), 2.19 (s, 3H), 2.01 (s, 3H). ESI-MS m/z calcd for $[C_{18}H_{20}ClN_3O_8Na]^+$ (M+Na)$^+$: 464.1; found: 464.1.

i34) 4-Chlorophenyl 2,4,6-tri-O-acetyl-3-azido-3-deoxy-α-D-galactopyranoside

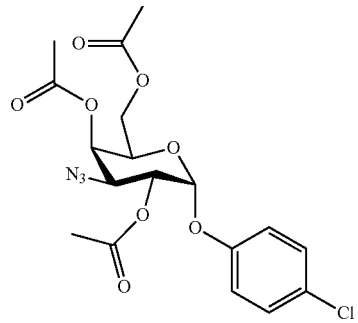

Yield 52%. $^1$H NMR (400 MHz, Chloroform-d) δ 7.28 (d, J=9.0 Hz, 2H), 6.78 (d, J=8.9 Hz, 2H), 5.73 (d, J=3.5 Hz, 1H), 5.51 (d, J=2.9 Hz, 1H), 5.21 (dd, J=10.9, 3.5 Hz, 1H), 4.31-4.23 (m, 2H), 4.14 (dd, J=11.4, 5.6 Hz, 1H), 4.02 (dd, J=11.4, 7.3 Hz, 1H), 2.19 (s, 3H), 2.17 (s, 3H), 1.98 (s, 3H). ESI-MS m/z calcd for $[C_{18}H_{20}ClN_3O_8Na]^+$ (M+Na)$^+$: 464.1; found: 464.1.

Example i35-i38 were made using a similar procedure as i1 from the corresponding nucleophile i35) Cyclohexyl 2,4,6-tri-O-acetyl-3-azido-3-deoxy-α-D-galactopyranoside

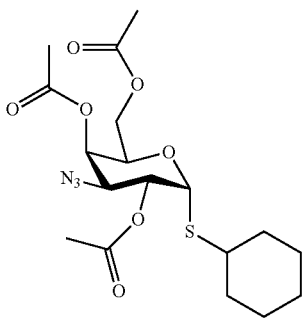

Yield 6%. $^1$H NMR (400 MHz, Chloroform-d) δ 5.82 (d, J=5.6 Hz, 1H), 5.41 (d, J=2.4 Hz, 1H), 5.18 (dd, J=10.9, 5.6 Hz, 1H), 4.57 (t, J=6.3 Hz, 1H), 4.12 (dd, J=11.5, 5.5 Hz, 1H), 4.03 (dd, J=11.4, 7.3 Hz, 1H), 3.88 (dd, J=10.9, 3.3 Hz, 1H), 2.83-2.73 (m, 1H), 2.15 (s, 3H), 2.14 (s, 3H), 2.05 (s, 3H), 2.03-1.23 (m, 10H). ESI-MS m/z calcd for $[C_{18}H_{27}N_3O_7SNa]^+$ (M+Na)$^+$: 452.1; found: 452.1.

i36) 2,4,5-Trichlorophenyl 2,4,6-tri-O-acetyl-3-azido-3-deoxy-α-D-galactopyranoside

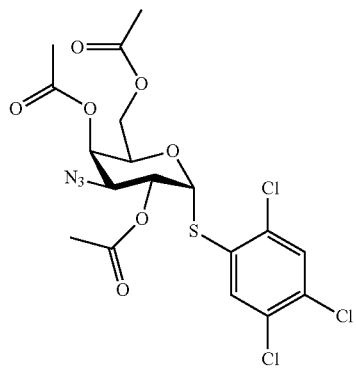

Yield 50%. ¹H NMR (400 MHz, Chloroform-d) δ 7.66 (s, 1H), 7.53 (s, 1H), 6.06 (d, J=5.6 Hz, 1H), 5.49 (d, J=2.9 Hz, 1H), 5.31 (dd, J=11.0, 5.6 Hz, 1H), 4.58 (dd, J=7.3, 5.2 Hz, 1H), 4.11 (dd, J=11.7, 4.9 Hz, 1H), 4.06-3.96 (m, 2H), 2.20 (s, 3H), 2.17 (s, 3H), 1.98 (s, 3H). ESI-MS m/z calcd for $[C_{18}H_{18}N_3O_7SNa]^+$ (M+Na)⁺: 548.0; found: 547.8.

i37) 2,5-Dichlorophenyl 2,4,6-tri-O-acetyl-3-azido-3-deoxy-1-thio-α-D-galactopyranoside

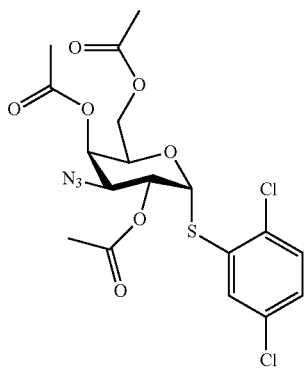

Yield 40%. ESI-MS m/z calcd for $[C_{18}H_{19}Cl_2N_3O_7SNa]^+$ (M+Na)⁺: 514.0; found: 513.9.

i38) 3-Hydroxyphenyl 2,4,6-tri-O-acetyl-3-azido-3-deoxy-1-thio-α-D-galactopyranoside

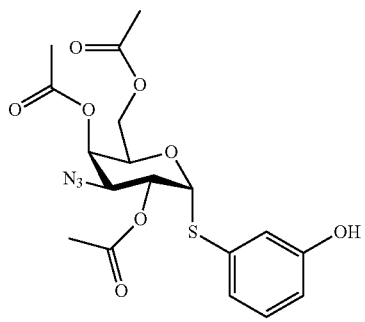

Not isolated but used in the next step directly. ESI-MS m/z calcd for $[C_{18}H_{21}N_3NaO_8S]^+$ (M+Na)⁺: 462.1; found: 462.1.

i40) 2-phenethyl 2,4,6-tri-O-acetyl-3-azido-3-deoxy-1-thio-α-D-galactopyranoside

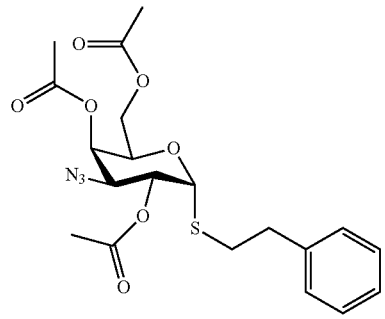

To a stirred suspension of 1,2,4,6-tetra-O-acetyl-3-azido-3-deoxy-3-D-galactopyranoside (200 mg, 0.54 mmol) in dry CH₂Cl₂ (5 mL), 2-phenylethanethiol (220 mg, 1.59 mmol) and BF₃.Et₂O (0.4 mL, 3.24 mmol) were added at 0° C. The mixture was stirred at 15° C. overnight. After diluted by CH₂Cl₂ (40 mL), the mixture was washed with satd. NaHCO₃ solution. The organic layers were dried over Na₂SO₄ and concentrated in vacuo. The residue was purified by chromatography (PE:EtOAc=3:1) to yield 2-phenethyl 2,4,6-tri-O-acetyl-3-azido-3-deoxy-1-thio-α-D-galactopyranoside 81 mg as a white solid.

¹H NMR (500 MHz, CDCl₃) δ 7.31-7.17 (m, 5H), 5.75 (d, J=6.0 Hz, 1H), 5.41 (d, J=2.5 Hz, 1H), 5.21 (dd, J=11.0, 5.5 Hz, 1H), 4.49 (t, J=6.0 Hz, 1H), 4.12 (dd, J=11.0, 5.0 Hz, 1H), 4.03 (dd, J=11.5, 7.5 Hz, 1H), 3.66 (dd, J=11.0, 4.0 Hz, 1H), 2.92-2.74 (m, 4H), 2.17 (s, 3H), 2.16 (s, 3H), 2.13 (s, 3H). ESI-MS m/z calcd for $[C_{20}H_{25}N_3NaO_7S]^+$ (M+Na)⁺: 474.1; found: 474.1.

i41) 3,4-dichlorophenyl-2,4,6-tri-O-acetyl-3-O-[(4-chlorophenyl)-4-oxobut-2-ynyl]-1-thio-α-D-galactopyranoside 1,2,3,4,6-penta-O-acetyl-β-D-galactopyranoside

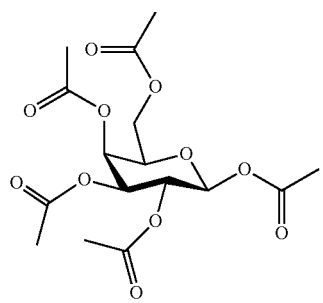

A suspension of anhydrous sodium acetate (13.7 g, 16.7 mmol) and acetic anhydride (20 mL) was refluxed for 5 minutes. After addition of D-(+)-galactose (3.0 g, 16.7 mmol) refluxing was continued for further 30 min. The hot solution was poured on ice water (300 mL) and the mixture was extracted with DCM (3×150 mL). Dried with MgSO$_4$, filtered, and evaporated of the solvent under reduced pressure to afford the crude product. Then the crude product was re-crystallized from hexane/EtOAc (2:1) to yield 1,2,3,4,6-penta-O-acetyl-β-D-galactopyranoside 4.2 g (64.6%) as a white solid.

$^1$H NMR (500 MHz, CDCl$_3$) δ 5.70 (d, J=8.3 Hz, 1H), 5.43 (d, J=2.6 Hz, 1H), 5.34 (dd, J=10.4, 8.4 Hz, 1H), 5.08 (dd, J=10.4, 3.4 Hz, 1H), 2.17 (s, 3H), 2.13 (s, 3H), 2.08-1.98 (m, 9H).

1-chloro 2,3,4,6-tetra-O-acetyl-β-D-galactopyranoside

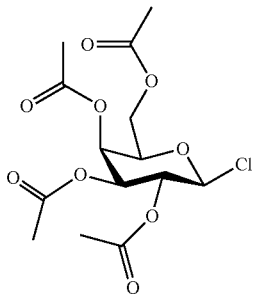

To a stirred suspension of 1,2,3,4,6-penta-O-acetyl-β-D-galactopyranoside (2.3 g, 5.9 mmol) and PCl$_5$ (1.35 g, 6.5 mmol) in dry CH$_2$Cl$_2$ (20 mL), BF$_3$.Et$_2$O (34 mg, 0.29 mmol) was added. After stirring for 30 min, the reaction mixture was diluted with CH$_2$Cl$_2$ (120 mL) and then washed with ice-cold water (60 mL), saturated ice-cold NaHCO$_3$ solution (2×50 mL), and again ice-cold water (2×30 mL), dried over anhydrous Na$_2$SO$_4$ and evaporated under reduced pressure. The residue was co-evaporated with toluene to yield 1-chloro-2,3,4,6-tetra-O-acetyl-P-D-galactopyranoside 2.1 g (97.2%) as colorless oil.

$^1$H NMR (500 MHz, CDCl$_3$) δ 5.42 (ddd, J=19.0, 6.7, 4.9 Hz, 2H), 5.33-5.23 (m, 1H), 5.02 (dd, J=10.2, 3.4 Hz, 1H), 4.17 (d, J=6.5 Hz, 2H), 4.06-3.97 (m, 1H), 2.19 (s, 3H), 2.10 (s, 3H), 2.06 (s, 3H), 2.00 (s, 3H).

3,4-dichlorophenyl 2,3,4,6-tetra-O-acetyl-1-thio-α-D-galactopyranoside

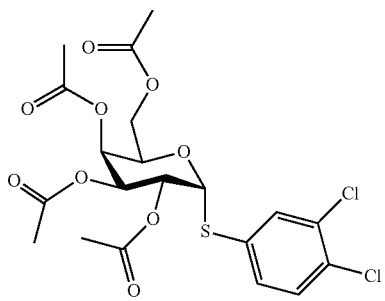

NaH (60% in mineral oil, 338 mg, and 14.7 mmol) was suspended in DMF (20 mL). 3,4-dichlorobenzenethiol (2.9 g, 16.3 mmol) was added. After 30 min, 1-chloro 2,3,4,6-tetra-O-acetyl-β-D-galactopyranoside (3.0 g, 8.2 mmol) The mixture was heated to 50° C. for 20 h. The mixture was diluted with CH$_2$Cl$_2$ (100 mL), citric acid (0.5 M, 20 ml) and water (20 mL). The organic phase was washed with water (3×30 mL) and concentrated. The residue was purified by column chromatography on silica gel (PE:EtOAc=3:1) to yield 3,4-dichloro-phenyl-2,3,4,6-tetra-O-acetyl-1-thio-α-D-galactopyranoside 2.7 g (66%) as a white solid.

$^1$H NMR (500 MHz, CDCl$_3$) δ 7.58 (d, J=2.1 Hz, 1H), 7.38 (d, J=8.4 Hz, 1H), 7.32 (d, 1H), 5.99 (d, J=5.6 Hz, 1H), 5.50 (d, J=2.4 Hz, 1H), 5.35 (dd, J=11.0, 5.6 Hz, 1H), 5.25 (dd, J=11.0, 3.3 Hz, 1H), 4.67 (t, J=6.2 Hz, 1H), 4.13-4.04 (m, 2H), 2.16 (s, 3H), 2.12 (s, 3H), 2.02 (s, 3H), 2.00 (s, 3H).

3,4-dichloro-phenyl 1-thio-α-D-galactopyranoside

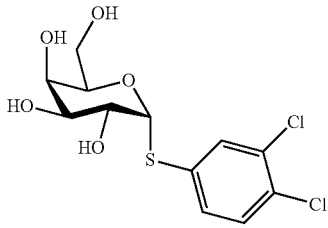

To a solution of 3,4-dichlorophenyl-2,3,4,6-tetra-O-acetyl-1-thio-α-D-galactopyranoside (2.7 g, 5.3 mmol) in methanol (30 ml) was added NaOMe (29 mg, 0.53 mmol) and the solution was stirred at room temperature for another 5 h. After completion, the mixture was neutralized (PH=7) with DOWEX 50 w×8-200 Ion exchange resin and filtered. The filtrate was concentrated to give a residue. The product was crystallized from CH$_2$Cl$_2$ (80 mL) to yield 3,4-dichloro-phenyl-1-thio-α-D-galactopyranoside 1.7 g (94%) as a white solid.

ESI-MS m/z calcd for [C$_{12}$H$_{18}$Cl$_2$NO$_5$S]$^+$ [M+NH$_4$]$^+$: 358.0; found: 358.0.

3,4-dichlorophenyl-3-O-propargyl-1-thio-α-D-galactopyranoside

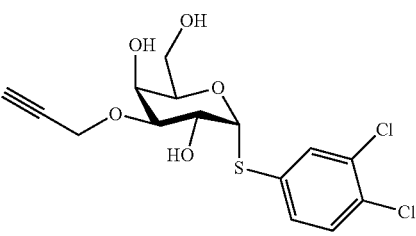

3,4-dichlorophenyl-1-thio-α-D-galactopyranoside (1.2 g, 3.5 mmol) in dry methanol (30 ml) was added dibutyl(oxo) tin (1.0 g, 4.2 mmol). The mixture was refluxed at 70° C. for 6 h. The reaction mixture became clear. The solvent was evaporated and dried in vacuo. 1,4-dioxane (50 mL), tetrabutylammonium iodide (1.3 g, 3.5 mmol), and methyl 2-bromoacetate (4.2 g, 35.2 mmol) was add to reaction above mixture and continued to heat at 105° C. for overnight. The mixture was concentrated and purified by combiflash (EtOAc:PE=4:1, ISCO 40 g, 40 ml/min, normal phase sillica, uv254) to yield 3,4-dichlorphenyl 3-O-propargyl-1-thio-α-D-galactopyranoside 520 mg (39%) as a white solid.

¹H NMR (500 MHz, DMSO-d₆) δ 7.75 (d, J=2.1 Hz, 1H), 7.55 (d, J=8.5 Hz, 1H), 7.45 (dd, J=8.4, 2.1 Hz, 1H), 5.69 (d, J=5.5 Hz, 1H), 5.54 (d, J=4.7 Hz, 1H), 4.80 (d, J=5.3 Hz, 1H), 4.65 (t, J=5.6 Hz, 1H), 4.31 (qd, J=16.0, 2.4 Hz, 2H), 4.15 (dt, J=10.1, 5.1 Hz, 1H), 4.07-3.91 (m, 2H), 3.62-3.40 (m, 3H), 3.40-3.27 (m, 2H).

3,4-dichlorophenyl-2,4,6-tri-O-acetyl-3-O-propargyl-1-thio-α-D-galactopyranoside

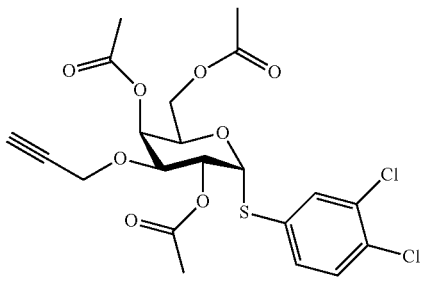

Acetic anhydride (1.4 g, 13.7 mmol) was added dropwise to a solution of 3,4-dichlorophenyl-3-O-propargyl-1-thio-α-D-galactopyranoside (520 mg, 1.37 mmol) in anhydrous pyridine (10 mL). The reaction was stirred under nitrogen for 20 h at 10° C. The mixture was concentrated under reduced pressure, and the residue was co-evaporated with toluene. The residue was purified by column chromatography on silica gel (PE:EtOAc=2:1) to yield 3,4-dichlorophenyl-2,4,6-tri-O-acetyl-3-O-propargyl-1-thio-D-galactopyranoside 530 mg (76.5%) as a yellow oil.

ESI-MS m/z calcd for $[C_{21}H_{26}Cl_2NO_8S]^+$ $[M+NH_4]^+$: 522.1; found: 522.0.

3,4-dichlorophenyl 2,4,6-tri-O-acetyl-3-O-[(4-chlorophenyl)-4-oxobut-2-ynyl]-1-thio-α-D-galactopyranoside

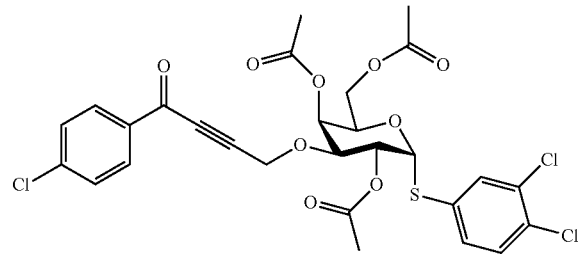

To a solution of 3,4-dichlorophenyl-2,4,6-tri-O-acetyl-3-O-[(4-chlorophenyl)-4-oxobut-2-ynyl]-1-thio-α-D-galactopyranoside (200 mg, 0.4 mmol) in THF (15 mL) was added benzoyl chloride (69 mg, 0.4 mmol), copper(I) iodide (15 mg, 0.08 mmol), PdCl₂(PPh₃)₂Cl₂ (29 mg, 0.04 mmol). The mixture was purged three times with N₂. Then the mixture was stirred at 10° C. for 20 min. Et₃N (40 mg, 0.4 mmol) was added via syringe to the reaction. Then the mixture was continued to stir at 10° C. for 20 h. The reaction was quenched with water (20 mL), extracted with dichloromethane (3×50 mL) and the aqueous phase was discarded. The extract was washed with brine (20 mL), dried over Na₂SO₄, filtered, and concentrated. The crude product was purified by combiflash (EtOAc:PE=1:20 to 1:5, ISCO, 40 g, 40 ml/min, normal phase, sillica, uv 254) to yield 3,4-dichlorophenyl-2,4,6-tri-O-acetyl-3-O-[(4-chlorophenyl)-4-oxobut-2-ynyl]-1-thio-α-D-galactopyranoside 160 mg (62.8%) as a yellow oil.

ESI-MS m/z calcd for $[C_{28}H_{29}Cl_3NO_9S]^+$ $[M+NH_4]^+$: 660.1; found: 660.0.

Example 42-53 were made from the intermediates i42-i53

Example 42

3,4-Dichlorophenyl 3-deoxy-3-[4-(2,3,4,5,6-pentafluorophenyl)-1H-1,2,3-triazol-1-yl]-1-thio-α-D-galactopyranosyl sulfoxide

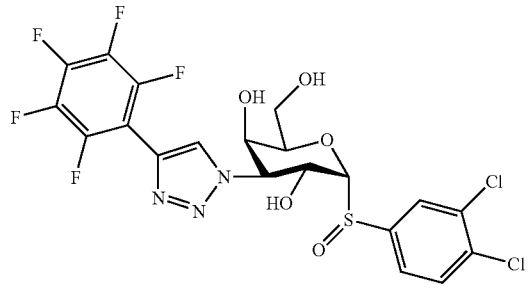

3,4-Dichlorophenyl 3-deoxy-3-[4-(2,3,4,5,6-pentafluorophenyl)-1H-1,2,3-triazol-1-yl]-1-thio-α-D-galactopyranoside, Example 52 (60 mg) was dissolved in CH₂Cl₂ (30 mL) and cooled with an ice/water bath. m-Chloroperbenzoic acid (30 mg) was dissolved in CH₂Cl₂ (5 mL) and added to the first solution. The cooling bath was removed. This mixture was stirred 30 min. Water 30 mL and sat. aq. NaHCO₃ (5 mL) was added. The mixture was separated and the organic phase was concentrated in vacuo. The residue was purified by HPLC. Freezedrying afforded the title compound 14 mg as a white solid. ¹H NMR (400 MHz, Methanol-d₄) δ 8.48 (s, 1H), 8.03 (t, J=1.1 Hz, 1H), 7.76 (d, J=1.1 Hz, 2H), 5.64 (dd, J=11.2, 2.8 Hz, 1H), 5.15 (dd, J=11.2, 5.6 Hz, 1H), 4.95 (d, J=5.6 Hz, 1H), 4.32-4.27 (m, 1H), 4.17 (t, J=6.0 Hz, 1H), 3.61-3.45 (m, 2H). ESI-MS m/z calcd for $[C_{20}H_{15}Cl_2F_5N_3O_5S]^+$ $(M+H)^+$: 574.00; found: 573.95.

Example 43

5-Chloropyridin-3-yl 3-deoxy-3-[4-(3,4,5-trifluorophenyl)-1H-1,2,3-triazol-1-yl]-1-thio-α-D-galactopyranoside

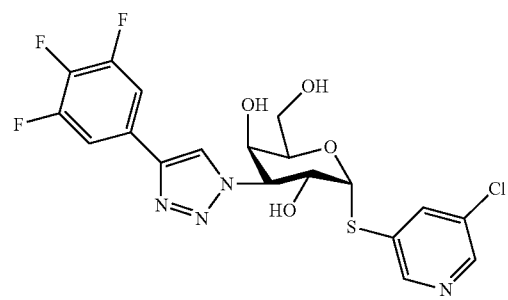

5-Chloropyridin-3-yl 2,4,6-tri-O-acetyl-3-deoxy-3-[4-(3,4,5-trifluorophenyl)-1H-1,2,3-triazol-1-yl]-1-thio-α-D-galactopyranoside, 143 (450 mg, 0.73 mmol) was dissolved in sodium methoxide/methanol (0.05 M, 20 mL). The reaction mixture was stirred at room temperature for 2 h followed by neutralisation (pH 7) by addition of DOWEX 50wx8-200 Ion exchange resin. The reaction mixture was filtered and the filtrate was concentrated to give crude material which was purified by preparative HPLC. The appropriate fractions where combined and lyophilized to give the title compound (220 mg, 61.80%) as a white solid.

$^1$H NMR (400 MHz, DMSO-$d_6$) δ 8.67 (s, 1H), 8.50 (d, J=2 Hz, 1H), 8.39 (d, J=2 Hz, 1H), 8.05 (t, 1H), 7.73-7.69 (m, 2H), 5.84 (dd, J=12.8, 4.8 Hz, 2H), 5.40 (d, J=6.4 Hz, 1H), 4.73-4.70 (m, 1H), 4.61 (dt, J=11.2, 5.3 Hz, 2H), 4.12 (t, J=6.0 Hz, 1H), 3.90 (s, 1H), 3.37 (dd, J=11.2, 5.6 Hz, 1H), 3.36-3.26 (m, 1H).

m/z calcd for $[C_{19}H_{16}ClF_3N_4O_4S]^+$ $[M+H]^+$: 489.0; found: 489.0.

Example 44

5-Bromopyridin-3-yl 3-deoxy-3-[4-(3,4,5-trifluorophenyl)-1H-1,2,3-triazol-1-yl]-1-thio-α-D-galactopyranoside

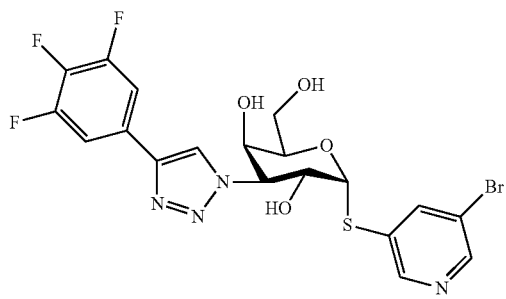

5-Bromopyridin-3-yl 2,4,6-tri-O-acetyl-3-deoxy-3-[4-(3,4,5-trifluorophenyl)-1H-1,2,3-triazol-1-yl]-1-thio-α-D-galactopyranoside (910 mg) was dissolved in MeOH (10.0 mL) followed by addition of Sodium methoxide (7.46 mg, 0.14 mmol). The mixture was stirred at room temperature for 1 h followed by acidification to pH5-6 using dowex 50 wx8 hydrogen form. The reaction mixture was filtered, washed with MeOH (20 mL) and concentrated in vacuo to afford crude product, which was purified by preparative-HPLC to give the title compound (445 mg, 60.5% yield).

$^1$H NMR (400 MHz, DMSO) δ 8.82 (s, 1H), 8.65 (dd, J=24.1, 1.7 Hz, 2H), 8.39-8.23 (m, 1H), 7.96-7.74 (m, 2H), 6.09-5.90 (m, 2H), 5.55 (d, J=6.3 Hz, 1H), 4.91-4.80 (m, 1H), 4.80-4.67 (m, 2H), 4.27 (t, J=6.1 Hz, 1H), 4.04 (d, J=3.7 Hz, 1H), 3.61-3.48 (m, 1H), 3.47-3.38 (m, 2H).

ESI-MS m/z calcd for $[C_{19}H_{16}BrF_3N_4O_4S]^+$ $[M+H]^+$: 532.0; found: 533.0.

Example 45

3-Chloro-5-cyanophenyl 3-deoxy-3-[4-(3,4,5-trifluorophenyl)-1H-1,2,3-triazol-1-yl]-1-thio-α-D-galactopyranoside

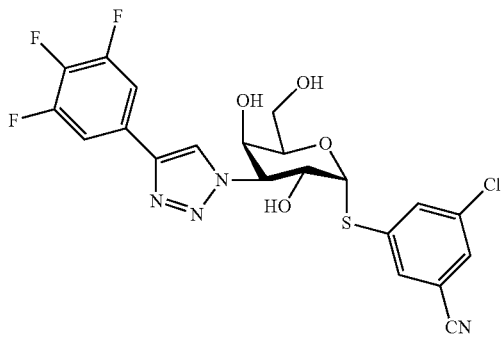

To a solution of 3-Chloro-5-cyanophenyl-2,4,6-tri-O-acetyl-3-deoxy-3-[4-(3,4,5-trifluorophenyl)-1H-1,2,3-triazol-1-yl]-1-thio-α-D-galactopyranoside, 145 (120.00 mg, 47.48 mmol) in methanol (11 mL) and water (2.2 mL) were added TEA (6.6 mL). After completion the reaction mixture was evaporated to dryness and the residue was purified by preparative HPLC to obtain the title compound (20 mg, 15%) as a white solid.

$^1$H NMR (400 MHz, DMSO) δ 8.82 (s, 1H), 8.05-7.95 (m, 2H), 7.95-7.91 (m, 1H), 7.91-7.77 (m, 2H), 6.10 (d, J=5.1 Hz, 1H), 5.97 (d, J=4.8 Hz, 1H), 5.55 (d, J=6.3 Hz, 1H), 4.87-4.69 (m, 3H), 4.24-4.16 (m, 1H), 4.05-4.00 (m, 1H), 3.55-3.48 (m, 1H), 3.44-3.38 (m, 1H).

m/z calcd for $[C_{21}H_{16}ClF_3N_4O_4S]^+$ $[M+H]^+$: 513.0; found: 513.0.

Example 46

3-Chloro-4-cyanophenyl 3-deoxy-3-[4-(3,4,5-trifluorophenyl)-1H-1,2,3-triazol-1-yl]-1-thio-α-D-galactopyranoside

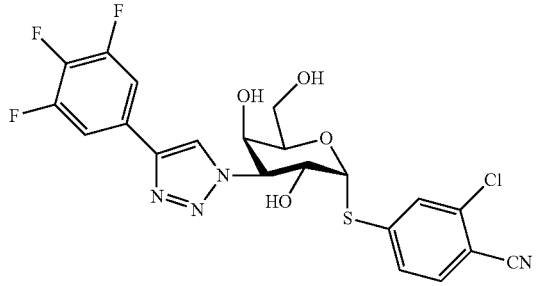

3-chloro-4-cyanophenyl 2,4,6-tri-O-acetyl-3-azido-3-deoxy-1-thio-α-D-galactopyranoside, i46 (98 mg, 0.20 mmol) was dissolved in acetonitrile (5 mL) and stirred at r.t. under argon. Copper(I) iodide (43 mg, 0.23 mmol) was added and after five minutes 1,2,3-trifluoro-5-[2-(trimethylsilyl)ethynyl]benzen (0.085 mL, 0.41 mmol). After an additional five minutes DIEA (0.040 mL, 0.23 mmol) was added and the mixture was heated to 70° C. After 2.5 h the reaction mixture was filtered through a short column of silica, eluting with EtOAc and then concentrated down. The residue was dissolved in methanolic sodium methoxide (0.05M, 30 mL) and stirred at r.t. After 18 h acetic acid (2 mL) was added and the mixture was concentrated down. The crude product was purified by preparative HPLC and lyophilized to give 46 mg (44%) of the title compound. ¹H NMR (400 MHz, Methanol-d₄) δ 8.55 (s, 1H), 7.85 (s, 1H), 7.74-7.61 (m, 4H), 6.11 (d, J=4.8 Hz, 1H), 5.05-4.94 (m, 2H), 4.38 (t, J=6.0 Hz, 1H), 4.20 (s, 1H), 3.77-3.66 (m, 2H). ESI-MS m/z calcd for $[C_{22}H_6ClF_3N_4O_4S]^+$ (M+H)⁺: 513.1; found: 513.0.

Example 47

3-Chloro-6-fluoro-4-cyanophenyl 3-deoxy-3-[4-(3,4,5-trifluorophenyl)-1H-1,2,3-triazol-1-yl]-1-thio-α-D-galactopyranoside

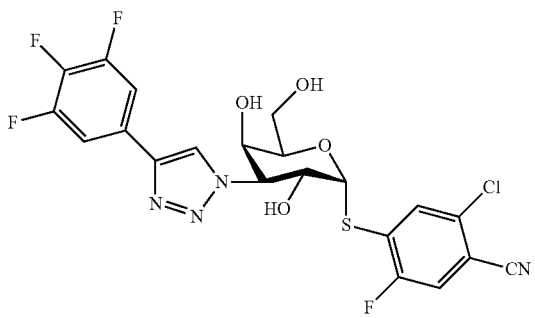

To a stirred solution of 3-Chloro-6-fluoro-4-cyanophenyl 2,4,6-tri-O-acetyl-3-deoxy-3-[4-(3,4,5-trifluorophenyl)-1H-1,2,3-triazol-1-yl]-1-thio-α-D-galactopyranoside, i47 (150 mg, 0.23 mmol) in MeOH (5 mL) was added triethylamine (3 mL) and H₂O (1 mL) was added at 0° C. The mixture was stirred at r.t. for 1 hour. The reaction mixture was concentrated and the residue was purified by Preparative HPLC to give 20 mg of the title compound.

¹H NMR (400 MHz, DMSO) δ 8.83 (s, 11H), 8.11-8.03 (m, 2H), 7.92-7.78 (m, 2H), 6.29 (d, J=5.5 Hz, 1H), 6.19-6.09 (m, 1H), 5.69-5.51 (m, 1H), 4.95-4.88 (m, 1H), 4.86-4.77 (m, 1H), 4.73-4.60 (m, 1H), 4.13-3.95 (m, 2H), 3.52-3.43 (m, 2H).

ESI-MS m/z calcd for $[C_{21}H_{16}ClF_4N_4O_4S]^+$ (M+H)⁺: 531.1; found: 531.1.

Example 48

3-Bromo-4-cyanophenyl 3-deoxy-3-[4-(3,4,5-trifluorophenyl)-1H-1,2,3-triazol-1-yl]-1-thio-α-D-galactopyranoside

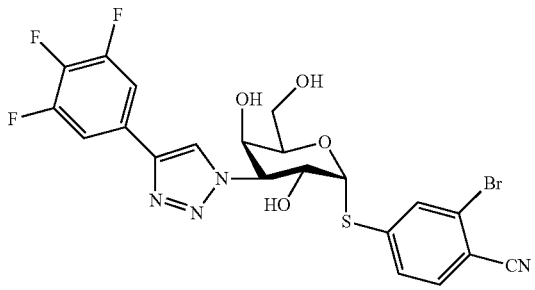

3-Bromo-4-cyanophenyl 2,4,6-tri-O-acetyl-3-deoxy-3-[4-(3,4,5-trifluorophenyl)-1H-1,2,3-triazol-1-yl]-1-thio-α-D-galactopyranoside (100 mg) was dissolved in MeOH (4 mL). TEA (2.4 ml) and H₂O (0.8 ml) was added. The mixture was stirred at rt over night followed by purification using preparative HPLC to give 20 mg (24.5%) of the title compound as white solid.

¹H NMR (400 MHz, DMSO) δ 8.82 (s, 1H), 8.03 (d, J=1.6 Hz, 1H), 7.94-7.80 (m, 3H), 7.69 (dd, J=8.3, 1.6 Hz, 1H), 6.20 (d, J=5.0 Hz, 1H), 6.00 (d, J=4.6 Hz, 1H), 5.58 (d, J=6.3 Hz, 1H), 4.92-4.72 (m, 2H), 4.69 (t, J=5.6 Hz, 1H), 4.14 (t, J=6.3 Hz, 1H), 4.02 (d, J=4.4 Hz, 1H), 3.59-3.50 (m, 1H), 3.43-3.37 (m, 2H).

ESI-MS m/z calcd for $[C_{21}H_{17}BrF_3N_4O_4S]^+$ (M+H)⁺: 557.0; found: 557.0.

Example 49

5-Bromo-6-trifluoromethyl-pyridin-3-yl 3-deoxy-3-[4-(3,4,5-trifluorophenyl)-1H-1,2,3-triazol-1-yl]-1-thio-α-D-galactopyranoside

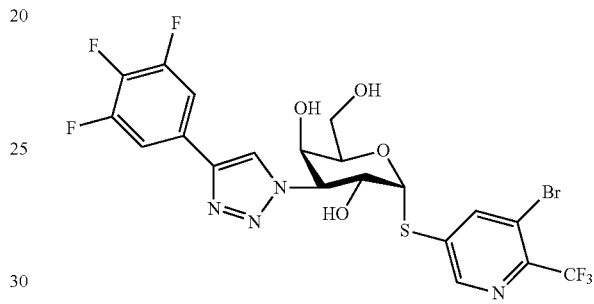

To a solution of 5-Bromo-6-trifluoromethyl-pyridin-3-yl 2,4,6-tri-O-acetyl-3-deoxy-3-[4-(3,4,5-trifluorophenyl)-1H-1,2,3-triazol-1-yl]-1-thio-α-D-galactopyranoside, 149 (90 mg, 0.12 mmol) in MeOH (5 mL) was added Sodium methoxide (0.67 mg, 0.01 mmol) at room temperature. The reaction mixture was stirred at room temperature for 1 h. The mixture was acidified with dowex 50 wx8 hydrogen form to pH 5~6. The solution was filtered, washed with MeOH (20 mL) and concentrated in vacuo to afford crude product, which was purified by Preparative HPLC to afford the title compound (12.77 mg, 17% yield).

¹H NMR (400 MHz, MeOD) δ 8.65 (d, J=1.8 Hz, 1H), 8.46 (s, 1H), 8.43-8.38 (m, 1H), 7.69-7.46 (m, 2H), 6.03 (d, J=5.1 Hz, 1H), 5.00-4.85 (m, 2H), 4.31 (t, J=6.1 Hz, 1H), 4.10 (d, J=1.8 Hz, 1H), 3.68-3.54 (m, 2H).

ESI-MS m/z calcd for $[C_{20}H_{15}BrF_6N_4O_4S]^+$ (M+H)⁺: 600.0; found: 601.0.

Example 50

5-Chloro-6-cyano-pyridin-3-yl 3-deoxy-3-[4-(3,4,5-trifluorophenyl)-1H-1,2,3-triazol-1-yl]-1-thio-α-D-galactopyranoside

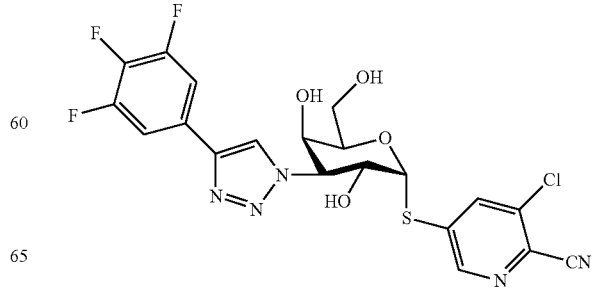

To a solution of 2,4,6-tri-O-acetyl-3-deoxy-3-[4-(3,4,5-trifluorophenyl)-1H-1,2,3-triazol-1-yl]-1-thio-α-D-galactopyranoside, 150 (12.00 mg, 0.02 mmol) in methanol (0.5 mL) and water (0.1 mL) were added TEA (0.3 mL). Upon completion the reaction mixture was evaporated to dryness and the residue was purified by preparative-HPLC to obtain the title compound (1.27 mg).

m/z calcd for [C20H15ClF3N5O4S]+ [M+H]+: 514.0; found: 514.0.

$^1$H NMR (400 MHz, MeOD) δ 8.62 (d, J=2 Hz, 1H), 8.46 (s, 1H), 8.40 (d, J=2 Hz, 1H), 7.56 (m, 2H), 6.11 (d, J=1.2 Hz, 1H), 4.95 (dd, J=11.6, 2.8 Hz, 1H), 4.88 (dd, J=11.2, 5.2 Hz, 1H), 4.25 (t, J=12, 6 Hz, 1H), 4.08 (d, J=1.6 Hz, 1H), 3.60 (d, J=6 Hz, 2H).

Example 51

5-Chloro-6-cyano-pyridazin-3-yl 3-deoxy-3-[4-(3,4,5-trifluorophenyl)-1H-1,2,3-triazol-1-yl]-1-thio-α-D-galactopyranoside

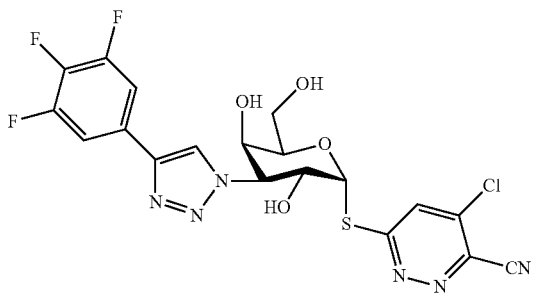

To a solution of acetyl chloride (0.5 ml) in methanol (5 mL) was added 2,4,6-tri-O-acetyl-3-deoxy-3-[4-(3,4,5-trifluorophenyl)-1H-1,2,3-triazol-1-yl]-1-thio-α-D-galactopyranoside, i51 (15 mg). The reaction was stirred for 4 h at room temperature. Followed by purification by preparative-TLC (DCM/MeOH=15/1) to obtain 0.95 mg of the title compound.

m/z calcd for [C19H14ClF3N6O4S]+ [M+H]+: 515.0; found: 515.0.

$^1$H NMR (400 MHz, MeOD) δ 8.60 (s, 1H), 8.30 (s, 1H), 7.68 (dd, J=8.8, 6.8 Hz, 2H), 7.56 (d, J=4 Hz, 1H), 5.11 (d, J=3.6 Hz, 2H), 4.20 (m, 2H), 3.71 (m, 2H).

Example 52

3,4-Dichlorophenyl 3-deoxy-1-thio-3-[4-(2,3,4,5,6-pentafluorophenyl)-1H-1,2,3-triazol-1-yl]-α-D-galactopyranoside

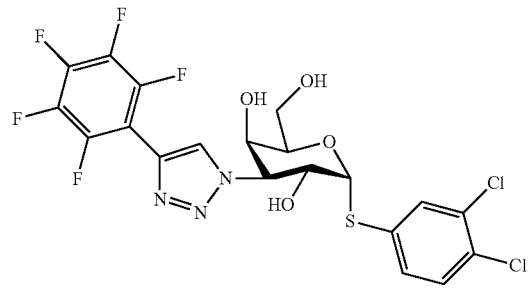

Example 53

3,4-Dichlorophenyl 2,4,6-tri-O-acetyl-3-azido-3-deoxy-1-thio-α-D-galactopyranoside (214 mg) was dissolved in MeCN (10 mL). Copper(I) iodide (15 mg) and pentafluorophenylacetylene (0.130 mL) were added and the mixture degassed (nitrogen). After 5 min, DIEA (0.300 mL) was added and the resulting mixture was stirred over night. The reaction mixture was filtered through a small plug of silica and concentrated in vacuo. The residue was suspended in MeOH (40 mL). 1M sodium methoxide in MeOH (1 mL) was added. After stirring at r.t. 2 h, acetic acid (1 mL) was added and the mixture concentrated in vacuo. The residue was dissolved in a small volume of MeCN/water, filtered and purified by HPLC (C$_{18}$/H$_2$O:MeCN:0.1% TFA). Freeze-drying afforded the title compound as a white powder (174 mg). $^1$H NMR (400 MHz, Methanol-d$_4$) δ 8.49 (d, J=1.6 Hz, 1H), 7.80 (d, J=2.0 Hz, 1H), 7.57-7.44 (m, 2H), 5.85 (d, J=5.3 Hz, 1H), 5.06 (dd, J=11.4, 2.8 Hz, 1H), 4.93 (dd, J=11.4, 5.4 Hz, 1H), 4.50 (t, J=6.0 Hz, 1H), 4.23 (s, 1H), 3.79-3.64 (m, 2H). ESI-MS m/z calcd for [C$_{20}$H$_{15}$Cl$_2$F$_5$N$_3$O$_4$S]+ (M+H)+: 558.00; found: 558.05.

Example 53

3,4-Dichlorophenyl 3-deoxy-3-[4-(2,3,4,5,6-pentafluorophenyl)-1H-1,2,3-triazol-1-yl]-α-D-galactopyranosyl sulfone

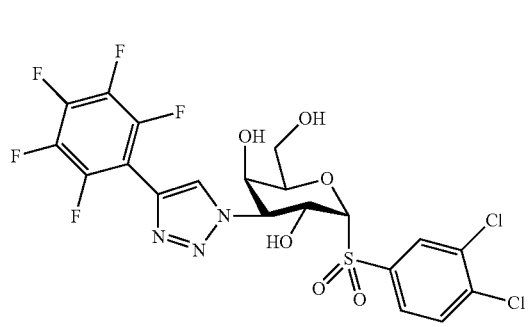

Following purification by HPLC in Example 42 7 mg of the title compound was isolated.

$^1$H NMR (400 MHz, Methanol-d$_4$) δ 8.50 (s, 1H), 8.16 (d, J=2.1 Hz, 1H), 7.92 (dd, J=8.4, 2.1 Hz, 1H), 7.80 (d, J=8.4 Hz, 1H), 5.82 (dd, J=11.4, 2.8 Hz, 1H), 5.34 (d, J=6.4 Hz, 1H), 5.15 (dd, J=11.5, 6.4 Hz, 1H), 4.53 (t, J=6.0 Hz, 1H), 4.31 (s, 1H), 3.60 (qd, J=11.5, 6.0 Hz, 2H). ESI-MS m/z calcd for [C$_{20}$H$_{15}$Cl$_2$F$_5$N$_3$O$_6$S]+ (M+H)+: 589.99; found: 590.00.

Example 54

5-Methoxy-6-cyano-pyridazin-3-yl 3-deoxy-3-[4-(3,4,5-trifluorophenyl)-1H-1,2,3-triazol-1-yl]-1-thio-α-D-galactopyranoside

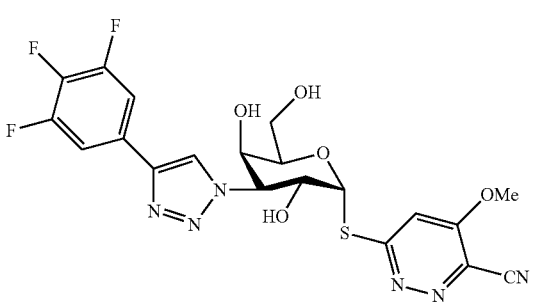

Following purification by preparative-TLC (DCM/MeOH=15/1) in Example 51, 0.5 mg of the title compound was isolated.

m/z calcd for [C20H17F3N6O5S]+ [M+H]+: 511.0; found: 511.0.

$^1$H NMR (400 MHz, DMSO-d$_6$) δ 8.47 (s, 1H), 7.56 (dd, J=8.8, 6.8 Hz, 2H), 7.49 (s, 1H), 6.32 (d, J=4 Hz, 1H), 4.95 (m, 2H), 4.14 (m, 1H), 4.08 (m, 4H), 3.59 (d, J=6 Hz, 1H).

Example 55

5-Hydroxy-6-cyano-pyridazin-3-yl 3-deoxy-3-[4-(3,4,5-trifluorophenyl)-1H-1,2,3-triazol-1-yl]-1-thio-α-D-galactopyranoside

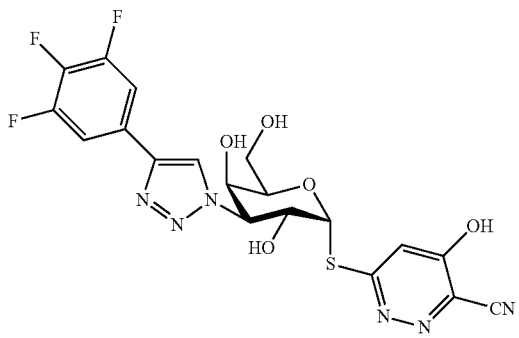

To a solution of acetyl chloride (2 ml) in methanol (20 mL) was added 2,4,6-tri-O-acetyl-3-deoxy-3-[4-(3,4,5-trifluorophenyl)-1H-1,2,3-triazol-1-yl]-1-thio-α-D-galactopyranoside, i50 (40 mg). The reaction was held at room temperature with stirring on for 4 h. The reaction mixture was concentrated and purified by preparative HPLC to obtain 7 mg of the title compound.

m/z calcd for [C19H15F3N6O5S]+ [M+H]+: 497.0; found: 497.0.

$^1$H NMR (400 MHz, DMSO-d$_6$) δ 8.59 (s, 1H), 7.68 (dd, J=8.8, 6.4 Hz, 2H), 7.28 (s, 1H), 6.35 (d, J=4 Hz, 1H), 7.50 (d, J=4 Hz, 2H), 4.27 (t, J=12.4, 6 Hz, 1H), 4.22 (s, 1H), 3.75-3.73 (m, 2H).

Synthesis of Intermediates i43-i51 i43) 5-Chloropyridin-3-yl 2,4,6-tri-O-acetyl-3-deoxy-3-[4-(3,4,5-trifluorophenyl)-1H-1,2,3-triazol-1-yl]-1-thio-α-D-galactopyranoside O-[(5-chloro-3-pyridyl)]N,N-dimethylcarbamothioate

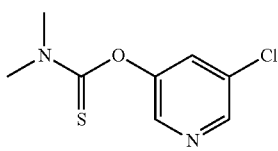

To a solution of 5-chloropyridin-3-ol (10 g, 0.10 mol) in N,N-dimethylformamide (200 mL) was added NaH (1.90 g, 0.10 mol) at 0° C. The reaction mixture was stirred at 0° C. 30 minutes followed by addition of Dimethylthiocarbamoyl chloride (10.50 g, 0.10 mol) followed by stirring at room temperature 20 h. The reaction was quenched with water (500 mL) and extracted with dichloromethane (500 mL×3). The combined organics were washed with brine (400 mL×3), dried over Na$_2$SO$_4$, filtered and the solvents where removed in vacuo. The crude product was purified by chromatography on a combiflash (EtOAc:PE=1:5) to give O-[(5-chloro-3-pyridyl)]N,N-dimethylcarbamothioate 6.2 g (28.7%) as brown oil.

m/z calcd for [C8H9ClN2OS]+ [M+H]+: 217.0; found: 217.0.

S-[(5-chloro-3-pyridyl)] N,N-dimethylcarbamothioate

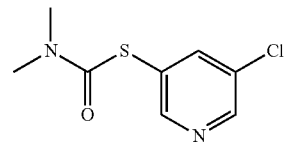

O-[(5-chloro-3-pyridyl)] N,N-dimethylcarbamothioate (6.2 g, 28.7 mmol) was taken up to in phenoxybenzene (30 mL) and added to 5 mL of refluxing phenoxybenzene. After 2 h, the reaction mixture was cooled and passed through 200 g SiO$_2$ to remove the phenoxybenzene, subsequent elution with PE:EtOAc=1:2 gave S-[(5-chloro-3-pyridyl)] N,N-dimethylcarbamothioate 4.5 g (73%) as yellow solid.

m/z calcd for [C8H9ClN2OS]+ [M+H]+: 217.0; found: 217.0.

5-chloropyridine-3-thiol

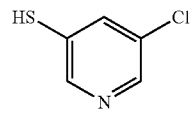

S-[(5-chloro-3-pyridyl)] N,N-dimethylcarbamothioate (3.5 g, 16.20 mmol) and NaOH (3.24 g, 81 mmol) was taken up into 160 mL ethanol/water=3:1 and heated at reflux for 2 h. The reaction mixture was concentrated to about 100 mL. EtOAc (300 mL) was added and the pH was adjusted to about 6 by addition of HCl (2M). The organic layer was isolated and dried over Na$_2$SO$_4$, concentrated, purified by chromatography on a combiflash (EtOAc:PE=1:5 to 1:2, ISCO, 40 g, 40 ml/min, normal phase sillica, uv254) to give 5-chloropyridine-3-thiol 2.0 g (85%) as yellow oil. m/z calcd for [C5H4ClNS]− [M−H]−: 144.0; found: 144.0.

5-Chloropyridin-3-yl 2,4,6-tri-O-Acetyl-3-azido-3-deoxy-1-thio-α-D-galactopyranoside

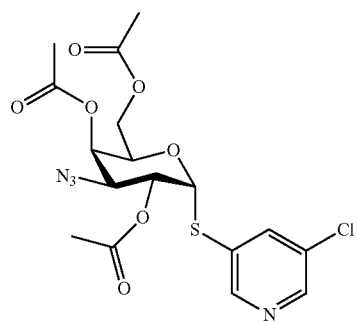

NaH (303.44 mg, 7.58 mmol) was suspended in DMF (25 mL). The 5-chloropyridine-3-thiol (1000 mg, 6.89 mmol) was added. After 30 min, the 3-azido-3-deoxy-2,4,6-tri-O-acetyl-1-chloro-β-D-galactopyranoside (1923.68 mg, 5.51 mmol) was added. The mixture was heated to 50° C. 3 h. The mixture was diluted with DCM (150 mL), 0.5M citric acid (150 mL) and water (150 mL). The organic phase was washed with water (100 mL) and concentrated. The residue was purified by column chromatography (PE:EtOAc=3:1) to give the title compound 900 mg (28.52%) as a white solid.

m/z calcd for $[C_{17}H_{19}ClN_4O_7S]^+$ $[M+H]^+$: 459.0; found: 459.0.

1,3-dideoxy-2,4,6-tri-O-acetyl-1-(5-chloropyridine-3-yl-thio)-3-[4-(3,4,5-trifluorophenyl)-1H-1,2,3-triazol-1-yl]-α-D-galactopyranoside

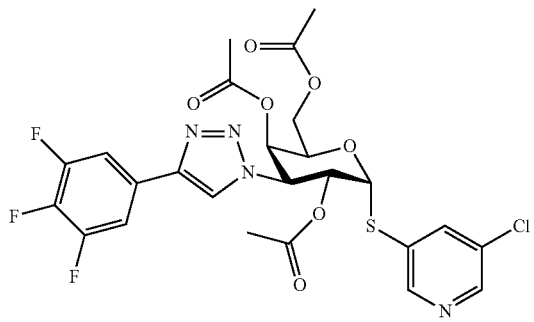

To a solution of 5-Chloropyridin-3-yl 2,4,6-tri-O-Acetyl-3-azido-3-deoxy-1-thio-α-D-galactopyranoside (600 mg, 1.30 mmol) in N,N-dimethylformamide (16 mL) was added trimethyl-[2-(3,4,5-trifluorophenyl)ethynyl]silane (597.00 mg, 2.62 mmol), and Copperiodide (74.70 mg, 0.4 mmol). The reaction vessel was purged 3 times with nitrogen. After completion the reaction was quenched with water (100 mL) and the reaction mixture was extracted with dichloromethane (100 mL×3). The combined organics where washed with brine (50 mL×1), dried over $Na_2SO_4$, filtered, and the solvents where evaporated in vacuo. The crude product was purified by combiflash (EtOAc:PE=1:10 to 1:2, ISCO 40 g, 40 ml/min, normal phase silica, UV254) to give the title compound 450 mg (56%) as a yellow solid.

m/z calcd for $[C_{25}H_{22}ClF_3N_4O_7S]^+$ $[M+H]^+$: 615.0; found: 615.0.

i44) 5-Bromopyridin-3-yl 2,4,6-tri-O-acetyl-3-deoxy-3-[4-(3,4,5-trifluorophenyl)-1H-1,2,3-triazol-1-yl]-1-thio-α-D-galactopyranoside O-[(5-bromo-3-pyridyl)] N,N-dimethylcarbamothioate

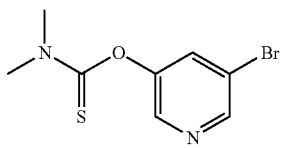

To a solution of 5-bromopyridin-3-ol (17.4 g, 0.10 mol) in DMF (0.15 L) was added sodium hydride (2.64 g, 0.11 mol, 96% in mineral oil) at 0° C., followed by stirring at 0° C. for 30 min. Dimethylthiocarbamoyl chloride (14.83 g, 0.12 mol) was added to the reaction mixture followed by stirring at room temperature over night. LC-MS analysis indicated formation of the target compound. The reaction mixture was quenched with water (100 mL) followed by extraction with EtOAc (100 mL×3). The combined organic layers were washed with brine (100 mL), dried over $Na_2SO_4$ and concentrated in vacuo. The crude product was purified by flash chromatography on a Biotage (EtOAc/PE=5%~40%, ISCO 120 g, 50 mL/min, normal phase silica gel, uv254) to afford the target compound O-[(5-bromo-3-pyridyl)] N,N-dimethylcarbamothioate (9.93 g, 36.5% yield) as yellow oil.

ESI-MS m/z calcd for $[C_8H_9BrN_2OS]^+$ $[M+H]^+$: 261.0; found: 261.0.

S-[(5-bromo-3-pyridyl)]N,N-dimethylcarbamothioate

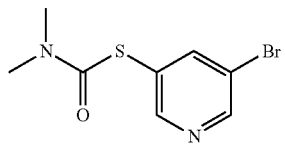

O-[(5-bromo-3-pyridyl)] N,N-dimethylcarbamothioate (9.93 g, 0.04 mol) was dissolved in phenoxybenzene (100 mL). The mixture was heated at reflux for 2 h. The reaction mixture was cooled to room temperature and directly purified by flash chromatography on a Biotage (EtOAc/PE=5%~50%, ISCO 120 g, 50 mL/min, normal phase silica gel, uv 254) to afford the target compound S-[(5-bromo-3-pyridyl)] N,N-dimethylcarbamothioate (4.63 g, 43.76% yield) as a yellow solid.

ESI-MS m/z calcd for $[C_8H_9BrN_2OS]^+$ $[M+H]^+$: 261.0; found: 261.0.

3-bromo-5-methoxy-benzenethiol

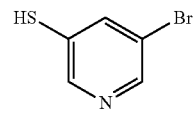

S-(3-chloro-5-methoxy-phenyl) N,N-dimethylcarbamothioate (1.044 g, 4 mmol) and KOH (897.21 mg, 16 mmol) was taken up in ethanol/water (40 mL, 3/1). The reaction mixture was heated at reflux for 2 h. LC-MS analysis indicated total consumption of the starting material. The mixture was concentrated followed by addition of 10% aq NaOH (30 mL). The reaction mixture was washed with ether (15 mL×3). The aqueous layer was acidified with aq $KHSO_4$ to adjust the pH~2, followed by extraction with EtOAc (20 mL×5). The combined organic layers were washed with brine, dried over $Na_2SO_4$ and concentrated in vacuo to afford crude product, which was used for next step directly without further purification.

ESI-MS m/z calcd for $[C_5H_4BrNS]^-$ $[M-H]^-$: 188.9; found: 188.0.

5-Bromopyridin-3-yl 2,4,6-tri-O-acetyl-3-azido-3-deoxy-1-thio-α-D-galactopyranoside

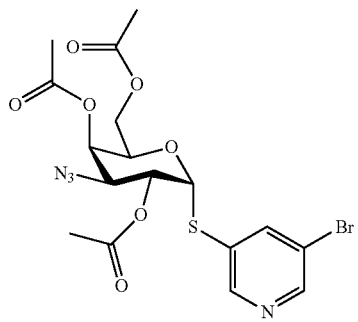

NaH (82.99 mg, 3.47 mmol) was added to a solution of 5-bromopyridine-3-thiol (658.67 mg, 3.47 mmol) in DMF (10 mL) at 0° C. The solution was stirred at rt for 30 min. Then 2,4,6-tri-O-acetyl-3-azido-1-chloro-3-deoxy-β-D-galactopyranoside (1.01 g, 2.89 mmol) was added. The reaction mixture was stirred at 50° C. for 2 h followed by cooling to room temperature. Water (50 mL) was added and the reaction mixture was extracted with EtOAc (15 mL×3). The combined organic layers were washed with brine, dried over Na$_2$SO$_4$ and concentrated in vacuo to afford crude product, which was purified by biotage (EtOAc/PE=5%~40%, ISCO 40 g, 30 mL/min, normal phase silica gel, uv 254) to afford the title compound (650 mg, 44.7% yield) as a white solid.

ESI-MS m/z calcd for [C$_{17}$H$_{19}$BrN$_4$O$_7$S]$^+$ [M+H]$^+$: 503.0; found: 503.0.

5-Bromopyridin-3-yl 2,4,6-tri-O-acetyl-3-deoxy-3-[4-(3,4,5-trifluorophenyl)-1H-1,2,3-triazol-1-yl]-1-thio-α-D-galactopyranoside

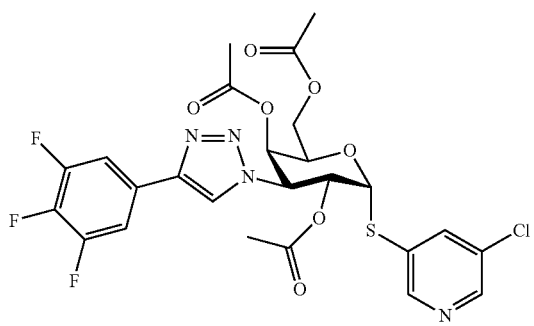

To a solution of 5-Bromopyridin-3-yl 2,4,6-tri-O-acetyl-3-azido-3-deoxy-1-thio-α-D-galactopyranoside (650 mg, 1.29 mmol) in DMF (15 mL) was added trimethyl-[2-(3,4,5-trifluorophenyl)ethynyl]silane (442.22 mg, 194 mmol), iodocopper (73.78 mg, 0.39 mmol), CsF (294.26 mg, 1.94 mmol) and N,N-diethylethanamine (653.39 mg, 6.46 mmol). The reaction vessel was purged 3 times with nitrogen. The reaction mixture was stirred at room temperature for 2 h. The mixture was filtered and washed with EtOAc (50 mL), The filtrate was concentrated in vacuo to afford the title compound as crude product, which was used for next step directly without further purification.

ESI-MS m/z calcd for [C$_{25}$H$_{22}$BrF$_3$N$_4$O$_7$S]$^+$ [M+H]$^+$: 658.0; found: 659.0.

i45) 3-Chloro-5-cyanophenyl 2,4,6-tri-O-acetyl-3-deoxy-3-[4-(3,4,5-trifluorophenyl)-1H-1,2,3-triazol-1-yl]-1-thio-α-D-galactopyranoside

O-3-chloro-5-cyanophenyl dimethylcarbamothioate

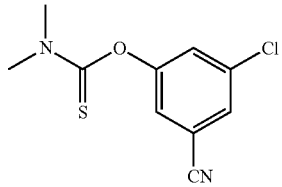

To a mixture of 3-chloro-5-hydroxy-benzonitrile (2.5 g, 16.28 mmol) in DMF (25 mL)) cooled to 0° C. was added sodiumhydride (0.43 g, 17.91 mmol) followed by dimethylthiocarbamoyl chloride (2.21 g, 17.91 mmol). The reaction mixture was stirred at room temperature for a 20 h followed by addition of water (50 ml), followed by extraction with DCM (100 ml*2). The combined organics were washed with brine, dried over Na$_2$SO$_4$ and evaporated to dryness to obtain crude product. Purification on silica gel (PE/EtOAc=10/1) to gay the target compound 2.5 g (63.80%) as a white solid.

S-3-chloro-5-cyanophenyl dimethylcarbamothioate

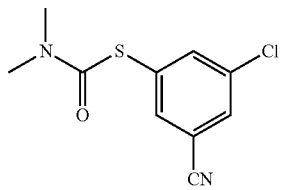

A solution of O-(3-chloro-5-cyano-phenyl) N,N-dimethylcarbamothioate (2.50 g, 10.39 mmol) in phenyl ether (20 ml) was stirred at 280° C. for 2 h. TLC analysis indicated the total consumption of the SM. The reaction mixture was cooled to room temperature and purified by silica gel chromatography to give product (2.20 g, 88%) as a solid.

3-chloro-5-mercaptobenzonitrile

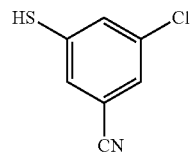

To a solution of S-(3-chloro-5-cyano-phenyl) N,N-dimethylcarbamothioate (300 mg, 1.25 mmol) in methanol (15 mL) was added 2M NaOH (8 ml). The reaction was stirred at 70° C. for 2 h. TLC analysis indicated the total consumption of the SM. Water (30 mL) and DCM (30 mL) were added. The phases where separated and the aqueous phase was further extracted with DCM (50 mL*2). The combined organics were washed with brine, dried over Na₂SO₄ followed by removal of the solvents in vacuo. The crude material was immediately used in the next step.

3-Chloro-5-cyanophenyl-2,4,6-tri-O-acetyl-3-azido-3-deoxy-1-thio-α-D-galactopyranoside

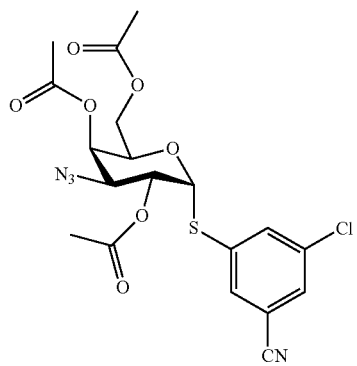

To a solution of 3-chloro-5-sulfanyl-benzonitrile (212 mg, 3 mmol) in DMF (15 mL) was added NaH (22.99 mg, 1.00 mmol). After stirring for 0.5 h, 2,4,6-tri-O-acetyl-3-azido-1-chloro-3-deoxy-β-D-galactopyranoside (218.53 mg, 0.62 mmol) was added and the reaction mixture was held at 50° C. with stirring for 2 h. TLC analysis indicated the total consumption of the SM. 10% citric acid aq. (30 mL) and DCM (30 mL) were added and the phases where separated. The aqueous phase was further extracted with DCM (50 mL*2). The combined organic layers were washed with brine, dried over Na₂SO₄ and the solvents where removed in vacuo. The crude material was purified by flash column chromatography to give the target compound 120 mg (20%) as white oil.

3-Chloro-5-cyanophenyl 2,4,6-tri-O-acetyl-3-deoxy-3-[4-(3,4,5-trifluorophenyl)-1H-1,2,3-triazol-1-yl]-1-thio-α-D-galactopyranoside

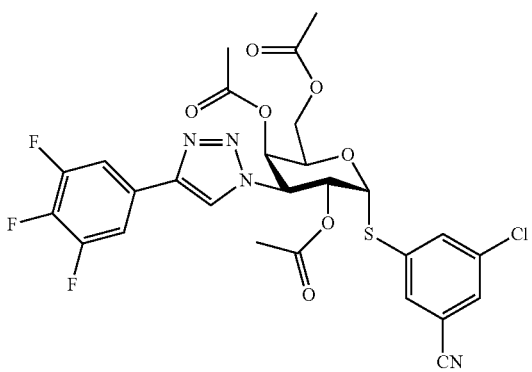

To a solution of 3-azido-1,3-dideoxy-2,4,6-tri-O-acetyl-1-(3-chloro-5-cyanophenyl-thio)-α-D-galactopyranoside (120 mg, 0.25 mmol) in DMF (3 mL) were added TEA (125.73 mg, 1.24 mmol), Copper(I)Iodide (14.20 mg, 0.07 mmol), trimethyl-[2-(3,4,5-trifluorophenyl)ethynyl]silane (113.46 mg, 0.50 mmol). The reaction mixture was stirred at 100° C. for 2 h. Water (80 mL) and DCM (80 mL) were added and the phases where separated. The aqueous phase was extracted with DCM (10 mL*2) and the combined organic phases were washed with water (20 mL) and brine (20 mL), dried over anhydrous sodium sulphate and removal of solvent in vacuo. The crude material was purified by column chromatography (PE/EtOAc=2/1) to obtain the title compound (100 mg, 45%).

i46) 3-chloro-4-cyanophenyl 2,4,6-tri-O-acetyl-3-azido-3-deoxy-1-thio-α-D-galactopyranoside

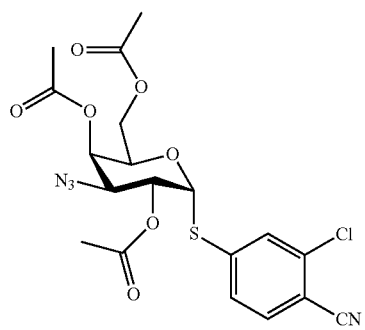

3-Chloro-4-cyanothiophenol 196 mg, 1.16 mmol) was dissolved in DMF (2 mL) followed by addition of NaH (58-62%, 50 mg, 1.30 mmol). The reaction mixture was stirred at r.t. for one hour followed by addition to a stirred solution of 2,4,6-tri-O-acetyl-3-azido-1-chloro-3-deoxy-β-D-galactopyranoside (280 mg, 0.80 mmol) in DMF (2 mL). The resulting mixture was heated to 55° C. for 100 minutes. EtOAc was added and the organics were washed four times with brine. The aqueous phase was extracted once with EtOAc and the combined organic phase was dried over Na₂SO₄ and the solvents where removed in vacuo. The residue was purified by flash chromatography (SiO₂, 0-60% EtOAc in petroleum ether to give the title compound, 98 mg as a white solid. ¹H NMR (400 MHz, Chloroform-d) δ 7.61-7.55 (m, 2H), 7.40 (dd, J=8.3, 1.6 Hz, 1H), 6.15 (d, J=5.5 Hz, 1H), 5.50-5.46 (m, 1H), 5.30 (dd, J=11.0, 5.6 Hz, 1H), 4.55-4.50 (m, 1H), 4.13 (dd, J=11.6, 4.9 Hz, 1H), 4.01 (dd, J=11.6, 7.7 Hz, 1H), 3.94 (dd, J=11.0, 3.2 Hz, 1H), 2.17 (s, 6H), 1.94 (s, 3H). ESI-MS m/z calcd for [C₁₉H₁₉ClN₄O₇SNa]⁺ (M+Na)⁺: 505.1; found: 505.0.

i47) 3-Chloro-6-fluoro-4-cyanophenyl 2,4,6-tri-O-acetyl-3-deoxy-3-[4-(3,4,5-trifluorophenyl)-1H-1,2,3-triazol-1-yl]-1-thio-α-D-galactopyranoside S-5-chloro-4-cyano-2-fluorophenyl O-ethyl carbonodithioate

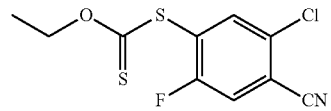 [SMILES: CCOC(=S)Sc1cc(Cl)c(C#N)cc1F]

4-amino-2-chloro-5-fluoro-benzonitrile (2.0 g, 11.73 mmol) was dissolved in 20 ml HCl at 0° C. Followed by slow addition of a water solution of NaNO₂ (810 mg, 11.73 mmol). The reaction mixture was stirred at 0° C. until the material was dissolved. The reaction mixture was filtered and slowly added to a 50° C. solution of Potassium ethyl xanthogenate (5.64 g, 35.18 mmol) in water (15 mL). The reaction mixture was stirred at 70° C. for 2 hours followed by extraction with EtOAc (100 mL*3). The combined organics were washed with brine, dried over $Na_2SO_4$, filtered and concentrated in vacuo to give 3.0 g of crude material which was used in the next step. ESI-MS m/z calcd for $[C_{10}H_8ClFNOS_2]^+$ (M+H)$^+$: 276.0; found: 276.0.

2-chloro-5-fluoro-4-mercaptobenzonitrile

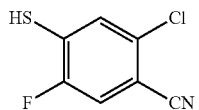 [SMILES: N#Cc1cc(F)c(S)cc1Cl]

O-ethyl (5-chloro-4-cyano-2-fluoro-phenyl)sulfanyl-methanethioate (1.0 g, 3.63 mmol) was dissolved in 20 mL ethanol and heated to 85° C. KOH (0.41 g, 7.25 mmol) was added slowly followed by stirring at 85° C. for 2 hours. After cooling to room temperature the reaction mixture was acidified to pH=4 using HCl (1M) followed by extraction with ethylacetate EtOAc (50 mL*3). The combined organic phases were washed with brine, dried over $Na_2SO_4$, filtered and concentrated in vacuo to give the title compound as a crude material, 1.0 g, which was used as is in the next step.

3-Chloro-6-fluoro-4-cyanophenyl 2,4,6-tri-O-acetyl-3-azido-3-deoxy-1-thio-α-D-galactopyranoside

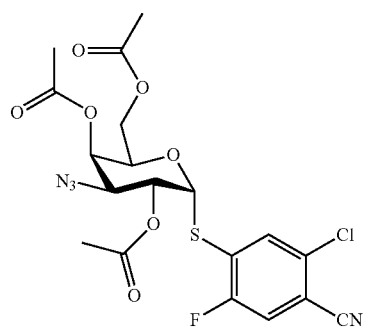

To a stirred solution of 2-chloro-5-fluoro-4-sulfanyl-benzonitrile (400 mg, 2.13 mmol) in DMF (5 ml), NaH (49 mg, 2.13 mmol) was added at 0° C. The reaction mixture was stirred at rt for 30 min followed by addition of 2,4,6-tri-O-acetyl-3-azido-1-chloro-3-deoxy-β-D-galactopyranoside (1.1 g, 3.41 mmol). The reaction mixture was stirred at 50° C. for 1 hour followed by removal of solvent in vacuo. The resulting crude was diluted with $CH_2Cl_2$ and washed with water and brine. The organic layer was dried over $Na_2SO_4$, filtered and the solvents where removed in vacuo. The crude product was purified by chromatography column (PE:EtOAc=3:1) to afford the title compound (130 mg, as white solid).

3-Chloro-6-fluoro-4-cyanophenyl 2,4,6-tri-O-acetyl-3-deoxy-3-[4-(3,4,5-trifluorophenyl)-1H-1,2,3-triazol-1-yl]-1-thio-α-D-galactopyranoside

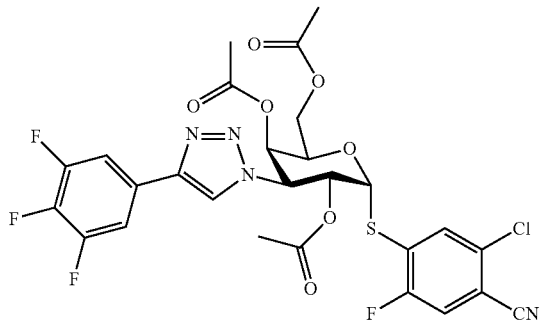

3-Chloro-6-fluoro-4-cyanophenyl 2,4,6-tri-O-acetyl-3-azido-3-deoxy-1-thio-α-D-galactopyranoside (130 mg, 0.26 mmol), trimethyl-[2-(3,4,5-trifluorophenyl)ethynyl]silane (120 mg, 0.52 mmol), Copper(I)Iodide (15 mg, 0.08 mmo) and Triethylamine (131 mg, 1.3 mmol) were added to a flask. DMF (3 mL) was added. The mixture was stirred at 100° C. for 1 hour under $N_2$ protection. Then the mixture was filtered and concentrated in vacuo. The residue was purified by flash chromatography to give title compound 160 mg. ESI-MS nm/z calcd for $[C_{27}H_{22}ClF_4N_4O_7S]^+$ (M+H)$^+$: 657.1; found: 657.1.

i48) 3-Bromo-4-cyanophenyl 2,4,6-tri-O-acetyl-3-deoxy-3-[4-(3,4,5-trifluorophenyl)-1H-1,2,3-triazol-1-yl]-1-thio-α-D-galactopyranoside 2-bromo-4-mercaptobenzonitrile

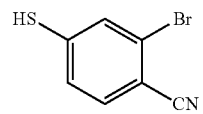

2-bromo-4-fluoro-benzonitrile (2 g, 10 mmol) was dissolved in DMF (5 mL). $Na_2S*10H_2O$ (2.58 g, 10 mmol) was added. The mixture was stirred at rt 1 h. Then 1M NaOH (100 mL) was added. The mixture was extracted by DCM (100 mL*2). Then the water phase was acided by 6 M HCl to pH=2. The mixture was extracted by DCM (200 mL*2). The organic phase was washed by brine, dried over $Na_2SO_4$, filtered and concentrated. The crude material was used for next step without further purification.

3-Bromo-4-cyanophenyl 2,4,6-tri-O-acetyl-3-azido-3-deoxy-1-thio-α-D-galactopyranoside

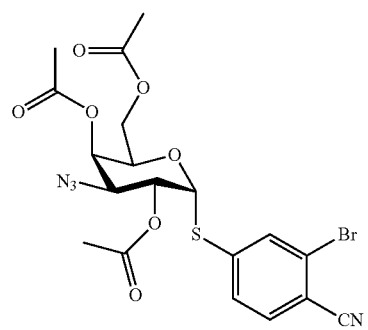

NaH (60%, 168.72 mg, 4.4 mmol) and 2-bromo-4-sulfanyl-benzonitrile (1 g crude) were added to a flask. DMF (5 mL) was added under $N_2$ protection at 0° C. The reaction mixture was stirred at 0° C. for 15 min. Then 2,4,6-tri-O-acetyl-3-azido-3-deoxy-1-thio-α-D-galactopyranoside (700 mg, 2 mmol) dissolved in DMF (5 ml) was added to the reaction mixture. The reaction was stirred at rt for 2 hours. EtOAc (200 ml) was added. The mixture was washed by water (100 mL), brine (100 mL), dried over $Na_2SO_4$, filtered and concentrated in vacuo. The residue was purified on silica gel column to give the title compound 240 mg (22.7%).

ESI-MS m/z calcd for $[CH_9H_{19}BrN_4NaO_7S]^+$ $(M+Na)^+$: 549.0; found: 549.0.

3-Bromo-4-cyanophenyl 2,4,6-tri-O-acetyl-3-deoxy-3-[4-(3,4,5-trifluorophenyl)-1H-1,2,3-triazol-1-yl]-1-thio-α-D-galactopyranoside

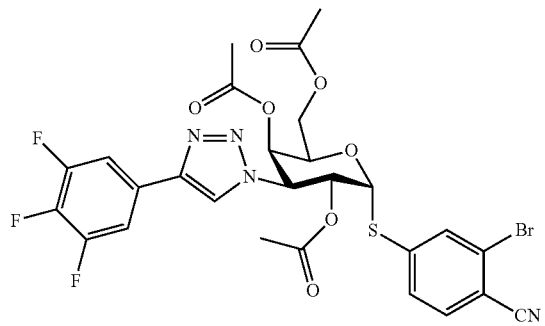

2,4,6-tri-o-acetyl-1-(3-bromo-4-cyanophenylthio)-3-azido-1,3-dideoxy-α-D-galactopyranoside (240 mg, 0.46 mmol), 2-(3,5-difluoro-4-methoxy-phenyl)ethynyl-trimethyl-silane (328.12 mg, 1.37 mmol), Copper(I)Iodide (26 mg, 0.14 mmol) and triethylamine (230.26 mg, 2.28 mmol) was dissolved in DMF (5 mL). The mixture was stirred at 100° C. for 1 hour. EtOAc (200 ml) was added. The mixture was filtered, washed by water (100 mL), dried by $Na_2SO_4$, filtered and concentrated. The residue was purified on silica gel column. 220 mg (70.7%) of the title compound was obtained.

ESI-MS m/z calcd for $[C_{27}H_{23}BrF_3N_4O_7S]^+$ $(M+H)^+$: 683.0; found: 683.1.

5-Bromo-6-trifluoromethyl-pyridin-3-yl 2,4,6-tri-O-acetyl-3-azido-3-deoxy-1-thio-α-D-galactopyranoside

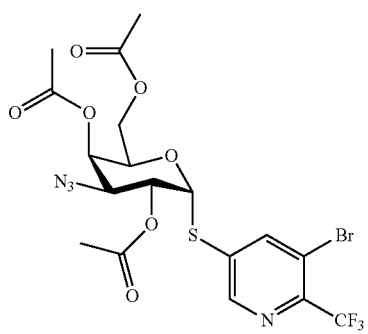

NaH (15.59 mg, 0.65 mmol) was added to a solution of 5-bromo-6-(trifluoromethyl)pyridine-3-thiol (140 mg, 0.54 mmol) in DMF (10 mL) at 0° C. The solution was stirred at rt for 30 min. Then 2,4,6-tri-O-acetyl-3-azido-1-chloro-3-deoxy-β-D-galactopyranoside (189.73 mg, 0.54 mmol) was added to mixture. The reaction was stirred at 50° C. for 2 h. The mixture was cooled to room temperature and water (20 mL) was added followed by extraction with EtOAc (15 mL×3). The combined organic layers were washed with brine, dried over $Na_2SO_4$ and concentrated in vacuo to afford crude product, which was purified by flash chromatography on a biotage (EtOAc/PE=5%~40%, ISCO 20 g, 15 mL/min, normal phase silica gel, uv 254) to afford crude 3-azido-1,3-dideoxy-2,4,6-tri-O-acetyl-1-(3-chloro-2-trifluoromethyl-pyridine-5-yl-thio)-α-D-galactopyranoside (70 mg, 22.58% yield).

ESI-MS m/z calcd for $[C_{18}H_{18}BrF_3N_4O_7S]^+$ $[M+H]^+$: 570.0; found: 571.0.

5-Bromo-6-trifluoromethyl-pyridin-3-yl 2,4,6-tri-O-acetyl-3-deoxy-3-[4-(3,4,5-trifluorophenyl)1H-1,2,3-triazol-1-yl]-1-thio-α-D-galactopyranoside

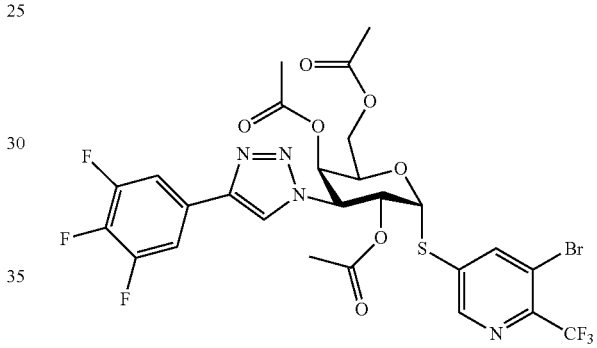

5-Bromo-6-trifluoromethyl-pyridin-3-yl 2,4,6-tri-O-acetyl-3-azido-3-deoxy-1-thio-α-D-galactopyranoside (70 mg, 0.12 mmol), trimethyl((3,4,5-trifluorophenyl)ethynyl)silane (27.97 mg, 0.12 mmol), CuI (7.0 mg, 0.04 mmol) and $Et_3N$ (18.60 mg, 0.18 mmol) were dissolved in DMF (10 mL) and the mixture was stirred at 50° C. for 2 h. Then the solvent was removed in vacuo to afford crude product (90 mg, >100% yield), which was used for next step without further purification.

ESI-MS m/z calcd for $[C_{26}H_{21}BrF_6N_4O_7S]^+$ $(M+H)^+$: 726.0; found: 727.0.

i50) 5-Chloro-6-cyano-pyridin-3-yl 2,4,6-tri-O-acetyl-3-deoxy-3-[4-(3,4,5-trifluorophenyl)-1H-1,2,3-triazol-1-yl]-1-thio-α-D-galactopyranoside 3-chloro-5-mercaptopicolinonitrile

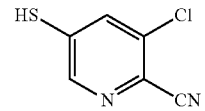

To a solution of 3,5-dichloropyridine-2-carbonitrile (50 mg, 0.29 mmol) in DMF (2 mL) was added $Na_2S$ (33.83 mg, 0.43 mmol). After completion of the reaction the mixture was added NaHSO₄ (aq) to adjust pH 4-5 followed by DCM (10 mL). The organic phase was washed with water (10 mL) and brine (10 mL), dried over anhydrous sodium sulphate. Removal of solvent gave the desired product (30 mg, crude).

m/z calcd for [C6H3ClN2S]⁻ [M−H]⁻: 169.0; found: 169.0.

5-Chloro-6-cyano-pyridin-3-yl 2,4,6-tri-O-acetyl-3-azido-3-deoxy-1-thio-α-D-galactopyranoside

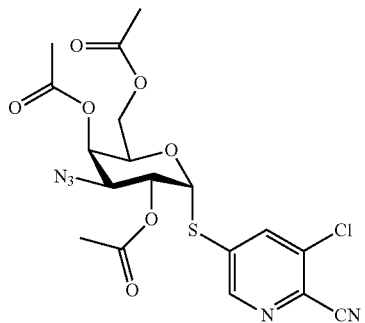

To a solution of 3-chloro-5-sulfanyl-pyridine-2-carbonitrile (30 mg, 0.17 mmol) in DMF (3 mL) was added NaH (3.94 mg, 0.17 mmol) at 0° C. After 10 min, 2,4,6-tri-O-acetyl-3-azido-1-chloro-3-deoxy-3-D-galactopyranoside (40 mg, 0.11 mmol) was added. The reaction mixture was stirred at room temperature for 4 h. Water (20 mL) and DCM (10 mL) were added. The aqueous phase was extracted with DCM (10 mL*2), and the combined organic phase was washed with water (20 mL), brine (20 mL), dried over anhydrous sodium sulphate and the solvents were removed in vacuo. The crude material was purified by flash chromatography (Petroleum Ether/EtOAc=3/1) to obtain the title compound (20 mg, 36.14%).

m/z calcd for [C18H18ClN5O7S]⁺ [M+H]⁺: 484.0; found: 484.0.

5-Chloro-6-cyano-pyridin-3-yl-2,4,6-tri-O-acetyl-3-deoxy-3-[4-(3,4,5-trifluorophenyl)-1H-1,2,3-triazol-1-yl]-1-thio-α-D-galactopyranoside

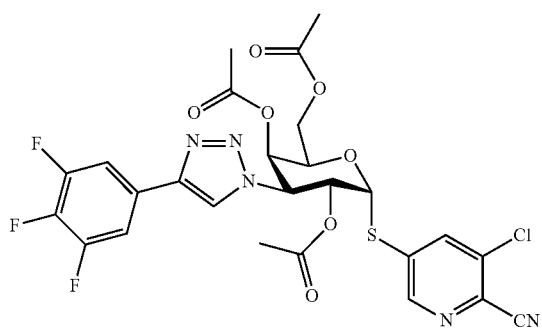

To a solution of 3-azido-1,3-dideoxy-2,4,6-tri-O-acetyl-1-(3-chloro-2-cyanopyridine-5-yl-thio)-α-D-galactopyranoside (20 mg, 0.04 mmol) in DMF (3 mL) were added TEA (20.91 mg, 0.21 mmol), Copper(I)Iodide (2.36 mg, 0.01 mmol), CsF (9.42 mg, 0.06 mmol), trimethyl-[2-(3,4,5-trifluorophenyl)ethynyl]silane(14.15 mg, 0.06 mmol). The reaction was stirred at room temperature for 2 h under N₂. Water (80 mL) and DCM (80 mL) were added. The aqueous phase was extracted with DCM (10 mL*2), the combined organic phase were washed with water (20 mL) and brine (20 mL), dried over anhydrous sodium sulphate followed by removal of the solvent in vacuo. The crude material was purified by column chromatography (Petroleum ether/Ethyl acetate=2/1) to obtain the title compound (12 mg, 45.36%).

m/z calcd for [C26H21ClF3N5O7S]⁺ [M+H]⁺: 640.0; found: 640.0.

i51) 5-Hydroxy-6-cyano-pyridazin-3-yl 2,4,6-tri-O-acetyl-3-deoxy-3-[4-(3,4,5-trifluorophenyl)-1H-1,2,3-triazol-1-yl]-1-thio-α-D-galactopyranoside Diethyl 2-diazo-3-oxopentanedioate

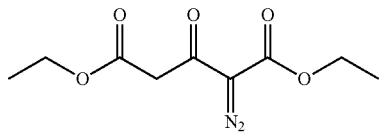

To a mixture of diethyl 3-oxopentanedioate (5 g, 24.73 mmol) and TEA (3.8 ml) in CH₃CN (100 ml) at 0° C. was added N-(4-azidosulfonylphenyl)acetamide (5.9 g, 24.73 mmol) in several portions. The reaction was stirred at room temperature for 1 h followed by filtration. The filter was washed with 1:1 hexane: ether and the filtrate was stirred on an ice bath for 30 min upon formation of additional precipitate. This was filtered off and the filter and washed with 1:1 hexane:ether. The filtrates where combined and the solvents where removed in vacuo to give the title compound as a yellow oil. (5.5 g, 97.47%)

m/z calcd for [C9H12N2O5]⁺ [M−N2]⁺: 200.0; found: 200.0.

ethyl 4,6-dihydroxypyridazine-3-carboxylate

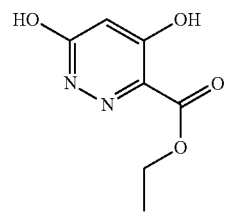

A mixture of diethyl 2-diazo-3-oxo-pentanedioate (1 g, 4.38 mmol) and PPh₃ (1.15 g, 4.38 mmol) in ether (50 ml) was stirred at room temperature for 48 h. Ether was removed in vacuo and HOAc (50 ml) and water (5 ml) was added to the residue. The mixture was refluxed for 10 h under N₂. The solvent was removed in vacuo to dryness. The residue was purified by column chromatography (DCM/MEOH=10/1) to obtain the desired product (2.1 g, 47%).

m/z calcd for [C7H8N2O4]⁺ [M+H]⁺: 185.0; found: 185.0.

4,6-dihydroxypyridazine-3-carboxamide

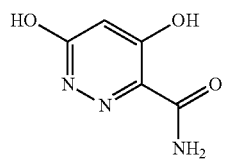

To a solution of ethyl 4,6-dihydroxypyridazine-3-carboxylate (2.1 g, 11.40 mmol) in 40 ml NH$_3$—CH$_3$OH was held at room temperature with stirring on for 20 h under N$_2$. The solvents were removed in vacuo, and the residue was used to next step directly. m/z calcd for [C5H5N3O3]$^+$ [M+H]$^+$: 156.0; found: 156.0.

4,6-dichloropyridazine-3-carbonitrile

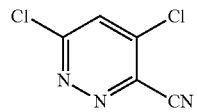

To a solution of 4,6-dihydroxypyridazine-3-carboxamide (800 mg, 5.16 mmol) in POCl$_3$ (10 mL) was stirred at 100° C. for 3 h under N$_2$. The reaction mixture was poured into ice water and extracted with DCM (40 ml*2). The combined organic phase was washed with brine (50 mL), dried over anhydrous sodium sulphate. Removal of solvent gave a residue. The residue was purified by column chromatography (PE/EtOAc=10/1) to obtain 4,6-dichloropyridazine-3-carbonitrile (280 mg).
m/z calcd for [C5HCl2N3]$^+$ [M+H]$^+$: 174.0; found: 174.0.

1,2,4,6-tetra-O-acetyl-1-3-deoxy-3-[4-(3,4,5-trifluorophenyl)-1H-1,2,3-triazol-1-yl]-β-D-galactopyranoside

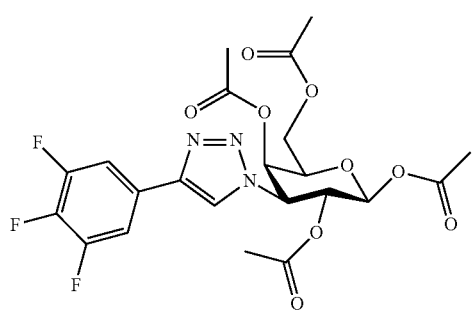

To a solution of 1,2,4,6-tetra-O-acetyl-3-azido-3-deoxy-β-D-galactopyranoside (2.00 g, 5.36 mmol) in DMF (20 mL) were added TEA (2.71 g, 26.80 mmol), Copper(I) Iodide (306.16 mg, 1.61 mmol), trimethyl-[2-(3,4,5-trifluorophenyl)ethynyl]silane(1.83 g, 8.04 mmol). The reaction was held at 100'C with stirring on for 2 h under N$_2$. Water (80 mL) and DCM (80 mL) were added. The aqueous phase was extracted with DCM (10 mL*2), the combined organic phase was washed with water (20 mL) and brine (20 mL), dried over anhydrous sodium sulphate. Removal of solvent gave a residue. The residue was purified by column chromatography (PE/EtOAc=2/1) to obtain title compound (2 g, 71%).

2,4,6-tri-O-acetyl-1-chloro-3-deoxy-3-[4-(3,4,5-trifluorophenyl)-1H-1,2,3-triazol-1-yl]-β-D-galactopyranoside

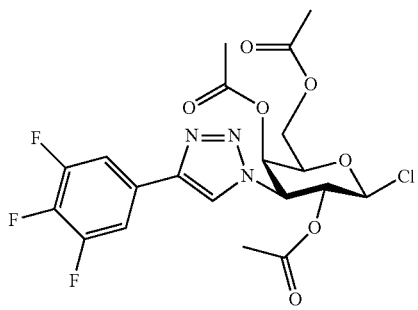

To a stirred suspension of 1,2,4,6-tetra-O-acetyl-1-3-deoxy-3-[4-(3,4,5-trifluorophenyl)-1H-1,2,3-triazol-1-yl]-β-D-galactopyranoside (2.00 g, 3.78 mmol) and PCl$_5$ (1.56 g, 7.56 mmol) in dry DCM (20 mL), BF$_3$-Et$_2$O (2 mL) was added. After stirring for 2 h, TLC analysis showed complete disappearance of the starting material. The reaction mixture was diluted with DCM (50 mL) and then washed with ice-cold water, sat. ice-cold NaHCO$_3$ solution (2×50 mL), and again ice-cold water successively, dried over anhydrous Na$_2$SO$_4$ and evaporated under reduced pressure to afford the crude product 1 g as a white solid. Which was used directly in the next step.

Acetyl 2,4,6-tri-O-acetyl-3-deoxy-3-[4-(3,4,5-trifluorophenyl)-1H-1,2,3-triazol-1-yl]-1-thio-α-D-galactopyranoside

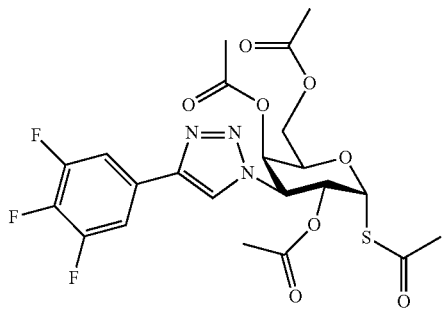

To a solution of 2,4,6-tri-O-acetyl-1-chloro-3-deoxy-3-[4-(3,4,5-trifluorophenyl)-1H-1,2,3-triazol-1-yl]-1-D-galactopyranoside (1.00 g, 1.98 mmol) in DMF (10 mL) were added Potassium thioacetate (452.31 mg, 3.96 mmol). The reaction mixture was stirred at room temperature for 20 h. Water (40 mL) and DCM (40 mL) were added. The aqueous phase was extracted with DCM (40 mL*2), and the combined organic phase was washed with water (50 mL) and brine (50 mL), dried over anhydrous sodium sulphate and evaporated to dryness. The crude products were purified by flash column chromatography (PE/EtOAc=3/2) to obtain title compound (450 mg, 42%).

2,4,6-tri-O-acetyl-3-deoxy-3-[4-(3,4,5-trifluorophenyl)-1H-1,2,3-triazol-1-yl]-1-thio-α-D-galactopyranoside

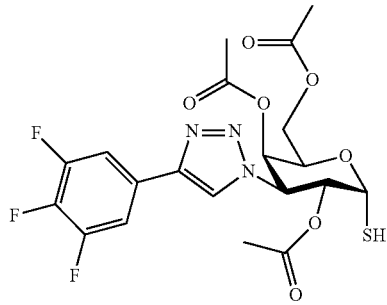

To a solution of Acetyl 2,4,6-tri-O-acetyl-3-deoxy-3-[4-(3,4,5-trifluorophenyl)-1H-1,2,3-triazol-1-yl]-1-thio-α-D-galactopyranoside (200 mg, 0.36 mmol) in DCM/methanol (30 mL) was cooled to 0° C. under $N_2$. Then sodium thiomethoxide (25.68 mg, 0.36 mmol) were added. The reaction mixture was stirred at 0° C. for 30 min. The pH was adjusted to 5-6 with d 0.3M HCl aq. The organic layer was washed with water (60 mL) and brine (60 mL), dried over anhydrous sodium sulphate. Removal of solvent gave the crude product (160 mg).

m/z calcd for $[C_{20}H_{20}F_3N_3O_7S]^+$ $[M+H]^+$: 504.0; found: 504.0.

5-Hydroxy-6-cyano-pyridazin-3-yl 2,4,6-tri-O-acetyl-3-deoxy-3-[4-(3,4,5-trifluorophenyl)-1H-1,2,3-triazol-1-yl]-1-thio-α-D-galactopyranoside

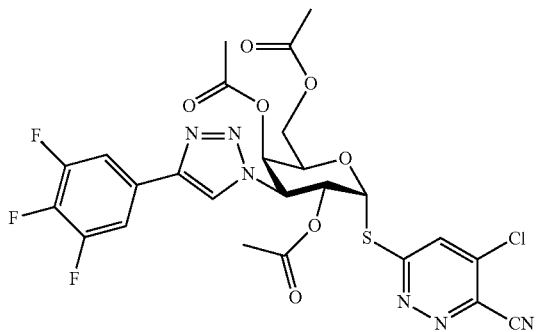

To a solution of 1,3-dideoxy-2,4,6-tri-O-acetyl-1-mercapto-3-[4-(3,4,5-trifluorophenyl)-1H-1,2,3-triazol-1-yl]-α-D-galactopyranoside (160 mg, 0.32 mmol) in DMF (20 mL) was added 4,6-dichloropyridazine-3-carbonitrile (82.96 mg, 0.48 mmol) at ice bath under $N_2$. Then NaH (10.96 mg, 0.48 mmol) was added. The mixture was held at room temperature with stirring for 4 h. Water (40 mL) and DCM (20 mL) were added. The aqueous phase was extracted with DCM (20 mL*2), the combined organic phase was washed with water (40 mL) and brine (40 mL), dried over anhydrous sodium sulphate and the solvents were removed in vacuo. The crude material was purified by purified by column chromatography (PE/EtOAc=2/1) to obtain the desired product (42 mg, 20%).

m/z calcd for $[C_{25}H_{20}ClF_3N_6O_7S]^+$ $[M+H]^+$: 641.0; found: 641.0.

Example 56

3-Chloro-2,4-difluorophenyl 3-deoxy-1-thio-3-[4-(3,4,5-trifluorophenyl)-1H-1,2,3-triazol-1-yl]-α-D-galactopyranoside

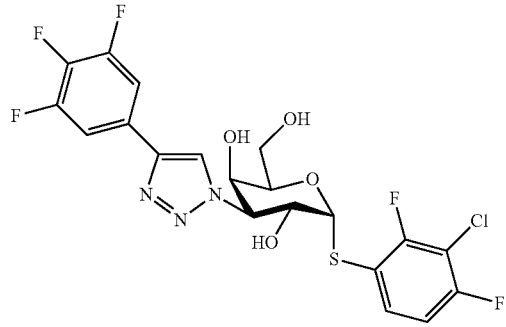

3-Chloro-2,4-difluoro-benzenethiol (110 mg) was dissolved in DMF (1 mL). Sodium hydride (54 mg, ca 60% in mineral oil) was added followed by 2,4,6-tri-O-acetyl-3-azido-1-chloro-3-deoxy-3-D-galactopyranosid (135 mg) dissolved in DMF (2 mL). The mixture was heated to 50° C. 1 h and then stirred at r.t. over night. It was partitioned between $Et_2O$ (100 mL) and water (3×150 mL). The organic phase was purified by flash chromatography ($SiO_2$, 5-95% EtOAc in heptane). This afforded the intermediate thioglycoside as an oil (96 mg). Copper(I) iodide (10 mg), 3,4,5-triflourophenylacetylene (0.080 mL) and DIEA (0.200 mL) were added and the resulting mixture stirred 2.5 h at r.t. The mixture was concentrated in vacuo. The residue was dissolved/suspended in EtOAc (5 mL) and filtered through a short column of silica. The solvent was removed in vacuo and the residue was dissolved in MeOH (20 mL). 1 M sodium methoxide in MeOH (2 mL) was added and the mixture left at r.t. over night. The mixture was concentrated in vacuo and the residue was dissolved in small volume MeCN/water, filtered and purified by HPLC ($C_{18}$/$H_2O$: MeCN:0.1% TFA). Freezedrying afforded the product as a white powder (63 mg). $^1$H NMR (400 MHz, Methanol-$d_4$) δ 8.54 (s, 1H), 7.74-7.58 (m, 3H), 7.14 (td, J=8.7, 1.8 Hz, 11H), 5.88 (d, J=5.4 Hz, 1H), 5.07 (dd, J=11.3, 2.8 Hz, 1H), 4.92 (dd, J=11.3, 5.4 Hz, 1H), 4.44 (t, J=6.2 Hz, 1H), 4.22 (d, J=2.8 Hz, 1H), 3.66 (dd, J=11.4, 5.9 Hz, 1H), 3.55 (dd, J=11.4, 6.4 Hz, 1H). ESI-MS m/z calcd for $[C_{20}H_{16}ClF_5N_3O_4S]^+$ $(M+H)^+$: 524.04; found: 524.00.

Example 57

3,4-Dichlorophenyl 3-deoxy-3-[4-(phenyl)-1H-1,2,3-triazol-1-yl]-1-thio-α-D-galactopyranoside

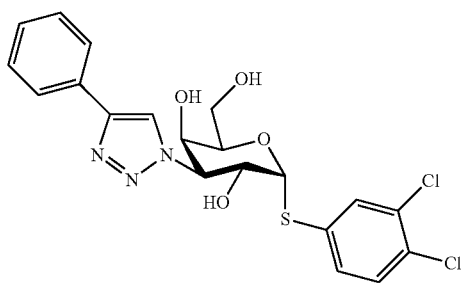

To a stirred solution of 2,4,6-tri-O-acetyl-3-deoxy-3-[4-(phenyl)-1-thio-α-D-galactopyranoside (100 mg) in MeOH (5 mL), NaOMe (9 mg) was added. The mixture was stirred at r.t. for 2 hours. Then the mixture was purified by reverse-phase chromatography to give 40 mg (50.8%) of 3,4-Dichlorophenyl 3-deoxy-3-[4-(phenyl)-1H-1,2,3-triazol-1-yl]-1-thio-α-D-galactopyranoside.

$^1$H NMR (400 MHz, DMSO) δ 8.58 (s, 1H), 7.92-7.86 (m, 2H), 7.84 (d, J=2.1 Hz, 1H), 7.60 (d, J=8.4 Hz, 1H), 7.53 (dd, J=8.4, 2.1 Hz, 1H), 7.45 (t, J=7.7 Hz, 2H), 7.33 (t, J=7.4 Hz, 1H), 5.89 (dd, J=19.3, 4.3 Hz, 2H), 5.48 (d, J=6.5 Hz, 1H), 4.87-4.75 (m, 2H), 4.71 (t, J=5.6 Hz, 1H), 4.25 (t, J=6.1 Hz, 1H), 4.04 (d, J=6.4 Hz, 1H), 3.60-3.50 (m, 1H), 3.48-3.37 (m, 1H). ESI-MS m/z calcd for $[C_{20}H_{20}Cl_2N_3O_4S]^+$ (M+H)$^+$: 468.1; found: 468.0.

Example 58

3,5-Dichloro-4-fluorophenyl 3-deoxy-3-[4-(3,4,5-trifluorophenyl)-1H-1,2,3-triazol-1-yl]-1-thio-α-D-galactopyranoside

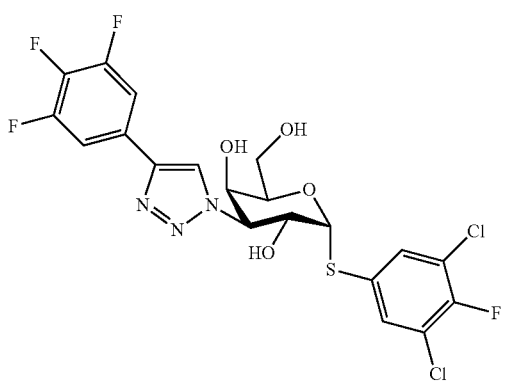

3,5-Dichloro-4-fluorophenyl 2,4,6-tri-O-acetyl-3-azido-3-deoxy-1-thio-α-D-galactopyranoside (50 mg, 0.1 mmol), trimethyl-[2-(3,4,5-trifluorophenyl)ethynyl]silane (43.87 mg, 0.2 mmol), Copper(I)Iodide (6 mg, 0.03 mmo) and triethylamine (49 mg, 0.48 mmol) were added to a flask. DMF (2.5 mL) was added. The mixture was stirred at 50° C. for 1 h under N$_2$ protection. LCMS showed that the target product was formed and no SM left. The mixture was filtered and concentrated in vacuum to afford crude intermediate. This was dissolved in MeOH (5 mL) and cooled to 0° C. followed by addition of sodium methoxide (5.0 mg, 0.09 mmol). The mixture was stirred at room temperature for 30 min. LCMS showed that the target product was formed and no SM left. Then the mixture was acidified with dowex 50 wx8 hydrogen form to PH=5~6. The solution was filtered and concentrated in vacuo to afford crude product, which was purified by Prep-HPLC to afford give the title compound (40 mg).

$^1$H NMR (400 MHz, CDCl$_3$) δ 8.12 (s, 1H), 7.53 (d, J=6.1 Hz, 2H), 7.49-7.40 (m, 2H), 5.83 (d, J=5.3 Hz, 1H), 4.97-4.86 (m, 1H), 4.74-4.67 (m, 1H), 4.66-4.59 (m, 1H), 4.49-4.42 (m, 1H), 4.42-4.31 (m, 1H), 4.06 (tt, J=12.2, 5.9 Hz, 2H).

ESI-MS m/z calcd for $[C_{20}H_{15}Cl_2F_4N_3O_4S]^+$ (M+H)$^+$: 539.0; found: 540.0.

Example 59

3,4-Dichloro-6-fluorophenyl 3-deoxy-3-[4-(3,4,5-trifluorophenyl)-1H-1,2,3-triazol-1-yl]-1-thio-α-D-galactopyranoside

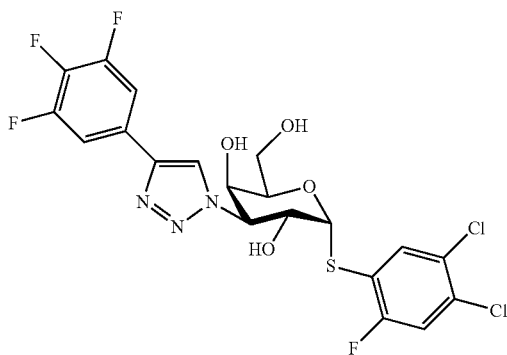

Sodium methoxide (4 mg, 0.07 mmol) was added to a stirred solution of 3,4-Dichloro-6-fluorophenyl 2,4,6-tri-O-acetyl-3-deoxy-3-[4-(3,4,5-trifluorophenyl)-1H-1,2,3-triazol-1-yl]-1-thio-α-D-galactopyranoside (150 mg, 0.23 mmol) in MeOH (5 mL) at 0° C. The mixture was stirred at room temperature for 1 h. LCMS showed no SM. The mixture was acidified with dowex 50 wx8 hydrogen form to PH=5~6. The solution was filtered and concentrated in vacuo to afford crude product, which was purified by preparative HPLC to afford the title compound (50 mg).

$^1$H NMR (400 MHz, DMSO) δ 8.82 (s, 1H), 7.99 (d, J=7.1 Hz, 1H), 7.97-7.82 (m, 2H), 7.77 (d, J=9.0 Hz, 1H), 6.14-5.96 (m, 2H), 5.53 (d, J=6.3 Hz, 1H), 4.89 (dd, J=11.3, 2.7 Hz, 1H), 4.81-4.72 (m, 1H), 4.67 (t, J=5.5 Hz, 1H), 4.18 (t, J=6.3 Hz, 1H), 4.07-4.00 (m, 1H), 3.55-3.42 (m, 1H), 3.42-3.34 (m, 1H) ESI-MS m/z calcd for $[C_{20}H_{15}Cl_2F_4N_3O_4S]^+$ (M+H)$^+$: 539.0; found: 540.0.

Example 60

3-Bromo-4-fluorophenyl 3-deoxy-3-[4-(3,4,5-trifluorophenyl)-1H-1,2,3-triazol-1-yl]-1-thio-α-D-galactopyranoside

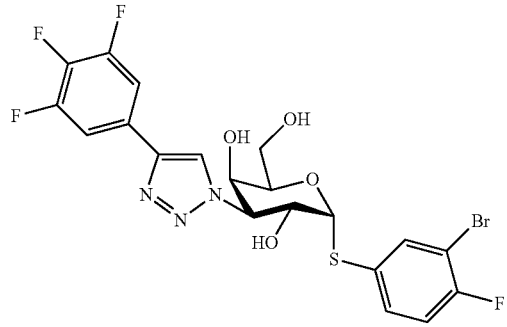

To a solution of 3-Bromo-4-fluorophenyl 2,4,6-tri-O-acetyl-3-deoxy-3-[4-(3,4,5-trifluorophenyl)-1H-1,2,3-triazol-1-yl]-1-thio-α-D-galactopyranoside (250 mg, 0.37 mmol) in methanol (10 mL) were added sodium methoxide (6.79 mg, 0.13 mol). The reaction was held at room temperature with stirring on for 2 h. The reaction mixture was evaporated to dryness. The crude product was purified by preparative HPLC to afford 3-Bromo-4-fluorophenyl 3-deoxy-3-[4-(3,4,5-trifluorophenyl)-1H-1,2,3-triazol-1-yl]-1-thio-α-D-galactopyranoside (40 mg, 36.15%) as a white solid.

$^1$H NMR (400 MHz, DMSO) δ 8.80 (s, 1H), 8.10-7.73 (m, 3H), 7.72-7.54 (m, 1H), 7.38 (t, J=8.7 Hz, 1H), 5.99-5.71 (m, 2H), 5.52 (d, J=6.3 Hz, 1H), 4.84-4.69 (m, 2H), 4.30 (t, J=6.0 Hz, 1H), 4.03 (d, J=4.2 Hz, 1H), 3.63-3.50 (m, 1H), 3.50-3.38 (m, 1H).

m/z calcd for [C20H16BrF4N3O4S]$^+$ [M+H]$^+$: 550.0; found: 550.0.

Example 61

3-Chloro-4-(trifluoromethyl)phenyl 3-deoxy-1-thio-3-[4-(3,4,5-trifluorophenyl)-1H-1,2,3-triazol-1-yl]-α-D-galactopyranoside

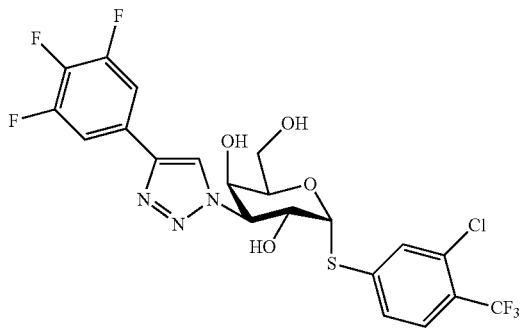

3-Chloro-4-(trifluoromethyl)phenyl 2,4,6-tri-O-acetyl-3-azido-3-deoxy-1-thio-α-D-galactopyranoside (32 mg) was dissolved in MeCN (3 mL) and stirred at r.t. under argon. Copper(I) iodide (20 mg) was added and after five minutes 1,2,3-trifluoro-5-[2-(trimethylsilyl)ethynyl]benzen (0.026 mL) was added. After an additional five minutes DIEA (0.011 mL) was added and the mixture was heated to 70° C. After 5 h the reaction mixture was filtered through a short column of silica, eluting with EtOAc and then concentrated in vacuo. The crude product was dissolved in methanolic NaOMe (0.05M, 10 mL) and stirred at r.t. After 18 h acetic acid (2 mL) was added and the mixture was concentrated in vacuo. The crude product was purified by preparative HPLC (C$_{18}$/H$_2$O:MeCN:0.1% TFA) and lyophilized to give 10 mg of 3-chloro-4-(trifluoromethyl)phenyl 3-deoxy-1-thio-3-[4-(3,4,5-trifluorophenyl)-1H-1,2,3-triazol-1-yl]-α-D-galactopyranoside. $^1$H NMR (400 MHz, Methanol-d$_4$) δ 8.55 (s, 1H), 7.84 (s, 1H), 7.74-7.61 (m, 4H), 6.05 (d, J=5.0 Hz, 1H), 4.98 (qd, J=11.4, 3.7 Hz, 2H), 4.43 (t, J=6.1 Hz, 1H), 4.20 (s, 1H), 3.71 (tt, J=11.4, 6.3 Hz, 2H). ESI-MS m/z calcd for [C$_{21}$H$_{17}$ClF$_3$N$_3$O$_4$S]$^+$ (M+H)$^+$: 556.1; found: 556.0.

Example 62

3,4,5-Trichlorophenyl 3-deoxy-1-thio-3-[4-(3,4,5-trifluorophenyl)-1H-1,2,3-triazol-1-yl]-α-D-galactopyranoside

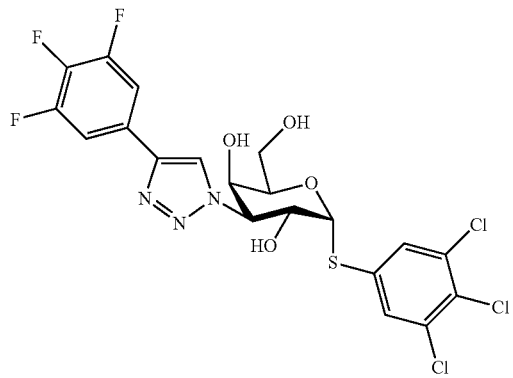

3,4,5-Trichlorophenyl 2,4,6-tri-O-acetyl-3-azido-3-deoxy-1-thio-α-D-galactopyranoside (64 mg) was dissolved in MeCN (5 mL) and stirred at r.t. under argon. Copper(I) iodide (18 mg) was added and after five minutes 1,2,3-trifluoro-5-[2-(trimethylsilyl)ethynyl]benzen (0.051 mL) was added. After an additional five minutes DIEA (0.022 mL) was added and the mixture was heated to 70° C. After 2 h 1,2,3-trifluoro-5-[2-(trimethylsilyl)ethynyl]benzen (0.051 mL) was added and the temperature decreased to 50° C. After 16 h the reaction mixture was filtered through a short column of silica, eluting with EtOAc and then concentrated in vacuo. The crude product was dissolved in methanolic NaOMe (0.05M, 20 mL) and stirred at r.t. After 2.5 h acetic acid (2 mL) was added and the mixture was concentrated in vacuo. The crude product was purified by preparative HPLC (C$_{18}$/H$_2$O:MeCN:0.1% TFA) and lyophilized to give 43 mg (64%) of 3,4,5-trichlorophenyl 3-deoxy-1-thio-3-[4-(3,4,5-trifluorophenyl)-1H-1,2,3-triazol-1-yl]-α-D-galactopyranoside. $^1$H NMR (400 MHz, Methanol-d$_4$) δ 8.54 (s, 1H), 7.76 (s, 2H), 7.69-7.60 (m, 2H), 5.92 (d, J=4.9 Hz, 1H), 5.03-4.89 (m, 2H), 4.46 (t, J=6.0 Hz, 1H), 4.20 (s, 1H), 3.79-3.65 (m, 2H). ESI-MS m/z calcd for [C$_{20}$H$_{16}$Cl$_3$F$_3$N$_3$O$_4$S]$^+$ (M+H)$^+$: 556.0; found: 556.0.

Example 63

5-Chloro-2-fluorophenyl 3-deoxy-1-thio-3-[4-(3,4,5-trifluorophenyl)-1H-1,2,3-triazol-1-yl]-α-D-galactopyranoside

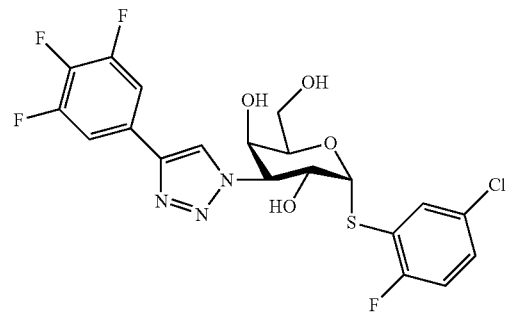

5-Chloro-2-fluorophenyl 2,4,6-tri-O-acetyl-3-azido-3-deoxy-1-thio-α-D-galactopyranoside (87 mg) was dissolved in MeCN (6 mL) and stirred at r.t. under $N_2$. Copper(I) iodide (13 mg) was added and after five minutes 1,2,3-trifluoro-5-[2-(trimethylsilyl)ethynyl]benzen (0.080 mL) was added. After an additional five minutes DIEA (0.035 mL) was added and the mixture was stirred at r.t. After 18 h the mixture was heated to 70° C. After 6 h the reaction mixture was filtered through a short column of silica, eluting with EtOAc and then concentrated in vacuo. The crude product was dissolved in methanolic NaOMe (0.05M, 20 mL) and stirred at r.t. After 18 h acetic acid (2 mL) was added and the mixture was concentrated in vacuo. The crude product was purified by preparative HPLC ($C_{18}$/$H_2$O:MeCN:0.1% TFA) and lyophilized to give 71 mg of 5-chloro-2-fluorophenyl 3-deoxy-1-thio-3-[4-(3,4,5-trifluorophenyl)-1H-1,2,3-triazol-1-yl]-α-D-galactopyranoside. $^1$H NMR (400 MHz, Methanol-d4) δ 8.55 (s, 1H), 7.73 (d, J=6.1 Hz, 1H), 7.65 (t, J=7.2 Hz, 2H), 7.39-7.29 (m, 1H), 7.15 (t, J=8.8 Hz, 1H), 5.95 (d, J=5.3 Hz, 1H), 5.06 (d, J=11.4 Hz, 1H), 4.94 (dd, J=11.2, 5.2 Hz, 1H), 4.44 (t, J=6.0 Hz, 1H), 4.23 (s, 1H), 3.68 (dd, J=11.1, 6.2 Hz, 1H), 3.57 (dd, J=11.2, 6.2 Hz, 1H). $^{13}$C NMR (101 MHz, Methanol-$d_4$) δ 163.6, 154.1, 151.7, 141.7, 139.3, 135.3, 130.6, 130.5, 123.6, 123.0, 118.1, 117.8, 110.9, 110.7, 89.6, 73.2, 69.5, 66.7, 65.4, 61.8. ESI-MS m/z calcd for $[C_{20}H_{17}ClF_4N_3O_4S]^+$ $(M+H)^+$: 506.1; found: 506.0.

Example 64

5-Bromo-2-fluorophenyl 3-deoxy-1-thio-3-[4-(3,4,5-trifluorophenyl)-1H-1,2,3-triazol-1-yl]-α-D-galactopyranoside

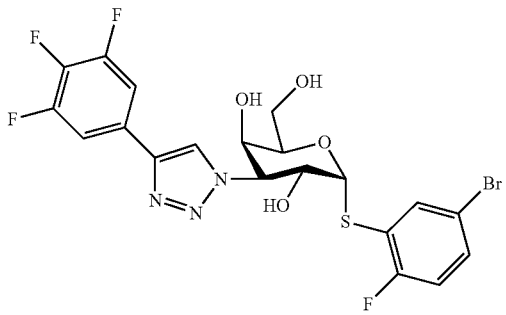

To a solution of 5-Bromo-2-fluorophenyl 2,4,6-tri-O-acetyl-3-deoxy-3-[4-(3,4,5-trifluorophenyl)-1H-1,2,3-triazol-1-yl]-1-thio-α-D-galactopyranoside (170 mg, 0.25 mol) in methanol (10 mL) were added sodium methoxide (6.79 mg, 0.13 mol). The reaction was held at room temperature with stirring on for 2 h. The reaction mixture was evaporated to dryness. The crude product was purified by preparative HPLC to afford 5-Bromo-2-fluorophenyl 3-deoxy-1-thio-3-[4-(3,4,5-trifluorophenyl)-1H-1,2,3-triazol-1-yl]-α-D-galactopyranoside (50 mg, 36.15%) as a white solid.

$^1$H NMR (400 MHz, MeOD) δ 8.57 (s, 1H), 7.89 (dd, J=6.4, 2.4 Hz, 1H), 7.72-7.63 (m, 2H), 7.58-7.46 (m, 1H), 7.12 (t, J=8.9 Hz, 1H), 5.95 (d, J=5.4 Hz, 1H), 5.16-5.02 (m, 1H), 4.98-4.93 (m, 1H), 4.46 (t, J=6.1 Hz, 1H), 4.23 (d, J=2.0 Hz, 1H), 3.79-3.64 (m, 1H), 3.64-3.54 (m, 1H).

m/z calcd for $[C20H16BrF4N3O4S]^+$ $[M+H]^+$: 550.0; found: 550.0.

Example 65

5-Chloro-2-methoxyphenyl 3-deoxy-1-thio-3-[4-(3,4,5-trifluorophenyl)-1H-1,2,3-triazol-1-yl]-α-D-galactopyranoside

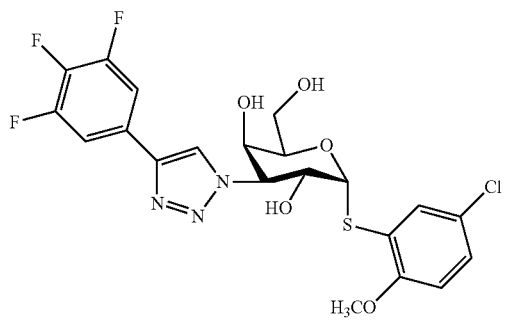

5-Chloro-2-methoxyphenyl 2,4,6-tri-O-acetyl-3-azido-3-deoxy-1-thio-α-D-galactopyranoside (59 mg) was dissolved in MeCN (5 mL) and stirred at r.t. under $N_2$. Copper(I) iodide (13 mg) was added and after five minutes 3,4,5-trifluorophenylacetylene (0.040 mL) was added. After an additional five minutes DIEA (0.022 mL) was added and the mixture was stirred at r.t. After 18 h the reaction mixture was filtered through a short column of silica, eluting with EtOAc and then concentrated in vacuo. The crude product was dissolved in methanolic NaOMe (0.05M, 20 mL) and stirred at r.t. After 5.5 h acetic acid (2 mL) was added and the mixture was concentrated in vacuo. The crude product was purified by preparative HPLC ($C_{18}$/$H_2$O:MeCN:0.1% TFA) and lyophilized to give 31 mg of 5-chloro-2-methoxyphenyl 3-deoxy-1-thio-3-[4-(3,4,5-trifluorophenyl)-1H-1,2,3-triazol-1-yl]-α-D-galactopyranoside. $^1$H NMR (400 MHz, Methanol-$d_4$) δ 8.54 (s, 1H), 7.70-7.58 (m, 3H), 7.27 (dd, J=8.8, 2.5 Hz, 1H), 6.98 (d, J=8.8 Hz, 1H), 5.96 (d, J=5.4 Hz, 1H), 5.07 (dd, J=11.3, 2.8 Hz, 1H), 4.92 (dd, J=11.4, 5.4 Hz, 1H), 4.45 (t, J=6.2 Hz, 1H), 4.22 (d, J=2.1 Hz, 1H), 3.89 (s, 3H), 3.68 (dd, J=11.1, 6.6 Hz, 1H), 3.54 (dd, J=11.2, 6.0 Hz, 1H). $^{13}$C NMR (101 MHz, Methanol-$d_4$) δ 159.1, 133.8, 129.4, 126.7, 124.6, 123.0, 113.2, 110.9, 110.7, 88.4, 72.9, 69.5, 66.8, 65.5, 61.7, 56.7. ESI-MS m/z calcd for $[C_{21}H_{20}ClF_3N_3O_5S]^+$ $(M+H)^+$: 518.1; found: 518.0.

Example 66

3-Iodophenyl 3-deoxy-1-thio-3-[4-(3,4,5-trifluorophenyl)-1H-1,2,3-triazol-1-yl]-α-D-galactopyranoside

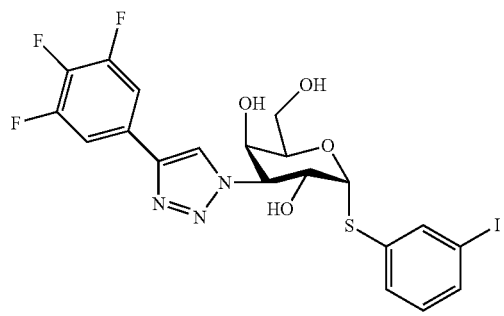

3-Iodophenyl 2,4,6-tri-O-acetyl-3-azido-3-deoxy-1-thio-α-D-galactopyranoside (50 mg) was dissolved in MeCN (10 mL). Copper(I) iodide (5 mg) and 3,4,5-trifluorophenylacetylene (0.100 mL) were added and the mixture degassed (N₂). Cesium fluoride (21 mg) was added and after 5 min, DIEA (0.200 mL) was added and the resulting mixture stirred 4 h. It was then filtered through a small plug of silica and concentrated in vacuo. The residue was suspended in MeOH (40 mL). 1M sodium methoxide in MeOH (1 mL) was added. After stirring at r.t. 2 h, acetic acid (1 mL) was added and the mixture concentrated in vacuo. The residue was dissolved in a small volume MeCN/water, filtered and purified by HPLC ($C_{18}$/$H_2O$:MeCN:0.1% TFA). Freezedrying afforded the title compound as a white powder (38 mg). $^1$H NMR (400 MHz, Methanol-$d_4$) δ 8.54 (s, 1H), 7.98 (t, J=1.6 Hz, 1H), 7.71-7.58 (m, 3H), 7.10 (t, J=7.9 Hz, 1H), 5.80 (d, J=5.2 Hz, 1H), 4.98 (dd, J=11.4, 2.8 Hz, 1H), 4.91 (dd, J=11.4, 5.1 Hz, 1H), 4.52 (t, J=6.2 Hz, 1H), 4.21 (d, J=2.7 Hz, 1H), 3.72 (qd, J=11.4, 6.1 Hz, 2H). ESI-MS m/z calcd for $[C_{20}H_{18}F_3IN_3O_4S]^+$ (M+H)$^+$: 579.99; found: 579.95.

Example 67

Picolinamide-5-yl 3-deoxy-3-[4-(3,4,5-trifluorophenyl)-1H-1,2,3-triazol-1-yl]-1-thio-α-D-galactopyranoside

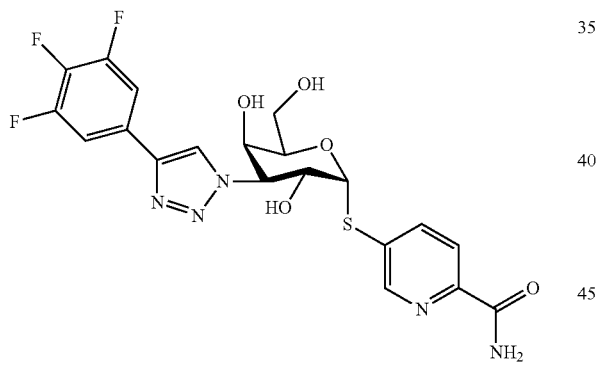

To a solution of 2-cyanopyridine-5-yl 3-deoxy-3-[4-(3,4,5-trifluorophenyl)-1H-1,2,3-triazol-1-yl]-1-thio-α-D-galactopyranoside (1.2 g, 1.98 mmol) in i-MeOH/Et₃N/H₂O (10/3/3)(20 mL) was held at room temperature with stirring on for 4 d. The mixture was evaporated to dryness. And the residue was triturated with ether and filtered. The reaction mixture was purified by preparative HPLC to give Picolinamide-5-yl 3-deoxy-3-[4-(3,4,5-trifluorophenyl)-1H-1,2,3-triazol-1-yl]-1-thio-α-D-galactopyranoside (20 mg, 1.87%).

m/z calcd for $[C_{20}H_{18}F_3N_5O_5S]^+$ [M+H]$^+$: 498.0; found: 498.0.

$^1$H NMR (400 MHz, MeOD) δ 8.78 (d, J=1.8 Hz, 1H), 8.59 (s, 1H), 8.21 (dd, J=8.2, 2.2 Hz, 1H), 8.07 (d, J=8.3 Hz, 1H), 7.68 (dd, J=8.8, 6.7 Hz, 2H), 6.02 (d, J=5.2 Hz, 1H), 5.06 (dd, J=11.4, 2.7 Hz, 1H), 4.97 (dd, J=11.4, 5.3 Hz, 1H), 4.49 (dt, J=6.0 Hz, 1H), 4.22 (d, 1H), 3.77-3.66 (m, 2H).

Example 68

3-Cyanophenyl 3-deoxy-1-thio-3-[4-(3,4,5-trifluorophenyl)-1H-1,2,3-triazol-1-yl]-α-D-galactopyranoside

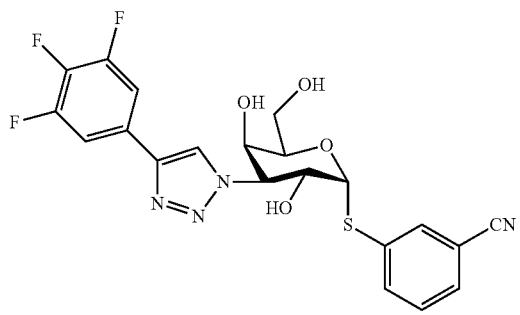

3-Cyanophenyl 2,4,6-tri-O-acetyl-3-deoxy-1-thio-3-[4-(3,4,5-trifluorophenyl)-1H-1,2,3-triazol-1-yl]-α-D-galactopyranoside (72 mg) was dissolved in methanolic NaOMe (0.05M, 10 mL) and stirred at r.t. After 2 h acetic acid (2 mL) was added and the mixture was concentrated in vacuo. The crude product was purified by preparative HPLC (Cis/H₂O:MeCN:0.1% TFA) then (Xterra/25 mM NH₃ in H₂O:MeCN) and lyophilized to give 15 mg of 3-cyanophenyl 3-deoxy-1-thio-3-[4-(3,4,5-trifluorophenyl)-1H-1,2,3-triazol-1-yl]-α-D-galactopyranoside.

$^1$H NMR (400 MHz, Methanol-$d_4$) δ 8.55 (s, 1H), 7.99 (s, 1H), 7.91 (d, J=8.0 Hz, 1H), 7.70-7.60 (m, 3H), 7.51 (t, J=7.9 Hz, 1H), 5.91 (d, J=5.2 Hz, 1H), 5.01 (dd, J=11.4, 2.5 Hz, 1H), 4.93 (dd, J=11.4, 5.2 Hz, 1H), 4.50 (t, J=6.0 Hz, 1H), 4.20 (s, 1H), 3.8-3.3 (m, 2H)

ESI-MS m/z calcd for $[C_2H_{17}F_3N_4O_4S]^+$ (M+H)$^+$: 479.1; found: 479.0.

Example 69

2-cyanopyridine-5-yl 3-deoxy-3-[4-(3,4,5-trifluorophenyl)-1H-1,2,3-triazol-1-yl]-1-thio-α-D-galactopyranoside

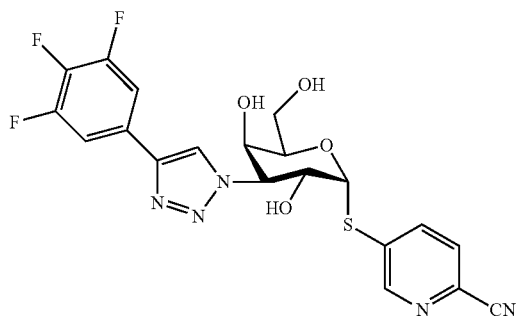

To a solution of 2-cyanopyridine-5-yl 2,4,6-tri-O-acetyl-3-deoxy-3-[4-(3,4,5-trifluorophenyl)-1H-1,2,3-triazol-1-yl]-1-thio-α-D-galactopyranoside (1.2 g, 1.98 mmol) in i-PrOH/Et₃N/H₂O (10/3/3)(20 mL) was stirred at room temperature for 4 days. The reaction mixture was evaporated to dryness. The residue was triturated with ether and filtered to afford a white solid 2-cyanopyridine-5-yl 3-deoxy-3-[4-(3,4,5-trifluorophenyl)-1H-1,2,3-triazol-1-yl]-1-thio-α-D-galactopyranoside (600 mg, 63.26%). m/z calcd for $[C_{20}H_{16}F_3N_5O_4S]^+$ [M+H]$^+$: 480.0; found: 480.0.

¹H NMR (400 MHz, MeOD) δ 8.83 (d, J=1.9 Hz, 1H), 8.58 (s, 1H), 8.22 (dd, J=8.2, 2.3 Hz, 1H), 7.81 (d, J=8.2 Hz, 1H), 7.67 (dt, J=11.4, 5.7 Hz, 2H), 6.15 (d, J=5.1 Hz, 1H), 5.07 (dd, J=11.4, 2.7 Hz, 1H), 4.99 (dd, J=11.4, 5.2 Hz, 1H), 4.40 (t, J=6.0 Hz, 1H), 4.21 (d, J=1.8 Hz, 1H), 3.75-3.65 (m, 2H).

Example 70

4-Chloro-2-thienyl 3-deoxy-3-[4-(3,4,5-trifluorophenyl)-1H-1,2,3-triazol-1-yl]-1-thio-α-D-galactopyranoside

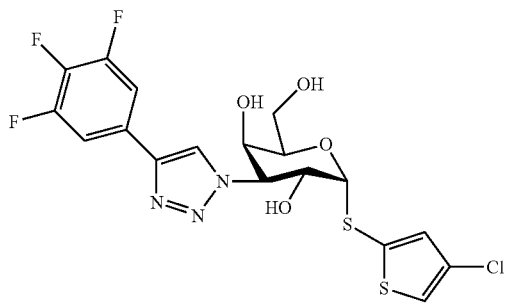

Sodium methoxide (0.53 mg, 0.01 mmol) was added to a solution of crude 4-chloro-2-thienyl 2,4,6-tri-O-acetyl-3-deoxy-3-[4-(3,4,5-trifluorophenyl)-1H-1,2,3-triazol-1-yl]-1-thio-α-D-galactopyranoside (61 mg, 0.10 mmol) in MeOH (5.0 mL) at room temperature. The mixture was stirred at room temperature for 1 h. The mixture was acidified with dowex 50 wx8 hydrogen form to PH=5~6. The solution was filtered, washed with MeOH (50 mL) and concentrated in vacuo to afford crude product, which was purified by preparative-HPLC to afford 4-chloro-2-thienyl 3-deoxy-3-[4-(3,4,5-trifluorophenyl)-1H-1,2,3-triazol-1-yl]-1-thio-α-D-galactopyranoside (6.64 mg, 13.7% yield).

¹H NMR (400 MHz, MeOD) δ 8.56 (s, 1H), 7.67 (dd, J=8.9, 6.6 Hz, 2H), 7.41 (d, J=1.2 Hz, 1H), 7.27 (d, J=1.2 Hz, 1H), 5.65 (d, J=5.2 Hz, 1H), 4.98 (dt, J=13.6, 6.8 Hz, 2H), 4.94-4.91 (m, 2H), 4.55 (t, J=5.9 Hz, 1H), 4.24 (d, J=1.6 Hz, 1H), 3.77 (qd, J=11.3, 6.2 Hz, 2H).

ESI-MS m/z calcd for $[C_8H_{15}ClF_3N_3O_4S_2]^+$ $[M+H]^+$: 493.0; found: 494.0.

Example 71

3-Carboxyphenyl 3-deoxy-3-[4-(3,4,5-trifluorophenyl)-1H-1,2,3-triazol-1-yl]-1-thio-α-D-galactopyranoside

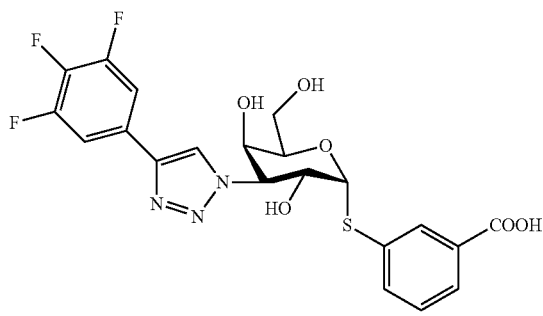

To a solution of (methyl 1-benzoate)-3-yl 2,4,6-tri-O-acetyl-3-deoxy-3-[4-(3,4,5-trifluorophenyl)-1H-1,2,3-triazol-1-yl]-1-thio-α-D-galactopyranoside (30 mg, 0.05 mmol) in NH4OH (2 mL) was held at room temperature with stirring on for 20 h. The crude product was purified by pre-HPLC to obtain 3-Carboxyphenyl 3-deoxy-3-[4-(3,4,5-trifluorophenyl)-1H-1,2,3-triazol-1-yl]-1-thio-α-D-galactopyranoside (10 mg, 42.7%).

¹H NMR (400 MHz, MeOD) δ 8.46 (s, 1H), 8.13 (s, 1H), 7.85 (d, J=7.7 Hz, 1H), 7.76 (d, J=7.5 Hz, 1H), 7.70-7.46 (m, 2H), 7.36 (t, J=7.7 Hz, 1H), 5.75 (d, J=5.3 Hz, 1H), 4.95-4.82 (m, 2H), 4.45 (t, J=6.3 Hz, 1H), 4.13 (s, 1H), 3.83-3.45 (m, 2H).

m/z calcd for $[C21H18F3N3O6S]^+$ $[M+H]^+$: 498.0; found: 498.0.

Example 72

Benzamide-3-yl 3-deoxy-3-[4-(3,4,5-trifluorophenyl)-1H-1,2,3-triazol-1-yl]-1-thio-α-D-galactopyranoside

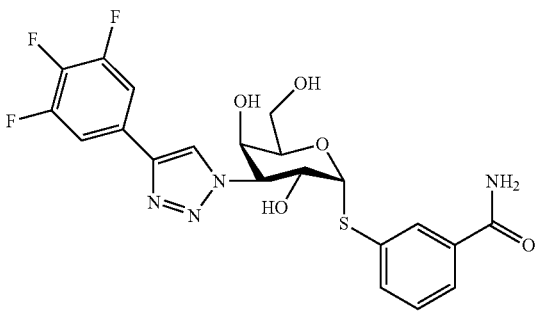

To a solution of 3-Carboxyphenyl 3-deoxy-3-[4-(3,4,5-trifluorophenyl)-1H-1,2,3-triazol-1-yl]-1-thio-α-D-galactopyranoside (4.00 mg, 0.01 mmol) in DMF (1 mL) were added NH4Cl (4.30 mg, 0.08 mmol), HATU (6.11 mg, 0.02 mmol), TEA (8.14 mg, 0.08 mmol). The reaction mixture was held at room temperature with stirring on for 20 h. The crude product was purified by pre-HPLC to obtain Benzamide-3-yl 3-deoxy-3-[4-(3,4,5-trifluorophenyl)-1H-1,2,3-triazol-1-yl]-1-thio-α-D-galactopyranoside (1.42 mg, 35.57%).

¹H NMR (400 MHz, MeOD) δ 8.46 (s, 1H), 8.02 (s, 1H), 7.70 (d, J=7.9 Hz, 2H), 7.67 (t, J=22.8 Hz, 2H), 7.56 (dd, J=8.7, 6.8 Hz, 1H), 7.56 (dd, J=8.7, 6.8 Hz, 1H), 7.35 (t, J=7.8 Hz, 1H), 5.75 (d, J=5.2 Hz, 1H), 4.92 (dd, J=11.4, 2.8 Hz, 1H), 4.83 (d, J=5.3 Hz, 1H), 4.48 (t, J=5.9 Hz, 1H), 4.11 (d, J=1.9 Hz, 1H), 3.77-3.52 (m, 2H).

m/z calcd for $[C21H19F3N4O5S]^+$ $[M+H]^+$: 497.0; found: 497.0.

Example 73

3,4-Dichlorophenyl 3-deoxy-3-[4-(3,4-difluorophenyl)-1H-1,2,3-triazol-1-yl]-1-thio-α-D-galactopyranoside

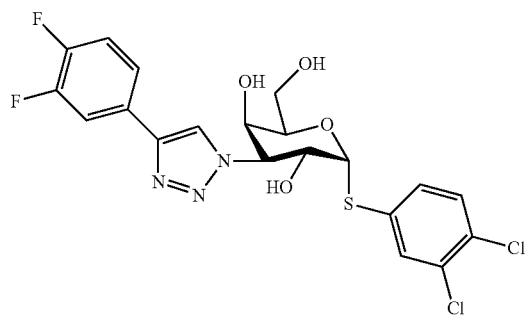

To a solution of 3,4-dichlorophenyl 2,4,6-tri-O-acetyl-3-deoxy-3-[4-(3,4-difluorophenyl)-1H-1,2,3-triazol-1-yl]-1-thio-α-D-galactopyranoside (400 mg, 0.63 mmol) in methanol (10 ml). Sodium methanolate solution (30%, 5 mg) was added and the solution was stirred at room temperature for 2 h. LC-MS analysis indicated the total consumption of the starting material. After completion, DOWEX 50wx8-200 Ion exchange resin was added (PH=7) and the reaction mixture was filtered. The filtrate was concentrated purified by combiflash (EtOAc:PE:=1:20 to 1:5 ISCO 40 g 40 ml/min normal phase sillica, uv254) to afford the target compound 55 mg as a white solid.

$^1$H NMR (500 MHz, DMSO) δ 7.99-7.95 (m, 1H), 7.85 (s, 1H), 7.79-7.75 (m, 1H), 7.60 (d, J=8.4 Hz, 1H), 7.54-7.52 (m, 2H), 5.94 (dd, J=20.4, 3.5 Hz, 2H), 5.50 (d, J=6.7 Hz, 1H), 4.81-4.75 (m, 3H), 4.27 (t, J=5.9 Hz, 1H), 4.06 (d, J=5.5 Hz, 1H), 3.50-3.48 (m, 1H), 3.37-3.33 (m, 1H).

ESI-MS m/z calcd for $[C_{20}H_{17}Cl_2F_2N_3O_4S]^+$ $[M+H]^+$: 504.0; found: 504.0.

Example 74

3,4-Dichlorophenyl 3-deoxy-3-[4-(3,4-difluorophenyl)-1H-1,2,3-triazol-1-yl]-1-thio-α-D-galactopyranoside

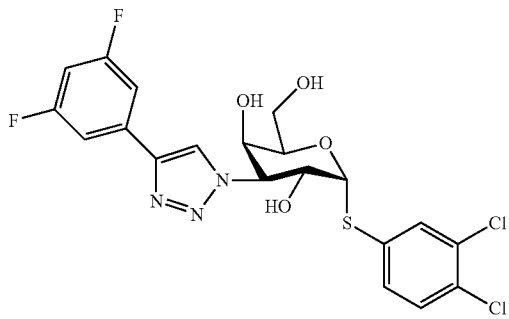

To a stirred solution of 3,4-Dichlorophenyl 2,4,6-tri-O-acetyl-3-deoxy-3-[4-(3,4-difluorophenyl)-1H-1,2,3-triazol-1-yl]-1-thio-α-D-galactopyranoside (160 mg, 0.25 mmol) in MeOH (5 mL), Sodium methoxide (4 mg, 0.07 mmol) was added at 0° C. The mixture was stirred at rt for 0.5 hours. LCMS showed that the target product was formed and no SM left. The mixture was concentrated and the residue was purified by Prep-HPLC to give 50 mg of the title compound.

$^1$H NMR (400 MHz, DMSO) δ 8.83 (s, 1H), 7.84 (d, J=2.1 Hz, 1H), 7.66-7.59 (m, 3H), 7.53 (dd, J=8.4, 2.1 Hz, 1H), 7.21 (t, J=9.4 Hz, 1H), 5.91 (dd, J=13.4, 4.6 Hz, 2H), 5.52 (d, J=6.3 Hz, 1H), 4.88-4.67 (m, 3H), 4.25 (t, J=6.3 Hz, 1H), 4.03 (d, J=4.8 Hz, 1H), 3.58-3.51 (m, 1H), 3.47-3.38 (m, 2H).

ESI-MS m/z calcd for $[C_{20}H_{18}Cl_2F_2N_3O_4S]^+$ $(M+H)^+$: 504.1; found: 504.0.

Example 75

3,4-Dichlorophenyl 3-deoxy-3-[4-(3-fluorophenyl)-1H-1,2,3-triazol-1-yl]-1-thio-α-D-galactopyranoside

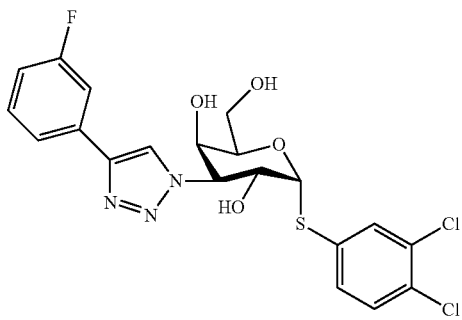

To a stirred solution of 3,4-Dichlorophenyl 2,4,6-tri-O-acetyl-3-deoxy-3-[4-(3-fluorophenyl)-1H-1,2,3-triazol-1-yl]-1-thio-α-D-galactopyranoside (140 mg) in MeOH (5 mL), NaOMe (12.35 mg) was added. The mixture was stirred at rt for 2 hours. Then the mixture was purified by reverse-phase chromatography to give 50 mg (45%) of the title compound.

$^1$H NMR (400 MHz, DMSO) δ 8.72 (s, 1H), 7.85 (d, J=1.8 Hz, 1H), 7.83-7.66 (m, 2H), 7.60 (d, J=8.4 Hz, 1H), 7.59-7.47 (m, 2H), 7.16 (td, J=8.4, 2.1 Hz, 1H), 6.04-5.82 (m, 2H), 5.50 (d, J=6.4 Hz, 1H), 4.80 (s, 2H), 4.72 (t, J=5.6 Hz, 1H), 4.25 (t. J=6.2 Hz, 1H), 4.03 (d, J=6.6 Hz, 1H), 3.64-3.50 (m, 1H), 3.46-3.38 (m, 1H).

ESI-MS m/z calcd for $[C_{20}H_{19}Cl_2F_3O_4S]^+$ $(M+H)^+$: 486.1; found: 486.2.

Example 76

3,3'-difluoro-cyklohexyl 3-deoxy-3-[4-(3,4,5-trifluorophenyl)-1H-1,2,3-triazol-1-yl]-1-thio-α-D-galactopyranoside

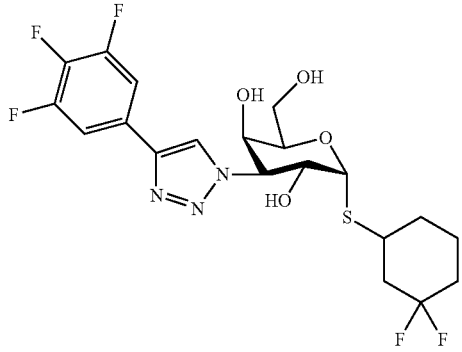

To a solution of 3,3'-difluoro-cyklohexyl 2,4,6-tri-O-acetyl-3-deoxy-3-[4-(3,4,5-trifluorophenyl)-1H-1,2,3-triazol-1-yl]-1-thio-α-D-galactopyranoside (10.00 mg, 0.01 mmol) in methanol (0.5 mL) and water (0.1 mL) were added TEA (0.3 mL). The reaction was evaporated to dryness and the residue was purified by pre-HPLC to obtain the title compound (1 mg).

$^1$H NMR (400 MHz, DMSO-d$_6$) δ 8.53 (s, 1H), 7.66 (dd, J=8.8, 6.4 Hz, 2H), 5.72 (d, J=2.8 Hz, 1H), 4.85-4.81 (m, 1H), 4.42 (t, J=6.8 Hz, 1H), 4.14 (d, J=2 Hz, 1H), 3.75 (d, J=6.4 Hz, 1H), 3.09-3.07 (m, 1H), 2.52 (m, 1H), 4.12 (t, J=6.0 Hz, 1H), 2.17-1.39 (m, 8H).

m/z calcd for [C20H22F5N3O4S]$^+$ [M+H]$^+$: 496.0; found: 496.0.

Example 77 n-Butyl 3-deoxy-3-[4-(3,4,5-trifluorophenyl)-1H-1,2,3-triazol-1-yl]-1-thio-α-D-galactopyranoside

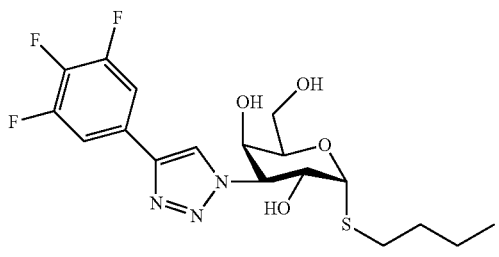

Sodium methoxide (2.7 mg, 0.05 mmol) was added to a solution of n-Butyl 2,4,6-tri-O-acetyl-3-deoxy-3-[4-(3,4,5-trifluorophenyl)-1H-1,2,3-triazol-1-yl]-1-thio-α-D-galactopyranoside (300 mg, 0.54 mmol) in MeOH (5.0 mL) at room temperature. The mixture was stirred at room temperature for 1 h. The mixture was acidified with dowex 50 wx8 hydrogen form to PH=5~6. The solution was filtered and concentrated in vacuo to afford crude product, which was purified by preparative-HPLC to afford the title compound (163.6 mg, 70% yield).

$^1$H NMR (400 MHz, MeOD) δ 8.36 (s, 1H), 7.58-7.42 (m, 2H), 5.42 (d, J=5.4 Hz, 1H), 4.79 (dd, J=11.3, 2.8 Hz, 1H), 4.66 (dd, J=11.3, 5.4 Hz, 1H), 4.25 (t, J=6.1 Hz, 1H), 3.97 (d, J=2.1 Hz, 1H), 3.59 (d, J=6.1 Hz, 2H), 2.53 (dtd, J=20.2, 12.8, 7.5 Hz, 2H), 1.60-1.45 (m, 2H), 1.40-1.27 (m, 2H), 0.81 (t, J=7.4 Hz, 3H).

ESI-MS m/z calcd for [C$_{18}$H$_{22}$F$_3$N$_3$O$_4$S]$^+$ (M+H)$^+$: 433.1; found: 434.2.

Example 78

3,4-Dichlorophenyl 3-deoxy-3-[4-(3,5-difluoro-4-methoxyphenyl)-1H-1,2,3-triazol-1-yl]-1-thio-α-D-galactopyranoside

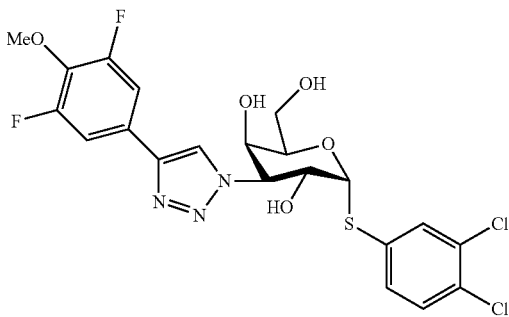

To a stirred solution of 3,4-Dichlorophenyl 2,4,6-tri-O-acetyl-3-deoxy-3-[4-(3,5-difluoro-4-methoxyphenyl)-1H-1,2,3-triazol-1-yl]-1-thio-α-D-galactopyranoside (150 mg) in MeOH (5 mL). NaOMe (12.35 mg) was added. The mixture was stirred at rt for 2 hours. The reaction mixture was Neutralized with H$^+$ resin, filtered and concentrated to afford product as a syrup. The crude product was purified by prep-HPLC to afford the title compound (50 mg, 45% yield).

$^1$H NMR (400 MHz, DMSO) δ 8.73 (s, 1H), 7.84 (d, J=2.1 Hz, 1H), 7.74-7.47 (m, 4H), 5.90 (dd, J=15.5, 4.5 Hz, 2H), 5.51 (d, J=6.4 Hz, 1H), 4.90-4.64 (m, 3H), 4.25 (t, J=6.1 Hz, 1H), 4.02 (d, J=4.8 Hz, 1H), 3.96 (s, 3H), 3.60-3.50 (m, 1H), 3.48-3.37 (m, 1H).

ESI-MS m/z calcd for [C$_{21}$H$_{19}$Cl$_2$F$_2$N$_3$O$_5$S]$^+$ [M+H]$^+$: 533.0; found: 534.2.

Example 79

2-hydroxy-pyridin-4-yl 3-deoxy-3-[4-(3,4,5-trifluorophenyl)-1H-1,2,3-triazol-1-yl]-1-thio-α-D-galactopyranoside

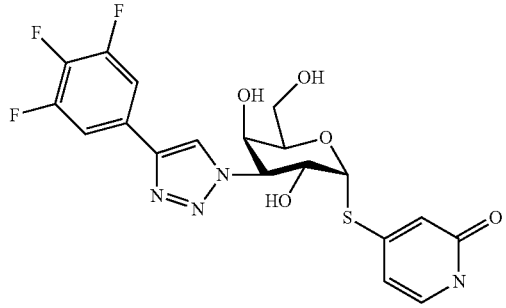

2-hydroxy-pyridin-4-yl 2,4,6-tri-O-acetyl-3-deoxy-3-[4-(3,4,5-trifluorophenyl)-1H-1,2,3-triazol-1-yl]-1-thio-α-D-galactopyranoside (100 mg) was dissolved in MeOH (10 mL). NaOMe (0.05 g) was added. The mixture was stirred at rt for 30 min. The reaction mixture was concentrated and the residue was purified by preparative HPLC to give 20 mg (28%) of the title compound.

$^1$H NMR (400 MHz, DMSO) δ 11.39 (s, 1H), 8.80 (s, 1H), 7.84 (dd, J=9.0, 6.8 Hz, 2H), 7.27 (d, J=6.9 Hz, 1H), 6.43 (d, J=1.7 Hz, 1H), 6.23 (dd, J=7.0, 1.8 Hz, 1H), 6.07 (d, J=2.6 Hz, 1H), 5.91 (s, 1H), 5.56 (s, 1H), 4.78 (s, 2H), 4.71 (s, 1H), 4.13 (t, J=6.4 Hz, 1H), 4.02 (s, 1H), 3.65-3.50 (m, 1H), 3.49-3.38 (m, 1H).

ESI-MS m/z calcd for [C$_{19}$H$_{18}$F$_3$N$_4$O$_5$S]$^+$ (M+H)$^+$: 471.1; found: 471.2.

Example 80

2-Chlorophenethyl 3-deoxy-3-[4-(3,4,5-trifluorophenyl)-1H-1,2,3-triazol-1-yl]-1-thio-α-D-galactopyranoside

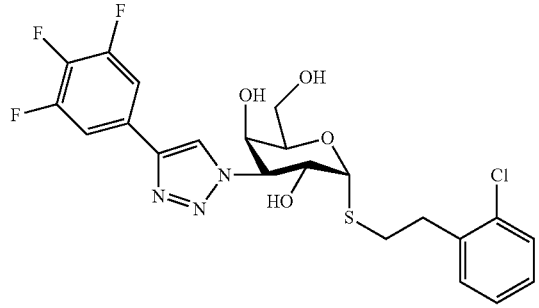

2-chlorophenethyl 2,4,6-tri-O-acetyl-3-deoxy-3-[4-(3,4,5-trifluorophenyl)-1H-1,2,3-triazol-1-yl]-1-thio-α-D-galactopyranoside (100 mg, 0.16 mmol) was dissolved in MeOH (12 mL). NaOMe (8.5 mg, 0.16 mmol) was added. The mixture was stirred at room temperature for 16 hours. Then the mixture was concentrated and the residue was purified on reverse phase column using a gradient of acetonitrile/0.01M NH$_4$HCO$_3$ from 0-52% to give 30 mg (37%) of the title compound.

$^1$H NMR (400 MHz, DMSO) δ 8.76 (s, 1H), 7.84 (dd, J=9.0, 6.8 Hz, 2H), 7.44 (dd, J=7.7, 1.5 Hz, 2H), 7.34-7.16 (m, 2H), 5.60 (d, J=5.2 Hz, 2H), 5.43 (d, J=6.1 Hz, 1H), 4.77-4.69 (m, 2H), 4.69-4.52 (m, 1H), 4.16 (t, J=6.2 Hz, 1H), 4.05-3.94 (m, 1H), 3.67-3.39 (m, 2H), 3.04 (t, J=7.7 Hz, 2H), 2.93-2.70 (m, 2H).

ESI-MS m/z calcd for [C$_{22}$H$_{22}$ClF$_3$N$_3$O$_4$S]$^+$ (M+H)$^+$: 516.1; found: 516.1.

Example 81

4-Chlorophenethyl 3-deoxy-3-[4-(3,4,5-trifluorophenyl)-1H-1,2,3-triazol-1-yl]-1-thio-α-D-galactopyranoside

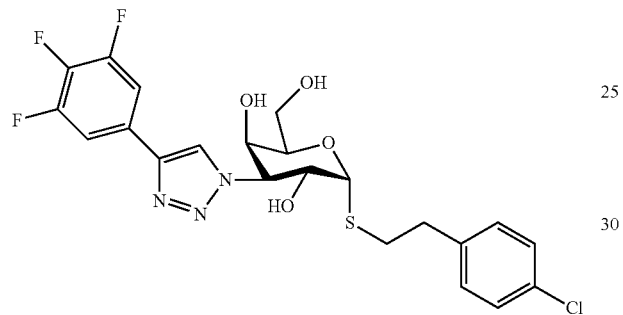

4-Chlorophenethyl 2,4,6-tri-O-acetyl-3-deoxy-3-[4-(3,4,5-trifluorophenyl)-1H-1,2,3-triazol-1-yl]-1-thio-α-D-galactopyranoside (100 mg, 0.16 mmol) was dissolved in MeOH (12 mL). NaOMe (8.5 mg, 0.16 mmol) was added. The mixture was stirred at rt for 16 hours. Then the mixture was concentrated and the residue was purified on C18 column to give 30 mg (37.3%) of the title compound as a white solid.

$^1$H NMR (400 MHz, DMSO) δ 8.75 (s, 1H), 7.83 (dd, J=9.0, 6.8 Hz, 2H), 7.45-7.20 (m, 4H), 5.57 (d, J=5.2 Hz, 2H), 5.43 (s, 1H), 4.87-4.72 (m, 2H), 4.72-4.60 (m, 1H), 4.14 (t, J=6.2 Hz, 1H), 3.96 (s, 1H), 3.65-3.43 (m, 2H), 2.96-2.71 (m, 4H).

ESI-MS m/z calcd for [C$_{22}$H$_{22}$ClF$_3$N$_3$O$_4$S]$^+$ (M+H)$^+$: 516.1; found: 516.1.

Example 82

2-Chlorobenzyl 3-deoxy-1-thio-3-[4-(3,4,5-trifluorophenyl)-1H-1,2,3-triazol-1-yl]-α-D-galactopyranoside

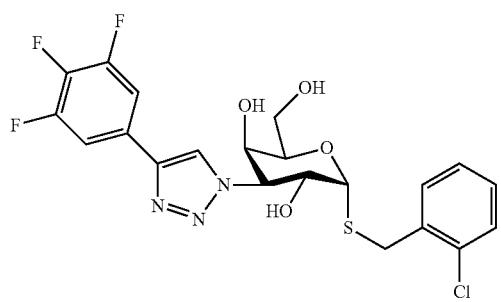

2-Chlorobenzyl 2,4,6-tri-O-acetyl-3-azido-3-deoxy-1-thio-α-D-galactopyranoside (132 mg) was dissolved in MeCN (10 mL). Copper(I) iodide (5 mg) and 3,4,5-trifluorophenylacetylene (0.100 mL) were added and the mixture degassed (N$_2$). After 5 min, DIEA (0.200 mL) was added and the resulting mixture stirred over night. It was then filtered through a small plug of silica and concentrated in vacuo. The residue was suspended in MeOH (40 mL). 1M sodium methoxide in MeOH (1 mL) was added. After stirring at r.t. 2 h, acetic acid (I mL) was added and the mixture concentrated in vacuo. The residue was dissolved in small volume MeCN/water, filtered and purified by HPLC (C$_{18}$/H$_2$O:MeCN:0.1% TFA). Freezedrying afforded the title compound as a white powder (123 mg). $^1$H NMR (400 MHz, Methanol-d$_4$) δ 8.49 (s, 1H), 7.61 (dd, J=8.6, 6.6 Hz, 2H), 7.52 (dd, J=6.4, 2.9 Hz, 1H), 7.40 (dd, J=6.5, 2.8 Hz, 1H), 7.31-7.20 (m, 2H), 5.50 (d, J=5.4 Hz, 1H), 4.97 (dd, J=11.3, 2.8 Hz, 1H), 4.82 (dd, J=11.3, 5.5 Hz, 1H), 4.46 (t, J=6.1 Hz, 1H), 4.17 (d, J=2.8 Hz, 1H), 4.03-3.90 (m, 2H), 3.77 (d, J=6.1 Hz, 2H). ESI-MS m/z calcd for [C$_{21}$H$_{20}$ClF$_3$N$_3$O$_4$S]$^+$ (M+H)$^+$: 502.07; found: 502.10.

Example 83

3,4-Dichlorobenzyl 3-deoxy-1-thio-3-[4-(3,4,5-trifluorophenyl)-1H-1,2,3-triazol-1-yl]-α-D-galactopyranoside

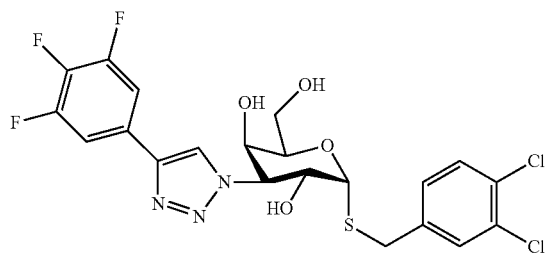

3,4-Dichlorobenzyl 2,4,6-tri-O-acetyl-3-azido-3-deoxy-1-thio-α-D-galactopyranoside (123 mg) was dissolved in MeCN (10 mL). Copper(I) iodide (10 mg) and 3,4,5-trifluorophenylacetylene (0.100 mL) were added and the mixture degassed (N$_2$). After 5 min, DIEA (0.200 mL) was added and the resulting mixture stirred over night. It was then filtered through a small plug of silica and concentrated in vacuo. The residue was suspended in MeOH (40 mL). 1M sodium methoxide in MeOH (1 mL) was added. After stirring at r.t. 2 h, acetic acid (1 mL) was added and the mixture concentrated in vacuo. The residue was dissolved in a small volume of MeCN/water, filtered and purified by HPLC (C$_{18}$/H$_2$O:MeCN:0.1% TFA). Freezedrying afforded the title compound as a white powder (84 mg). $^1$H NMR (400 MHz, Methanol-d$_4$) δ 8.49 (s, 1H), 7.68-7.57 (m, 31H), 7.46 (d, J=8.2 Hz, 1H), 7.36 (dd, J=8.3, 1.9 Hz, 1H), 5.36 (d, J=5.5 Hz, 1H), 4.97 (dd, J=11.3, 2.9 Hz, 1H), 4.80 (dd, J=11.3, 5.5 Hz, 1H), 4.41 (t, J=6.1 Hz, 1H), 4.15 (d, J=2.8 Hz, 1H), 3.91-3.83 (m, 1H), 3.83-3.71 (m, 3H). ESI-MS m/z calcd for [C$_{21}$H$_{19}$Cl$_2$F$_3$N$_3$O$_4$S]$^+$ (M+H)$^+$: 536.03; found: 536.00.

Example 84

3-Chlorophenethyl 3-deoxy-3-[4-(3,4,5-trifluorophenyl)-1H-1,2,3-triazol-1-yl]-1-thio-α-D-galactopyranoside

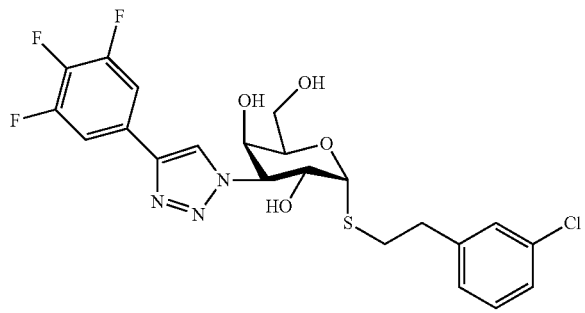

3-Chlorophenethyl 2,4,6-tri-O-acetyl-3-deoxy-3-[4-(3,4,5-trifluorophenyl)-1H-1,2,3-triazol-1-yl]-1-thio-α-D-galactopyranoside (120 mg, 0.19 mmol) was dissolved in MeOH (12 mL). NaOMe (10.1 mg, 0.19 mmol) was added. The mixture was stirred at rt for 16 hours. Then the mixture was concentrated and the residue was purified on C18 column using a gradient of acetonitrile/0.01M $NH_4HCO_3$ from 0-52% to give 33 mg (34.2%) of the title compound as a white solid.

$^1$H NMR (400 MHz, DMSO) δ 8.76 (s, 1H), 7.84 (dd, J=9.0, 6.8 Hz, 2H), 7.39-7.23 (m, 4H), 5.58 (t, J=5.7 Hz, 2H), 5.42 (d, J=6.4 Hz, 1H), 4.81-4.70 (m, 2H), 4.70-4.60 (m, 1H), 4.15 (t, J=6.1 Hz, 1H), 3.96 (dd, J=6.1, 2.5 Hz, 1H), 3.64-3.45 (m, 2H), 3.01-2.71 (m, 4H).

ESI-MS m/z calcd for $[C_{22}H_{22}ClF_3N_3O_4S]^+$ $(M+H)^+$: 516.1; found: 516.1.

Example 85

4-Chlorobenzyl 3-deoxy-1-thio-3-[4-(3,4,5-trifluorophenyl)-1H-1,2,3-triazol-1-yl]-α-D-galactopyranoside

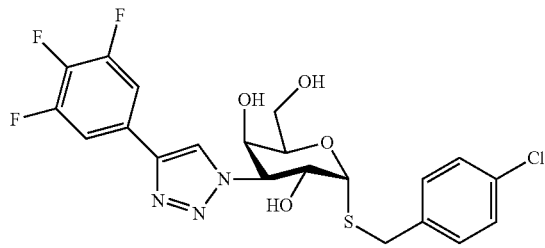

4-Chlorobenzyl 2,4,6-tri-O-acetyl-3-azido-3-deoxy-1-thio-α-D-galactopyranoside (98 mg) was dissolved in MeCN (10 mL). Copper(I) iodide (5 mg) and 3,4,5-trifluorophenylacetylene (0.100 mL) were added and the mixture degassed (nitrogen). After 5 min, DIEA (0.200 mL) was added and the resulting mixture stirred over night. It was then filtered through a small plug of silica and concentrated in vacuo. The residue was suspended in MeOH (40 mL). 1M sodium methoxide in MeOH (1 mL) was added. After stirring at r.t. 2 h, acetic acid (1 mL) was added and the mixture concentrated in vacuo. The residue was dissolved in small volume MeCN/water, filtered and purified by HPLC ($C_{18}/H_2O$:MeCN:0.1% TFA). Freezedrying afforded the title compound as a white powder (85 mg). $^1$H NMR (400 MHz, Methanol-$d_4$) δ 8.48 (s, 1H), 7.62 (dd, J=8.5, 6.7 Hz, 2H), 7.41 (d, J=8.1 Hz, 2H), 7.35-7.27 (m, 2H), 5.38 (d, J=5.4 Hz, 1H), 4.97 (dd, J=11.4, 2.9 Hz, 1H), 4.80 (dd, J=11.3, 5.6 Hz, 1H), 4.43 (t, J=6.0 Hz, 1H), 4.15 (d, J=2.9 Hz, 1H), 3.92-3.83 (m, 1H), 3.82-3.72 (m, 3H). ESI-MS nm/z calcd for $[C_{21}H_{20}ClF_3N_3O_4S]^+$ $(M+H)^+$: 502.07; found: 502.10.

Example 86

Propyl 3-deoxy-3-[4-(3,4,5-trifluorophenyl)-1H-1,2,3-triazol-1-yl]-1-thio-α-D-galactopyranoside

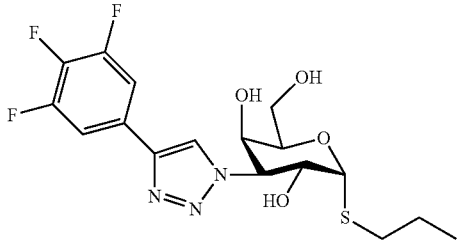

MeONa (1.08 mg, 0.02 mmol) was added to a solution of propyl 2,4,6-tri-O-acetyl-3-deoxy-3-[4-(3,4,5-trifluorophenyl)-1H-1,2,3-triazol-1-yl]-1-thio-α-D-galactopyranoside (100 mg, 0.18 mmol) in MeOH (5.0 mL) at room temperature. The mixture was stirred at room temperature for 1 h. The mixture was acidified with dowex 50 wx8 hydrogen form to PH=5~6. The solution was filtered and concentrated in vacuo to afford crude product, which was purified by Preparative HPLC to afford the title compound (68.7 mg, 91% yield).

$^1$H NMR (400 MHz, MeOD) δ 8.36 (s, 1H), 7.49 (dd, J=8.8, 6.7 Hz, 2H), 5.42 (d, J=5.4 Hz, 1H), 4.79 (dd, J=11.3, 2.9 Hz, 1H), 4.66 (dd, J=11.3, 5.4 Hz, 1H), 4.25 (t, J=6.0 Hz, 1H), 3.97 (d, J=2.3 Hz, 1H), 3.59 (d, J=6.1 Hz, 2H), 2.50 (dtd, J=20.3, 12.9, 7.5 Hz, 2H), 0.90 (t, J=7.3 Hz, 3H).

ESI-MS m/z calcd for $[C_{17}H_{20}F_3N_3O_4S]^+$ $(M+H)^+$: 419.1; found: 420.2.

Example 87

2-Aminopyridin-4-yl 3-deoxy-3-[4-(3,4,5-trifluorophenyl)-1H-1,2,3-triazol-1-yl]-1-thio-α-D-galactopyranoside

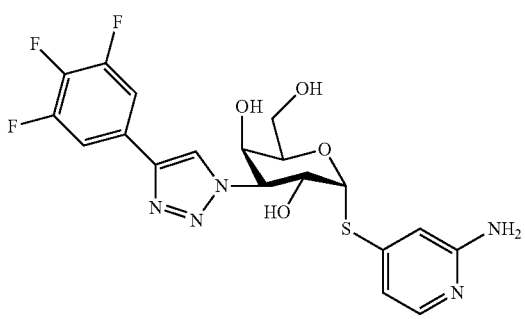

Sodium methoxide (3.37 mg, 0.06 mmol) was added to a solution of 2-Aminopyridin-4-yl 2,4,6-tri-O-acetyl-3-deoxy-3-[4-(3,4,5-trifluorophenyl)-1H-1,2,3-triazol-1-yl]-1-thio-α-D-galactopyranoside (124 mg, 0.21 mmol) in MeOH (5.0 mL) at room temperature. The mixture was stirred at room temperature for 1 h. The mixture was acidified with dowex 50 wx8 hydrogen form to PH=5~6. The solution was filtered and concentrated in vacuo to afford crude product, which was purified by Prep-HPLC to afford the title compound (4.95 mg, 5.06% yield).

1H NMR (400 MHz, MeOD) δ 8.46 (s, 1H), 7.64 (d, J=5.5 Hz, 1H), 7.56 (dd, J=8.9, 6.7 Hz, 2H), 6.73 (s, 1H), 6.66 (dd, J=5.8, 1.6 Hz, 1H), 6.00 (d, J=4.4 Hz, 1H), 4.91-4.82 (m, 2H), 4.29 (t, J=6.1 Hz, 1H), 4.09 (d, J=2.4 Hz, 1H), 3.69-3.58 (m, 2H).

ESI-MS m/z calcd for $[C_{19}H_{18}F_3N_5O_4S]^+$ $(M+H)^+$: 469.1; found: 470.2.

Example 88

5-dimethylamino-naphatlen-2-yl 3-deoxy-3-[4-(3,4,5-trifluorophenyl)-1H-1,2,3-triazol-1-yl]-1-thio-α-D-galactopyranoside

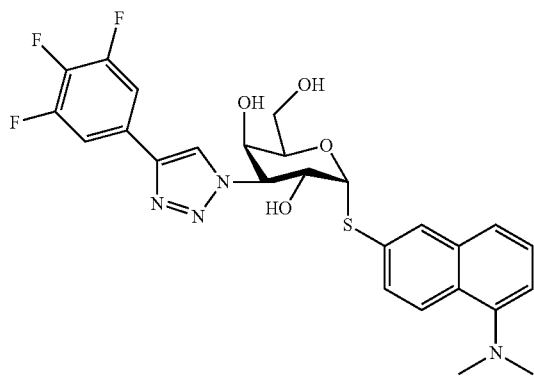

To a solution of 5-dimethylamino-naphatlen-2-yl 2,4,6-tri-O-acetyl-3-deoxy-3-[4-(3,4,5-trifluorophenyl)-1H-1,2,3-triazol-1-yl]-1-thio-α-D-galactopyranoside (50 mg, 0.07 mol) in MeOH/H$_2$O (0.6 mL) was added TEA (0.3 ml). The reaction was held at room temperature with stirring on for 2 h. The solvent was evaporated to dryness. The residue was purified by preparative-HPLC to obtain the desired product.

1H NMR (400 MHz, MeOD) δ8.41 (s, 1H), 8.01 (d, J=8.9 Hz, 1H), 7.94 (d, J=1.7 Hz, 1H), 7.58-7.43 (m, 3H), 7.33 (d, J=8.2 Hz, 1H), 7.24 (t, J=7.8 Hz, 1H), 6.97 (d, J=6.9 Hz, 1H), 5.74 (d, J=5.3 Hz, 1H), 4.89 (dd, J=11.4, 2.8 Hz, 1H), 4.81-4.76 (m, 1H), 4.48 (t, J=6.2 Hz, 1H), 4.07 (d, J=2.0 Hz, 1H), 3.68-3.43 (m, 2H), 2.71 (s, 6H).

m/z calcd for $[C26H25F3N4O4S]^+$ $[M+H]^+$: 547.0; found: 547.0.

Example 89

Ethyl 3-deoxy-1-thio-3-[4-(3,4,5-trifloorophenyl)-1H-1,2,3-triazol-1-yl]-α-D-galactopyranoside

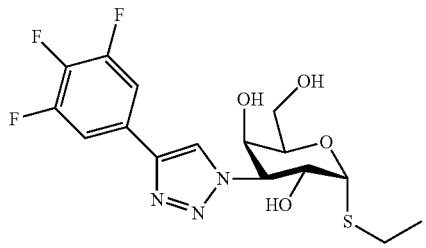

Ethyl 2,4,6-tri-O-acetyl-3-azido-3-deoxy-1-thio-α-D-galactopyranoside (43 mg) was dissolved in MeCN (5 mL) and stirred at r.t. under N$_2$. Copper(I) iodide (9 mg) was added and after five minutes 1,2,3-trifluoro-5-[2-(trimethylsilyl)ethynyl]benzen (0.050 mL) was added. After an additional five minutes DIEA (0.020 mL) was added and the mixture was heated to 45° C. After 2 h the heat was increased to 80° C. for 70 min and then decreased to 30° C. After three days the reaction mixture was filtered through a short column of silica, eluting with EtOAc and then concentrated in vacuo. The crude product was dissolved in methanolic NaOMe (0.05M, 20 mL) and stirred at r.t. After 100 min acetic acid (2 mL) was added and the mixture was concentrated in vacuo. The crude product was purified by preparative HPLC (C$_{18}$/H$_2$O:MeCN:0.1% TFA) and lyophilized to give 42 mg of ethyl 3-deoxy-1-thio-3-[4-(3,4,5-trifluorophenyl)-1H-1,2,3-triazol-1-yl]-α-D-galactopyranoside. $^1$H NMR (400 MHz, Methanol-d$_4$) δ 8.50 (s, 1H), 7.72-7.58 (m, 2H), 5.61 (d, J=5.4 Hz, 1H), 4.94 (dd, J=11.3, 2.3 Hz, 1H), 4.85-4.77 (m, 1H), 4.40 (t, J=6.0 Hz, 1H), 4.13 (s, 1H), 3.74 (d, J=6.1 Hz, 2H), 2.80-2.59 (m, 2H), 1.34 (t, J=7.4 Hz, 3H). $^{13}$C NMR (101 MHz, Methanol-d$_4$) δ 123.0, 110.9, 110.6, 86.9, 72.5, 69.8, 66.6, 65.6, 62.4, 24.5, 15.2. ESI-MS m/z calcd for $[C_{16}H_{19}F_3N_3O_4S]^+$ $(M+H)^+$: 406.1; found: 406.1.

Example 90

5-Bromopyridin-3-yl 3-deoxy-3-[4-(3,4,5-trifluorophenyl)-1H-1,2,3-triazol-1-yl]-α-D-galactopyranosyl sulfoxide, isomer 1

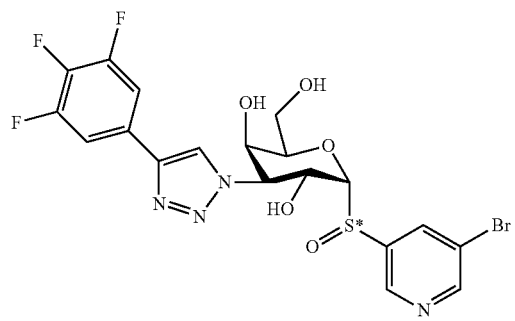

isomer 1

NaOMe (2.32 mg, 0.04 mmol) was added in to a mixture of 5-Bromopyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 1 (145 mg, 0.21 mmol) in MeOH (10 mL). Then it was stirred at room temperature for 1 h. The mixture was acidified with dowex 50 wx8 hydrogen form to PH=5~6. The solution was filtered, washed with MeOH (20 mL) and concentrated in vacuo to afford crude product, which was purified by trituration in $CH_2Cl_2$ and $Et_2O$ to afford 1,3-dideoxy-1-(5-bromopyridine-3-yl-thio)-3-[4-(3,4,5-trifluorophenyl)-1H-1,2,3-triazol-1-yl]-α-D-galacto pyranoside (69.41 mg, 58.86% yield). The chirality of the stereocenter located at the sulfurus atom marked * was not determined.

$^1$H NMR (400 MHz, MeOD) δ 8.93 (d, J=1.8 Hz, 1H), 8.85 (d, J=2.1 Hz, 1H), 8.56 (s, 1H), 8.50 (t, J=1.9 Hz, 1H), 7.79-7.51 (m, 1H), 5.61 (dd, J=11.1, 2.6 Hz, 1H), 5.18 (dd, J=11.0, 5.6 Hz, 1H), 5.09 (d, J=5.6 Hz, 1H), 4.27 (d, J=2.3 Hz, 1H), 4.21 (t, J=5.9 Hz, 1H), 3.64-3.46 (m, 1H).

ESI-MS m/z calcd for $[C_{19}H_{16}BrF_3N_4O_5S]^+$ $[M+H]^+$: 548.0; found: 549.0.

Example 91

5-Bromopyridin-3-yl 3-deoxy-3-[4-(3,4,5-trifluorophenyl)-1H-1,2,3-triazol-1-yl]-α-D-galactopyranosyl sulfoxide, isomer 2 isomer 2

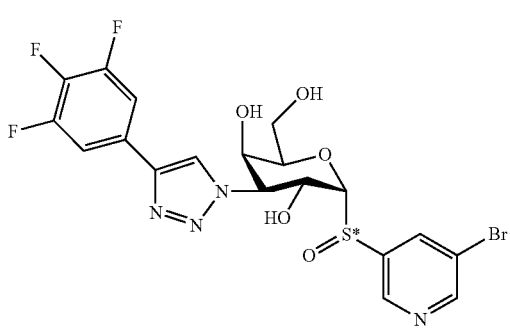

NaOMe (0.64 mg, 0.01 mmol) was added in to a mixture of 5-Bromopyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 2 (40 mg, 0.06 mmol) in MeOH (5 mL). Then it was stirred at room temperature for 1 h. The mixture was acidified with dowex 50 wx8 hydrogen form to PH=5~6. The solution was filtered, washed with MeOH (20 mL) and concentrated in vacuo to afford crude product, which was purified by trituration in CH2Cl2 and Et2O to afford the title compound (3.32 mg, 10.21% yield). The chirality of the stereocenter located at the sulfurus atom marked * was not determined.

$^1$H NMR (400 MHz, MeOD) δ 8.84 (dd, J=13.6, 1.9 Hz, 1H), 8.62 (s, 1H), 8.49 (t, J=2.0 Hz, 1H), 7.69 (dd, J=8.8, 6.6 Hz, 1H), 5.77 (dd, J=11.2, 2.7 Hz, 1H), 5.24 (dd, J=11.3, 6.6 Hz, 1H), 5.02 (t, J=6.0 Hz, 1H), 4.95 (d, J=6.5 Hz, 1H), 4.26 (s, 1H), 3.56 (s, 1H), 3.56-3.50 (m, 1H).

ESI-MS m/z calcd for $[C_{19}H_{16}BrF_3N_4O_5S]^+$ $[M+H]^+$: 548.0; found: 549.0.

Example 92

5-Bromopyridin-3-yl 3-deoxy-3-[4-(3,4,5-trifluorophenyl)-1H-1,2,3-triazol-1-yl]-α-D-galactopyranosyl sulfone

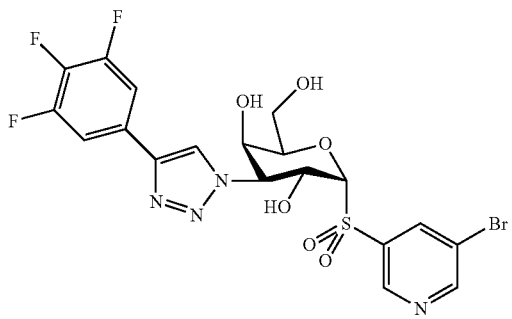

5-Bromo-3-pyridyl 3-deoxy-3-[4-(3,4,5-trifluorophenyl)-1H-1,2,3-triazol-1-yl]-1-thio-α-D-galactopyranoside (9 mg) was dissolved/suspended in $CH_2Cl_2$ (3 mL) at r.t. and m-chloroperbenzoic acid (4.6 mg in 0.460 mL $CH_2Cl_2$) was added. After 20 h more m-chloroperbenzoic acid (8.4 mg in 0.840 mL $CH_2Cl_2$) was added. After 4 h the temperature was increased to 30° C. for an additional 20 h. MeCN (1 mL) was added followed by $H_2O_2$ (27%, 0.5 mL) and the mixture was stirred for 6.5 h. The mixture was filtered through a short silica column, eluting with 15% MeOH in EtOAc, concentrated in vacuo. The crude product was purified by preparative HPLC ($C_{18}$/$H_2O$:MeCN:0.1% TFA) and lyophilized to give 3 mg of the title compound.

$^1$H NMR (400 MHz, Methanol-$d_4$) δ 9.07 (s, 1H), 8.97 (s, 1H), 8.56 (d, J=9.3 Hz, 2H), 7.70-7.61 (m, 2H), 5.73 (d, J=11.5 Hz, 1H), 5.43 (d, J=6.4 Hz, 1H), 5.15 (dd, J=11.4, 6.5 Hz, 1H), 4.55 (s, 1H), 4.28 (s, 1H), 3.62 (d, J=6.2 Hz, 2H).

$^{13}$C NMR (101 MHz, Methanol-$d_4$) δ 156.3, 148.9, 140.9, 122.8, 121.9, 110.9, 93.8, 78.1, 69.2, 66.2, 64.1, 62.3. ESI-MS m/z calcd for $[C_{19}H_{17}BrF_3N_4O_6S]^+$ $(M+H)^+$: 565.0; found: 565.0.

Example 93

5-Chloropyridin-3-yl 3-deoxy-3-[4-(3,4,5-trifluorophenyl)-1H-1,2,3-triazol-1-yl]-α-D-galactopyranosyl sulfoxide, isomer 1 isomer 1

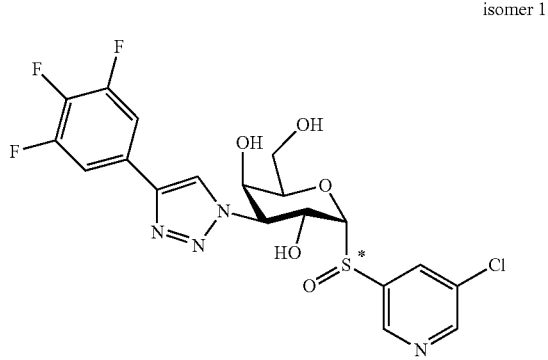

To a solution of 5-Chloropyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 1 (18 mg, 0.03 mmol) in MeOH/Et3N/H2O (5/3/1)(0.5 mL) was stirred at room temperature for 4 h. The mixture was evaporated to dryness, and the residue was triturated with ether and filtered to afford the title compound as a white solid (5 mg, 34.72%). The chirality of the stereocenter located at the sulfurus atom marked * was not determined.

$^1$H NMR (400 MHz, MeOD) δ8.79 (d, J=1.7 Hz, 1H), 8.76 (d, J=2.3 Hz, 1H), 8.62 (s, 1H), 8.36 (t, J=2.0 Hz, 1H), 7.69 (dd, J=8.8, 6.6 Hz, 2H), 5.77 (dd, J=11.3, 2.7 Hz, 1H), 5.24 (dd, J=11.3, 6.6 Hz, 1H), 5.02 (t, J=5.9 Hz, 1H), 4.96 (d, J=6.6 Hz, 1H), 4.26 (d, 1H), 3.60-3.47 (m, 2H).

m/z calcd for $[C_{19}H_{16}ClF_3N_4O_5S]^+$ $[M+H]^+$: 505.0; found: 505.0.

Example 94

5-Chloropyridin-3-yl 3-deoxy-3-[4-(3,4,5-trifluorophenyl)-1H-1,2,3-triazol-1-yl]-α-D-galactopyranosyl sulfoxide, isomer 2

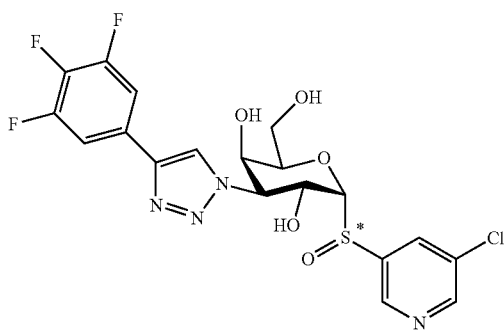

isomer 2

To a solution of 5-Chloropyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 2 (100 mg, 0.16 mmol) in MeOH/Et3N/H2O (5/3/1)(2 mL) was stirred at temperature for 4 h. The mixture was evaporated to dryness, and the residue was triturated with ether and filtered to afford the title compound as a white solid (47 mg, 59%). The chirality of the stereocenter located at the sulfurus atom marked * was not determined.

$^1$H NMR (400 MHz, MeOD) δ 8.73 (d, J=1.8 Hz, 1H), 8.58 (d, J=2.2 Hz, 1H), 8.39 (s, 1H), 8.20 (t, J=2.0 Hz, 1H), 7.50 (dd, J=8.8, 6.7 Hz, 2H), 5.44 (dd, J=11.1, 2.8 Hz, 1H), 5.01 (dd, J=11.1, 5.6 Hz, 1H), 4.92 (d, J=5.6 Hz, 1H), 4.10 (d, J=2.0 Hz, 1H), 4.03 (t, J=5.8 Hz, 1H), 3.39 (qd, J=11.6, 5.9 Hz, 2H).

m/z calcd for $[C_{19}H_{16}ClF_3N_4O_5S]^+$ $[M+H]^+$: 505.0; found: 505.0.

Example 95

5-Dimethylamino-naphtalen-2-yl 3-deoxy-3-[4-(3,4,5-trifluorophenyl)-1H-1,2,3-triazol-1-yl]-α-D-galactopyranosyl sulfone

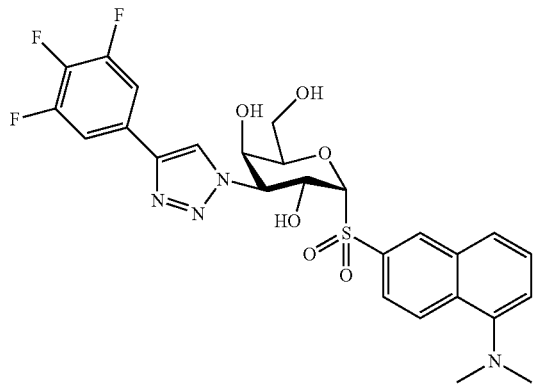

To a solution of 5-Dimethylamino-naphtalen-2-yl 2,4,6-tri-O-acetyl-3-deoxy-3-[4-(3,4,5-trifluorophenyl)-1H-1,2,3-triazol-1-yl]-1-thio-α-D-galactopyranoside (20 mg, 0.03 mmol) was added TEA (0.3 ml) in MeOH/H$_2$O (0.5 ml/0.1 ml). The reaction was stirred at room temperature for 1 h. The mixture was purified by pre-HPLC to obtain the title compound (6 mg).

1H NMR (400 MHz, MeOD) δ 8.58 (s, 2H), 8.45 (d, J=9.0 Hz, 1H), 7.99 (dd, J=9.0, 1.8 Hz, 1H), 7.77 (d, J=8.2 Hz, 1H), 7.73-7.63 (m, 2H), 7.59 (t, J=7.9 Hz, 1H), 7.36 (d, J=7.3 Hz, 1H), 5.87 (dd, J=11.5, 2.8 Hz, 1H), 5.36 (d, J=6.3 Hz, 1H), 5.20-5.11 (m, 1H), 4.65 (t, J=6.1 Hz, 1H), 4.33 (d, J=1.8 Hz, 1H), 3.62-3.56 (m, 1H), 3.53-3.46 (m, 1H), 2.92 (s, 6H).

m/z calcd for $[C26H25F3N4O6S]^+$ $[M+H]^+$: 578.0; found: 578.0.

Example 96

3,4-dichlorophenyl-3-deoxy-3-(3,4,5-trifluorobenzamido)-1-thio-α-D-galactopyranoside

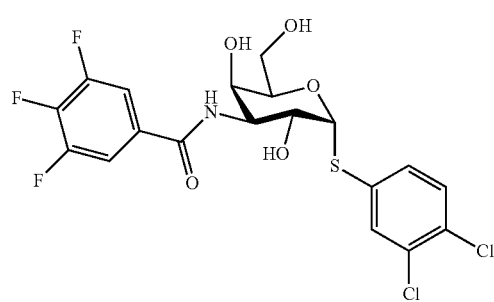

To a stirred solution of 3,4-dichlorophenyl 2,4,6-tri-O-acetyl-3-deoxy-3-(3,4,5-trifluorobenzamido)-1-thio-α-D-galactopyranoside (50 mg, 0.08 mmol) in MeOH (2 mL) and DCM (0.5 mL) at 0° C. was added sodium methoxide (13 mg, 0.37 mmol). The mixture was stirred at rt for 2 hours. The was adjusted with 2M HCl to pH=7. The mixture was concentrated and the residue was purified on reversed phase column. To give the title compound (18 mg, 45% yield).

$^1$H NMR (400 MHz, DMSO) δ 8.52-8.39 (m, 1H), 7.96-7.84 (m, 2H), 7.79 (d, J 2.0 Hz, 1H), 7.57 (d, J=8.4 Hz, 1H), 7.48 (dd, J=8.4, 2.1 Hz, 1H), 5.81 (d, J=5.3 Hz, 1H), 5.40 (d, J=4.4 Hz, 1H), 5.14 (d, J=5.4 Hz, 1H), 4.64 (t, J=5.7 Hz, 1H), 4.38-4.26 (m, 1H), 4.14-3.95 (m, 2H), 3.92-3.87 (m, 1H), 3.60-3.47 (m, 1H), 3.36 (s, 1H). ESI-MS m/z calcd for $[C_{19}H_{17}Cl_2F_3NO_5S]^+$ (M+H)$^+$: 498.0; found: 498.1.

Example 97

3,4-Dichlorophenyl 3-deoxy-3-[4-(ethoxycarbonyl)-1H-1,2,3-triazol-1-yl]-1-thio-α-D-galactopyranoside

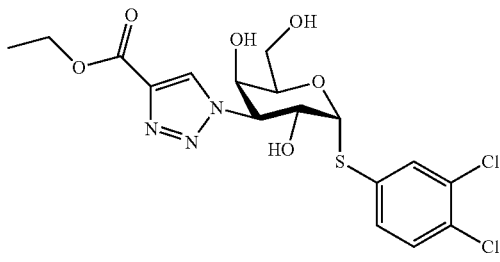

3,4-Dichlorophenyl 2,4,6-tri-O-acetyl-3-deoxy-3-[4-ethoxycarbonyl)-1H-1,2,3-triazol-1-yl]-1-thio-α-D-galactopyranoside (117 mg, 0.20 mmol) was dissolved in EtOH (10 mL). TEA (200 mg) and water (1 ml) were added. The mixture was stirred at 90° C. for 48 hours. The mixture was concentrated in vacuo and the residue was purified by prep-HPLC to give 22 mg of the title compound.

$^1$H NMR (400 MHz, DMSO) δ 8.66 (s, 1H), 7.83 (d, J=2.0 Hz, 1H), 7.60 (d, J=8.4 Hz, 1H), 7.52 (dd, J=8.5, 2.0 Hz, 1H), 5.97-5.83 (m, 2H), 5.45 (d, J=6.8 Hz, 1H), 4.90-4.78 (m, 2H), 4.74 (t, J=5.6 Hz, 1H), 4.32 (q, J=7.1 Hz, 2H), 4.24 (t, J=6.2 Hz, 1H), 4.01 (d, J=6.2 Hz, 1H), 3.60-3.49 (m, 1H), 3.44-3.36 (m, 1H), 1.31 (t, J=7.1 Hz, 3H).

ESI-MS m/z calcd for $[C_{17}H_{20}Cl_2N_3O_6S]^+$ (M+H)$^+$: 464.0; found: 464.0.

Example 98

3,4-Dichlorophenyl 3-deoxy-3-[4-(ethylaminocarbonyl)-1H-1,2,3-triazol-yl]-1-thio-α-D-galactopyranoside

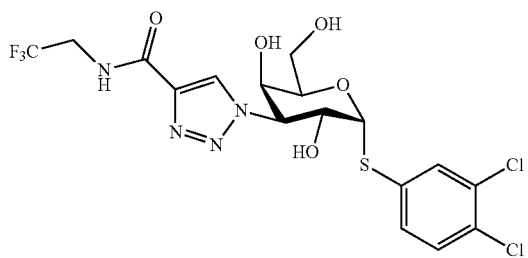

3,4-Dichlorophenyl 3-deoxy-3-[4-carboxy)-1H-1,2,3-triazol-1-yl]-1-thio-α-D-galactopyranoside (80 mg, 0.18 mmol), 2,2,2-trifluoroethanamine (36 mg, 0.37 mmol) was dissolved in DMF (2 mL). HATU (140 mg, 0.37 mmol), N-ethyl-N-isopropyl-propan-2-amine (120 mg, 0.92 mmol) were added. The reaction mixture was stirred at rt for 2 hours followed by purification by preparative-HPLC to give 40 mg of the title compound.

$^1$H NMR (400 MHz, DMSO) δ 9.18 (t, 1H), 8.58 (s, 1H), 7.83 (d, J=2.0 Hz, 1H), 7.66-7.45 (m, 2H), 5.89 (d, J=5.0 Hz, 2H1), 5.56-5.38 (m, 1H), 4.93-4.68 (m, 2H), 4.24 (t, J=6.2 Hz, 1H), 4.15-3.90 (m, 3H), 3.58-3.44 (m, 2H).

ESI-MS m/z calcd for $[C_{17}H_{18}C_2F_3N_4O_5S]^+$ (M+H)$^+$: 517.0; found: 517.0.

Example 99

3,4-Dichlorophenyl 3-O-[(5,6-Difluoro-2-oxo-3-chromenyl)methyl]-1-thio-α-D-galactopyranoside

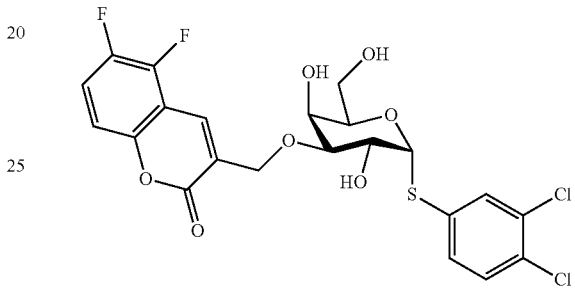

To a solution of 3,4-dichlorophenyl-2,4,6-tri-O-acetyl-3-O-propargyl-1-thio-α-D-galactopyranoside (300 mg, 0.59 mmol) in tetrahydrofuran (15 mL) was added 2,3-difluoro-6-hydroxybenzaldehyde (93.85 mg, 0.59 mmol), N-diazo-4-methyl-benzenesulfonamide (117.07 mg, 0.5 mmol), copperiodide (11.31 mg, 0.06 mmol). The reaction mixture was purged three times with $N_2$. The reaction mixture was stirred at room temperature for 1 h. N,N-diethylethanamine (120.14 mg, 1.19 mmol) was added via addition funnel to the mixture. Then the mixture was stirred at room temperature for 20 h. Solvents were evaporated in vacuo and the residue was dissolved in DCM (150 mL) and washed successively with aqueous $NH_4Cl$ (2×30 mL) and brine (30×2 mL). The organic layer was separated, dried over $Na_2SO_4$ and evaporated in vacuo. The residue was purified by flash chromatography (PE:EtOAc=2:3) to give the corresponding tosyl sulfoninimid intermediate 290 mg (59.97%) as yellow oil. ESI-MS m/z calcd for $[C_{35}H_{31}Cl_2F_2NO_{11}S_2]^+$ [M+H]$^+$: 814.0; found: 814.0.

The intermediate tosyl sulfonamide intermediate (55 mg, 0.07 mmol) was dissolved in $NaOCH_3$/methanol (5 mL, 0.05 M). Then the mixture was stirred at room temperature for 20 h. After completion, DOWEX50wx8-200 Ion exchange resin was added (PH=7) and the mixture was filtered. The filtrate was concentrated in vacuo followed by purification by preparative HPLC to give the title compound 5 mg (14.2%) as a white solid.

$^1$H NMR (500 MHz, DMSO-d$_6$) δ 8.34 (s, 1H), 7.81-7.67 (m, 2H), 7.55 (d, J=8.4 Hz, 1H), 7.46 (dd, J=8.5, 2.1 Hz, 1H), 7.36 (d, J=6.9 Hz, 1H), 5.73 (t, J=5.3 Hz, 2H), 4.92 (d, J=4.9 Hz, 1H), 4.74-4.47 (m, 3H), 4.32-4.19 (m, 1H), 4.11 (m, 1H), 4.01 (t, J=6.1 Hz, 1H), 3.58 (dt, J=11.6, 5.9 Hz, 1H), 3.49 (dd, J=10.1, 2.9 Hz, 1H), 3.45-3.38 (m, 1H).
ESI-MS m/z calcd for $[C_{22}H_{18}Cl_2F_2O_7S]^+$ [M+H]$^+$: 534.0; found: 534.0.

Example 100

5-Chloropyridin-3-yl 3-deoxy-3-[4-(3,4-difluorophenyl)-1H-1,2,3-triazol-1-yl]-1-thio-α-D-galactopyranoside

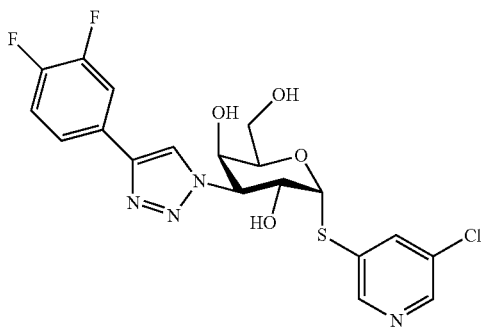

Sodium Methoxide (1.09 mg, 0.02 mmol) was added to a solution of 5-Chloropyridin-3-yl 2,4,6-tri-O-acetyl-3-deoxy-3-[4-(3,4-difluorophenyl)-1H-1,2,3-triazol-1-yl]-1-thio-α-D-galactopyranoside (120 mg, 0.20 mmol) in MeOH (5.0 mL) at room temperature. The mixture was stirred at room temperature for 1 h. The mixture was acidified with dowex 50 wx8 hydrogen form to PH=5~6. The solution was filtered, washed with MeOH (20 mL) and concentrated in vacuo to afford crude product, which was purified by preparative-HPLC to afford the title compound (82.5 mg, 87% yield).

$^1$H NMR (400 MHz, MeOD) δ 8.66 (d, J=1.8 Hz, 1H), 8.51 (s, 114), 8.48 (t, J=4.6 Hz, 1H), 8.21 (t, J=2.1 Hz, 1H), 7.80 (ddd, J=11.7, 7.7, 2.1 Hz, 1H), 7.72-7.64 (m, 1H), 7.37 (dt, J=10.4, 8.5 Hz, 1H), 5.94 (d, J=5.1 Hz, 1H), 5.04 (dd, J=11.4, 2.7 Hz, 1H), 4.99-4.92 (m, 1H), 4.51 (t, J=6.1 Hz, 1H), 4.22 (d, J=1.7 Hz, 1H), 3.78-3.66 (m, 2H).

ESI-MS m/z calcd for $[C_{19}H_{17}ClF_2N_4O_4S]^+$ $[M+H]^+$: 470.1; found: 471.0.

Example 101

5-Bromopyridin-3-yl 3-deoxy-3-[4-(3,4-difluorophenyl)-1H-1,2,3-triazol-1-yl]-1-thio-α-D-galactopyranoside

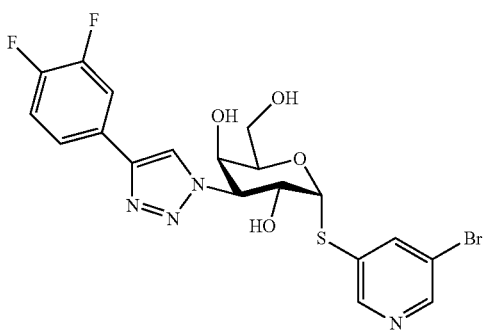

Sodium methoxide (0.84 mg, 0.02 mmol) was added to a solution of Bromopyridin-3-yl 2,4,6-tri-O-acetyl-3-deoxy-3-[4-(3,4-difluorophenyl)-1H-1,2,3-triazol-1-yl]-1-thio-α-D-galactopyranoside (100 mg, 0.16 mmol) in MeOH (5.0 mL) at room temperature. The mixture was stirred at room temperature for 1 h. The mixture was acidified with dowex 50 wx8 hydrogen form to PH=5~6. The solution was filtered, washed with MeOH (20 mL) and concentrated in vacuo to afford crude product, which was purified by Prep-HPLC to afford 1,3-dideoxy-1-(5-bromopyridine-3-yl-thio)-3-[4-(3,4-difluorophenyl)-1H-1,2,3-triazol-1-yl]-α-D-galacto pyranoside (10.96 mg, 13.64% yield).

$^1$H NMR (400 MHz, MeOD) δ 8.70 (d, J=1.9 Hz, 1H), 8.58 (d, J=2.1 Hz, 1H), 8.51 (s, 1H), 8.35 (t, J=2.0 Hz, 1H), 7.80 (ddd, J=11.7, 7.7, 2.1 Hz, 1H), 7.73-7.63 (m, 1H), 7.37 (dt, J=10.4, 8.4 Hz, 1H), 5.93 (d, J=5.1 Hz, 1H), 5.03 (dd, J=11.4, 2.7 Hz, 1H), 4.96 (dd, J=11.4, 5.2 Hz, 1H), 4.51 (t, J=6.0 Hz, 1H), 4.22 (d, J=1.7 Hz, 1H), 3.77-3.63 (m, 2H).

ESI-MS m/z calcd for $[C_{19}H_{17}BrF_2N_4O_4S]^+$ $[M+H]^+$: 514.0; found: 515.1.

Example 102

3,4-Dichlorophenyl 3-deoxy-3-[4-(propyl-carbonyl)-1H-1,2,3-triazol-1-yl]-1-thio-α-D-galactopyranoside

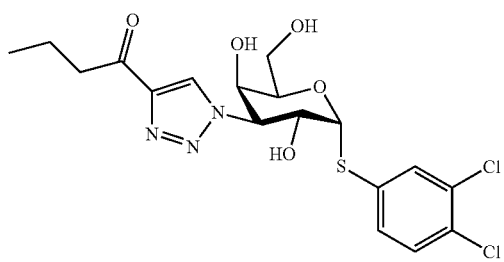

To a stirred solution of 2,4,6-tri-O-acetyl-3-deoxy-3-[4-(propyl-carbonyl)-1H-1,2,3-triazol-1-yl]-1-thio-α-D-galactopyranoside (300 mg, 0.51 mmol) in MeOH (5 mL), Sodium methoxide (8 mg, 0.15 mmol) was added at 0° C. The mixture was stirred at rt for 0.5 hours. LCMS showed that the target product was formed and no SM left. The reaction was purified by prep-HPLC to give the title compound 25 mg.

$^1$H NMR (400 MHz, DMSO) δ 8.66 (s, 1H), 7.83 (d, J=2.0 Hz, 1H), 7.60 (d, J=8.4 Hz, 1H), 7.52 (dd, J=8.5, 2.1 Hz, 1H), 5.89 (t, J=4.2 Hz, 2H), 5.44 (d, J=6.8 Hz, 1H), 4.89-4.76 (m, 2H), 4.73 (t, J=5.6 Hz, 1H), 4.24 (t, J=6.4 Hz, 1H), 4.00 (d, J=6.1 Hz, 1H), 3.58-3.47 (m, 1H), 3.46-3.36 (m, 1H), 2.99 (t, J=7.2 Hz, 2H), 1.86-1.52 (m, 2H), 0.93 (t, J=7.4 Hz, 3H).

ESI-MS m/z calcd for $[C_{18}H_{22}Cl_2N_3O_5S]^+$ $(M+H)^+$: 462.1; found: 462.0.

Example 103

5-Chloro-6-trifluoromethyl-pyridine-3-yl 3-deoxy-3-[4-(3,4,5-trifluorophenyl)-1H-1,2,3-triazol-1-yl]-1-thio-α-D-galactopyranoside

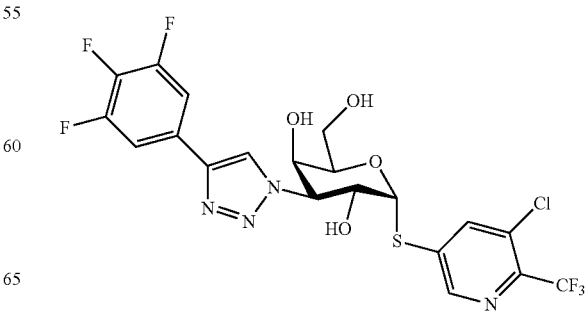

To a solution of 5-chloro-6-trifluoromethyl-pyridine-3-yl 2,4,6-tri-O-acetyl-3-azido-3-deoxy-1-thio-α-D-galactopyranoside (110 mg, 0.21 mmol) in MeCN (15 mL) was added 3,4,5-trifluorophenylacetylene (71.49 mg, 0.32 mmol), iodocopper (11.93 mg, 0.06 mmol), CsF (47.57 mg, 0.31 mmol) and N,N-diethylethanamine (134.92 mg, 1.04 mmol). The reaction vessel was purged 3 times with nitrogen. Then the mixture was stirred at room temperature for 2 h. The mixture was filtered and washed with EtOAc (50 mL), The filtrated was concentrated in vacuo to afford crude intermediate, which was used for next step directly without further purification. MeONa (1.13 mg, 0.02 mmol) was added to a solution of crude 1,3-dideoxy-2,4,6-tri-O-acetyl-1-(5-chloro-6-(trifluoromethyl)pyridin-3-ylthio)-3-[4-(3,4,5-trifluorophenyl)-1H-1,2,3-triazol-1-yl]-α-D-galactopyranoside in MeOH (5 mL) at room temperature. The mixture was stirred at room temperature for 1 h. The mixture was acidified with dowex 50 wx8 hydrogen form to PH=5~6. The solution was filtered, washed with MeOH (20 mL) and concentrated in vacuo to afford crude product, which was purified by Prep-HPLC, Prep-TLC and chromatography to afford the title compound (15 mg, 13% yield)

$^1$H NMR (400 MHz, MeOD) δ 8.73 (d, J=1.8 Hz, 1H), 8.58 (s, 1H), 8.36 (d, J=1.3 Hz, 1H), 7.67 (dt, J=11.3, 5.6 Hz, 2H), 6.16 (d, J=5.2 Hz, 1H), 5.07 (dd, J=11.4, 2.7 Hz, 1H), 4.99 (dd, J=11.4, 5.2 Hz, 1H), 4.42 (t, J=6.1 Hz, 1H), 4.21 (d, J=1.7 Hz, 1H), 3.72 (d, J=6.0 Hz, 2H).

ESI-MS m/z calcd for $[C_{20}H_{15}ClF_6N_4O_4S]^+$ (M+H)$^+$: 556.0; found: 557.2.

Example 104

5-Chloro-2-trifluoromethyl-pyridine-3-yl 3-deoxy-3-[4-(3,4,5-trifluorophenyl)-1H-1,2,3-triazol-1-yl]-1-thio-α-D-galactopyranoside

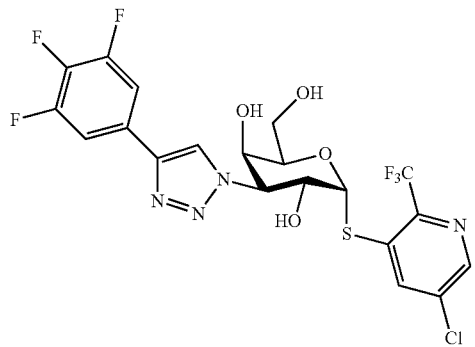

Following purification by Prep-HPLC, Prep-TLC and chromatography in Example 103, 2.69 mg (2.31% yield) of the title compound was isolated.

$^1$H NMR (400 MHz, MeOD) δ 8.46 (s, 1H), 8.42 (d, J=2.0 Hz, 1H), 8.40 (s, 1H), 7.56 (dd, J=8.9, 6.6 Hz, 2H), 5.99 (d, J=4.7 Hz, 1H), 4.95-4.86 (m, 2H), 4.30 (t, J=6.3 Hz, 1H), 4.11 (s, 1H), 3.60 (dd, J=6.0, 2.4 Hz, 2H).

ESI-MS m/z calcd for $[C_{20}H_{15}ClF_6N_4O_4S]^+$ (M+H)$^+$: 556.0; found: 557.2.

Example 105

5-Chloro-6-cyano-pyridine-3-yl 3-deoxy-3-[4-(3,4-difluorophenyl)-1H-1,2,3-triazol-1-yl]-1-thio-α-D-galactopyranoside

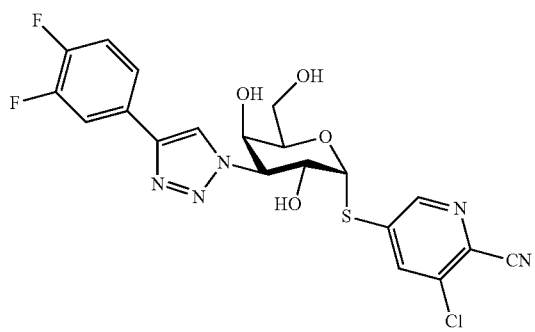

To a solution of 5-Chloro-6-cyano-pyridine-3-yl 2,4,6-tri-O-acetyl-3-deoxy-3-[4-(3,4-difluorophenyl)-1H-1,2,3-triazol-1-yl]-1-thio-α-D-galactopyranoside (60 mg) in methanol/TEA/H$_2$O (0.5/0.3/0.1 mL) was stirred at room temperature for 4 h. The mixture was evaporated to dryness and the crude material was purified by preparative-HPLC (on C-18 column using a gradient of CH$_3$CN/10 mM NH$_4$HCO$_3$ from 0-40%) to obtained the title compound (20 mg, 41.8%).

m/z calcd for $[C_{20}H_{16}ClF_2N_5O_4S]^+$ [M+H]$^+$: 496.0; found: 496.0.

$^1$H NMR (400 MHz, MeOD) δ 8.74 (d, J=1.8 Hz 1H), 8.52 (s, 1H), 8.36 (d, J=1.8 Hz, 1H), 7.84-7.76 (m, 1H), 7.69 (d, J=6.9 Hz, 1H), 7.37 (dd, J=18.9, 8.5 Hz, 1H), 6.23 (d, J=5.0 Hz, 1H), 5.06 (dd, J=11.2, 2.6 Hz, 1H), 5.01 (dd, J=11.4, 5.0 Hz, 1H), 4.37 (t, J=6.0 Hz, 1H), 4.20 (d, J=1.2 Hz, 1H), 3.72 (d, J=6.0 Hz, 2H).

Example 106

3-Chloro-4-cyanophenyl 3-deoxy-3-[4-(3,4-difluorophenyl)-1H-1,2,3-triazol-1-yl]-1-thio-α-D-galactopyranoside

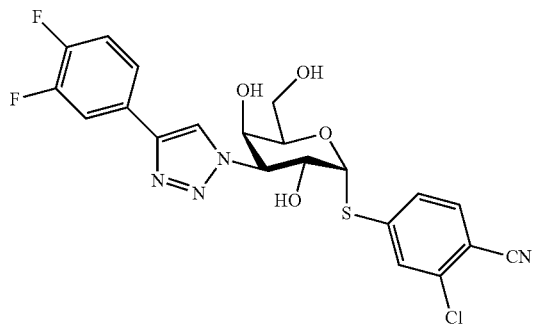

5-Chloro-6-cyano-pyridine-3-yl 2,4,6-tri-O-acetyl-3-deoxy-3-[4-(3,4-difluorophenyl)-1H-1,2,3-triazol-1-yl]-1-thio-α-D-galactopyranoside (70 mg) in methanol/TEA/H$_2$O (2.5/1.5/0.5 mL) was stirred at room temperature for 4 h. The mixture was evaporated to dryness and the crude was purified by prep-HPLC (on C-18 column using a gradient of CH₃CN/10 mM NH₄HCO₃ from 0-43%) to obtained the title compound (50 mg, 34.86%). m/z calcd for $[C_{21}H_{17}ClF_2N_4O_4S]^+$ $[M+H]^+$: 495.0; found: 495.0.

¹H NMR (400 MHz, MeOD) δ 8.51 (s, 1H), 7.88 (d, J=1.5 Hz, 1H), 7.80 (dd, J=11.5, 7.6, 2.0 Hz, 1H), 7.70 (dt, J=8.2, 4.9 Hz, 3H), 7.37 (dt, J=10.3, 8.5 Hz, 1H), 6.13 (d, J=4.6 Hz, 1H), 5.03 (dd, J=11.5, 2.4 Hz, 1H), 4.99 (dd, J=11.5, 4.6 Hz, 1H), 4.40 (t, J=6.1 Hz, 1H), 4.22 (d, 1H), 3.79-3.67 (m, 2H).

Synthesis of Intermediates i57-i106 i57) 3,4-Dichlorophenyl 2,4,6-tri-O-acetyl-3-deoxy-3-[4-(3,4,5-trifluorophenyl)-1H-1,2,3-triazol-1-yl]-1-thio-α-D-galactopyranoside

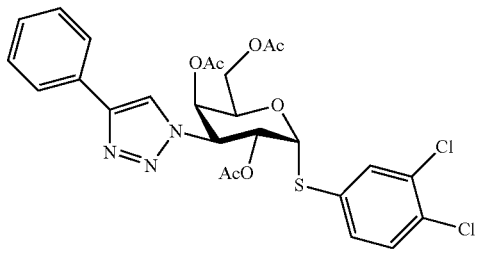

3,4-dichlorophenyl 2,4,6-tri-O-acetyl-3-azido-3-deoxy-1-thio-α-D-galactopyranoside (300 mg, 0.61 mmol), ethynylbenzene (186.71 mg, 1.83 mmol), copper(I)Iodide (34.81 mg, 0.18 mmol) and triethylamine (308.3 mg, 3.05 mmol) was dissolved in DMF (5 mL). The mixture was stirred at 100° C. for 1 hour. EtOAc (200 ml) was added. The reaction mixture was filtered, washed with water (100 mL), dried over sodium sulphate, filtered and the solvents were removed in vacuo. The residue was purified on silica gel column. 250 mg (69%) of 3,4-dichlorophenyl 2,4,6-tri-O-acetyl-3-deoxy-3-[4-(phenyl)-1-thio-α-D-galactopyranoside was obtained. ESI-MS m/z calcd for $[C_{26}H_{26}Cl_2N_3O_7S]^+$ $(M+H)^+$: 594.1; found: 594.1.

i58) 3,5-Dichloro-4-fluorophenyl 2,4,6-tri-O-acetyl-3-azido-3-deoxy-1-thio-α-D-galactopyranoside

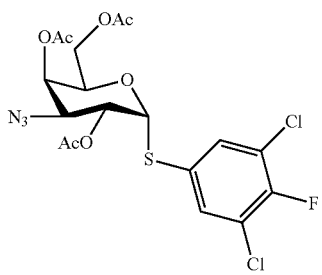

To a stirred solution of 3,5-dichloro-4-fluoro-benzenethiol (500 mg, 2.54 mmol) in dry DMF (4 mL) was added NaH (61 mg, 2.54 mmol) at 0° C. The mixture was stirred at room temperature for 30 min. Then 2,4,6-tri-O-acetyl-3-azido-1-chloro-3-deoxy-3-D-galactopyranoside (591 mg, 1.69 mmol) was added. The mixture was stirred at 50° C. overnight. The solvents were removed in vacuo and the resulting crude was diluted with CH₂Cl₂ and washed with water and brine. The organic layer was dried over Na₂SO₄, filtered and evaporated. The crude product was purified by chromatography column (PE:EtOAc=3:1) to afford the title compound (120 mg).

i59) 3,4-Dichloro-6-fluorophenyl 2,4,6-tri-O-acetyl-3-deoxy-3-[4-(3,4,5-trifluorophenyl)-1H-1,2,3-triazol-1-yl]-1-thio-α-D-galactopyranoside 4,5-Dichloro-2-fluoroaniline

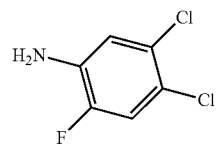

1,2-dichloro-3-fluoro-5-nitro-benzene (5 g, 23.8 mmol), NH₄Cl (14 g, 261.9 mmol) was dissolved in EtOH/H₂O (160 mL, 15/1). The solution heated to 85° C. followed by addition of Fe in portions. After addition the reaction mixture was heated (85° C.) for 1 h. The reaction mixture was extracted with EtOAc (10 mL×3). The combined organic layers were washed with brine (15 mL), dried over Na₂SO₄, and concentrated in vacuum to give crude product. Purification by flash chromatography gave 3,4-dichloro-5-fluoro-aniline (4 g).

S-4,5-dichloro-2-fluorophenyl O-ethyl carbonodithioate

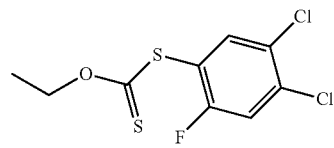

4,5-dichloro-2-fluoro-aniline (2.0 g, 11.1 mmol) was dissolved in con HCl (20 mL) at 0° C., Then NaNO₂ (770 mg, 11.1 mmol) in water (2 mL) was added slowly. The solution was stirred at 0° C. until the solution was clear. Potassium ethyl xanthogenate (2.67 g, 16.7 mmol) in water (15 mL) was added to mixture. The solution was stirred at 50° C. for 2 hs. The resulting solution was extracted with EtOAc (10 mL×3). The combined organic layers were washed with brine (15 mL), dried over Na₂SO₄, and concentrated in vacuo to give crude product, which was purified by flash chromatography to afford S-4,5-dichloro-2-fluorophenyl O-ethyl carbonodithioate (3.0 g)

4,5-dichloro-2-fluorobenzenethiol

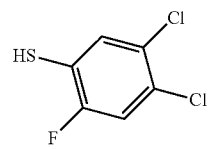

KOH (1.77 g, 32 mmol) was added to a mixture of O-ethyl (4,5-dichloro-2-fluoro-phenyl)sulfanylmethanethioate (3 g, 10.5 mmol) in EtOH (20 mL). The solution was stirred at 85° C. for 2 h. The mixture was acidified with conc. HCl to pH=4~5. The resulting solution was extracted with EtOAc (50 mL×3). The combined organic layers were washed with brine (50 mL), dried over Na₂SO₄, and concentrated in vacuum to give crude product, which was purification by flash chromatography to afford 3,5-dichloro-4-fluoro-benzenethio (2 g).

3,4-Dichloro-6-fluorophenyl 2,4,6-tri-O-acetyl-3-azido-3-deoxy-1-thio-α-D-galactopyranoside

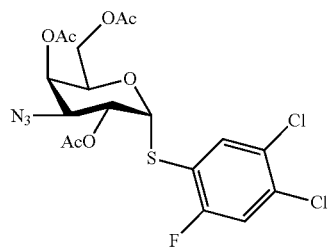

To a stirred solution of 4,5-dichloro-2-fluoro-benzenethiol (2.0 g, 10.15 mmol) in dry DMF (4 mL) was added NaH (233.33 mg, 10.15 mmol) at 0° C. The mixture was stirred at rt for 30 min. Then 2,4,6-tri-O-acetyl-3-azido-1-chloro-3-deoxy-β-D-galactopyranoside (360 mg, 2.66 mmol) was added to the mixture. The mixture was stirred at 50° C. overnight. The resulting solution was extracted with CH₂Cl₂ (10 mL×3). The combined organic layers were washed with brine (15 mL), dried over Na₂SO₄, and concentrated in vacuum to give crude product, which was purification by flash chromatography (PE:EtOAc=3:1) to afford the title compound (300 mg, white solid).

3,4-Dichloro-6-fluorophenyl 2,4,6-tri-O-acetyl-3-deoxy-3-[4-(3,4,5-trifluorophenyl)-1H-1,2,3-triazol-1-yl]-1-thio-α-D-galactopyranoside

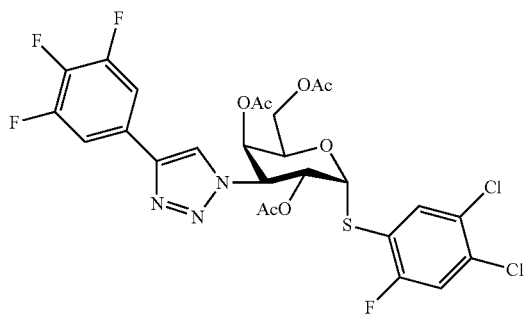

3,4-Dichloro-6-fluorophenyl 2,4,6-tri-O-acetyl-3-azido-3-deoxy-1-thio-α-D-galactopyranoside (360 mg, 0.71 mmol), trimethyl-[2-(3,4,5-trifluorophenyl)ethynyl]silane (320 mg, 1.41 mmol), Copper(I)Iodide (30 mg, 0.16 mmo) and triethylamine (220 mg, 2.1 mmol) were added to a flask. DMF (3 mL) was added. The mixture was stirred at 50° C. for 1 h under a N₂ atmosphere. LCMS showed no SM. The resulting solution was extracted with EtOAc (10 mL×3). The combined organic layers were washed with brine (15 mL), dried over Na₂SO₄, and concentrated in vacuum to give crude product, which was purification by flash chromatography to give the title compound (160 mg).

i60) 3-Bromo-4-fluorophenyl 2,4,6-tri-O-acetyl-3-deoxy-3-[4-(3,4,5-trifluorophenyl)-1H-1,2,3-triazol-1-yl]-1-thio-α-D-galactopyranoside O-3-bromo-4-fluorophenyl dimethylcarbamothioate

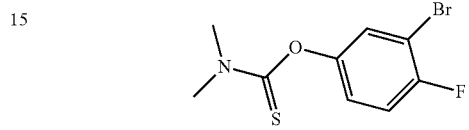

To a solution of 3-bromo-4-fluoro-phenol (3000 mg, 15.79 mmol) in DMF (20 mL) were added NaH (180.55 mg, 17.36 mmol). After 10 mins, N,N-dimethylcarbamothioyl chloride (694.73 mg, 7.85 mmol) was added. The reaction mixture was held at room temperature with stirring on for 20 h. Water (80 mL) and DCM (80 mL) were added. The organic layer was washed with brine, dried (Na2SO4) and evaporated to dryness. The crude products were purified by flash column chromatography to obtain O-3-bromo-4-fluorophenyl dimethylcarbamothioate (3100 mg, 70.87%) as a white solid.

S-3-bromo-4-fluorophenyl dimethylcarbamothioate

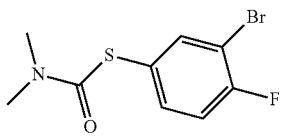

To a solution of O-3-bromo-4-fluorophenyl dimethylcarbamothioate (3100 mg, 11.19 mmol) in phenoxybenzene (20 mL) was held at 280° C. with stirring on for 2 h. The reaction mixture was cooled to room temperature. The crude product was purified by flash chromatography to obtain S-3-bromo-4-fluorophenyl dimethylcarbamothioate (2800 mg, 90.32%) as a yellow solid.

2.3 3-bromo-4-fluorobenzenethiol

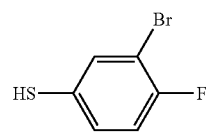

To a solution of S-3-bromo-4-fluorophenyl dimethylcarbamothioate (1200 mg, 4.33 mmol) in methanol (15 mL) was added 10% NaOH aq. (8 ml). The reaction was held at 50° C. with stirring on for 4 h. TLC analysis indicated the total consumption of the SM. The reaction mixture was cooled to room temperature and adjusted pH to 3, then DCM (15 ml) was added. The organic layer was evaporated to dryness and used in the next step.

3-Bromo-4-fluorophenyl 2,4,6-tri-O-acetyl-3-azido-3-deoxy-1-thio-α-D-galactopyranoside

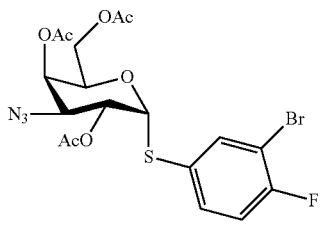

To a solution of 3-bromo-4-fluorobenzenethiol (891.98 mg, 4.33 mmol) in DMF (10 mL) was added NaH (138.56 mg, 3.46 mmol) at 0° C. under a $N_2$ atmosphere. After 10 min, 2,4,6-tri-O-acetyl-3-azido-1-chloro-3-deoxy-β-D-galactopyranoside (755.59 mg, 2.17 mmol) was added. The reaction mixture was stirred at 50° C. for 4 h. The mixture was diluted with DCM (30 mL) and washed with 10% citric acid (20 mL). The organic layer was evaporated to dryness. The crude product was purified by flash column chromatography to obtain 3-Bromo-4-fluorophenyl 2,4,6-tri-O-acetyl-3-azido-3-deoxy-1-thio-α-D-galactopyranoside (300 mg, 26.64%) as a white solid.

3-Bromo-4-fluorophenyl 2,4,6-tri-O-acetyl-3-deoxy-3-[4-(3,4,5-trifluorophenyl)-1H-1,2,3-triazol-1-yl]-1-thio-α-D-galactopyranoside

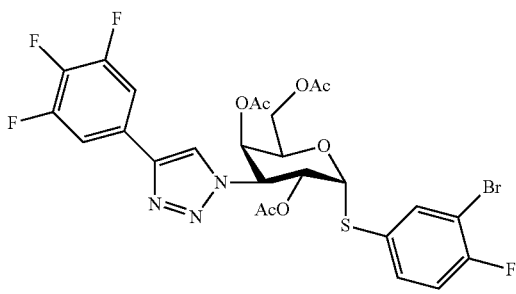

To a solution of 3-Bromo-4-fluorophenyl 2,4,6-tri-O-acetyl-3-azido-3-deoxy-1-thio-α-D-galactopyranoside (300 mg, 0.57 mmol) in DMF (6 mL) was added TEA (194.47 mg, 1.92 mmol), Copper(I)Iodide (21.96 mg, 0.12 mmol), 3,4,5-trifluorophenylacetylene (175.49 mg, 0.77 mmol). The reaction was stirred at 100° C. for 2 h. TLC analysis indicated the total consumption of the SM. Water (10 mL) and DCM (20 mL) were added. The aqueous phase was extracted with DCM (20 mL*2), and the combined organic phase was washed with brine, dried ($Na_2SO_4$) and evaporated to dryness. The crude products were purified by flash column chromatography to give the target compound (250 mg, 64.97%) as a brown solid.

i61) 3-Chloro-4-(trifluoromethyl)phenyl 2,4,6-tri-O-acetyl-3-azido-3-deoxy-1-thio-α-D-galactopyranoside 3-Chloro-4-(trifluoromethyl)-thiophenol

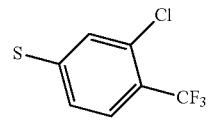 [SMILES: FC(F)(F)c1ccc(S)cc1Cl]

Sodium sulfide (206 mg) was dissolved in DMF (2 mL) and 2-chloro-4-fluoro-1-(trifluoromethyl)benzene (0.250 mL) was added. After 24 h of stirring, Water was added and the mixture was extracted twice with petroleum ether/EtOAc 1:1, dried $Na_2SO_4$ and concentrated to give 382 mg 3-chloro-4-(trifluoromethyl)-thiophenol. The crude product was used in the next step without further purification.

3-Chloro-4-(trifluoromethyl)phenyl 2,4,6-tri-O-acetyl-3-azido-3-deoxy-1-thio-α-D-galactopyranoside

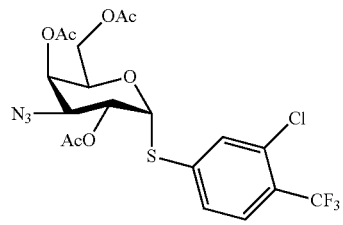

3-Chloro-4-(trifluoromethyl)thiophenol (382 mg) was dissolved in DMF (3 mL) and NaH (78 mg, ca 60% in mineral oil) was added and the mixture was stirred at r.t. After 1 h the mixture was added to 2,4,6-tri-O-acetyl-3-azido-1-chloro-3-deoxy-1-D-galactopyranosid (545 mg) dissolved in DMF (3.5 mL) and the resulting mixture was heated to 55° C. After 95 min the reaction was removed from heat and allow to reach r.t. slowly over night. The mixture was diluted with EtOAc and washed four times with brine. The aqueous phase was extracted twice with EtOAc and the combined organic phase was concentrated in vacuo. The residue was purified by flash chromatography ($SiO_2$, 0-75% EtOAc in petroleum ether) to give 32 mg 3-chloro-4-(trifluoromethyl)phenyl 2,4,6-tri-O-acetyl-3-azido-3-deoxy-1-thio-α-D-galactopyranoside. ESI-MS m/z calcd for $[C_{19}H_{19}ClF_3N_3O_8SNa]^+$ (M+Na)$^4$: 548.0; found: 548.0.

i62) 3,4,5-Trichlorophenyl 2,4,6-tri-O-acetyl-3-azido-3-deoxy-1-thio-α-D-galactopyranoside 3,4,5-Trichlorothiophenol

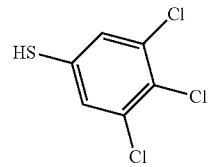

Potassium ethyl xanthate (285 mg) was dissolved in water (3 mL) and heated to 70° C. and 3,4,5-trichlorobenzenediazonium tetrafluoroborate (251 mg) was added in portions. After 100 min the mixture was diluted with a small amount of water and extracted three times with Et$_2$O, dried through a phase separator and concentrated in vacuo. The residue was dissolved in methanolic NaOH (0.05 M, 9 mL) and heated to reflux. After 18 h the mixture was allowed to reach r.t. and concentrated in vacuo. The residue was suspended in water (5 mL) and HCl (conc., aq., 5 mL) was added followed by Zn powder (415 mg) and the mixture was heated to reflux for 2 h. Extracted twice with Et$_2$O, dried Na$_2$SO$_4$ and concentrated to give 158 mg of 3,4,5-trichlorothiophenol. $^1$H NMR (500 MHz, DMSO-d$_6$) δ 7.63 (s, 2H), 6.15 (bs, 1H).

3,4,5-Trichlorophenyl 2,4,6-tri-O-acetyl-3-azido-3-deoxy-1-thio-α-D-galactopyranoside

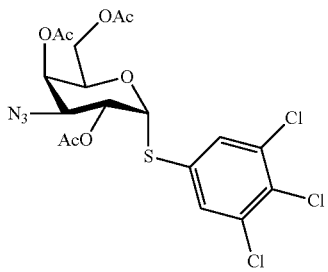

3,4,5-Trichlorothiophenol (158 mg) was dissolved in DMF (2 mL) and NaH (88 mg, ca 60% in mineral oil) was added and the mixture was stirred at r.t. After 80 min the mixture was added to 2,4,6-tri-O-acetyl-3-azido-1-chloro-3-deoxy-3-D-galactopyranosid (130 mg) dissolved in DMF (1.5 mL) and the resulting mixture was heated to 55° C. After 100 min the reaction was removed from heat and allow to reach r.t. slowly over 3.75 h. The mixture was diluted with EtOAc and washed four times with brine. The aqueous phase was extracted once with EtOAc and the combined organic phase was concentrated in vacuo. The residue was purified by flash chromatography (SiO$_2$, 0-60% EtOAc in petroleum ether) to give 64 mg 3,4,5-trichlorophenyl 2,4,6-tri-O-acetyl-3-azido-3-deoxy-1-thio-α-D-galactopyranoside. $^1$H NMR (400 MHz, Chloroform-d) δ 7.49 (s, 2H), 6.01 (d, J=5.5 Hz, 1H), 5.48 (d, J=3.0 Hz, 1H), 5.28 (dd, J=11.0, 5.5 Hz, 1H), 4.58 (dd, J=7.6, 4.8 Hz, 1H), 4.14 (dd, J=11.7, 4.6 Hz, 1H), 4.03 (dd, J=11.7, 7.9 Hz, 1H), 3.92 (dd, J=10.9, 3.2 Hz, 1H), 2.19 (s, 3H), 2.17 (s, 3H), 2.01 (s, 3H). ESI-MS m/z calcd for [C$_{18}$H$_{18}$Cl$_3$N$_3$O$_7$SNa]$^+$ (M+Na)$^+$: 548.0; found: 548.0.

i63) 5-Chloro-2-fluorophenyl 2,4,6-tri-O-acetyl-3-azido-3-deoxy-1-thio-α-D-galactopyranoside 5-Chloro-2-fluorothiophenol

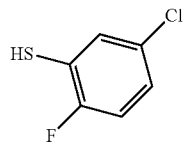

5-Chloro-2-fluorobenzenesulfonyl chloride (233 mg) was dissolved in CH$_2$Cl$_2$ (20 mL). Triphenylphosphine (841 mg) was added and the mixture was stirred at r.t. After 18 h the mixture was extracted with NaOH (2M). The organic phase was concentrated in vacuo, redissolved in Et$_2$O and extracted once more with NaOH (2M). The combined aqueous phases was acidified to pH 1 with HCl (conc., aq.) and extracted three times with CH$_2$Cl$_2$. The combined organic phase was dried through a phase separator and concentrated to give 141 mg of 5-chloro-2-fluorothiophenol. $^1$H NMR (400 MHz, DMSO-d$_6$) δ 7.62-7.55 (m, 1H), 7.32-7.19 (m, 2H), 5.86 (s, 1H).

5-Chloro-2-fluorophenyl 2,4,6-tri-O-acetyl-3-azido-3-deoxy-1-thio-α-D-galactopyranoside

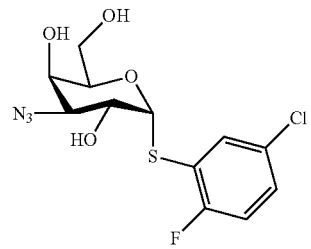

5-Chloro-2-fluorothiophenol (141 mg) was dissolved in DMF (3 mL) and NaH (39 mg, ca 60% in mineral oil) was added and the mixture was stirred at r.t. After 45 min the mixture was added to 2,4,6-tri-O-acetyl-3-azido-1-chloro-3-deoxy-3-D-galactopyranosid (187 mg) dissolved in DMF (2 mL) and the resulting mixture was heated to 55° C. After 60 min the reaction was removed from the heat and allowed to reach r.t. slowly over night. The mixture was diluted with EtOAc and washed four times with brine. The aqueous phase was extracted twice with EtOAc and the combined organic phase was concentrated in vacuo. The residue was purified by flash chromatography (SiO$_2$, 5-70% EtOAc in petroleum ether) to give 87 mg 5-chloro-2-fluorophenyl 2,4,6-tri-O-acetyl-3-azido-3-deoxy-1-thio-α-D-galactopyranoside. $^1$H NMR (400 MHz, Chloroform-d) δ 7.50 (dd, J=6.1, 2.5 Hz, 1H), 7.32-7.22 (m, 1H), 7.04 (t, J=8.7 Hz, 1H), 5.99 (d, J=5.5 Hz, 1H), 5.53-5.45 (m, 1H), 5.29 (dd, J=10.9, 5.5 Hz, 1H), 4.66-4.57 (m, 1H), 4.10 (dd, J=11.6, 5.0 Hz, 1H), 4.06-3.92 (m, 2H), 2.20 (s, 3H), 2.15 (s, 3H), 1.99 (s, 3H).

i64) 5-Bromo-2-fluorophenyl 2,4,6-tri-O-acetyl-3-deoxy-3-[4-(3,4,5-trifluorophenyl)-1H-1,2,3-triazol-1-yl]-1-thio-α-D-galactopyranoside O-5-bromo-2-fluorophenyl dimethylcarbamothioate

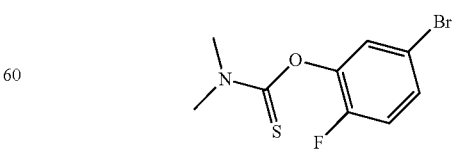

To a solution of 5-bromo-2-fluoro-phenol (1000 mg, 5.24 mmol) in DMF (10 mL) were added NaH (180.55 mg, 7.85 mmol). After 10 mins, N,N-dimethylcarbamothioyl chloride (970.73 mg, 7.85 mmol) was added. The reaction mixture was stirred at room temperature for 20 h. Water (30 mL) and DCM (30 mL) were added. The organic layer was washed with brine, dried (Na₂SO₄) and evaporated to dryness. The crude products were purified by flash column chromatography to obtain O-(5-bromo-2-fluoro-phenyl) N,N-dimethylcarbamothioate (900 mg, 61.80%) as a white solid.

S-5-bromo-2-fluorophenyl dimethylcarbamothioate

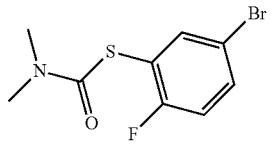

To a solution of O-(5-bromo-2-fluoro-phenyl) N,N-dimethylcarbamothioate (900 mg, 3.24 mmol) in phenoxybenzene (8 mL) was held at 280° C. with stirring on for 2 h. The reaction mixture was cooled to room temperature. The crude product was purified by flash column chromatography to obtain S-(5-bromo-2-fluoro-phenyl) N,N-dimethylcarbamothioate (730 mg, 81.11%) as a yellowy solid.

5-bromo-2-fluorobenzenethiol

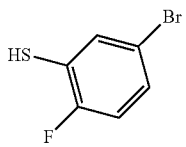

To a solution of S-(5-bromo-2-fluoro-phenyl) N,N-dimethylcarbamothioate (730 mg, 2.62 mmol) in methanol (10 mL) was added 10% NaOH aq. (8 ml). The reaction was held at 50° C. with stirring on for 4 h. TLC analysis indicated the total consumption of the SM. The reaction mixture was cooled to room temperature and adjusted pH to 3, then DCM (15 ml) was added. The organic layer was evaporated to dryness and used directly in the next step.

5-bromo-2-fluorophenyl 2,4,6-tri-O-acetyl-3-azido-3-deoxy-1-thio-α-D-galactopyranoside

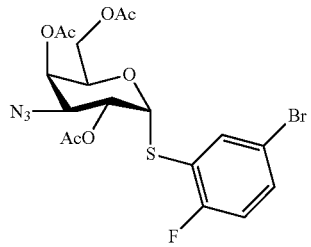

To a solution of 5-bromo-2-fluoro-benzenethiol (664.7 mg, 3.21 mmol) in DMF (10 mL) were added NaH (59.04 mg, 2.57 mmol) at 0° C. under N2. After 10 min, 2,4,6-tri-O-acetyl-3-azido-1-chloro-3-deoxy-β-D-galactopyranoside (561.31 mg, 1.60 mmol) was added. The reaction mixture was stirred at 50° C. stirring for 4 h. The mixture was diluted with DCM (20 ml) and washed with 10% citric acid (15 ml). The organic layer was evaporated to dryness. The crude product was purified by flash column chromatography to obtain 5-Bromo-2-fluorophenyl 2,4,6-tri-O-acetyl-3-azido-3-deoxy-1-thio-α-D-galactopyranoside (400 mg, 47.90%) as a white solid.

5-Bromo-2-fluorophenyl 2,4,6-tri-O-acetyl-3-deoxy-3-[4-(3,4,5-trifluorophenyl)-1H-1,2,3-triazol-1-yl]-1-thio-α-D-galactopyranoside

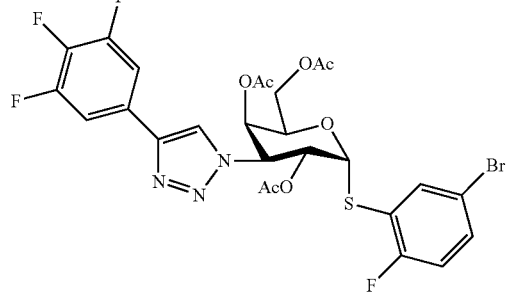

To a solution of 5-bromo-2-fluorophenyl 2,4,6-tri-O-acetyl-3-azido-3-deoxy-1-thio-α-D-galactopyranoside (200 mg, 0.25 mmol) in DMF (6 mL) were added TEA (194.47 mg, 1.92 mmol), Copper(I)Iodide (21.96 mg, 0.12 mmol), 3,4,5-trifluorophenylacetylene (175.49 mg, 0.77 mmol). The reaction was stirred at 100° C. for 2 h. TLC analysis indicated the total consumption of the SM. Water (10 mL) and DCM (20 mL) were added. The aqueous phase was extracted with DCM (20 mL*2), and the combined organic phase was washed with brine, dried (Na₂SO₄) and evaporated to dryness. The crude products were purified by flash column chromatography to give the target compound of 5-Bromo-2-fluorophenyl 2,4,6-tri-O-acetyl-3-deoxy-3-[4-(3,4,5-trifluorophenyl)-1H-1,2,3-triazol-1-yl]-1-thio-α-D-galactopyranoside (170 mg, 65%) as a brown solid.

i65) 5-Chloro-2-methoxyphenyl 2,4,6-tri-O-acetyl-3-azido-3-deoxy-1-thio-α-D-galactopyranoside 5-Chloro-2-mehoxythiophenol

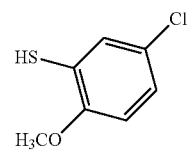

5-Chloro-2-methoxybenzenesulfonyl chloride (260 mg) was dissolved in THF (2.5 mL) and stirred at r.t. Triphenylphosphine (990 mg) was added followed by water (0.340 mL). After 2 h the mixture was diluted with Et₂O and extracted with NaOH (2M). The aqueous phase was washed once with Et₂O. The aqueous phase was then acidified to pH 1 with HCl (conc., aq.) and extracted twice with CH₂Cl₂. The combined organic phase was dried through a phase separator and concentrated to give 175 mg of 5-chloro-2-mehoxythiophenol. ¹H NMR (400 MHz, DMSO-d₆) δ 7.43

(d, J=2.5 Hz, 1H), 7.14 (dd, J=8.7, 2.5 Hz, 1H), 6.97 (d, J=8.8 Hz, 1H), 5.14 (s, 1H), 3.81 (s, 3H).

5-Chloro-2-methoxyphenyl 2,4,6-tri-O-acetyl-3-azido-3-deoxy-1-thio-α-D-galactopyranoside

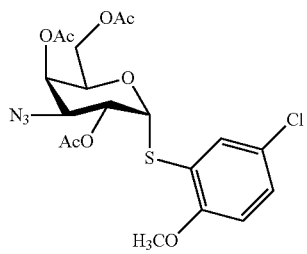

5-Chloro-2-mehoxythiophenol (144 mg) was dissolved in DMF (3 mL) and NaH (36 mg, ca 60% in mineral oil) was added and the mixture was stirred at r.t. After 3 h the mixture was added to 2,4,6-tri-O-acetyl-3-azido-1-chloro-3-deoxy-β-D-galactopyranosid (130 mg) dissolved in DMF (2 mL) and the resulting mixture was heated to 55° C. After 75 min the reaction was removed from heat and allow to reach r.t. slowly over night. The mixture was diluted with EtOAc and washed four times with brine. The aqueous phase was extracted twice with EtOAc and the combined organic phase was concentrated in vacuo. The residue was purified by flash chromatography (SiO$_2$, 5-70% EtOAc in petroleum ether) to give 65 mg 5-chloro-2-methoxyphenyl 2,4,6-tri-O-acetyl-3-azido-3-deoxy-1-thio-α-D-galactopyranoside. $^1$H NMR (400 MHz, Chloroform-d) δ 7.44 (d, J=2.5 Hz, 1H), 7.23 (dd, J=8.7, 2.5 Hz, 1H), 6.80 (d, J=8.8 Hz, 1H), 6.12 (d, J=5.5 Hz, 1H), 5.46 (d, J=3.0 Hz, 1H), 5.31 (dd, J=10.9, 5.5 Hz, 1H), 4.66-4.58 (m, 1H), 4.11-4.01 (m, 2H), 3.96 (dd, J=11.5, 7.7 Hz, 1H), 3.86 (s, 3H), 2.19 (s, 3H), 2.16 (s, 3H), 1.96 (s, 3H). ESI-MS m/z calcd for [C$_{19}$H$_{22}$ClN$_3$O$_8$SNa]$^+$ (M+Na)$^+$: 510.1; found: 510.0.

i66) 3-Iodophenyl 2,4,6-tri-O-acetyl-3-azido-3-deoxy-1-thio-α-D-galactopyranoside O-(3-Iodophenyl) N,N-dimethylcarbamothioate

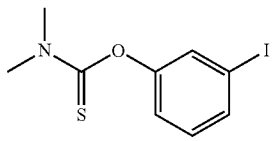

NaH (102 mg, ca 60% in mineral oil) was suspended in DMF (7 mL). 3-Iodophenol (502 mg) was added and the mixture stirred 10 min. N,N-Dimethylthiocarbamoyl chloride (420 mg) was added and the mixture heated to 80° C. 1.5 h. The mixture was allowed to cool, then partitioned between diethyl ether (150 mL) and water (150 mL). The organic phase was washed with water (2×150 mL), aq. sat. NaHCO$_3$ (150 mL) and brine (150 mL), dried (MgSO$_4$), filtered and concentrated in vacuo. The residue was purified by flash chromatography (SiO$_2$, 5-75% EtOAc in heptane). This gave as a white solid (523 mg).

S-(3-Iodophenyl) N,N-dimethylcarbamothioate

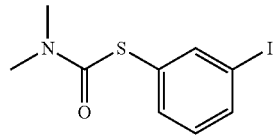

O-(3-iodophenyl) N,N-dimethylcarbamothioate (401 mg) under a argon atmosphere was heated to 260° C. for 1 h. The residue was purified by flash chromatography (SiO$_2$, 2-75% EtOAc in petroleum ether). This afforded a yellow liquid (185 mg).

3-Iodobenzenethiophenol

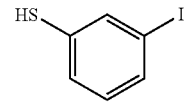

S-(3-Iodophenyl) N,N-dimethylcarbamothioate (170 mg) was dissolved in MeOH (20 mL). 2M aq. sodium hydroxide (2.0 mL) was added and the mixture stirred at reflux 3 h. 1M aq. HCl (4 mL) was added and the mixture partitioned between ether (150 mL) and water (150 mL). The organic phase was washed with brine (100 mL), dried (MgSO$_4$) and concentrated in vacuo. This afforded a yellow oil (122 mg). $^1$H NMR (400 MHz, Chloroform-d) δ 7.69 (t, J=1.6 Hz, 1H), 7.54 (dt, J=7.9, 1.2 Hz, 1H), 7.36-7.24 (m, 1H), 7.01 (t, J=7.9 Hz, 1H), 3.51 (s, 1H).

3-Iodophenyl 2,4,6-tri-O-acetyl-3-azido-3-deoxy-1-thio-α-D-galactopyranoside

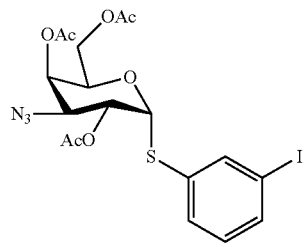

NaH (50 mg, ca 60% in mineral oil) was suspended in DMF (2 mL). 3-Iodobenzenethiophenol (122 mg) in DMF (4 mL) was added. After 5 min, the thiolate was added to 2,4,6-tri-O-acetyl-3-azido-1-chloro-3-deoxy-β-D-galactopyranoside (197 mg) in a vial. The mixture was heated to 50° C. 1 h, then stirred at r.t. over night. The mixture was diluted with CH$_2$Cl$_2$ (15 mL) and extracted with water (2×10 mL). The organic phase was concentrated. The residue was purified by flash chromatography (SiO$_2$, 1-50% EtOAc in heptane). This afforded a white solid (103 mg). $^1$H NMR (400 MHz, Chloroform-d) δ 7.80 (s, 1H), 7.61 (dt, J=8.3, 1.2 Hz, 1H), 7.44-7.38 (m, 1H), 7.03 (dd, J=8.4, 7.2 Hz, 1H), 5.98 (d, J=5.5 Hz, 1H), 5.47 (s, 1H), 5.28 (dd, J=11.0, 5.6 Hz, 1H), 4.62 (dd, J=7.4, 5.4 Hz, H), 4.12 (dd, J=11.5, 5.2 Hz, 1H), 4.05-3.91 (m, 2H), 2.18 (s, 3H), 2.16 (s, 3H), 2.00 (s, 3H).

i68) 3-Cyanophenyl 2,4,6-tri-O-acetyl-3-deoxy-1-thio-3-[4-(3,4,5-trifluorophenyl)-1H-1,2,3-triazol-1-yl]-α-D-galactopyranoside O-3-Cyanophenyl N,N-dimethylthiocarbamate

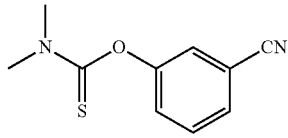

3-Hydroxybenzonitrile (277 mg) was dissolved in DMF (2 mL) and stirred at r.t. NaH (93 mg, ca 60% in mineral oil) was added in portion and the mixture was cooled to 0° C. After stirring for 10 min, dimethylthiocarbamoyl chloride (390 mg) was added. After 5 min the mixture was removed from cold and heated to 80° C. After 2 h the mixture was poured into NaHCO$_3$ (sat. aq.) and extracted with EtOAc. The organic phase was washed twice with brine, and the aqueous phase was extracted once with EtOAc. The combined organic phase was dried (Na$_2$SO$_4$) and concentrated. The residue was purified by flash chromatography (SiO$_2$, 5-95% EtOAc in petroleum ether) to give 392 mg O-3-cyanophenyl N,N-dimethylthiocarbamate. $^1$H NMR (400 MHz, Chloroform-d) δ 7.58-7.53 (m, 1H), 7.50 (t, J=7.9 Hz, 1H), 7.38 (s, 1H), 7.34 (ddt, J=7.8, 3.1, 1.5 Hz, 1H), 3.47 (s, 3H), 3.37 (s, 3H).

S-3-Cyanophenyl N,N-dimethylthiocarbamate

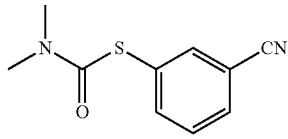

O-3-Cyanophenyl N,N-dimethylthiocarbamate. (345 mg) was heated to 220° C. under N$_2$ for 1 h and then 240° C. for 5.5 h. The residue was purified by flash chromatography (SiO$_2$, 5-70% EtOAc in petroleum ether) to give 149 mg S-3-cyanophenyl N,N-dimethylthiocarbamate.

3-Sulfanylbenzonitrile

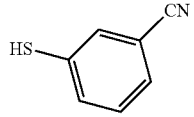

S-3-Cyanophenyl N,N-dimethylthiocarbamate (149 mg) was dissolved in MeOH (20 mL) and NaOH (2M, 2.0 mL) was added and the mixture was heated to reflux. After 3.75 h the mixture was neutralized with HCl (1M, aq.), diluted with brine and extracted three times with CH$_2$Cl$_2$. The organic phase was dried through a phase separator and concentrated to give 93 mg 3-sulfanylbenzonitrile. $^1$H NMR (400 MHz, Chloroform-d) δ 7.55 (s, 1H), 7.49 (d, J=7.9 Hz, 1H), 7.44 (d, J=7.7 Hz, 1H), 7.34 (t, J=7.9 Hz, 1H).

3-Cyanophenyl 2,4,6-tri-O-acetyl-3-azido-3-deoxy-1-thio-α-D-galactopyranoside

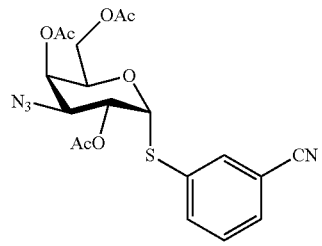

3-Sulfanylbenzonitrile (93 mg) was dissolved in DMF (3 mL) and NaH (29 mg, ca 60% in mineral oil) was added and the mixture was stirred at r.t. After 80 min the mixture was added to 2,4,6-tri-O-acetyl-3-azido-1-chloro-3-deoxy-3-D-galactopyranoside (125 mg) dissolved in DMF (2 mL) and the resulting mixture was heated to 55° C. After 65 min the reaction was removed from the heat and allowed to reach r.t. slowly over night. The mixture was diluted with EtOAc and washed four times with brine. The aqueous phase was extracted twice with EtOAc and the combined organic phase was concentrated in vacuo. The residue was purified by flash chromatography (SiO$_2$, 5-75% EtOAc in petroleum ether) to give 79 mg 3-cyanophenyl 2,4,6-tri-O-acetyl-3-azido-3-deoxy-1-thio-α-D-galactopyranoside. $^1$H NMR (400 MHz, Chloroform-d) δ 7.76 (s, 1H), 7.68 (d, J=8.0 Hz, 1H), 7.57 (d, J=7.7 Hz, 1H), 7.43 (t, J=7.8 Hz, 1H), 6.02 (d, J=5.5 Hz, 1H), 5.49 (s, 1H), 5.28 (dd, J=10.9, 5.5 Hz, 1H), 4.66-4.57 (m, 1H), 4.14 (dd, J=11.6, 4.9 Hz, 1H), 4.06-3.91 (m, 2H), 2.19 (s, 3H), 2.17 (s, 3H), 2.00 (s, 3H).

3-Cyanophenyl 2,4,6-tri-O-acetyl-3-deoxy-1-thio-3-[4-(3,4,5-trifluorophenyl)-1H-1,2,3-triazol-1-yl]-α-D-galactopyranoside

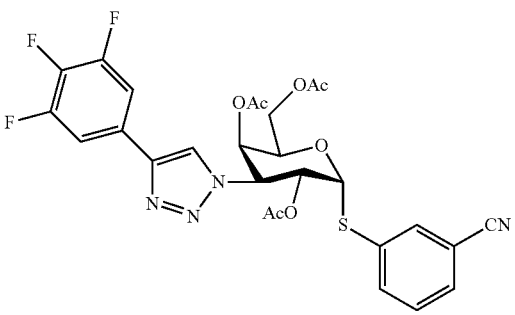

3-Cyanophenyl 2,4,6-tri-O-acetyl-3-azido-3-deoxy-1-thio-α-D-galactopyranoside (79 mg) was dissolved in MeCN (5 mL) and stirred at r.t. under N$_2$. Copper(I) iodide (25 mg) was added and after five minutes 3,4,5-trifluorophenylacetylene (0.050 mL) was added. After an additional five minutes DIEA (0.035 mL) was added and the mixture was stirred at r.t. After 18 h the reaction mixture was concentrated in vacuo. The crude product was purified by flash chromatography (SiO$_2$, 5-70% EtOAc in petroleum ether) to give 72 mg 3-cyanophenyl 2,4,6-tri-O-acetyl-3-deoxy-1-thio-3-[4-(3,4,5-trifluorophenyl)-1H-1,2,3-triazol-1-yl]-α-D-galactopyranoside. $^1$H NMR (400 MHz, Chloroform-d) δ 7.81 (d, J=2.0 Hz, 2H), 7.74 (d, J=8.0 Hz, 1H), 7.62 (d, J 7.8 Hz, 1H), 7.46 (dt, J=12.5, 7.9 Hz, 3H), 6.20 (d, J=5.6 Hz, 1H), 6.10 (dd, J=11.6, 5.6 Hz, 1H), 5.63 (d, J=2.4 Hz, 1H), 5.22 (dd, J=11.6, 3.1 Hz, 1H), 4.85 (t, J=6.3 Hz, 1H), 4.17 (dd, J=11.6, 5.2 Hz, 1H), 4.07 (dd, J=11.6, 7.4 Hz, 1H), 2.07 (s, 3H), 2.01 (s, 3H), 1.98 (s, 3H). ESI-MS nm/z calcd for [C$_{27}$H$_{24}$F$_3$N$_4$O$_7$S]$^+$ (M+H)$^+$: 605.1; found: 605.1.

i69) 2-cyanopyridine-5-yl 2,4,6-tri-O-acetyl-3-deoxy-3-[4-(3,4,5-trifluorophenyl)-1H-1,2,3-triazol-1-yl]-1-thio-α-D-galactopyranoside 5-mercaptopicolinonitrile

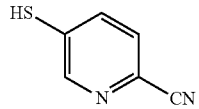

To a solution of 5-fluoropicolinonitrile (5 g, 40.95 mmol) in DMF (200 mL) was added Na$_2$S.9H$_2$O (14.8 g, 61.43 mmol). The reaction was stirred at room temperature for 20 h. The mixture was added NaHSO$_4$ aq to adjust pH 4-5 and MTBE (100 ml) was added. The organic phase was washed with water (100 mL) and brine (100 mL), dried over anhydrous sodium sulphate. Removal of solvent gave the desired product (4.5 g, crude).

m/z calcd for [C$_6$H$_4$N$_2$S]$^-$ [M–H]$^-$: 135.0; found: 135.0.

2-cyanopyridine-5-yl 2,4,6-tri-O-acetyl-3-azido-3-deoxy-1-thio-α-D-galactopyranoside

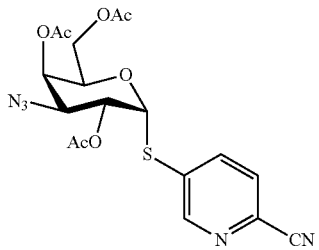

To a solution of 5-mercaptopicolinonitrile (4.5 g, 33.09 mmol) in DMF (200 mL) was added NaH (1.1 g, 36.40 mmol) at 0° C. After 10 min, 2,4,6-tri-O-acetyl-3-azido-1-chloro-3-deoxy-β-D-galactopyranoside (5.7 g, 16.55 mmol) was added. The mixture was stirred at room temperature for 4 h. Water (200 mL) and DCM (100 mL) were added. The aqueous phase was extracted with DCM (100 mL×2), the combined organic phase was washed with water (200 mL) and brine (200 mL), dried over anhydrous sodium sulphate. Removal of solvent gave a residue. The residue was purified by column chromatography (PE/EtOAc-3/1) to obtain the desired product (2.1 g, 28%).

m/z calcd for [C$_{18}$H$_{19}$N$_5$O$_7$S]$^+$ [M+H]$^+$: 450.0; found: 450.0.

2-cyanopyridine-5-yl 2,4,6-tri-O-acetyl-3-deoxy-3-[4-(3,4,5-trifluorophenyl)-1H-1,2,3-triazol-1-yl]-1-thio-α-D-galactopyranoside

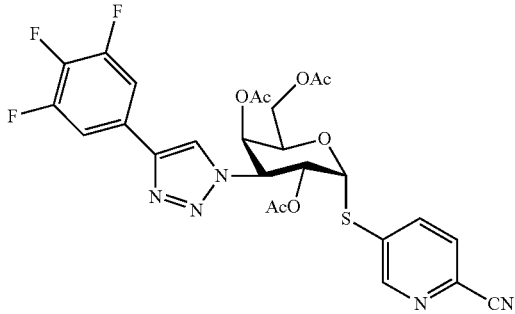

To a solution of 2-cyanopyridine-5-yl 2,4,6-tri-O-acetyl-3-azido-3-deoxy-1-thio-α-D-galactopyranoside (2.1 g, 4.68 mmol) in DMF (20 mL) were added TEA (3.2 mL), Copper (I)Iodide (268 mg, 1.40 mmol), CsF (1.1 g, 7.02 mmol), 3,4,5-trifluorophenylacetylene (1.6 g, 7.02 mmol). The reaction was stirred at room temperature for 20 h under inert atmosphere (N$_2$). Water (30 mL) and DCM (30 mL) were added. The aqueous phase was extracted with DCM (20 mL×2), the combined organic phases were washed with water (40 mL) and brine (40 mL), dried over anhydrous sodium sulphate. Removal of solvent gave a residue. The residue was purified by column chromatography (PE/EtOAc=2/1) to obtain the desired product (1.2 g, 42.85%).

m/z calcd for [C$_{26}$H$_{22}$F$_3$N$_5$O$_7$S]$^+$ [M+H]$^+$: 606.0; found: 606.0.

$^1$H NMR (400 MHz, CDCl$_3$) δ 8.77 (d, J=1.8 Hz, 1H), 7.96 (dd, J=8.2, 2.3 Hz, 1H), 7.78 (s, 1H), 7.67 (d, J=8.2 Hz, 1H), 7.44 (dd, J=8.1, 6.5 Hz, 2H), 6.30 (d, J=5.6 Hz, 1H), 6.15 (dd, J=11.6, 5.6 Hz, 1H), 5.62 (d, J=2.3 Hz, 1H), 5.21 (dd, J=11.7, 3.1 Hz, 1H), 4.81-4.76 (m, 1H), 4.11 (ddd, J=19.1, 11.7, 6.3 Hz, 2H), 2.08 (s, 3H), 1.98 (d, J=1.7 Hz, 6H).

i70) 4-Chloro-2-thienyl 2,4,6-tri-O-acetyl-3-deoxy-3-[4-(3,4,5-trifluorophenyl)-1H-1,2,3-triazol-1-yl]-1-thio-α-D-galactopyranoside 4-chlorothiophene-2-thiol

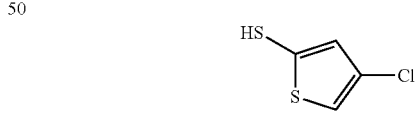

To a solution of 4,5-dichlorothiophene-2-sulfonyl chloride (2500 mg, 9.94 mmol) in dry toluene (30 mL) in a three-neck round-bottom flask with a nitrogen inlet, reflux condenser, and calcium chloride guard tube, was added Ph$_3$P (7820.5 mg, 29.82 mmol) in portions (CAUTION: reaction is highly exothermic and may start refluxing). The reaction was stirred for 10 min and allowed to cool to below 50° C. Water (10 mL) was added and the mixture was stirred for 10 min. The aqueous layer was discarded and the organic layer was extracted with 10% NaOH (2×30 mL). The alkaline aqueous extract was washed with toluene (2×20 mL), acidified with dilute HCl and extracted with DCM (2×15 mL).

The organic layer was dried over Na$_2$SO$_4$ and the solvent was evaporated under reduced pressure to afford 4-chlorothiophene-2-thiol (50 mg, 3.34% yield).

4-Chloro-2-thienyl 2,4,6-tri-O-acetyl-3-azido-3-deoxy-1-thio-α-D-galactopyranoside

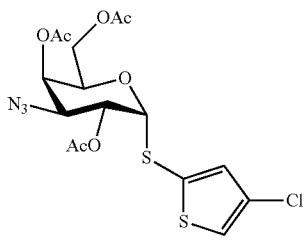

NaH (7.95 mg, 0.33 mmol, 96% in mineral) was added to a solution of 4-chlorothiophene-2-thiol (50 mg, 0.33 mmol) in DMF (4 mL) at 0° C. Then it was stirred at 50° C. for 30 min. 2,4,6-tri-O-Acetyl-3-azido-1-chloro-3-deoxy-β-D-galactopyranoside (94.47 mg, 0.27 mmol) in DMF (1 mL) was added to mixture. The mixture was stirred at 50° C. for 2 h. Then it was cooled to room temperature, water (10 mL) was added to mixture. The resulting solution was extracted with EtOAc (10 mL×3). The combined organic layers were washed with brine (15 mL), dried over Na$_2$SO$_4$, concentrated in vacuum to give crude product. Purification by flash chromatography afforded the crude product 4-Chloro-2-thienyl 2,4,6-tri-O-acetyl-3-azido-3-deoxy-1-thio-α-D-galactopyranoside (50 mg, 32.47%).

ESI-MS m/z calcd for [C$_{16}$H$_{18}$ClN$_3$O$_7$S$_2$]$^+$ (M+H)$^+$: 464.0; found: 464.0.

4-Chloro-2-thienyl 2,4,6-tri-O-acetyl-3-deoxy-3-[4-(3,4,5-trifluorophenyl)-1H-1,2,3-triazol-1-yl]-1-thio-α-D-galactopyranoside

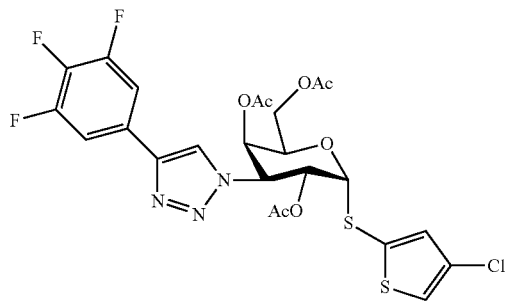

4-Chloro-2-thienyl 2,4,6-tri-O-acetyl-3-azido-3-deoxy-1-thio-α-D-galactopyranoside (50 mg, 0.11 mmol), 3,4,5-trifluorophenylacetylene (36.91 mg, 0.16 mmol), CuI (6.16 mg, 0.03 mmol) and Et3N (54.53 mg, 0.54 mmol) were dissolved in DMF (5 mL) and the mixture was stirred at 50° C. for 2 h. Then it was cooled to room temperature. The mixture was filtered, the filtrated was concentrated in vacuo to afford crude product, which was used for next step without further purification.

ESI-MS m/z calcd for [C$_{24}$H$_{21}$ClF$_3$N$_3$O$_7$S$_2$]$^+$[M+H]$^+$: 619.0; found: 620.0.

i71) (Methyl-1-benzoate)-3-yl 2,4,6-tri-O-acetyl-3-deoxy-3-[4-(3,4,5-trifluorophenyl)-1H-1,2,3-triazol-1-yl]-1-thio-α-D-galactopyranoside Methyl 3-mercaptobenzoate

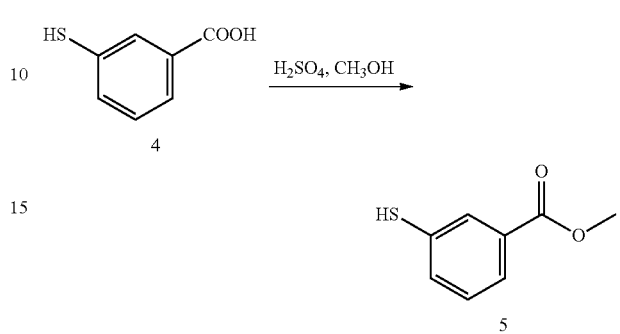

To a solution of 3-sulfanylbenzoic acid (200 mg, 1.30 mmol) in methanol (10 mL) were added H$_2$SO$_4$ (1 ml). The reaction mixture was stirred at 85° C. for 1 h. Water (20 mL) and EtOAc (30 mL) were added. The aqueous phase was extracted with Ethyl acetate (20 mL*2), the combined organic phases were washed with brine, dried over Na$_2$SO$_4$, filtered and evaporated to dryness to obtain methyl 3-sulfanylbenzoate.

(Methyl 1-benzoate)-3-yl 2,4,6-tri-O-acetyl-3-azido-3-deoxy-1-thio-α-D-galactopyranoside

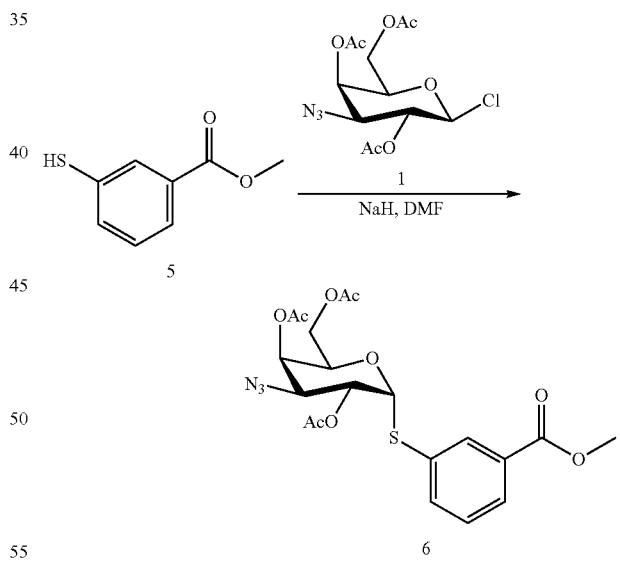

To a solution of methyl 3-sulfanylbenzoate (200 mg, 1.19 mmol) in DMF (10 mL) were added NaH (21.87 mg, 0.95 mmol). After 0.5 h, 2,4,6-tri-O-acetyl-3-azido-1-chloro-3-deoxy-β-D-galactopyranoside (207.9 mg, 0.59 mmol) was added. The mixture was stirred at room temperature for 2 h. Water (20 mL) and DCM (20 mL) were added. The aqueous phase was extracted with DCM (20 mL*2), the combined organic phases were washed with water (30 mL), brine (30 mL), dried over anhydrous sodium sulphate. Solvents were evaporated and the residue was purified by flash column chromatography (PE/EtOAc=3/1) to obtain (Methyl 1-benzoate)-3-yl 2,4,6-tri-O-acetyl-3-azido-3-deoxy-1-thio-α-D-galactopyranoside (60 mg, 11%).

(Methyl 1-benzoate)-3-yl 2,4,6-tri-O-acetyl-3-deoxy-3-[4-(3,4,5-trifluorophenyl)-1H-1,2,3-triazol-1-yl]-1-thio-α-D-galactopyranoside

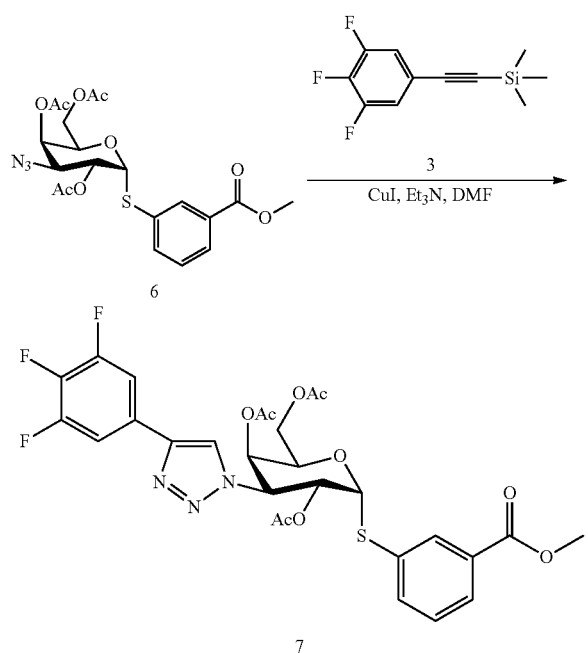

To a solution of (Methyl 1-benzoate)-3-yl 2,4,6-tri-O-acetyl-3-azido-3-deoxy-1-thio-α-D-galactopyranoside (60 mg, 0.12 mmol) in DMF (5 mL) were added CuI (7.12 mg, 0.04 mmol), 3,4,5-trifluorophenylacetylene (42.67 mg, 0.19 mmol) and TEA (63.05 mg, 0.62 mmol). The reaction mixture was stirred at 100° C. for 2 h. Water (20 mL) and DCM (20 mL) were added. The aqueous phase was extracted with DCM (20 mL*2), the combined organic phase was washed with water (30 mL) and brine (30 mL), dried over anhydrous sodium sulphate. Removal of solvent gave a residue. The residue was purified by flash column chromatography (PE/EtOAc=3/1) to obtain (methyl 1-benzoate)-3-yl 2,4,6-tri-O-acetyl-3-deoxy-3-[4-(3,4,5-trifluorophenyl)-1H-1,2,3-triazol-1-yl]-1-thio-α-D-galactopyranoside (30 mg, 38%).

i73) 3,4-Dichlorophenyl 2,4,6-tri-O-acetyl-3-deoxy-3-[4-(3,4-difluorophenyl)-1H-1,2,3-triazol-1-yl]-1-thio-α-D-galactopyranoside

[(3,4-difluorophenyl)-ethynyl]-trimethylsilane

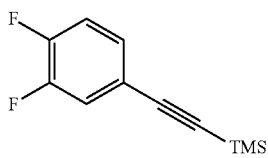 [SMILES: C[Si](C)(C)C#Cc1ccc(F)c(F)c1]

To a solution of 1,2-difluoro-4-iodo-benzene (3 g, 1 mol) in THF (50 ml) was added ethynyl(trimethyl)silane (2.46 g, 2 mol), iodocopper (475 mg, 0.2 mol), Palladium chloride; triphenylphosphine (878 mg, 0.1 mol), N-ethyl-N-isopropyl-propan-2-amine (2.55 g, 0.2 mol). The mixture was purged three times with N₂. The mixture was stirred at RT overnight. LC-MS analysis indicated the target compound was formed. The reaction was quenched with water (50 ml). The mixture was extracted with dichloromethane and the aqueous phase was discarded. The mixture was washed with brine (50 ml) and the aqueous phase was discarded. The material was dried over Na₂SO₄, filtered, and concentrated to dryness. The crude product was purified by combiflash to afford the target compound 350 mg crude of 3.8 g (72.1%).

HNMR (500 MHz, CDCl₃) δ 7.06-7.07 (m, 1H), 6.95-6.70 (m, 1H), 6.87-6.89 (m, 1H), 0.69 (s, 9H).

3,4-Dichlorophenyl 2,4,6-tri-O-acetyl-3-deoxy-3-[4-(3,4-difluorophenyl)-1H-1,2,3-triazol-1-yl]-1-thio-α-D-galactopyranoside

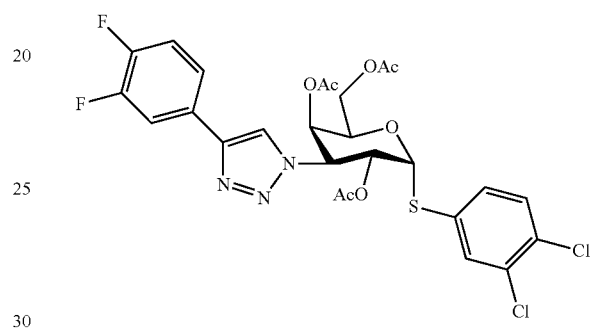

To a solution of 3,4-dichlorophenyl 2,4,6-tri-O-acetyl-3-azido-3-deoxy-1-thio-α-D-galactopyranoside (200 mg, 4.31 mmol) in N,N-dimethylformamide (10 ml) was added [(3,4-difluorophenyl)-ethynyl]-trimethylsilane (246.67 mg, 8.62 mmol), N,N-diethylethanamine (40 mg, 4.31 mmol), copper iodide (22 mg, 1.29 mmol). The mixture was purged three times with N₂. The mixture was stirred at 100° C. for 30 min. LC-MS analysis indicated the target compound was formed. The reaction was quenched with water (50 ml). The mixture was extracted with dichloromethane and the aqueous phase was discarded. The mixture was washed with brine (50 ml) and the aqueous phase was discarded. The material was dried over Na₂SO₄, filtered, and concentrated to dryness. The crude product was purified by combiflash (EtOAc:PE=1:3 to 3:1 ISCO 40 g 40 ml/min normal phase sillica, uv254) to afford the target compound 250 mg.

ESI-MS m/z calcd for [C26H23Cl2F2N3O7S]⁺ [M+H]⁺: 630.0; found: 630.0.

i74) 3,4-Dichlorophenyl 2,4,6-tri-O-acetyl-3-deoxy-3-[4-(3,4-difluorophenyl)-1H-1,2,3-triazol-1-yl]-1-thio-α-D-galactopyranoside

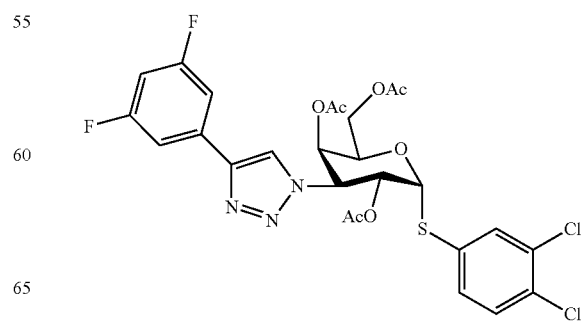

3,4-Dichlorophenyl 2,4,6-tri-O-acetyl-3-azido-3-deoxy-1-thio-α-D-galactopyranoside (150 mg, 0.3 mmol), 3,5-difluorophenylacetylene (90 mg, 0.61 mmol), Copper(I) Iodide (20 mg, 0.09 mmo) and Triethylamine (154 mg, 1.52 mmol) were added to a flask. DMF (3 mL) was added. The mixture was stirred at 100° C. for 1 hour under inert atmosphere ($N_2$). The mixture was filtered and concentrated in vacuum to give 160 mg of the title compound.

ESI-MS m/z calcd for $[C_{26}H_{24}Cl_2F_2N_3O_7S]^+$ (M+H)$^+$: 630.1; found: 630.0.

i75) 3,4-Dichlorophenyl 2,4,6-tri-O-acetyl-3-deoxy-3-[4-(3-fluorophenyl)-1H-1,2,3-triazol-1-yl]-1-thio-α-D-galactopyranoside

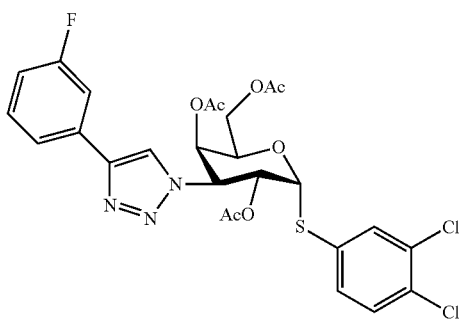

3,4-Dichlorophenyl 2,4,6-tri-O-acetyl-3-azido-3-deoxy-1-thio-α-D-galactopyranoside (150 mg, 0.3 mmol), 1-ethynyl-3-fluoro-benzene (109.8 mg, 0.91 mmol), Copper(I) Iodide (17.41 mg, 0.09 mmol) and Triethylamine (154.15 mg, 1.52 mmol) was dissolved in DMF (5 mL). The mixture was stirred at 100° C. for 1 hour. LCMS showed that the product was formed and no SM left. EtOAc (200 ml) was added. The mixture was filtered, washed by water (100 mL), dried by Na2SO4, filtered and concentrated. The residue was purified on silica gel column to give 140 mg (75%) of the title compound.

ESI-MS m/z calcd for $[C_{26}H_{25}Cl_2FN_3O_7S]^+$ (M+H)$^+$: 612.1; found: 612.1.

i76) 3,3'-difluoro-cyclohexyl 2,4,6-tri-O-acetyl-3-deoxy-3-[4-(3,4,5-trifluorophenyl)-1H-1,2,3-triazol-1-yl]-1-thio-α-D-galactopyranoside 1,2,4,6-tetra-O-acetyl-3-[4-(3,4,5-trifluorophenyl)-1H-1,2,3-triazol-1-yl]-3-deoxy-β-D-galactopyranoside

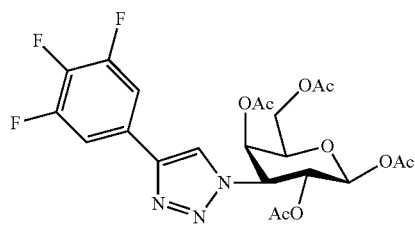

To a solution of 1,2,4,6-tetra-O-acetyl-3-azido-3-deoxy-β-D-galactopyranoside (2.00 g, 5.36 mmol) in DMF (20 mL) were added TEA (2.71 g, 26.80 mmol), Copper(I) Iodide (306.2 mg, 1.61 mmol), 3,4,5-trifluorophenylacetylene (1.83 g, 8.04 mmol). The reaction was held at 100° C. with stirring on for 2 h under $N_2$. Water (80 mL) and DCM (80 mL) were added. The aqueous phase was extracted with DCM (10 mL*2), the combined organic phase was washed with water (20 mL) and brine (20 mL), dried over anhydrous sodium sulphate. Removal of solvent gave a residue. The residue was purified by column chromatography (PE/EtOAc=2/1) to obtain the title compound (2 g, 71%).

2,4,6-tri-O-acetyl-1-chloro-3-deoxy-3-[4-(3,4,5-trifluorophenyl)-1H-1,2,3-triazol-1-yl]-β-D-galactopyranoside

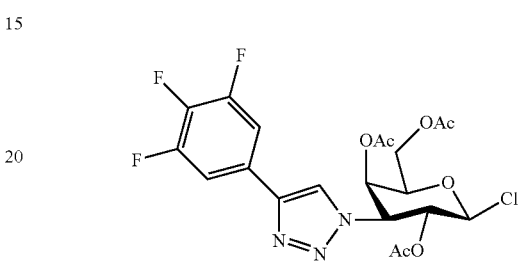

To a stirred suspension of 1.9 g, 3.78 mmol) and $PCl_5$ (1.56 g, 7.56 mmol) in dry DCM (20 mL), $BF_3.Et_2O$ (2 mL) was added. After stirring for 2 h, TLC analysis showed complete disappearance of the starting material. The reaction mixture was diluted with DCM (50 mL) and then washed with ice-cold water, sat. ice-cold $NaHCO_3$ solution (2×50 mL), and again ice-cold water successively, dried over anhydrous $Na_2SO_4$ and evaporated under reduced pressure to afford the crude product 1 g as a white solid. This was used directly in the next step.

Acetyl 2,4,6-tri-O-acetyl-3-deoxy-3-[4-(3,4,5-trifluorophenyl)-1H-1,2,3-triazol-1-yl]-1-thio-α-D-galactopyranoside

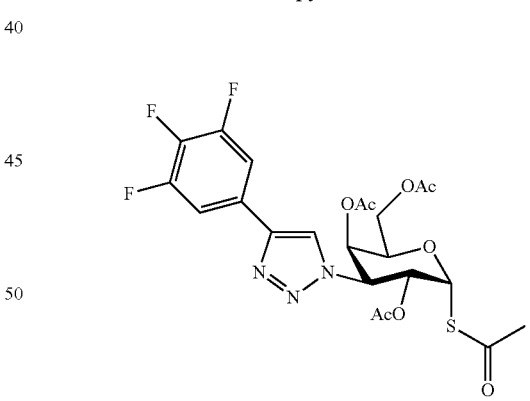

To a solution of 2,4,6-tri-O-acetyl-1-chloro-3-deoxy-3-[4-(3,4,5-trifluorophenyl)-1H-1,2,3-triazol-1-yl]-β-D-galactopyranoside (1.00 g, 1.98 mmol) in DMF (10 mL) was added potassium thioacetate (452.3 mg, 3.96 mmol). The reaction mixture was stirred at room temperature for 20 h. Water (40 mL) and DCM (40 mL) were added. The aqueous phase was extracted with DCM (40 mL*2), the combined organic phase was washed with water (50 mL) and brine (50 mL), dried over anhydrous sodium sulphate and evaporated to dryness. The crude products were purified by flash column chromatography (PE/EtOAc-3/2) to obtain the title compound (450 mg, 42%).

3-oxo-cyclohexyl 2,4,6-tri-O-acetyl-3-deoxy-3-[4-(3,4,5-t trifluorophenyl)-1H-1,2,3-triazol-1-yl]-1-thio-α-D-galactopyranoside

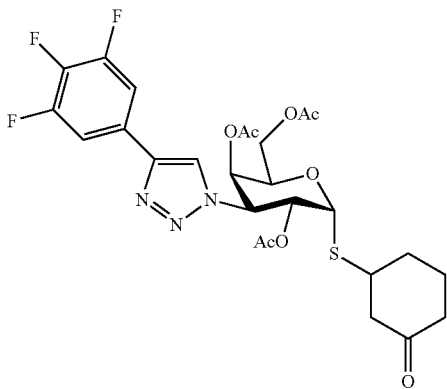

To a solution of acetyl 2,4,6-tri-O-acetyl-3-deoxy-3-[4-(3,4,5-trifluorophenyl)-1H-1,2,3-triazol-1-yl]-1-thio-α-D-galactopyranoside (450 mg, 0.83 mmol) in DCM (10 mL) were added cyclohex-2-en-1-one (158.7 mg, 1.66 mmol) and diethylamine (1.21 g, 16.6 mmol). The reaction mixture was stirred at room temperature for 2 h. Water (30 mL) and DCM (30 mL) were added. The aqueous phase was extracted with DCM (30 mL*2), the combined organic phase was washed with brine, dried (Na$_2$SO$_4$) and evaporated to dryness to obtain the title compound (200 mg, 40%).

3,3'-difluoro-cyclohexyl 2,4,6-tri-O-acetyl-3-deoxy-3-[4-(3,4,5-trifluorophenyl)-1H-1,2,3-triazol-1-yl]-1-thio-α-D-galactopyranoside

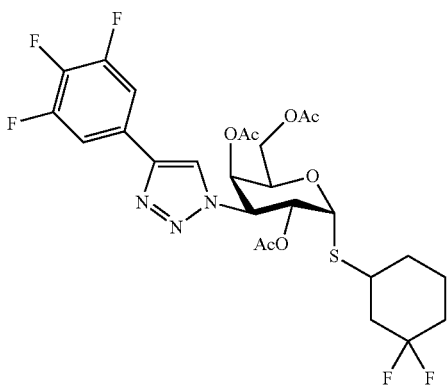

To a solution of 3-oxo-cyclohexyl 2,4,6-tri-O-acetyl-3-deoxy-3-[4-(3,4,5-trifluorophenyl)-1H-1,2,3-triazol-1-yl]-1-thio-α-D-galactopyranoside (60 mg, 0.10 mmol) in DCM (5 mL) were added DAST (80.7 mg, 0.50 mmol). The reaction was stirred at 35° C. for 2 h. The crude product was purified by preparative-TLC to obtain the title compound (30 mg, 48%).

i77) n-Butyl 2,4,6-tri-O-acetyl-3-deoxy-3-[4-(3,4,5-trifluorophenyl)-1H-1,2,3-triazol-1-yl]-1-thio-α-D-galactopyranoside n-Butyl 2,4,6-tri-O-acetyl-3-azido-3-deoxy-1-thio-α-D-galactopyranoside

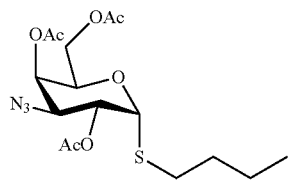

To a solution of 1,2,4,6-tetra-O-acetyl-3-azido-3-deoxy-β-D-galactopyranoside (373 mg, 1.0 mmol) in CHCl$_3$ (10 mL) were added butane-1-thiol (79.38 mg, 0.88 mmol), followed by BF$_3$.OEt$_2$ (1419.3 mg, 10.0 mmol). Reaction was allowed to proceed at room temperature in dark room for 1 h. Excess BF$_3$—OEt$_2$ was decomposed by the addition of cold water (10 mL), and the mixture was then extracted with EtOAc (10 mL×3). The combined organic layers were dried over Na$_2$SO$_4$ and concentrated in vacuo to afford crude product afford the title compound (380 mg, 94% yield).

ESI-MS m/z calcd for $[C_{16}H_{25}N_3O_7S]^+$ $[M+H]^+$: 403.1; found: 404.2.

n-Butyl 2,4,6-tri-O-acetyl-3-deoxy-3-[4-(3,4,5-trifluorophenyl)-1H-1,2,3-triazol-1-yl]-1-thio-α-D-galactopyranoside

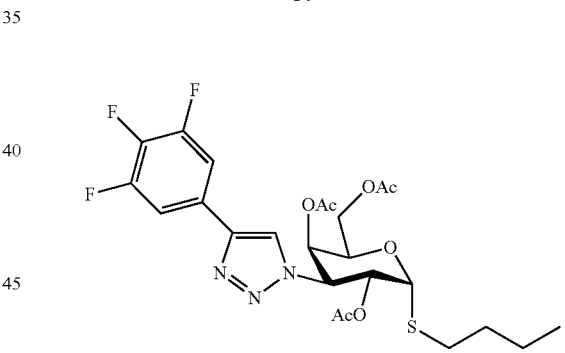

To a solution of n-Butyl 2,4,6-tri-O-acetyl-3-azido-3-deoxy-1-thio-α-D-galactopyranoside (380 mg, 0.94 mmol) in MeCN (10 mL) was added 3,4,5-trifluorophenylacetylene (321.5 mg, 1.41 mmol), iodocopper (53.3 mg, 0.28 mmol), CsF (214.2 mg, 1.41 mmol) and Et$_3$N (475.6 mg, 4.7 mmol). The reaction vessel was purged 3 times with nitrogen. Then the mixture was stirred at room temperature for 2 h. The mixture was extracted with EtOAc (10 mL×3). The combined organic layers were washed with brine, dried over Na$_2$SO$_4$ and concentrated in vacuo to afford crude product, which was purified by flash chromatography to afford the title compound (300 mg, 57.0% yield). $^1$H NMR (400 MHz, MeOD) δ 8.36 (s, 1H), 7.46 (dd, J=8.7, 6.7 Hz, 2H), 5.80 (dt, J=8.1, 5.6 Hz, 2H), 5.42 (d, J=2.3 Hz, 1H), 5.23 (d, J=3.0 Hz, 1H), 5.21 (d, J=3.2 Hz, 1H), 4.68 (t, J=6.4 Hz, 1H), 4.01 (qd, J=11.4, 6.4 Hz, 2H), 2.51 (dtd, J=20.2, 12.9, 7.3 Hz, 2H), 1.88 (s, 6H), 1.73 (s, 3H), 1.55-1.40 (m, 2H), 1.39-1.20 (m, 2H), 0.81 (t, J=7.3 Hz, 3H).

ESI-MS m/z calcd for $[C_{24}H_{28}F_3N_3O_7S]^+$ (M+H)$^+$: 559.2; found: 560.2.

i78) 3,4-Dichlorophenyl 2,4,6-tri-O-acetyl-3-deoxy-3-[4-(3,5-difluoro-4-methoxyphenyl)-1H-1,2,3-triazol-1-yl]-1-thio-α-D-galactopyranoside ((3,5-difluoro-4-methoxyphenyl)ethynyl)trimethylsilane

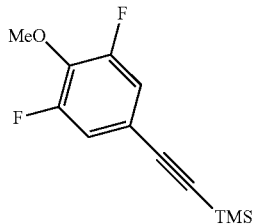 [SMILES: COc1c(F)cc(C#C[Si](C)(C)C)cc1F]

The mixture of 5-bromo-1,3-difluoro-2-methoxy-benzene (2.6 g, 11.7 mmol), ethynyl (trimethyl)silane (1.145 g, 11.7 mmol), N,N-Diisopropylethylamine (1.205 g, 9.33 mmol), Copper(I)Iodide (177.6 mg, 0.93 mmol) and Bis(Triphenylphosphine)palladium (11) chloride (340.4 mg, 0.47 mmol) in THF (20 mL) were heated at 60° C. under a nitrogen atmosphere for 16 hours. Added water (50 mL) and extracted by EtOAc (60 mL), washed EtOAc phase with water (50 mL), brine (50 mL), dried over Na$_2$SO$_4$, filtered and concentrated to give a residue. The residue was purified by slica gel column (pure PE) to afford the title compound as an oil.

3,4-Dichlorophenyl 2,4,6-tri-O-acetyl-3-deoxy-3-[4-(3,5-difluoro-4-methoxyphenyl)-1H-1,2,3-triazol-1-yl]-1-thio-α-D-galactopyranoside

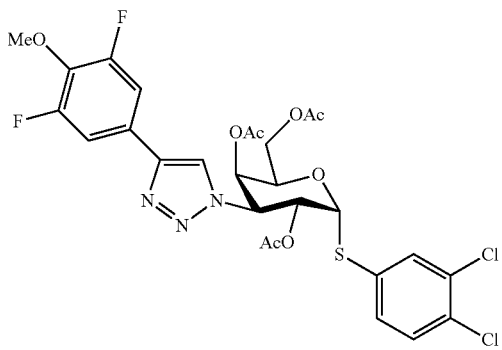

3,4-Dichlorophenyl 2,4,6-tri-O-acetyl-3-azido-3-deoxy-1-thio-α-D-galactopyranoside (150 mg, 0.3 mmol), 2-(3,5-difluoro-4-methoxy-phenyl)ethynyl-trimethyl-silane (219.66 mg, 0.91 mmol), Copper(I)Iodide (17.41 mg, 0.09 mmol) and triethylamine (154.15 mg, 1.52 mmol) was dissolved in DMF (5 mL). The mixture was stirred at 100° C. for 1 hour. LCMS showed that the product was formed and no SM left. EtOAc (50 mL) was added. The mixture was filtered, washed by water (100 mL), dried by Na$_2$SO$_4$, filtered and concentrated. The residue was purified on silica gel column to afford the title compound (120 mg, 59.6% yield).

ESI-MS m/z calcd for $[C_{27}H_{25}Cl_2F_2N_3O_8S]^+$ (M+H)$^+$: 659.1; found: 660.1.

i79) 2-hydroxy-pyridin-4-yl 2,4,6-tri-O-acetyl-3-deoxy-3-[4-(3,4,5-trifluorophenyl)-1H-1,2,3-triazol-1-yl]-1-thio-α-D-galactopyranoside O-2-hydroxypyridin-4-yl dimethylcarbamothioate

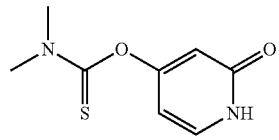

To a solution of pyridine-2,4-diol (2.2 g, 0.02 mol) in THF (20 mL), Dabco (2.22 g, 0.02 mol) and N,N-dimethylcarbamothioyl chloride (2.45 g, 0.02 mol) were added. The mixture was stirred at rt for 16 h. The solvents were removed in vacuo and the resulting crude was diluted with CH$_2$Cl$_2$ and washed with water and brine. The organic layer was dried over Na$_2$SO$_4$, filtered and evaporated. The crude product was purified by silica gel column to give 0.9 g (22.9%) of the title compound.

ESI-MS nm/z calcd for $[C_8H_{11}N_2O_2S]^+$ (M+H)$^+$: 199.1; found: 199.0.

S-1-(4-methoxybenzyl)-2-oxo-1,2-dihydropyridin-4-yl dimethylcarbamothioate

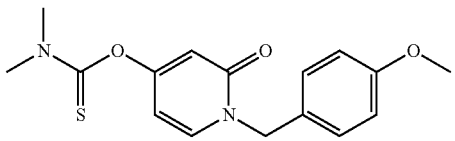

To a solution of O-[(2-hydroxy-4-pyridyl)] N,N-dimethylcarbamothioate (400 mg) in DMF (6 mL), NaH (60%, 0.15 g) was added at 0° C. The mixture was stirred at 0° C. for 15 min. 1-(bromomethyl)-4-methoxy-benzene (1.22 g, 0.01 mol) was added. The mixture was stirred at rt for 2 hours. EtOAc (100 ml) was added. the mixture was washed by water (40 mL), brine (40 mL), dried over Na$_2$SO$_4$, filtered and concentrated. The residue was purified on silica gel column. 0.4 g (62.3%) of the title compound was obtained.

ESI-MS m/z calcd for $[C_{16}H_{19}N_2O_3S]^+$ (M+H)$^+$: 319.1; found: 319.1.

S-1-(4-methoxybenzyl)-2-oxo-1,2-dihydropyridin-4-yl dimethylcarbamothioate

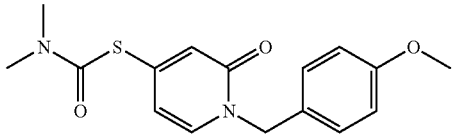

S-1-[[1-[(4-methoxyphenyl)methyl]-2-oxo-1-pyridyl]] N,N-dimethylcarbamothioate (0.3 g) was dissolved in phenoxybenzene (3 mL). The mixture was stirred at 280° C. for 2 hours. LCMS showed that the desired product was formed and no SM left. The mixture was purified by flash chromatography on silica to give 0.25 g (83.3%) of the title compound.

ESI-MS m/z calcd for [C16H19N2O3S]+ (M+H)+: 319.1; found: 319.1.

4-mercapto-1-(4-methoxybenzyl)pyridin-2(1H)-one

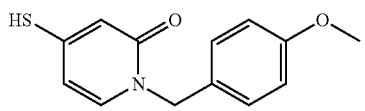 [SMILES: COc1ccc(Cn2ccc(S)cc2=O)cc1]

To a solution of S-[[1-[(4-methoxyphenyl)methyl]-2-oxo-4-pyridyl]] N,N-dimethylcarbamothioate (0.25 g) in EtOH (10 mL), KOH (0.09 g) was added. The mixture was stirred at 85° C. for 2 hours. The mixture was cooled to rt. Neutralization with H+ resin, filtered and concentrated to afford product as an oil. The residue was used for next step.

ESI-MS nm/z calcd for $[C_{13}H_{14}NO_2S]^+$ (M+H)$^+$: 248.1; found: 248.0.

1-(4-methoxybenzyl)-2-oxo-1,2-dihydropyridin-4-yl 2,4,6-tri-O-acetyl-3-azido-3-deoxy-1-thio-α-D-galactopyranoside

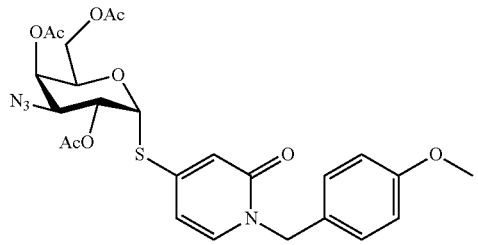

To a solution of 1-[(4-methoxyphenyl)methyl]-4-sulfanyl-pyridin-2-one (0.25 g) in DMF (3 mL), NaH (60%, 0.12 g) was added. The mixture was stirred at rt for 15 min. 2,4,6-tri-O-acetyl-3-azido-1-chloro-3-deoxy-β-D-galactopyranoside (350 mg) was added. the mixture was stirred at rt for 2 hours. EtOAc (100 mL) was added. The mixture was washed by water (50 mL), brine (50 mL), dried over Na2SO4, filtered and concentrated. The residue was purified on silica gel column. 0.3 g (53.5%) of title compound was obtained.

ESI-MS m/z calcd for $[C_{25}H_{29}N_4O_9S]^+$ (M+H)$^+$: 561.2; found: 561.2.

1-(4-methoxybenzyl)-2-oxo-1,2-dihydropyridin-4-yl 2,4,6-tri-O-acetyl-3-deoxy-3-[4-(3,4,5-trifluorophenyl)-1H-1,2,3-triazol-1-yl]-1-thio-α-D-galactopyranoside

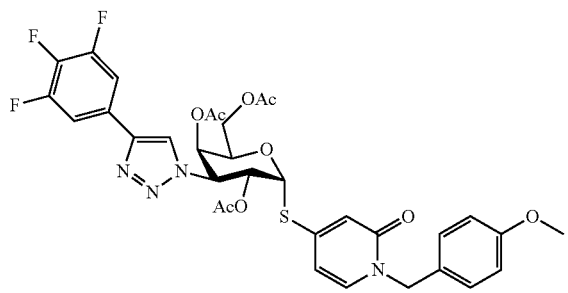

1-(4-methoxybenzyl)-2-oxo-1,2-dihydropyridin-4-yl 2,4,6-tri-O-acetyl-3-azido-3-deoxy-1-thio-α-D-galactopyranoside (0.32 g) was dissolved in CH3CN (6 ml). Then CuI (0.03 g), 3,4,5-trifluorophenylacetylene (0.13 g), and DIEA (0.22 g) were added. The mixture was stirred at rt for 5 min. CsF (0.09 g) was added. The mixture was stirred at rt over night. 0.12 g (29.6%) of the title compound was obtained.

ESI-MS m/z calcd for $[C_{33}H_{32}F_3N_4O_9S]^+$ (M+H)$^+$: 717.2; found: 717.2.

2-hydroxy-pyridin-4-yl 2,4,6-tri-O-acetyl-3-deoxy-3-[4-(3,4,5-trifluorophenyl)-1H-1,2,3-triazol-1-yl]-1-thio-α-D-galactopyranoside

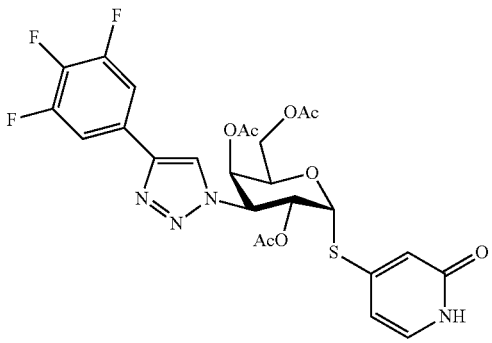

1-(4-methoxybenzyl)-2-oxo-1,2-dihydropyridin-4-yl 2,4,6-tri-O-acetyl-3-deoxy-3-[4-(3,4,5-trifluorophenyl)-1H-1,2,3-triazol-1-yl]-1-thio-α-D-galactopyranoside (100 mg, 0.14 mmol) was dissolved in TFA (5 mL). The mixture was stirred at in a single node microwave oven at 110° C. for 2 hours. The TFA was removed in vacuum. The residue was used for next step.

ESI-MS m/z calcd for $[C_{25}H_{24}F_3N_4O_8S]^+$ (M+H)$^+$: 597.1; found: 597.1.

i80) 2-chlorophenethyl 2,4,6-tri-O-acetyl-3-deoxy-3-[4-(3,4,5-trifluorophenyl)-1H-1,2,3-triazol-1-yl]-1-thio-α-D-galactopyranoside

2-chlorophenethyl 2,4,6-tri-O-acetyl-3-azido-3-deoxy-1-thio-α-D-galactopyranoside

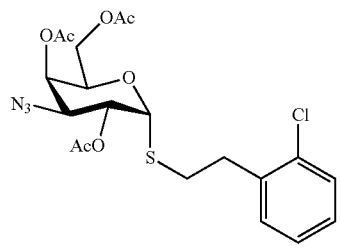

Acetyl 2,4,6-tri-O-acetyl-3-azido-3-deoxy-1-thio-α-D-galactopyranoside (0.5 g) was dissolved in DMF (4 mL). 1-(2-bromoethyl)-2-chloro-benzene (0.33 g) was added. diethylamine (2 mL) was added at 0° C. The mixture was stirred at 0° C. for 2 hours. EtOAc (200 mL) was added. The mixture was washed by water (100 mL). The organic phase was dried over $Na_2SO_4$, filtered and concentrated. The residue was purified on silica gel column to give 0.3 g (48%) of the title compound.

$^1$H NMR (400 MHz, $CDCl_3$) δ 7.39-7.31 (m, 1H), 7.24-7.12 (m, 3H), 5.76 (d, J=5.6 Hz, 1H), 5.42 (d, J=2.5 Hz, 1H), 5.22 (dd, J=10.9, 5.6 Hz, 1H), 4.51 (t, J=6.7 Hz, 1H), 4.05-3.88 (m, 2H), 3.05-2.94 (m, 2H), 2.91-2.71 (m, 2H), 2.16 (s, 3H), 2.14 (s, 3H), 1.98 (s, 3H). ESI-MS m/z calcd for $[C_{20}H_{24}ClN_3O_7SNa]^+$ $(M+Na)^+$: 508.1; found: 508.0.

2-chlorophenethyl 2,4,6-tri-O-acetyl-3-deoxy-3-[4-(3,4,5-trifluorophenyl)-1H-1,2,3-triazol-1-yl]-1-thio-α-D-galactopyranoside

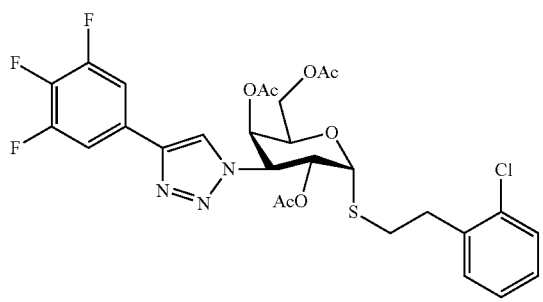

2-chlorophenethyl 2,4,6-tri-O-acetyl-3-azido-3-deoxy-1-thio-α-D-galactopyranoside (350 mg, 0.72 mmol) and 3,4,5-trifluorophenylacetylene (164.4 mg, 0.72 mmol) were dissolved in $CH_3CN$ (20 mL). Then Copper(I)Iodide (137.2 mg, 0.72 mmol), TEA (72.9 mg, 0.72 mmol) and CsF (109.4 mg, 0.72 mmol) were added. The mixture was stirred at rt over night. The mixture was concentrated and the residue was purified on silica gel using a gradient of EtOAc/PE from 0-30% to give 120 mg (25.9%) of the title compound.

ESI-MS m/z calcd for $[C_{28}H_{28}ClF_3N_3O_7S]^+$ $(M+H)^+$: 642.1; found: 642.1.

i81) 4-Chlorophenethyl 2,4,6-tri-O-acetyl-3-deoxy-3-[4-(3,4,5-trifluorophenyl)-1H-1,2,3-triazol-1-yl]-1-thio-α-D-galactopyranoside

Acetyl 2,4,6-tri-O-acetyl-3-azido-3-deoxy-1-thio-α-D-galactopyranoside

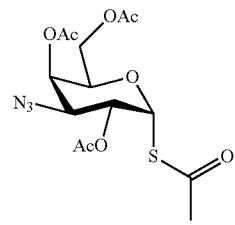

2,4,6-tri-O-acetyl-3-azido-1-chloro-3-deoxy-1-D-galactopyranoside (3 g, 8.58 mmol) was dissolved in DMF (8 mL). Potassium thioacetate (1469.5 mg, 12.87 mmol) was added. The mixture was stirred at rt for 16 hours. EtOAc (200 mL) was added. The mixture was washed with water (100 mL) and brine. The organic phase was dried over $Na_2SO_4$, filtered and concentrated. The residue was purified on silica gel column using a gradient of EtOAc/PE from 0-35%. 1.2 g of the title compound was obtained.

ESI-MS n/z calcd for $[C_{14}H_{23}N_4O_8S]^+$ $(M+NH_4)^+$: 407.1; found: 407.2.

4-Chlorophenethyl 2,4,6-tri-O-acetyl-3-azido-3-deoxy-1-thio-α-D-galactopyranoside

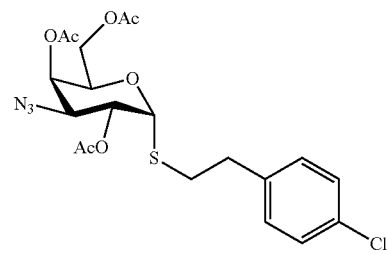

Acetyl 2,4,6-tri-O-acetyl-3-azido-3-deoxy-1-thio-α-D-galactopyranoside (400 mg, 1.03 mmol) was dissolved in DMF (4 mL). 1-(2-bromoethyl)-4-chloro-benzene (225.5 mg, 1.03 mmol) was added. Diethylamine (2 ml) was added at 0° C. The mixture was stirred at 0° C. for 2 hours. EtOAc (200 mL) was added. The mixture was washed by water (100 mL). The organic phase was dried over $Na_2SO_4$, filtered and concentrated. The residue was purified on silica gel column to give 300 mg (60.10%) of the title compound.

$^1$H NMR (400 MHz, $CDCl_3$) δ 7.35-7.2 (m, 2H), 7.15-7.06 (m, 2H), 5.75 (d, J=5.6 Hz, 1H), 5.41 (d, J=2.5 Hz, 1H), 5.19 (dd, J=10.8, 5.6 Hz, 1H), 4.46 (t, J=6.3 Hz, 1H), 4.11 (dd, J=11.5, 5.6 Hz, 1H), 4.02 (dd, J=11.5, 7.2 Hz, 1H), 3.90 (dd, J=10.9, 3.3 Hz, 1H), 2.96-2.76 (m, 3H), 2.76-2.63 (m, 1H).

ESI-MS m/z calcd for $[C_{20}H_{24}ClN_3O_7SNa]^+$ $(M+Na)^+$: 508.1; found: 508.0.

231

4-Chlorophenethyl 2,4,6-tri-O-acetyl-3-deoxy-3-[4-(3,4,5-trifluorophenyl)-1H-1,2,3-triazol-1-yl]-1-thio-α-D-galactopyranoside

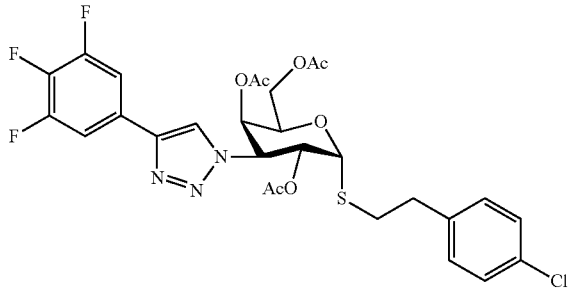

4-Chlorophenethyl 2,4,6-tri-O-acetyl-3-azido-3-deoxy-1-thio-α-D-galactopyranoside (350 mg, 0.72 mmol) and 3,4,5-trifluorophenylacetylene (164.42 mg, 0.72 mmol) were dissolved in CH$_3$CN (20 mL). Then Copper(I)Iodide (137.17 mg, 0.72 mmol), TEA (72.88 mg, 0.72 mmol) and CsF (109.41 mg, 0.72 mmol) were added. The mixture was stirred at rt over night. The mixture was concentrated and the residue was purified on silica gel using a gradient of EtOAc/PE from 0-30% to give 200 mg (43.2%) of the title compound.

ESI-MS m/z calcd for $[C_{28}H_{28}ClF_3N_3O_7S]^+$ (M+H)$^+$: 642.1; found: 642.1.

i82) 2-Chlorobenzyl 2,4,6-tri-O-acetyl-3-azido-3-deoxy-1-thio-α-D-galactopyranoside

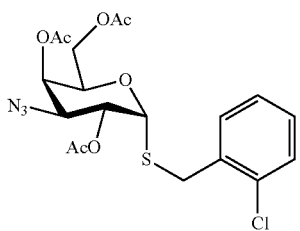

1,2,4,6-Tetra-O-acetyl-3-azido-3-deoxy-β-D-galactopyranoside (287 mg) was dissolved in dichloroethane (10 mL). 2-Chlorobenzylmercaptane (0.200 mL) and BF$_3$.OEt$_2$ (0.400 mL) were added. The vial was closed and heated to 65° C. over night. It was allowed to cool, then washed with water (15 mL). The organic phase was purified by flash chromatography (SiO$_2$, 1-50% EtOAc in heptane). This afforded 2-chlorobenzyl 2,4,6-tri-O-acetyl-3-azido-3-deoxy-1-thio-α-D-galactopyranoside (132 mg). $^1$H NMR (400 MHz, Chloroform-d) δ 7.41-7.34 (m, 1H), 7.30 (dt, J=8.1, 3.9 Hz, 1H), 7.28-7.16 (m, 2H), 5.63 (d, J=5.6 Hz, 1H), 5.42 (d, J=3.3 Hz, 1H), 5.19 (dd, J=10.9, 5.6 Hz, 1H), 4.53 (t, J=6.5 Hz, 1H), 4.11 (dd, J=11.4, 5.9 Hz, 1H), 4.02-3.76 (m, 5H), 2.13 (d, J=1.0 Hz, 3H), 2.06 (s, 3H), 2.05 (d, J=1.2 Hz, 3H).

232 i83) 3,4-Dichlorobenzyl 2,4,6-tri-O-acetyl-3-azido-3-deoxy-1-thio-α-D-galactopyranoside

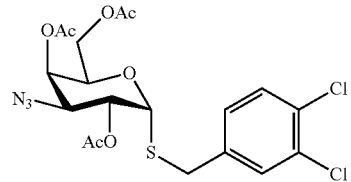

1,2,4,6-Tetra-O-acetyl-3-azido-3-deoxy-3-D-galactopyranoside (229 mg) was dissolved in dichloroethane (10 mL). 3,4-Dichlorobenzylmercaptane (0.200 mL) and BF$_3$.OEt$_2$ (0.400 mL) were added. The vial was closed and heated to 65° C. over night. The mixture was allowed to cool, then washed with water (15 mL). The organic phase was collected and purified by flash chromatography (SiO$_2$, 1-50% EtOAc in heptane). This afforded 3,4-dichlorobenzyl 2,4,6-tri-O-acetyl-3-azido-3-deoxy-1-thio-α-D-galactopyranoside (123 mg) as a clear oil. $^1$H NMR (400 MHz, Chloroform-d) δ 7.41-7.32 (m, 2H), 7.11 (dd, J=8.3, 2.1 Hz, 1H), 5.51 (d, J=5.6 Hz, 1H), 5.46-5.40 (m, 1H), 5.18 (dd, J=10.8, 5.6 Hz, 1H), 4.47 (t, J=6.4 Hz, 1H), 4.12 (dd, J=11.5, 5.7 Hz, 1H), 3.98 (dd, J=11.5, 7.0 Hz, 1H), 3.91 (dd, J=10.9, 3.3 Hz, 1H), 3.70-3.56 (m, 2H), 2.14 (d, J=0.9 Hz, 3H), 2.08 (s, 3H), 2.06 (s, 3H).

i84) 3-Chlorophenethyl 2,4,6-tri-O-acetyl-3-deoxy-3-[4-(3,4,5-trifluorophenyl)-1H-1,2,3-triazol-1-yl]-1-thio-α-D-galactopyranoside 3-Chlorophenethyl 2,4,6-tri-O-acetyl-3-azido-3-deoxy-1-thio-α-D-galactopyranoside

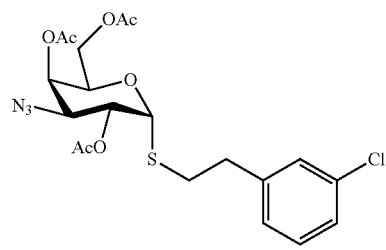

2,4,6-tri-o-acetyl-1-(acetylthio)-3-azido-1,3-dideoxy-α-D-galactopyranoside (0.5 g mol) was dissolved in DMF (4 mL). 2-(3-chlorophenyl)ethanethiol (0.33 g) was added diethylamine (2 ml) was added at 0° C. The mixture was stirred at 0° C. for 2 hours. EtOAc (200 mL) was added. The mixture was washed by water (100 mL). The organic phase was dried over Na$_2$SO$_4$, filtered and concentrated. The residue was purified on silica gel column to give 0.3 g (48.1%) of the title compound.

$^1$H NMR (400 MHz, CDCl$_3$) δ 7.26-7.16 (m, 3H), 7.10-7.04 (m, 1H), 5.75 (d, J=5.6 Hz, 1H), 5.41 (d, J=2.6 Hz, 1H), 5.20 (dd, J=10.8, 5.6 Hz, 1H), 4.48 (t, J=6.4 Hz, 1H), 4.22-4.08 (m, 2H), 4.05 (d, J=7.3 Hz, 1H), 3.91 (dd, J=10.9, 3.4 Hz, 1H), 2.97-2.78 (m, 3H), 2.78-2.68 (m, 1H), 2.16 (s, 3H), 2.14 (s, 3H), 2.00 (s, 3H).

ESI-MS m/z calcd for $[C_{20}H_{24}ClN_3O_7SNa]^+$ (M+Na)$^+$: 508.1; found: 508.0.

3-Chlorophenethyl 2,4,6-tri-O-acetyl-3-deoxy-3-[4-(3,4,5-trifluorophenyl)-1H-1,2,3-triazol-1-yl]-1-thio-α-D-galactopyranoside

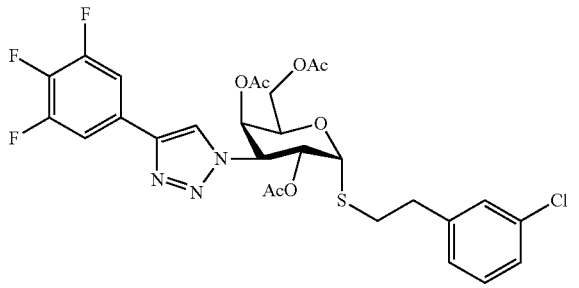

3-Chlorophenethyl 2,4,6-tri-O-acetyl-3-azido-3-deoxy-1-thio-α-D-galactopyranoside (350 mg, 0.72 mmol) and 3,4,5-trifluorophenylacetylene (164.42 mg, 0.72 mmol) were dissolved in CH$_3$CN (20 mL). Then Copper(I)Iodide (137.17 mg, 0.72 mmol), TEA (72.88 mg, 0.72 mmol) and CsF (109.41 mg, 0.72 mmol) were added. The mixture was stirred at rt over night. The mixture was concentrated and the residue was purified on silica gel using a gradient of EtOAc/PE from 0-30% to give 130 mg (28.1%) of the title compound.

ESI-MS m/z calcd for [C$_{28}$H$_{28}$ClF$_3$N$_3$O$_7$S]$^+$ (M+H)$^+$: 642.1; found: 642.1.

i85 4-Chlorobenzyl 2,4,6-tri-O-acetyl-3-azido-3-deoxy-1-thio-α-D-galactopyranoside

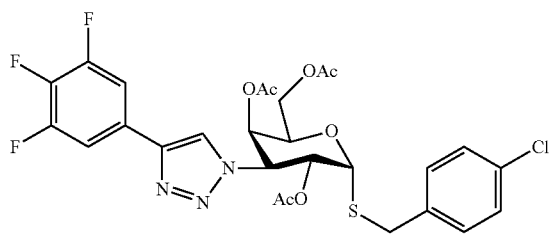

1,2,4,6-Tetra-O-acetyl-3-azido-3-deoxy-β-D-galactopyranoside (181 mg) was dissolved in dichloroethane (10 mL). 4-Chlorobenzylmercaptane (0.150 mL) and BF$_3$.OEt$_2$ (0.200 mL) were added. The vial was closed and heated to 65° C. over night. Allowed to cool, then concentrated in vacuo. Pyridine (10 mL) and acetic anhydride (1 mL) were added, and the mixture then stirred 1 h. It was again concentrated in vacuo. The residue was purified by flash chromatography (SiO$_2$, 1-50% EtOAc in heptane). 4-Chlorobenzyl 2,4,6-tri-O-acetyl-3-azido-3-deoxy-1-thio-α-D-galactopyranoside was isolated as a clear oil (58 mg). $^1$H NMR (400 MHz, Chloroform-d) δ 7.28 (d, J=8.3 Hz, 2H), 7.21 (d, J=8.3 Hz, 2H), 5.52 (d, J=5.6 Hz, 1H), 5.43 (d, J=3.3 Hz, 1H), 5.19 (dd, J=10.8, 5.6 Hz, 1H), 4.50 (t, J=6.4 Hz, 1H), 4.12 (dd, J=11.4, 5.7 Hz, 1H), 3.99 (dd, J=11.5, 7.1 Hz, 1H), 3.92 (dd, J=10.8, 3.4 Hz, 1H), 3.73-3.60 (m, 2H), 2.14 (s, 3H), 2.08 (s, 3H), 2.07 (s, 3H).

I86) Propyl 2,4,6-tri-O-acetyl-3-deoxy-3-[4-(3,4,5-trifluorophenyl)-1H-1,2,3-triazol-1-yl]-1-thio-α-D-galactopyranoside Propyl 2,4,6-tri-O-acetyl-3-azido-3-deoxy-1-thio-α-D-galactopyranoside

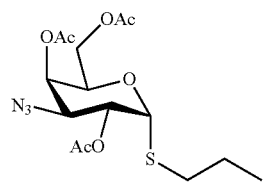

To a solution of 1,2,4,6-tetra-O-acetyl-3-azido-3-deoxy-β-D-galactopyranoside (150 mg, 0.40 mmol) in CHCl$_3$ (10 mL) were added propane-1-thiol (28 mg, 0.35 mmol), followed by BF$_3$.OEt$_2$ (568 mg, 4.0 mmol). Reaction was allowed to proceed at room temperature in a dark room for 1 h. Excess BF$_3$.OEt$_2$ was decomposed by the addition of cold water (10 mL), and the mixture was then extracted with EtOAc (10 mL×3). The combined organic layers were dried over anhyd Na$_2$SO$_4$ and concentrated in vacuo to afford crude product. (150 mg, 96% yield).

ESI-MS m/z calcd for [C$_{15}$H$_{23}$N$_3$O$_7$S]$^+$ [M+NH$_4$]$^+$: 389.1; found: 407.2.

Propyl 2,4,6-tri-O-acetyl-3-deoxy-3-[4-(3,4,5-trifluorophenyl)-1H-1,2,3-triazol-1-yl]-1-thio-α-D-galactopyranoside

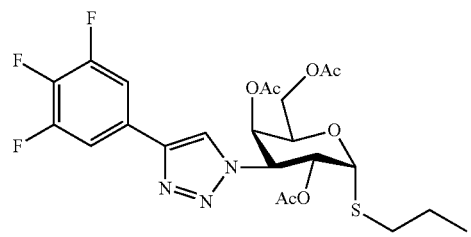

To a solution of propyl 2,4,6-tri-O-acetyl-3-azido-3-deoxy-1-thio-α-D-galactopyranoside (150 mg, 0.39 mmol) in MeCN (10 mL) was added 3,4,5-trifluorophenylacetylene (135 mg, 0.59 mmol), iodocopper (23 mg, 0.12 mmol), CsF (89 mg, 0.59 mmol) and Et$_3$N (197 mg, 1.95 mmol). The reaction vessel was purged 3 times with nitrogen. Then the mixture was stirred at room temperature for 2 h. The mixture was extracted with EtOAc (10 mL×3). The combined organic layers were washed with brine, dried over Na$_2$SO$_4$ and concentrated in vacuo to afford crude product, which was purified by flash chromatography to afford the title compound (100 mg, 47% yield).

ESI-MS m/z calcd for [C$_{23}$H$_{26}$F$_3$N$_3$O$_7$S]$^+$ (M+H)$^+$: 545.5; found: 546.2.

i87) 2-Aminopyridin-4-yl 2,4,6-tri-O-acetyl-3-deoxy-3-[4-(3,4,5-trifluorophenyl)-1H-1,2,3-triazol-1-yl]-1-thio-α-D-galactopyranoside 2-nitropyridine-4-thiol

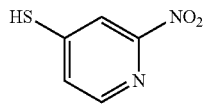

4-chloro-2-nitro-pyridine (5000 mg, 31.54 mmol) and NaHS (2122 mg, 37.84 mmol) were dissolvent in DMF (50 mL). Then it was stirred at 50° C. overnight. Aq NaOH (50 mL) was added to the mixture. The mixture was extracted with EtOAc (10 mL×3). The aqueous was acidified with aq NaHSO$_4$ to PH~4. Then it was extracted with EtOAc (15 mL×3). The combined organic layers were washed with brine, dried over Na$_2$SO$_4$ and concentrated in vacuo to afford crude product, which was purified by washed with EtOAc (10 mL) to afford 2-nitropyridine-4-thiol (1700 mg, 35% yield).

ESI-MS m/z calcd for $[C_5H_4N_2O_2S]^-$ [M−H]$^-$: 156.0; found: 155.0.

2-Nitropyridin-4-yl 2,4,6-tri-O-acetyl-3-azido-3-deoxy-1-thio-α-D-galactopyranoside

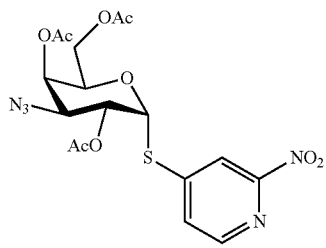

K$_2$CO$_3$ (708 mg, 5.12 mmol) was added to a solution of 2-nitropyridine-4-thiol (800 mg, 5.12 mmol) in DMF (15 mL) at 0° C. The solution was stirred at rt for 30 min. Then 2,4,6-tri-O-acetyl-3-azido-1-chloro-3-deoxy-β-D-galactopyranoside (1433 mg, 4.1 mmol) was added to the mixture. The reaction was stirred at 50° C. overnight. The mixture was extracted with EtOAc (10 mL×3). The combined organic layers were washed with brine, dried over Na$_2$SO$_4$ and concentrated in vacuo to afford crude product, which was purified by FLASH CHROMATOGRAPHY to afford the title compound (450 mg, 19% yield).

ESI-MS m/z calcd for $[C_{17}H_{19}N_5O_9S]^+$ [M+H]$^+$: 469.1; found: 470.1.

2-nitropyridin-4-yl 2,4,6-tri-O-acetyl-3-deoxy-3-[4-(3,4,5-trifluorophenyl)-1H-1,2,3-triazol-1-yl]-1-thio-α-D-galactopyranoside

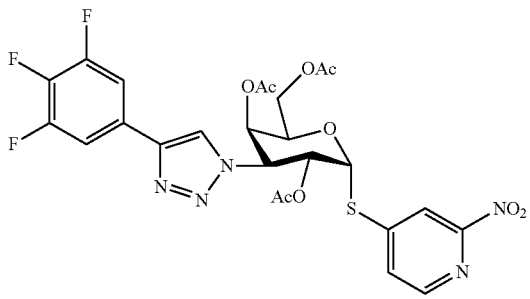

To a solution of 2-nitropyridin-4-yl 2,4,6-tri-O-acetyl-3-azido-3-deoxy-1-thio-α-D-galactopyranoside (450 mg, 0.96 mmol) in MeCN (10 mL) was added 3,4,5-trifluorophenylacetylene (328 mg, 1.44 mmol), Copper iodide (54.8 mg, 0.29 mmol), CsF (218 mg, 1.44 mmol) and Et$_3$N (485 mg, 4.79 mmol). The reaction vessel was purged thrice with nitrogen. Then the mixture was stirred at room temperature for 3 h. The mixture was extracted with EtOAc (10 mL×3). The combined organic layers were washed with brine, dried over Na$_2$SO$_4$ and concentrated in vacuo to afford crude product, which was purified by flash chromatography to afford the title compound (175 mg, 29% yield).

ESI-MS m/z calcd for $[C_{25}H_{22}F_3N_5O_9S]^+$ (M+H)$^+$: 625.1.0; found: 626.2.

2-Aminopyridin-4-yl 2,4,6-tri-O-acetyl-3-deoxy-3-[4-(3,4,5-trifluorophenyl)-1H-1,2,3-triazol-1-yl]-1-thio-α-D-galactopyranoside

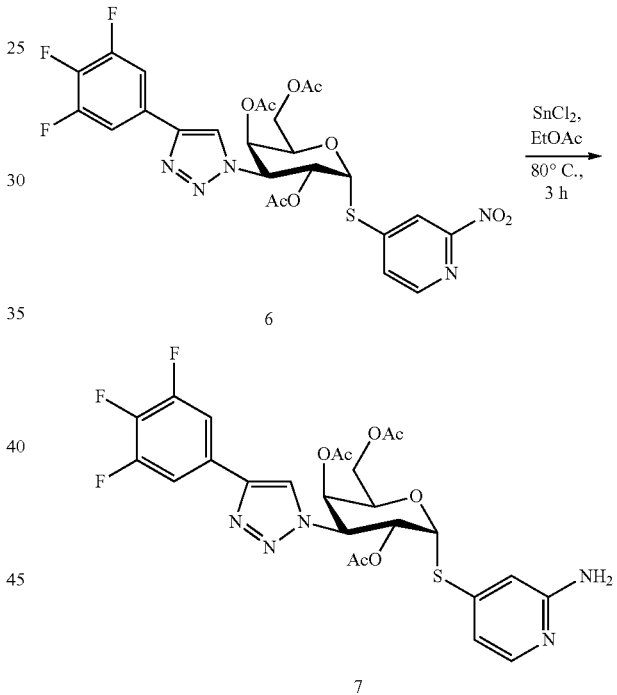

SnCl$_2$.2H$_2$ (189.4 mg, 0.84 mmol) was added into a solution of 2-nitropyridin-4-yl 2,4,6-tri-O-acetyl-3-deoxy-3-[4-(3,4,5-trifluorophenyl)-1H-1,2,3-triazol-1-yl]-1-thio-α-D-galactopyranoside (175 mg, 0.28 mmol) in EtOAc (10 mL). The solution was stirred at 80° C. for 3 h. Water (20 mL) was added to the mixture, then it was basified with aq NaHCO$_3$. The mixture was extracted with EtOAc (10 mL×3). The combined organic layers were washed with brine, dried over Na$_2$SO$_4$ and concentrated in vacuo to afford crude product, which was purified by flash chromatography to afford 1,3-dideoxy-2,4,6-tri-O-acetyl-1-(2-aminopyridin-4-ylthio)-3-[4-(3,4,5-trifluorophenyl)-1H-1,2,3-triazol-1-yl]-α-D-galactopyranoside (124 mg, 74% yield).

ESI-MS m/z calcd for $[C_{25}H_{24}F_3N_5O_7S]+$ (M+H)+: 595.1.0; found: 596.2.

i88) 5-Dimethylamino-naphatlen-2-yl 2,4,6-tri-O-acetyl-3-deoxy-3-[4-(3,4,5-trifluorophenyl)-1H-1,2,3-triazol-1-yl]-1-thio-α-D-galactopyranoside 6-(tert-butyldimethylsilyloxy)naphthalen-1-amine

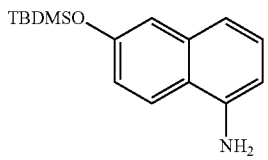 [SMILES: CC(C)(C)[Si](C)(C)Oc1ccc2c(N)cccc2c1]

A solution of 5-aminonaphthalen-2-ol (500 mg, 3.14 mmol) and imidazole (213.8 mg, 3.14 mmol) in DCM (10 ml) was added dropwise a solution of TBDMS-Chloride (710.1 mg, 4.71 mmol) in DCM (10 mL) with stirring at 10° C. The reaction mixture was stirred at r.t over 2 h followed by addition of water (30 ml). The phases were separated and the organic layer was washed with brine, dried over ($Na_2SO_4$) and the solvents where evaporated to give crude material.
ESI-MS m/z calcd for $[C16H23NOSi]^+$ $(M+H)^+$: 274.0; found: 274.0.

6-(tert-butyldimethylsilyloxy)-N,N-dimethylnaphthalen-1-amine

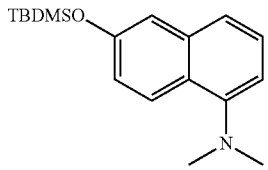 [SMILES: CN(C)c1cccc2cc(O[Si](C)(C)C(C)(C)C)ccc12]

A solution of 6-[tert-butyl(dimethyl)silyl]oxynaphthalen-1-amine (800 mg, 2.93 mmol) and $K_2CO_3$ (2021.7 mg, 2.93 mmol) in acetone (20 ml) was added methyl iodide (1245.7 mg, 2.93 mmol) dropwise at 10° C. The reaction mixture was stirred at reflux for 24 h, followed by addition of water (30 ml). The phases where separated and the organic layer was washed with brine, dried over ($Na_2SO_4$) and the solvents where evaporated.
ESI-MS m/z calcd for $[C18H27NOSi]^+$ $(M+H)^+$: 302.0; found: 302.0.

5-(dimethylamino)naphthalen-2-ol

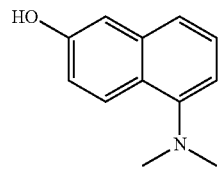

To a stirred solution of 6-[tert-butyl(dimethyl)silyl]oxy-N,N-dimethyl-naphthalen-1-amine (750 mg, 2.49 mmol) in tetrahydrofuran (20 ml) was added TBAF (2355 mg, 7.46 mmol) at rt. The reaction mixture was stirred at r.t over 24 h followed by evaporation of the solvents to give crude material.

ESI-MS m/z calcd for $[Cl2H13NO]^+$ $(M+H)^+$: 188.0; found: 188.0.

O-5-(dimethylamino)naphthalen-2-yl dimethylcarbamothioate

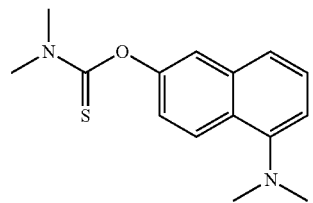

To a stirred solution of 5-(dimethylamino)naphthalen-2-ol (1000 mg, 5.34 mmol) and 1,4-diazabicyclooctane (1795 mg, 16.02 mmol) in tetrahydrofuran (30 ml) was added N,N-dimethylcarbamothioyl chloride (1320 mg, 10.68 mmol) at it. The reaction mixture was stirred at r.t over 16 h. The reaction mixture was evaporated to dryness and purified by biotage flash (PE:EtOAc=10%-50%) to give 800 mg (54.6%) of the title compound.
ESI-MS m/z calcd for $[C15H18N2OS]^+$ $(M+H)^+$: 275.0; found: 275.0.

S-5-(dimethylamino)naphthalen-2-yl dimethylcarbamothioate

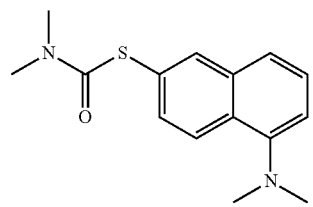

A solution of O-[[5-(dimethylamino)-2-naphthyl]] N,N-dimethylcarbamothioate (700 mg, 2.55 mmol)) in Phenyl ether (5 ml) was stirred at 250° C. over 2 h. The reaction mixture was purified by column chromatography on silica gel eluted with PE/EtOAc (100:0~70:30) to give 600 mg (85.7%) of the title compound.
ESI-MS m/z calcd for $[C_{15}H_{18}N_2OS]^+$ $(M+H)^+$: 275.0; found: 275.0.

5-(dimethylamino)naphthalene-2-thiol

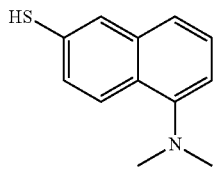

S-[[5-(dimethylamino)-2-naphthyl]] N,N-dimethylcarbamothioate (700 mg, 2.55 mmol) and NaOH (408.16 mg, 10.2 mmol) was taken up in 16 mL THF/MeOH/water=1:1:1 and heated at reflux for 2 h. TLC analysis indicated the total consumption of the starting material. The mixture was concentrated to about 10 mL, taken up to 50 mL EtOAc, added with 2M hydrochloric acid to adjust the pH to about 6. The organic layer was dried over Na$_2$SO$_4$, concentrated to afford the target compound 500 mg (96%) of the title compound as a yellow oil which was used immediately in the next step.

5-Dimethylamino-naphatlen-2-yl 2,4,6-tri-O-acetyl-3-azido-3-deoxy-1-thio-α-D-galactopyranoside

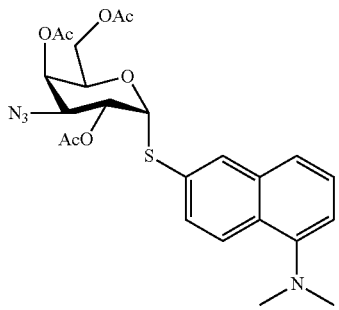

NaH (56.5 mg, 2.46 mmol) was suspended in DMF (20 ml) followed by addition of 5-(dimethylamino)naphthalene-2-thiol (500 mg, 2.46 mmol). Then 2,4,6-tri-O-acetyl-3-azido-1-chloro-3-deoxy-β-D-galactopyranoside (860.1 mg, 2.46 mmol) was added. The mixture was stirred at rt over 2 h. The reaction mixture was diluted with CH$_2$C2 (DCM) (50 ml), 0.5M citric acid (50 ml) and water (50 ml). The phases were separated and the organic phase was washed with water (10 ml) and concentrated in vacuo. The residue was purified by column chromatography (SiO2/PE:EtOAc 10:1=3:1) to give 910 mg (72%) of the title compound as a white solid.

ESI-MS m/z calcd for [C24H28N4O7S]$^+$ (M+H)$^+$: 517.0; found: 517.0.

5-Dimethylamino-naphatlen-2-yl 2,4,6-tri-O-acetyl-3-deoxy-3-[4-(3,4,5-trifluorophenyl)-1H-1,2,3-triazol-1-yl]-1-thio-α-D-galactopyranoside

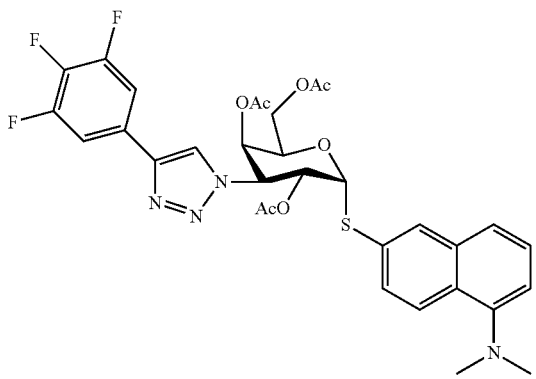

A mixture of 5-Dimethylamino-naphatlen-2-yl 2,4,6-tri-O-acetyl-3-azido-3-deoxy-1-thio-α-D-galactopyranoside (0.91 g) and 3,4,5-trifluorophenylacetylene (0.4 g) were dissolved in CH$_3$CN (20 ml). Then CsF (0.09 g), and DIEA (0.5 g) were added. The mixture was stirred at rt for 5 min followed by addition of Copper iodide (0.07 g) was added. The mixture was stirred at rt over night. Then the mixture was concentrated and purified by column chromatography (SiO2/PE:EtOAc 10:1=3:1) to give 810 mg (68.3%) of the title compound.

1H NMR (400 MHz, CDCl3) δ 8.20 (d, J=8.9 Hz, 1H), 7.96 (d, J=1.6 Hz, 1H), 7.80 (s, 1H), 7.60-7.35 (m, 5H), 7.26 (s, 1H), 7.13-7.03 (m, 1H), 6.25 (d, J=5.5 Hz, 1H), 6.11 (dd, J=11.6, 5.5 Hz, 1H), 5.63 (d, J=2.3 Hz, 1H), 5.32 (dd, J=11.6, 3.1 Hz, 1H), 4.96 (t, J=6.4 Hz, 1H), 4.23-3.99 (m, 2H), 2.89 (s, 6H), 2.06 (s, 3H), 1.99 (s, 3H), 1.81 (s, 3H)

m/z calcd for [C32H31F3N4O7S]$^+$ [M+H]H$^+$: 673.0; found: 673.0.

i89) Ethyl 2,4,6-tri-O-acetyl-3-azido-3-deoxy-1-thio-α-D-galactopyranoside

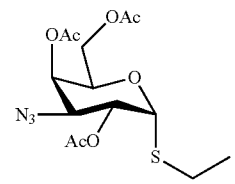

1,2,4,6-Tetra-O-acetyl-3-azido-3-deoxy-β-D-galactopyranose (208 mg) was dissolved in CH$_2$Cl$_2$ and molecular sieves (MS3 Å) was added. The mixture was cooled to 0° C. under N$_2$ and EtSH (0.080 mL) was added followed by BF$_3$.OEt$_2$ (0.070 mL). After 2 h the reaction mixture was allowed to reach r.t. After four days NEt$_3$ was added and the mixture was filtered to remove MS3 Å and concentrated in vacuo. The residue was purified by flash chromatography (SiO$_2$, 1-50% EtOAc in petroleum ether) to give 97 mg ethyl 2,4,6-tri-O-acetyl-3-azido-3-deoxy-1-thio-β-D-galactopyranoside. This was redissolved in CH$_2$Cl$_2$ (3 mL) and BF$_3$.OEt$_2$ (0.070 mL) was added. After four days NEt$_3$ was added and the mixture was concentrated in vacuo. The residue was purified by flash chromatography (SiO$_2$, 5-50% EtOAc in petroleum ether) to give 43 mg ethyl 2,4,6-tri-O-acetyl-3-azido-3-deoxy-1-thio-α-D-galactopyranoside. $^1$H NMR (400 MHz, Chloroform-d) δ 5.74 (d, J=5.5 Hz, 1H), 5.42 (s, 1H), 5.20 (dd, J=10.8, 5.5 Hz, 1H), 4.53 (t, J=6.3 Hz, 1H), 4.13 (dd, J=11.4, 5.6 Hz, 1H), 4.04 (dd, J=11.3, 7.2 Hz, 1H), 3.96-3.86 (m, 1H), 2.66-2.47 (m, 2H), 2.15 (s, 3H), 2.14 (s, 3H), 2.05 (s, 3H), 1.28 (t, J=7.4 Hz, 3H).

i90) (5-Bromopyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 1 and i91) (5-Bromopyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 2

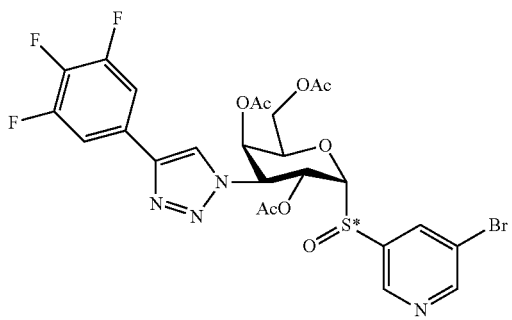

mCPBA (242.91 mg, 1.20 mmol) was added it to a solution of 5-Bromopyridin-3-yl 2,4,6-tri-O-acetyl-3-deoxy-3-[4-(3,4,5-trifluorophenyl)-1H-1,2,3-triazol-1-yl]-1-thio-α-D-galactopyranoside (526 mg, 0.80 mmol) in CH$_2$Cl$_2$ (15 mL) at 0° C. After stirring at 0° C. for 2 h, 10% aq NaOH was added it to mixture. Then it was extracted with CH$_2$Cl$_2$ (15 mL×3). The combined organic layers were washed with brine, dried over Na$_2$SO$_4$ and concentrated in vacuo to afford crude product which was separated by preparative TLC (EtOAc/petroleum ether/CH$_2$Cl$_2$) to give isomer 1 (145 mg) and isomer 2 (40 mg). The exact chirality of the stereocenter located at the sulfurus atom marked * was not determined for isomer 1 and isomer 2.

i90) (5-Bromopyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 1

1H NMR (400 MHz, MeOD) δ 8.84 (d, J=1.8 Hz, 1H), 8.82 (d, J=2.0 Hz, 1H), 8.49 (s, 1H), 8.40 (t, J=2.0 Hz, 1H), 7.58-7.49 (m, 2H), 6.24 (dd, J=11.6, 5.6 Hz, 1H), 5.97 (dd, J=11.6, 3.0 Hz, 1H), 5.29 (d, J=5.6 Hz, 1H), 4.57 (t, J=6.4 Hz, 1H), 3.89 (ddd, J=18.8, 11.8, 6.1 Hz, 2H), 1.93 (s, 3H), 1.90 (s, 3H), 1.66 (s, 3H).
ESI-MS m/z calcd for [C$_{25}$H$_{22}$BrF$_3$N$_4$O$_8$S]$^+$ [M+H]$^+$: 674.0; found: 675.1.

i91) (5-Bromopyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 2

1H NMR (400 MHz, MeOD) δ 8.82 (d, J=1.8 Hz, 1H), 8.81 (d, J=2.1 Hz, 1H), 8.50 (s, 1H), 8.34 (t, J=2.0 Hz, 1H), 7.63-7.43 (m, 1H), 6.46 (dd, J=11.7, 6.6 Hz, 1H), 6.12 (dd, J=11.7, 2.9 Hz, 1H), 5.63 (d, J=1.8 Hz, 1H), 5.37-5.33 (m, 1H), 5.19 (d, J=6.6 Hz, 1H), 3.81 (ddd, J=19.4, 12.0, 6.4 Hz, 2H), 1.96 (s, 3H), 1.93 (s, 3H), 1.89 (s, 3H).
ESI-MS m/z calcd for [C$_{25}$H$_{22}$BrF$_3$N$_4$O$_8$S]$^+$ [M+H]$^+$: 674.0; found: 675.1.

i93) 5-Chloropyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 1 and i94) 5-Chloropyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 2

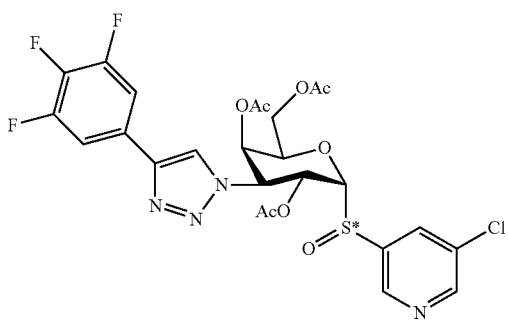

To a solution of 5-Chloropyridin-3-yl 2,4,6-tri-O-acetyl-3-deoxy-3-[4-(3,4,5-trifluorophenyl)-1H-1,2,3-triazol-1-yl]-1-thio-α-D-galactopyranoside (400 mg, 0.65 mmol) in DCM (20 mL) were added mCPBA (171 mg, 0.98 mmol). The reaction was stirred at room temperature for 4 h. The mixture was concentrated and the crude product was purified by flash chromatography (EtOAc:PE=1:10 to 1:2, Silica 40 g, 40 ml/min, normal phase sillica, uv254) to obtain the title compound as isomer 1(18 mg) and isomer 2(100 mg).

i93) 5-Chloropyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, Isomer 1

$^1$H NMR (400 MHz, CDCl$_3$) δ 8.75 (dd, J=23.8, 2.0 Hz, 2H), 8.04 (t, J=2.1 Hz, 1H), 7.87 (s, 1H), 7.54-7.42 (m, 2H), 6.49 (dd, J=11.5, 6.6 Hz, 1H), 6.06 (dd, J=11.6, 2.9 Hz, 1H), 5.62 (d, J=1.5 Hz, 1H), 5.53 (t, J=6.2 Hz, 1H), 5.03 (d, J=6.6 Hz, 1H), 3.91 (dd, J=6.1, 3.1 Hz, 2H), 2.11 (s, 3H), 2.05 (d, J=5.7 Hz, 6H).
m/z calcd for [C$_{25}$H$_{22}$ClF$_3$N$_4$O$_8$S]$^+$ [M+H]$^+$: 631.0; found: 631.0.

i94) 5-Chloropyridin-3-yl 2,4,6-tri-O-acetyl-3-deoxy-3-[4-(3,4,5-trifluorophenyl)-1H-1,2,3-triazol-1-yl]-1-α-D-galactopyranoside sulfoxide, isomer 2

$^1$H NMR (400 MHz, CDCl$_3$) δ 8.70 (dd, J=6.9, 2.0 Hz, 2H), 8.10 (t, J=2.1 Hz, 1H), 7.82 (s, 1H), 7.43 (dd, J=8.1, 6.5 Hz, 2H), 6.35 (dd, J=11.5, 5.6 Hz, 1H), 6.05 (dd, J=11.5, 3.1 Hz, 1H), 5.70 (d, J=1.9 Hz, 1H), 5.23 (d, J=5.6 Hz, 1H), 4.87 (t, J=6.2 Hz, 1H), 4.12 (dd, J=12.7, 6.8 Hz, 2H), 2.10 (s, 3H), 2.04 (s, 3H), 1.61 (s, 3H).
m/z calcd for [C$_{25}$H$_{22}$ClF$_3$N$_4$O$_8$S]$^+$ [M+H]$^+$: 631.0; found: 631.0.

i95) (N,N-Dimethylnaphtalen-5-amine N-Oxide)-2-yl 2,4,6-tri-O-acetyl-3-deoxy-3-[4-(3,4,5-trifluorophenyl)-1H-1,2,3-triazol-1-yl]-1-thio-α-D-galactopyranosyl sulfone

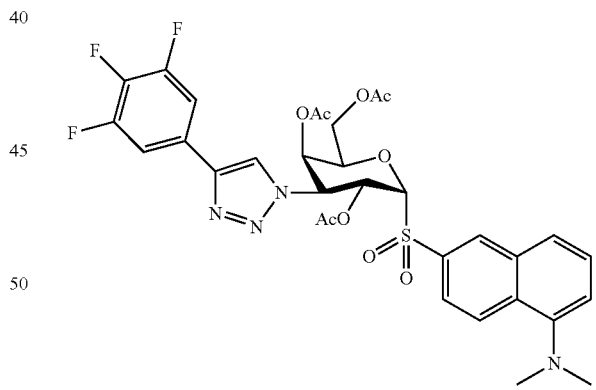

To a solution of 5-Dimethylamino-naphatlen-2-yl 2,4,6-tri-O-acetyl-3-deoxy-3-[4-(3,4,5-trifluorophenyl)-1H-1,2,3-triazol-1-yl]-1-thio-α-D-galactopyranoside (200 mg, 0.30 mmol) in DCM (10 mL) was added mCPBA (256.5 mg, 1.49 mmol). The reaction mixture was stirred at room temperature for 1 h, followed by addition of DCM (20 ml). The reaction mixture was washed with sat. Na$_2$S$_2$O$_3$ aq. (2*30 ml), sat. aq. NaHCO$_3$ (2*30 mL). The organic layer was dried over anhydrous sodium sulphate. Removal of solvent gave crude N-oxide (200 mg). m/z calcd for [C$_{32}$H$_{31}$F$_3$N$_4$O$_{10}$S]$^+$ [M+H]$^+$: 721.0; found: 721.0. The material was dissolved in methanol (3 mL) was added Pd/C (5 mg). The reaction was stirred at room temperature for 4 h under a hydrogen atmosphere. The mixture was filtered and the filtrate was evaporated to dryness. The residue was purified by preparative-TLC to obtain the desired product (10 mg) m/z calcd for [C32H31F3N4O9S]+ [M+H]+: 705.0; found: 705.0.

i96) 3,4-dichlorophenyl 2,4,6-tri-O-acetyl-3-deoxy-3-(3,4,5-trifluorobenzamido)-1-thio-α-D-galactopyranoside 3,4-dichlorophenyl 2,4,6-tri-O-acetyl-3-azido-3-deoxy-1-thio-α-D-galactopyranoside

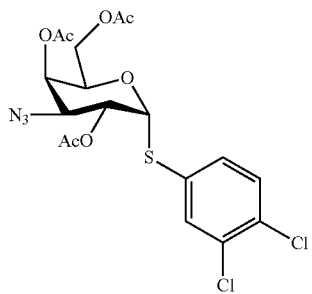

To a stirred solution of 3,4-dichlorobenzenethiol (0.95 g, 5.32 mmol) in dry DMF (4 ml) was added NaH (0.12 g, 5.32 mmol) at 0° C. The mixture was stirred at rt for 30 minutes followed by addition of 2,4,6-tri-O-acetyl-3-azido-1-chloro-3-deoxy-β-D-galactopyranoside (0.93 g, 2.66 mmol). The reaction mixture was stirred at 50° C. overnight. Solvents were removed in vacuo and the resulting crude was diluted with CH$_2$Cl$_2$ and washed with water and brine. The organic layer was dried over Na$_2$SO$_4$, filtered and evaporated. The crude product was purified by silica gel column to give the title compound as a white solid (300 mg).

ESI-MS m/z calcd for [C$_{18}$H$_{20}$Cl$_2$N$_3$O$_7$S]$^+$ (M+H)$^+$: 492.0; found: 492.0.

2,4,6-Tri-O-acetyl-3-amino-3-deoxy-1-thio-α-D-galactopyranoside

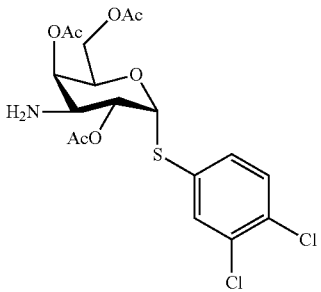

3,4-dichlorophenyl 2,4,6-tri-O-acetyl-3-azido-3-deoxy-1-thio-α-D-galactopyranoside (300 mg, 0.61 mmol) was dissolved in MeOH (15 mL) and DCM (5 mL). Pd/C (10% Pd, 650 mg). The mixture was stirred at rt under H$_2$ pressure for 16 hours. TLC indicated complete reaction. Pd/C was filtered and the filter was concentrated. The crude residue (220 mg) was used for next step.

ESI-MS m/z calcd for [C$_{18}$H$_{22}$Cl$_2$NO$_7$S]$^+$ (M+H)$^+$: 466.0; found: 466.0.

3,4-dichlorophenyl 2,4,6-tri-O-acetyl-3-deoxy-3-(3,4,5-trifluorobenzamido)-1-thio-α-D-galactopyranoside

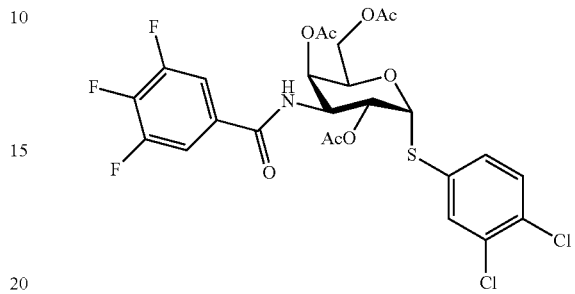

2,4,6-Tri-O-acetyl-3-deoxy-3-amino-1-thio-α-D-galactopyranoside (115 mg, 0.25 mol), HATU (187 mg, 0.49 mmol) and 3,4,5-trifluorobenzoic acid (52 mg, 0.30 mmol) were dissolved in DMF (2 ml). N,N-Diisopropylethylamine (159 mg, 1.23 mmol) was added. The mixture was stirred at rt for 3 hours. Then water (50 mL) was added. The mixture was extracted by EtOAc (120 ml). The EtOAc phase was washed by brine (100 mL), dried over Na2SO4, filtered and concentrated. The residue was purified by silica gel column (PE:EtOAc=1:2) to obtain the title compound (50 mg, yield 33%).

ESI-MS m/z calcd for [C$_{25}$H$_{23}$Cl$_2$F$_3$NO$_8$S]$^+$ (M+H)$^+$: 624.0; found: 624.1.

i98) 3,4-Dichlorophenyl 3-deoxy-3-[4-carboxy)-1H-1,2,3-triazol-1-yl]-1-thio-α-D-galactopyranoside 3,4-Dichlorophenyl 2,4,6-tri-O-acetyl-3-deoxy-3-[4-(ethoxycarbonyl)-1H-1,2,3-triazol-1-yl]-1-thio-α-D-galactopyranoside

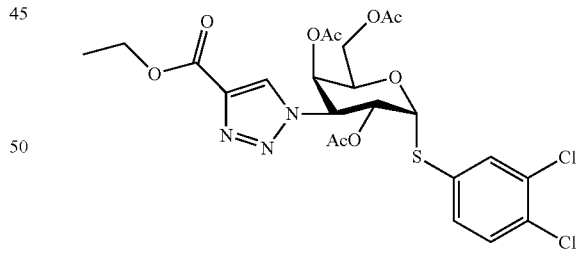

3,4-dichlorophenyl 2,4,6-tri-O-acetyl-3-azido-3-deoxy-1-thio-α-D-galactopyranoside (1.3 g, 2.64 mmol), Ethyl propiolate (777 mg, 7.92 mmol), Copper(I)Iodide (151 mg, 0.79 mmol) and Triethylamine (1336 mg, 13.2 mmol) was dissolved in DMF (15 mL). The mixture was stirred at 100° C. for 1 hour. EtOAc (200 ml) was added. The mixture was filtered, washed by water (100 mL), dried by Na$_2$SO$_4$, filtered and concentrated. The residue was purified by flash chromatography on silica to give 860 mg (55%) of the title compound.

ESI-MS min calcd for [C$_{23}$H$_{26}$Cl$_2$N$_3$O$_9$S]$^+$ (M+H)$^+$: 590.1; found: 590.1.

3,4-Dichlorophenyl 3-deoxy-3-[4-carboxy)-1H-1,2,3-triazol-1-yl]-1-thio-α-D-galactopyranoside

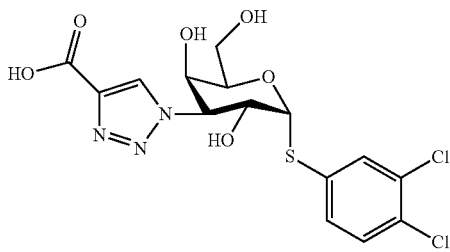

3,4-Dichlorophenyl 2,4,6-tri-O-acetyl-3-deoxy-3-[4-(ethoxycarbonyl)-1H-1,2,3-triazol-1-yl]-1-thio-α-D-galactopyranoside (400 mg, 0.68 mmol) was dissolved in MeOH (10 mL). KOH (152.04 mg, 2.71 mmol) in water (3 ml) was added. The mixture was stirred at rt for 6 hours. Then the mixture was acidified using 2M HCl to PH=6. The mixture was purified by reverse-phase column chromatography to give 260 mg (88%) of the title compound.

ESI-MS m/z calcd for $[C_{15}H_{16}Cl_2N_3O_6S]^+$ $(M+H)^+$: 436.0; found: 436.0.

i100) 5-Chloropyridin-3-yl 2,4,6-tri-O-acetyl-3-deoxy-3-[4-(3,4-difluorophenyl)-1H-1,2,3-triazol-1-yl]-1-thio-α-D-galactopyranoside

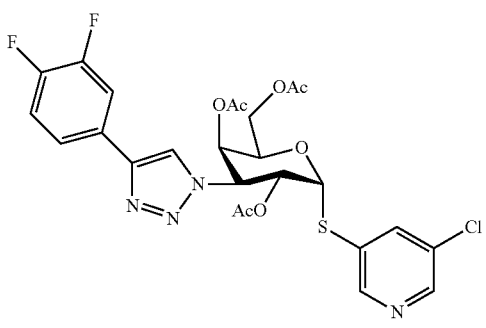

To a solution of 5-Chloropyridin-3-yl 2,4,6-tri-O-acetyl-3-azido-3-deoxy-1-thio-α-D-galactopyranoside (310 mg, 0.68 mmol) in MeCN (15 mL) was added [(3,4-difluorophenyl)-ethynyl]-trimethylsilane (170.5 mg, 0.81 mmol), Copper iodide (38.6 mg, 0.20 mmol), CsF (153.93 mg, 1.01 mmol) and N,N-diethylethanamine (436.6 mg, 3.38 mmol). The reaction vessel was purged twice with nitrogen. The reaction mixture was stirred at room temperature overnight. The mixture was filtered and washed with EtOAc (50 mL), The filtrate was concentrated in vacuo to afford crude product, which was purified by FLASH CHROMATOGRAPHY to afford the title compound (120 mg, 30% yield).

ESI-MS m/z calcd for $[C_{25}H_{23}ClF_2N_4O_7S]^+$ $[M+H]^+$: 596.1; found: 597.1.

i101) 5-Bromopyridin-3-yl 2,4,6-tri-O-acetyl-3-deoxy-3-[4-(3,4-difluorophenyl)-1H-1,2,3-triazol-1-yl]-1-thio-α-D-galactopyranoside

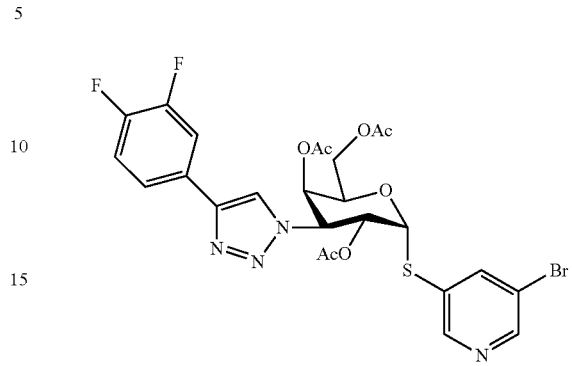

To a solution of 5-Bromopyridin-3-yl 2,4,6-tri-O-acetyl-3-azido-3-deoxy-1-thio-α-D-galactopyranoside (280 mg, 0.56 mmol) in MeCN (15 mL) was added [(3,4-difluorophenyl)-ethynyl]-trimethylsilane (140.39 mg, 0.67 mmol), Copper iodide (31.78 mg, 0.17 mmol), CsF (126.76 mg, 0.83 mmol) and N,N-diethylethanamine (215.69 mg, 1.67 mmol). The reaction vessel was purged twice with nitrogen. Then the mixture was stirred at room temperature overnight. The mixture was filtered and washed with EtOAc (50 mL), The filtrate was concentrated in vacuo to afford crude product, which was purified by FLASH CHROMATOGRAPHY to give the title compound (100 mg, 28.02% yield).

ESI-MS m/z calcd for $[C_{25}H_{23}BrF_2N_4O_7S]^+$ $[M+H]^+$: 640.0; found: 640.1.

i102) 2,4,6-tri-O-acetyl-3-deoxy-3-[4-(propyl-carbonyl)-1H-1,2,3-triazol-1-yl]-1-thio-α-D-galactopyranoside 3,4-Dichlorophenyl 2,4,6-tri-O-acetyl-3-deoxy-3-[4-(1-hydroxybutyl)-1H-1,2,3-triazol-1-yl]-1-thio-α-D-galactopyranoside

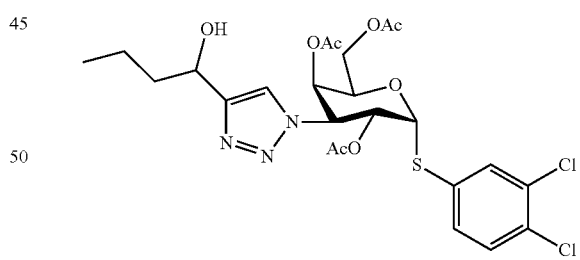

3,4-Dichlorophenyl 2,4,6-tri-O-acetyl-3-azido-3-deoxy-1-thio-α-D-galactopyranoside (300 mg, 0.61 mmol), hex-1-yne-3-ol (120 mg, 1.22 mmol), Copper(I)Iodide (34.81 mg, 0.18 mmo) and Triethylamine (308 mg, 3.05 mmol) were added to a flask. DMF (3 mL) was added. The mixture was stirred at 100° C. for 1 hour under a nitrogen atmosphere. The mixture was filtered and concentrated in vacuum. Water (50 mL) and EtOAc (120 ml) was added and the phases were separated. The organic phase was washed by brine (100 mL), dried over $Na_2SO_4$, filtered and concentrated. The residue was purified by silica gel column to give the title compound.

2,4,6-tri-O-acetyl-3-deoxy-3-[4-(propyl-carbonyl)-H-1,2,23-triazol-1-yl]-1-thio-α-D-galactopyranoside

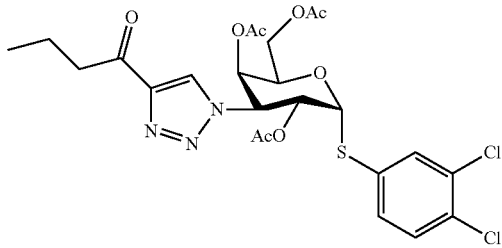

Dess-Martin periodinane (387 mg, 0.91 mmol, 1.2 eq.) was added to a solution of 3,4-Dichlorophenyl 2,4,6-tri-O-acetyl-3-deoxy-3-[4-(1-hydroxybutyl-carbonyl)-1H-1,2,3-triazol-1-yl]-1-thio-α-D-galactopyranoside (450 mg, 0.76 mmol, 1.0 eq.) in DCM (5 ml) and the mixture was stirred overnight at r.t. Diethyl ether (50 ml) was added and the organic layer was washed with aq. $Na_2S_2O_3$ (2 M, 50 ml), aq. $K_2CO^3$ (2 M, 50 ml), and water (50 ml). The combined organic layers were dried ($Na_2SO_4$), concentrated in vacuo and dried in vacuum to give the crude target product (357 mg).

ESI-MS n/z calcd for $[C_{24}H_{28}Cl_2N_3O_8S]^+$ $(M+H)^+$: 588.1; found: 588.1.

i103) 5-Chloro-6-trifluoromethyl-pyridine-3-yl 2,4,6-tri-O-acetyl-3-azido-3-deoxy-1-thio-α-D-galactopyranoside 3,5-dichloro-2-iodopyridine

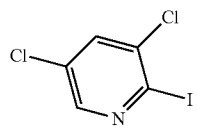

A mixture of 2-bromo-3,5-dichloropyridine (5.672 g, 25 mmol), sodium iodide (11241.7 mg, 75 mmol) and chlorotrimethylsilane (2716 mg, 25 mmol) in MeCN (50 mL) was heated under reflux for 45 min. The reaction mixture was then poured into a 2.0 M aqueous solution of sodium hydroxide (10 mL) and extracted with diethyl ether (20 mL×3). The combined organic layers were washed with brine and evaporated to afford crude product, which was purified by biotage (EtOAc/PE=1%~10%, ISCO 40 g, 25 mL/min, normal phase silica gel, uv 254) to afford the target compound 3,5-dichloro-2-iodopyridine (3800 mg, 55.5% yield) as a white solid.

$^1$H NMR (400 MHz, MeOD) δ8.35 (t, J=4.5 Hz, 1H), 8.01 (d, J=2.3 Hz, 1H).

GC-MS m/z calcd for [C5H2Cl2IN]: 272.9; found: 273.0.

3,5-dichloro-2-(trifluoromethyl)pyridine

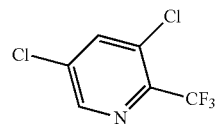 [SMILES: FC(F)(F)c1ncc(Cl)cc1Cl]

KF (87.18 mg, 1.5 mmol) and CuI (285.80 mg, 1.5 mmol) were thoroughly mixed before being heated under vacuum (1 mm Hg) with the flame of a Bunsen burner with gentle shaking until an homogeneous greenish color was obtained. NMP (25 mL), trimethyl(trifluoromethyl)silane (213.88 mg, 1.5 mmol). The mixture was stirred at 50° C. for 45 min. 3,5-dichloro-2-iodopyridine (2250 mg, 7.45 mmol) was added. The mixture was stirred at 50° C. overnight. The reaction was followed by GC-MS, which indicated formed product. Water (50 mL) was added to mixture and extracted with Ethyl acetate (5 mL×3). The combined organic layers were washed with brine and evaporated to afford crude product, which was purified by biotage (EtOAc/PE=1%~50%, ISCO 12 g, 10 mL/min, normal phase silica gel, uv 254) to afford compound 3,5-dichloro-2-(trifluoromethyl)pyridine (198 mg, 91.63% yield) as brown oil.

$^1$H NMR (400 MHz, MeOD) δ 8.66 (d, J=2.0 Hz, 1H), 8.34-8.24 (m, 1H).

GC-MS m/z calcd for $[C_6H_2Cl_2F_3N]$: 215.0; found: 215.0.

2.3 5-chloro-6-(trifluoromethyl)pyridine-3-thiol

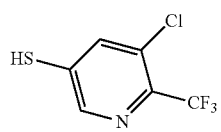 [SMILES: FC(F)(F)c1ncc(S)cc1Cl]

3,5-dichloro-2-(trifluoromethyl)pyridine (1080 mg, 5.0 mmol) and NaHS (336.4 mg, 6.0 mmol) were dissolved in DMF (15 mL). The reaction mixture was stirred at room temperature for 3 h followed by adjustment to pH~9 by addition of 10% aq NaOH. The reaction mixture was extracted with $Et_2O$ (10 mL×3) and the aqueous layer was acidified with 2 M $NaHSO_4$ to PH~3. The mixture was extracted with ethyl acetate (15 mL×3). The combined organic layers were washed with brine and evaporated to afford crude product, which was purified by biotage (EtOAc/PE=1%~50%, ISCO 20 g, 15 mL/min, normal phase silica gel, uv 254) to afford 5-chloro-6-(trifluoromethyl)pyridine-3-thiol (650 mg, 61% yield) as brown oil, which was used for next without further purification.

$^1$H NMR (400 MHz, MeOD) δ 8.48 (d, J=1.4 Hz, 1H), 8.02 (d, J=17.1 Hz, 2H).

ESI-MS m/z calcd for $[C_6H_3ClF_3NS]^+$ $(M-H)^-$: 213.0; found: 211.9.

249

5-Chloro-6-trifluoromethyl-pyridine-3-yl 2,4,6-tri-O-acetyl-3-azido-3-deoxy-1-thio-α-D-galactopyranoside

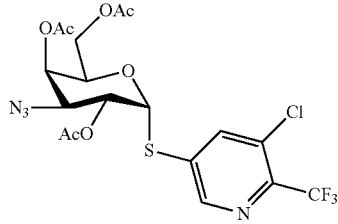

NaH (20.5 mg, 0.86 mmol) was added to a solution of 5-chloro-6-(trifluoromethyl)pyridine-3-thiol (183.2 mg, 0.86 mmol) in DMF (10 mL) at 0° C. The solution was stirred at room temperature for 30 min. Then 2,4,6-tri-O-acetyl-3-azido-1-chloro-3-deoxy-β-D-galactopyranoside (250 mg, 0.71 mmol) was added to mixture. The reaction was stirred at 50° C. for 2 h. The mixture was cooled to room temperature and water (50 mL) was added. Then it was extracted with EtOAc (10 mL×3). The combined organic layers were washed with brine, dried over $Na_2SO_4$ and concentrated in vacuo to afford crude product, which was purified by biotage (EtOAc/PE=5%~40%, ISCO 12 g, 10 mL/min, normal phase silica gel, uv 254) to afford the target compound 3-azido-1,3-dideoxy-2,4,6-tri-O-acetyl-1-(5-chloro-6-(trifluoromethyl)pyridin-3-ylthio)-α-D-galactopyranoside (110 mg, 29% yield).

ESI-MS m/z calcd for $[C_{18}H_{18}ClF_3N_4O_7S]^+$ $[M+H]^+$: 526.1; found: 527.2.

i105) 5-Chloro-6-cyano-pyridine-3-yl 2,4,6-tri-O-acetyl-3-deoxy-3-[4-(3,4-difluorophenyl)-1H-1,2,3-triazol-1-yl]-1-thio-α-D-galactopyranoside 3-chloro-5-mercaptopicolinonitrile

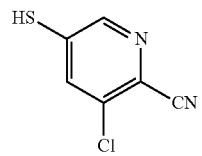

To a solution of 3,5-dichloropicolinonitrile (300 mg, 1.74 mmol) in DMF (8 mL) was added $Na_2S*9H_2O$ (487 mg, 1.74 mmol). The reaction was stirred at room temperature for 20 h. The pH was adjusted to pH 4-5 using $NaHSO_4$ aq followed by addition of MTBE (15 mL). The phases were separated and the organic phase was washed with water (20 mL) and brine (20 mL), dried over anhydrous sodium sulphate and the solvents were evaporated to give the desired product.

m/z calcd for $[C_6H_3ClN_2S]^-$ $[M-H]^-$: 169.0; found: 169.0.

250

5-Chloro-6-cyano-pyridine-3-yl 2,4,6-tri-O-acetyl-3-azido-3-deoxy-1-thio-α-D-galactopyranoside

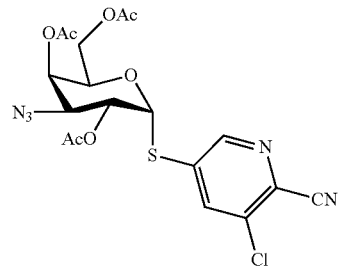

To a solution of 3-chloro-5-mercaptopicolinonitrile (250 mg, 1.47 mmol) in DMF (4 mL) was added NaH (64 mg, 1.62 mmol) at 0° C. After 10 min, 5-Chloro-6-cyano-pyridine-3-yl 2,4,6-tri-O-acetyl-3-azido-3-deoxy-1-thio-α-D-galactopyranoside (256 mg, 0.73 mmol) was added. The reaction mixture was stirred at room temperature for 4 h. Water (20 mL) and DCM (10 mL) were added. The aqueous phase was extracted with DCM (10 mL×2) and the combined organic phases were washed with water (20 mL) and brine (20 mL), dried over anhydrous sodium sulphate. The solvents were evaporated followed by purification by column chromatography (PE/EtOAc=3/1) to obtain the desired product (80 mg, 23%).

m/z calcd for $[C_{18}H_{18}ClN_5O_7S]^+$ $[M+H]^+$: 484.0; found: 484.0.

5-Chloro-6-cyano-pyridine-3-yl 2,4,6-tri-O-acetyl-3-deoxy-3-[4-(3,4-difluorophenyl)-1H-1,2,3-triazol-1-yl]-1-thio-α-D-galactopyranoside

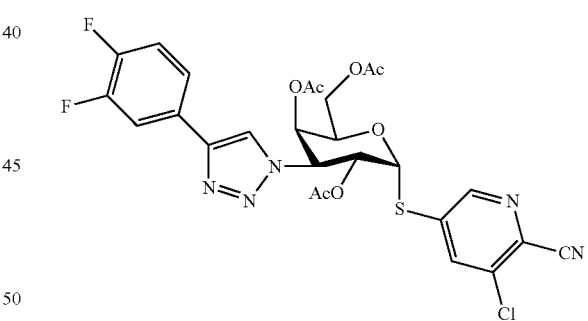

To a solution of 5-Chloro-6-cyano-pyridine-3-yl 2,4,6-tri-O-acetyl-3-deoxy-3-[4-(3,4-difluorophenyl)-1H-1,2,3-triazol-1-yl]-1-thio-α-D-galactopyranoside (100 mg, 0.21 mmol) in DMF (5 mL) were added TEA (104.6 mg, 1.03 mmol), Copper(I)Iodide (11.8 mg, 0.06 mmol), CsF (47.1 mg, 0.31 mmol), [(3,4-difluorophenyl)-ethynyl]-trimethylsilane (65.2 mg, 0.31 mmol). The reaction was stirred at room temperature for 2 h under $N_2$. Water (20 mL) and DCM (20 mL) were added. The aqueous phase was extracted with DCM (10 mL×2), the combined organic phases were washed with water (20 mL) and brine (20 mL), dried over anhydrous sodium sulphate. Removal of solvent gave a residue. The residue was purified by column chromatography (PE/EtOAc=3/1) to obtain the desired product (60 mg, 46.68%).

m/z calcd for [C$_{26}$H$_{22}$ClF$_2$N$_5$O$_7$S]$^+$ [M+H]$^+$: 622.0; found: 622.0.

i106) 5-Chloro-6-cyano-pyridine-3-yl 2,4,6-tri-O-acetyl-3-deoxy-3-[4-(3,4-difluoropbenyl)-1H-1,2,3-triazol-1-yl]-1-thio-α-D-galactopyranoside 2-chloro-4-mercaptobenzonitrile

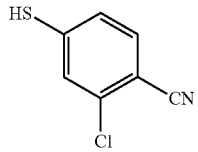

To a solution of 2-chloro-4-fluoro-benzonitrile (4 g, 25.71 mmol) in DMF (20 mL) were added Na$_2$S (3.01 g, 38.57 mmol). The mixture was held at room temperature with stirring on for 20 h. Then the mixture was added 1 M HCl to adjust to pH 6-7. MTBE (20 ml) and water (20 ml) was added. The aqueous phase was extracted with MTBE (20 mL×2), the combined organic phases were washed with sat. NaHCO$_3$ (50 mL) and brine (50 mL), dried over anhydrous sodium sulphate. Removal of solvent gave a yellow solid (3.7 g). The residue was used to next step directly.

m/z calcd for [C$_7$H$_4$ClNS]$^-$ [M−H]$^-$: 168.0; found: 168.0.

3-Chloro-4-cyanophenyl 2,4,6-tri-O-acetyl-3-azido-3-deoxy-1-thio-α-D-galactopyranoside

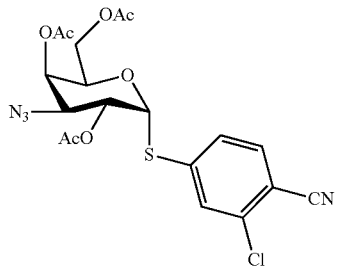

To a solution of 2-chloro-4-sulfanyl-benzonitrile (3.4 g, 20 mmol) in DMF (40 mL) was added NaH (529 mg, 22 mmol) at 0° C. After 10 min, 2,4,6-tri-O-acetyl-3-azido-1-chloro-3-deoxy-R-D-galactopyranoside (3.5 g, 10 mmol) was added. The mixture was stirred at room temperature for 4 h. Water (80 mL) and DCM (80 mL) were added. The aqueous phase was extracted with DCM (40 mL×2), the combined organic phases were washed with water (100 mL) and brine (100 mL), dried over anhydrous sodium sulphate. Removal of solvent gave a residue. The residue was purified by column chromatography (PE/EtOAc-3/1) to obtain the desired product (2 g, 21%).

m/z calcd for [C$_{19}$H$_{19}$ClN$_4$O$_7$S]$^+$ [M+H]$^+$: 483.0; found: 483.0.

5-Chloro-6-cyano-pyridine-3-yl 2,4,6-tri-O-acetyl-3-deoxy-3-[4-(3,4-difluorophenyl)-1H-1,2,3-triazol-1-yl]-1-thio-α-D-galactopyranoside

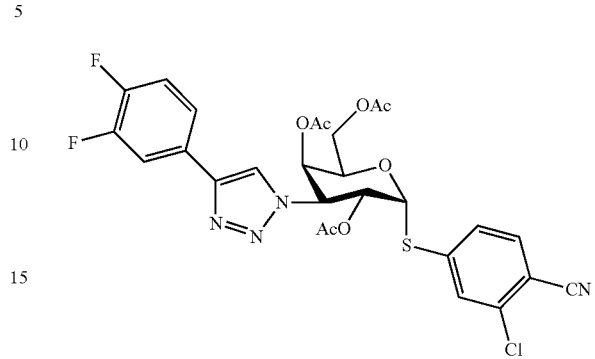

To a solution of 3-Chloro-4-cyanophenyl 2,4,6-tri-O-acetyl-3-azido-3-deoxy-1-thio-α-D-galactopyranoside (200 mg, 0.41 mmol) in DMF (5 mL) were added DIPEA (267.6, 2.07 mmol), Copper(I)Iodide (23.6 mg, 0.12 mmol), CsF (94.4 mg, 0.62 mmol), [(3,4-difluorophenyl)-ethynyl]-trimethylsilane (130.6 mg, 0.62 mmol). The reaction was stirred at room temperature for 2 h under N$_2$. Water (20 mL) and DCM (20 mL) were added. The aqueous phase was extracted with DCM (10 mL×2), the combined organic phases were washed with water (50 mL) and brine (50 mL), dried over anhydrous sodium sulphate. Removal of solvent gave a residue. The residue was purified by column chromatography (PE/EtOAc=2/1) to obtain the desired product. (180 mg, 69.9%).

m/z calcd for [C$_{27}$H$_{23}$ClF$_2$N$_4$O$_7$S]$^+$ [M+H]: 621.0; found: 621.0.

$^1$H NMR (400 MHz, CDCl$_3$) δ 7.77 (s, 1H), 7.68-7.59 (m, 2H), 7.54-7.48 (m, 1H), 7.46 (dd, J=8.2, 1.7 Hz, 1H), 7.22 (dd, J=13.3, 5.0 Hz, 1H), 6.33 (d, J=5.6 Hz, 1H), 6.13 (dd, J=11.7, 5.6 Hz, 1H), 5.62 (d, J=2.3 Hz, 1H), 5.20 (dd, J=11.7, 3.1 Hz, 1H), 4.78-4.73 (m, 1H), 4.21-4.03 (m, 2H), 2.08 (s, 3H), 1.96 (d, J=1.3 Hz, 6H).

REFERENCES

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. *Infect. Immun*. Vol. 69: 832-837.

Barondes, S. H., Cooper, D. N. W., Gitt, M. A., and Leffler, H. (1994). Galectins. Structure and function of a large family of animal lectins. *J. Biol. Chem.* 269:20807-20810.

Blois, S. M., Ilarregui, J. M., Tometten, M., Garcia, M., Orsal, A. S., Cordo-Russo, R., Toscano, M. A., Bianco, G. A., Kobelt, P., Handjiski, B., et al. (2007). A pivotal role for galectin-1 in fetomaternal tolerance. *Nat Med* 13: 1450-1457.

Chen, W.-S., Leffler H., Nilsson, U. J., Panjwani, N. (2012). Targeting Galectin-1 and Galectin-3 Attenuates VEGF-A-induced Angiogenesis; *Mol. Biol. Cell* (suppl), Abstract No. 2695.

Cumpstey, I., Carlsson, S., Leffler, H. and Nilsson, U. J. (2005) Synthesis of a phenyl thio-β-D-galactopyranoside library from 1,5-difluoro-2,4-dinitrobenzene: discovery of efficient and selective monosaccharide inhibitors of galectin-7. *Org. Biomol. Chem.* 3: 1922-1932.

Cumpstey, I., Sundin, A., Leffler, H. and Nilsson, U. J. (2005) $C_2$-Symmetrical thiodigalactoside bis-benzamido derivatives as high-affinity inhibitors of galectin-3: Efficient lectin inhibition through double arginine-arene interactions. *Angew. Chem. Int. Ed.* 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. *Chem. Eur. J.* 14: 4233-4245.

Dam, T. K., and Brewer, C. F. (2008). Effects of clustered epitopes in multivalent ligand-receptor interactions. *Biochemistry* 47: 8470-8476.

Delacour. D., Greb, C., Koch, A., Salomonsson, E., Leffler, H., Le Bivic, A., and Jacob, R. (2007). Apical Sorting by Galectin-3-Dependent Glycoprotein Clustering. *Traffic* 8: 379-388.

Delaine, T., Cumpstey, I., Ingrassia, L., Le Mercier, M., Okechukwu, P., Leffler, H., Kiss, R., and Nilsson, U. J. (2008). Galectin-Inhibitory Thiodigalactoside Ester Derivatives Have Anti-Migratory Effects in Cultured Lung and Prostate Cancer Cells. *J Med Chem* 51; 8109-8114.

Demotte, N., Wieers. G., van der Smissen, P., Moser, M., Schmidt, C., Thielemans, K., et al., (2010). *Cancer Res.* 70; 7476-7488.

Farkas, I.; Szabó, I. F.; Bognár, R.; Anderle, D. Carbohydr. Res. 1976, 48, 136-138.

Garner, O. B., and Baum, L. G. (2008). Galectin-glycan lattices regulate cell-surface glycoprotein organization and signalling. *Biochem Soc Trans* 36: 1472-1477.

Giguere, D., Patnam, R., Bellefleur, M.-A., St.-Pierre, C., Sato, S., and Roy, R. (2006). Carbohydrate triazoles and isoxazoles as inhibitors of galectins-1 and -3. *Chem Commun:* 2379-2381.

Glinsky, G. V., Price, J. E., Glinsky, V. V., Mossine, V. V., Kiriakova, G., and Metcalf, J. B. (1996). *Cancer Res* 56: 5319-5324.

Glinsky, V. V., Kiriakova, G., Glinskii, O. V., Mossine, V. V., Mawhinney, T. P., Turk, J. R., Glinskii, A. B., Huxley, V. H., Price, J. E., and Glinsky, G. V. (2009). Synthetic Galectin-3 Inhibitor Increases Metastatic Cancer Cell Sensitivity to Taxol-Induced Apoptosis In Vitro and In Vivo. *Neoplasia* 11; 901-909.

Huflejt, M. E. and Leffler, H. (2004) Galectin-4 in normal tissues and cancer. *Glycoconj. J.* 20: 247-255.

Ingrassia et al. (2006) A Lactosylated Steroid Contributes in Vivo Therapeutic Benefits in Experimental Models of Mouse Lymphoma and Human Glioblastoma. *J. Med. CHem.* 49: 1800-1807.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast *Cancer. Clin. Cancer Res.* 9: 2374-2383.

Kouo, T., Huang, L., Pucsek, A. B., Cao, M., Solt, S., Armstrong, T., Jaffee, E. (2015) *Cancer Immonol. Res.* 3: 412-23

Lau, K. S., and Dennis, J. W. (2008). N-Glycans in cancer progression. *Glycobiology* 18: 750-760.

Lau, K. S., Partridge, E. A., Grigorian, A., Silvescu, C. I., Reinhold, V. N., Demetriou, M., and Dennis, J. W. (2007). Complex N-glycan number and degree of branching cooperate to regulate cell proliferation and differentiation. *Cell* 129: 123-134.

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Lin, C.-I., Whang, E. E., Donner, D. B., Jiang, X., Price, B. D., Carothers, A. M., Delaine, T., Leffler, H., Nilsson, U. J., Nose, V., et al. (2009). Galectin-3

Targeted Therapy with a Small Molecule Inhibitor Activates Apoptosis and Enhances Both Chemosensitivity and Radiosensitivity in Papillary Thyroid Cancer. *Mol Cancer Res* 7: 1655-1662.

MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. *J. Immun.* 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. *Am. J. Resp. Crit. Care Med.*, in press.

Massa, S. M., Cooper, D. N. W., Leffler, H., Barondes, S. H. (1993) L-29, an endogenous lectin, binds to glycoconjugate ligands with positive cooperativity. *Biochemistry* 32: 260-267.

Melero, I., Berman, D. M., Aznar, M. A., Korman, A. J., Gracia, J. L. P., Haanen, J. (2015) *Nature Reviews Cancer,* 15: 457-472

Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. *Science* 306: 120-124.

Perone, M. J., Bertera, S., Shufesky, W. J., Divito, S. J., Montecalvo, A., Mathers, A. R., Larregina, A. T., Pang, M., Seth, N., Wucherpfennig, K. W., et al. (2009). Suppression of autoimmune diabetes by soluble galectin-1. *J Immunol* 182: 2641-2653.

Pienta, K. J., Naik, H., Akhtar, A., Yamazaki, K., Reploge, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Ramos-Soriano, J.; Niss, U.; Angulo, J.; Angulo, M.; Moreno-Vargas, A. J.; Carmona, A. T.; Ohlson, S.; Robina, I. Chem. Eur. J. 2013, 19, 17989-18003.

Ruvolo, P. P. *Biochim. Biophys Acta*. Molecular cell research (2015) E-pub ahead of print, title: Galectin-3 as a guardian of the tumor microenvironment, published on-line 8 Apr. 2015: (http://www.sciencedirect.com/science/article/pii/S0167488915002700), Saegusa, J., Hsu, D. K., Chen, H. Y., Yu, L., Fermin, A., Fung, M. A., and Liu, F. T. (2009). Galectin-3 is critical for the development of the allergic inflammatory response in a mouse model of atopic dermatitis. *Am J Pathol* 174: 922-931.

Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejier, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Sörme, P., Qian, Y., Nyholm, P.-G., Leffler. H., Nilsson, U. J. (2002) Low micromolar inhibitors of galectin-3 based on 3'-derivatization of N-acetyllactosamine. *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., Magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Thijssen, V. L., Poirer, F., Baum, L. G., and Griffioen, A. W. (2007). Galectins in the tumor endothelium: opportunities for combined cancer therapy. *Blood* 110: 2819-2827.

Toscano, M. A., Bianco, G. A., Ilarregui, J. M., Croci, D. O., Correale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8: 825-834.

We claim:

1. A D-galactopyranose compound of formula (1)

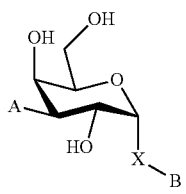

(1)

wherein
the pyranose ring is a-D-galactopyranose,
A is selected from

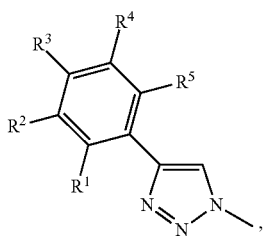

2

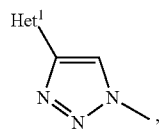

3

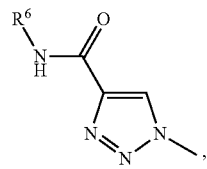

4

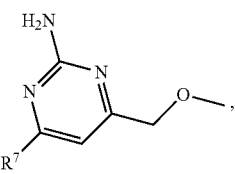

5

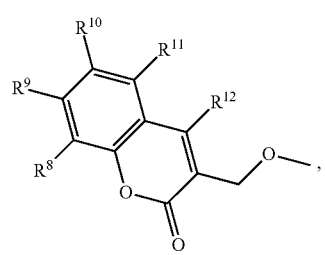

6

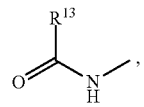

7

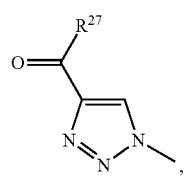

8 wherein $Het^1$ is selected from a five or six membered heteroaromatic ring, optionally substituted with a group selected from Br; F; Cl; CN; $NR^{19}R^{20}$, wherein $R^{19}$ and $R^{20}$ are independently selected from H, $C_{1-3}$ alkyl, cyclopropyl, iso-propyl, —C(=O)—$R^{21}$, wherein $R^{21}$ is selected from H and $C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-iso-propyl optionally substituted with a F; and $OC_{1-3}$ alkyl optionally substituted with a F;

wherein $R^1$-$R^5$ are independently selected from H, CN, $NH_2$, F, methyl optionally substituted with a F, and $OCH_3$ optionally substituted with a F;

wherein $R^6$ is selected from $C_{1-6}$ alkyl optionally substituted with a halogen, branched $C_{3-6}$ alkyl and $C_{3-7}$ cycloalkyl;

wherein $R^7$ is selected from a five or six membered heteroaromatic ring, optionally substituted with a group selected from Br, F, Cl, methyl optionally substituted with a F, and $OCH_3$ optionally substituted with a F, and a phenyl optionally substituted with a group selected from Br, F, Cl, methyl optionally substituted with a F, and $OCH_3$ optionally substituted with a F;

wherein $R^8$-$R^{12}$ are independently selected from H, F, methyl optionally substituted with a F, and $OCH_3$ optionally substituted with a F;

wherein $R^{13}$ is a five or six membered heteroaromatic ring optionally substituted with a group selected from H, OH, F, methyl optionally substituted with a F, and OCH₃ optionally substituted with a F, or an aryl optionally substituted with a group selected from H, OH, F, methyl optionally substituted with a F, and OCH₃ optionally substituted with a F;

X is selected from S, SO, SO₂, C=O, and CR⁷R⁸ wherein R⁷ and R⁸ are independently selected from hydrogen, OH, or halogen;

wherein R²⁷ is selected from a $C_{1-6}$ alkyl, branched $C_{3-6}$ alkyl, $C_{1-6}$ alkoxy and branched $C_{3-6}$ alkoxy;

B is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, OCH₃ optionally substituted with a F, OCH₂CH₃ optionally substituted with a F, OH, and R¹⁴—CONH— wherein R¹⁴ is selected from $C_{1-3}$ alkyl and cyclopropyl; or a $C_{1-6}$ alkyl substituted with a phenyl, optionally substituted with a substituent selected from CN, a halogen, methyl optionally substituted with a F, OCH₃ optionally substituted with a F, OCH₂CH₃ optionally substituted with a F, OH, and R¹⁵—CONH— wherein R¹⁵ is selected from $C_{1-3}$ alkyl and cyclopropyl; b) an aryl, optionally substituted with a group selected from a halogen; CN; —COOH; —CONR²²R²³, wherein R²² and R²³ are independently selected from H, $C_{1-3}$ alkyl, cyclopropyl, and isopropyl; $C_{1-3}$ alkyl, optionally substituted with a F; cyclopropyl, optionally substituted with a F; isopropyl, optionally substituted with a F; O$C_{1-3}$ alkyl, optionally substituted with a F; O-cyclopropyl, optionally substituted with a F; O-isopropyl, optionally substituted with a F; NR²⁸R²⁹, wherein R²⁸ and R²⁹ are independently selected from H, $C_{1-3}$ alkyl and isopropyl; OH; and R¹⁶—CONH— wherein R¹⁶ is selected from $C_{1-3}$ alkyl and cyclopropyl; c) a $C_{5-7}$ cycloalkyl, optionally substituted with a substituent selected from a halogen, CN, methyl optionally substituted with a F, OCH₃ optionally substituted with a F, OCH₂CH₃ optionally substituted with a F, OH, and R¹⁷—CONH— wherein R¹⁷ is selected from $C_{1-3}$ alkyl and cyclopropyl; and d) a heterocycle, optionally substituted with a group selected from a halogen; CN; —COOH; —CONR²⁴R²⁵, wherein R²⁴ and R²⁵ are independently selected from H, $C_{1-3}$ alkyl, cyclopropyl, and isopropyl; $C_{1-3}$ alkyl, optionally substituted with a F; cyclopropyl, optionally substituted with a F; isopropyl, optionally substituted with a F; O$C_{1-3}$ alkyl, optionally substituted with a F; O-cyclopropyl, optionally substituted with a F; O-isopropyl, optionally substituted with a F; NR³⁰R³¹, wherein R³⁰ and R³¹ are independently selected from H, $C_{1-3}$ alkyl and isopropyl; OH; and R¹⁸—CONH— wherein R¹⁸ is selected from $C_{1-3}$ alkyl and cyclopropyl; e) a $C_{1-6}$ alkyl or branched $C_{3-6}$ alkyl; or a pharmaceutically acceptable salt or solvate thereof.

2. The compound of claim 1, wherein A is selected from formula 2 wherein R¹-R⁵ are independently selected from H, F, methyl optionally substituted with a F, and OCH₃ optionally substituted with a F.

3. The compound of claim 1, wherein A is selected from formula 2 wherein W and R⁵ are selected from H and R²-R⁴ are selected from F or wherein R¹-R⁵ are all F or wherein R² and R³ are F and R¹, R⁴ and R⁵ are H, or wherein R² and R⁴ are F and R¹, R³ and R⁵ are H, or wherein R² is F and R¹, R³-R⁵ are H, or wherein R² and R⁴ are F, R³ is OCH₃, and R¹ and R⁵ are H.

4. The compound of claim 1, wherein A is selected from formula 3 wherein Het¹ is selected from a six membered heteroaromatic ring, optionally substituted with a group selected from Br, F, and Cl.

5. The compound of claim 1, wherein A is selected from formula 3 wherein Het¹ is selected from a pyridinyl substituted with a F.

6. The compound of claim 1, wherein A is selected from formula 4 wherein R⁶ is selected from $C_{1-6}$ alkyl optionally substituted with a halogen, and branched $C_{3-6}$ alkyl.

7. The compound of claim 1, wherein A is selected from formula 5 wherein R⁷ is selected from phenyl optionally substituted with a group selected from Br, F, Cl, methyl optionally substituted with a F, and OCH₃ optionally substituted with a F.

8. The compound of claim 1, wherein A is selected from formula 5 wherein R⁷ is selected from phenyl substituted with a Cl.

9. The compound of claim 1, wherein A is selected from formula 6 wherein R⁸-R¹² are independently selected from H and F.

10. The compound of claim 1, wherein A is selected from formula 6 wherein R⁸-R₁₂ are H, or wherein R¹⁰-R¹¹ are F and R⁸, R⁹, and R¹² are H.

11. The compound of claim 1, wherein A is selected from formula 7 wherein R¹³ is an aryl, optionally substituted with a group selected from F.

12. The compound of claim 1, wherein A is selected from formula 7 wherein R¹³ is phenyl, optionally substituted with one, two or three F.

13. The compound of claim 1, wherein A is selected from formula 8 wherein R²⁷ is selected from a $C_{1-6}$ alkyl, branched $C_{3-6}$ alkyl, $C_{1-6}$ alkoxy and branched $C_{3-6}$ alkoxy.

14. The compound of claim 1, wherein X is selected from S, SO, and SO₂.

15. The compound of claim 1, wherein B is selected from a $C_{1-6}$ alkyl substituted with a phenyl, said phenyl optionally substituted with a group selected from Br, F, Cl, methyl optionally substituted with a F, and OCH₃ optionally substituted with a F.

16. The compound of claim 1, wherein B is selected from a $C_{1-6}$ alkyl substituted with a phenyl, said phenyl optionally substituted with a group selected from Cl.

17. The compound of claim 1, wherein B is selected from a $C_{1-6}$ alkyl.

18. The compound of claim 1, wherein B is selected from an aryl, optionally substituted with a group selected from a halogen; CN; methyl optionally substituted with a F; OCH₃ optionally substituted with a F; OCH₂CH₃ optionally substituted with a F; OH; R¹⁶—CONH— wherein R¹⁶ is selected from $C_{1-3}$ alkyl and cyclopropyl; —COOH; NR²⁸R²⁹, wherein R²⁸ and R²⁹ are independently selected from H, $C_{1-3}$ alkyl and isopropyl; and -CONH₂.

19. The compound of claim 1, wherein B is selected from a naphthyl optionally substituted with NR²⁸R²⁹, wherein R²⁸ and R²⁹ are independently selected from H, $C_{1-3}$ alkyl and isopropyl.

20. The compound of claim 1, wherein B is selected from a phenyl or phenyl substituted with one, two or three substituents selected from Cl, F, Br, I, CN, methyl, OH, CF₃, OCH2CH₃, OCH3, OCF₃, COOH, CONH₂, and R¹⁶—CONH— wherein R¹⁶ is selected from $C_{1-3}$ alkyl.

21. The compound of claim 1, wherein B is selected from a heterocycle, optionally substituted with a group selected from a halogen; CN; methyl optionally substituted with a F; OCH₃ optionally substituted with a F; OCH₂CH₃ optionally substituted with a F; OH; CONH₂; NR³⁰R³¹, wherein R³⁰ and $R^{31}$ are independently selected from H, $C_{1-3}$ alkyl and isopropyl; and $R^{18}$—CONH— wherein $R^{18}$ is selected from $C_{1-3}$ alkyl and cyclopropyl.

22. The compound of claim 1, wherein B is selected from a pyridinyl, thiophenyl, and a pyridazinyl, optionally substituted with a group selected from Cl, Br, $CF_3$, $OCH_3$, OH, $NH_2$, $CONH_2$, and CN.

23. The compound of claim 1, wherein B is selected from a $C_{5-7}$ cycloalkyl, optionally substituted with a substituent selected from a halogen, methyl optionally substituted with a F, $OCH_3$ optionally substituted with a F, $OCH_2CH_3$ optionally substituted with a F, OH, and $R^{17}$—CONH— wherein $R^{17}$ is selected from $C_{1-3}$ alkyl and cyclopropyl.

24. The compound of claim 1, wherein B is a cyclohexyl or a cyclohexyl substituted with a substituent selected from halogen.

25. The compound of claim 1, selected from:
3,4-Dimethylphenyl 3-deoxy-3-[4-(3,4,5-trifluorophenyl)-1H-1,2,3-triazol-1-yl]-1-thio-α-D-galactopyranoside,
3-Bromophenyl 3-deoxy-3-[4-(3,4,5-trifluorophenyl)-1H-1,2,3-triazol-1-yl]-1-thio-α-D-galactopyranoside,
3-Ethoxyphenyl 3-deoxy-3-[4-(3,4,5-trifluorophenyl)-1H-1,2,3-triazol-1-yl]-1-thio-α-D-galactopyranoside,
4-Pyridyl 3-deoxy-3-[4-(3,4,5-trifluorophenyl)-1H-1,2,3-triazol-1-yl]-1-thio-α-D-galactopyranoside,
2,4-Dichlorophenyl 3-deoxy-3-[4-(3,4,5-trifluorophenyl)-1H-1,2,3-triazol-1-yl]-1-thio-α-D-galactopyranoside,
4-Acetanilidyl 3-deoxy-3-[4-(3,4,5-trifluorophenyl)-1H-1,2,3-triazol-1-yl]-1-thio-α-D-galactopyranoside,
4-Methoxyphenyl 3-deoxy-3-[4-(3,4,5-trifluorophenyl)-1H-1,2,3-triazol-1-yl]-1-thio-α-D-galactopyranoside,
2,3-Dichlorophenyl 3-deoxy-3-[4-(3,4,5-trifluorophenyl)-1H-1,2,3-triazol-1-yl]-1-thio-α-D-galactopyranoside,
3,4-Dichlorophenyl 3-deoxy-3-[4-(3,4,5-trifluorophenyl)-1H-1,2,3-triazol-1-yl]-1-thio-α-D-galactopyranoside,
Benzyl 3-deoxy-1-thio-3-[4-(3,4,5-trifluorophenyl)-1H-1,2,3-triazol-1-yl]-1-thio-α-D-galactopyranoside,
3-Methoxyphenyl 3-deoxy-3-[4-(3,4,5-trifluorophenyl)-1H-1,2,3-triazol-1-yl]-1-thio-α-D-galactopyranoside,
2-Naphtyl 3-deoxy-3-[4-(3,4,5-trifluorophenyl)-1H-1,2,3-triazol-1-yl]-1-thio-α-D-galactopyranoside,
3-Methylphenyl 3-deoxy-3-[4-(3,4,5-trifluorophenyl)-1H-1,2,3-triazol-1-yl]-1-thio-α-D-galactopyranoside,
3-(Trifluoromethyl)phenyl 3-deoxy-3-[4-(3,4,5-trifluorophenyl)-1H-1,2,3-triazol-1-yl]-1-thio-α-D-galactopyranoside,
4-Bromophenyl 3-deoxy-3-[4-(3,4,5-trifluorophenyl)-1H-1,2,3-triazol-1-yl]-1-thio-α-D-galactopyranoside,
3,5-Dichlorophenyl 3-deoxy-3-[4-(3,4,5-trifluorophenyl)-1H-1,2,3-triazol-1-yl]-1-thio-α-D-galactopyranoside,
2,6-Dimethylphenyl 3-deoxy-3-[4-(3,4,5-trifluorophenyl)-1H-1,2,3-triazol-1-yl]-1-thio-α-D-galactopyranoside,
1-Naphthyl 3-deoxy-1-thio-3-[4-(3,4,5-trifluorophenyl)-1H-1,2,3-triazol-1-yl]-1-thio-α-D-galactopyranoside,
3-Chlorophenyl 3-deoxy-3-[4-(3,4,5-trifluorophenyl)-1H-1,2,3-triazol-1-yl]-1-thio-α-D-galactopyranoside,
3-(Trifluoromethoxy)phenyl 3-deoxy-3-[4-(3,4,5-trifluorophenyl)-1H-1,2,3-triazol-1-yl]-1-thio-α-D-galactopyranoside,
2-Pyridyl 3-deoxy-3-[4-(3,4,5-trifluorophenyl-1H-1,2,3-triazol-1-yl]-)-1-thio-α-D-galactopyranoside,
4-Chlorophenyl 3-deoxy-3-[4-(3,4,5-trifluorophenyl)-1H-1,2,3-triazol-1-yl]-1-thio-α-D-galactopyranoside,
3,4-Dichlorophenyl 3-deoxy-3-[4-(3,4,5-trifluorophenyl)-1H-1,2,3-triazol-1-yl]-α-D-galactopyranosyl sulfoxide,
3,4-Dichlorophenyl 3-deoxy-3-[4-(3,4,5-trifluorophenyl)-1H-1,2,3-triazol-1-yl]-α-D-galactopyranosyl sulfone,
4-Chlorophenyl 3-deoxy-3-[4-(3,4,5-trifluorophenyl)-1H-1,2,3-triazol-1-yl]-α-D-galactopyranosyl sulfoxide,
Phenyl 3-deoxy-3-[4-(3,4,5-trifluorophenyl)-1H-1,2,3-triazol-1-yl]-1-thio-α-D-galactopyranoside,
3-Chloro-4-fluorophenyl 3-deoxy-3-[4-(3,4,5-trifluorophenyl)-1H-1,2,3-triazol-1-yl]-1-thio-α-D-galactopyranoside,
4-Tolyl 3-deoxy-3-[4-(3,4,5-trifluorophenyl)-1H-1,2,3-triazol-1-yl]-1-thio-α-D-galactopyranoside,
4-Fluorophenyl 3-deoxy-3-[4-(3,4,5-trifluorophenyl)-1H-1,2,3-triazol-1-yl]-1-thio-α-D-galactopyranoside,
4-Trifluoromethoxyphenyl 3-deoxy-3-[4-(3,4,5-trifluorophenyl)-1H-1,2,3-triazol-1-yl]-1-thio-α-D-galactopyranoside,
Cyclohexyl 3-deoxy-3-[4-(3,4,5-trifluorophenyl)-1H-1,2,3-triazol-1-yl]-1-thio-α-D-galactopyranoside,
2,4,5-Trichlorophenyl 3-deoxy-3-[4-(3,4,5-trifluorophenyl)-1H-1,2,3-triazol-1-yl]-1-thio-α-D-galactopyranoside,
2,5-Dichlorophenyl 3-deoxy-3-[4-(3,4,5-trifluorophenyl)-1H-1,2,3-triazol-1-yl]-1-thio-α-D-galactopyranoside,
3-Hydroxy-phenyl 3-deoxy-3-[4-(3,4,5-trifluorophenyl)-1H-1,2,3-triazol-1-yl]-1-thio-α-D-galactopyranoside,
3-Bromophenyl 3-deoxy-3-[4-(3,4,5-trifluorophenyl)-1H-1,2,3-triazol-1-yl]-α-D-galactopyranosyl sulfoxide,
2-Phenethyl 3-deoxy-3-[4-(3,4,5-trifluorophenyl)-1H-1,2,3-triazol-1-yl]-1-thio-α-D-galactopyranoside,
3,4-Dichlorophenyl 3-O-[(2-amino-(4-chlorophenyl)pyrimidin-6-yl) methylene]-1-thio-α-D-galactopyranoside,
3,4-Dichlorophenyl 3-deoxy-3-[4-(2,3,4,5,6-pentafluorophenyl)-1H-1,2,3-triazol-1-yl]-α-D-galactopyranosyl sulfoxide,
5-Chloropyridin-3-yl 3-deoxy-3-[4-(3,4,5-trifluorophenyl)-1H-1,2,3-triazol-1-yl]-1-thio-α-D-galactopyranoside,
5-Bromopyridin-3-yl 3-deoxy-3-[4-(3,4,5-trifluorophenyl)-1H-1,2,3-triazol-1-yl]-1-thio-α-D-galactopyranoside,
3-Chloro-5-cyanophenyl 3-deoxy-3-[4-(3,4,5-trifluorophenyl)-1H-1,2,3-triazol-1-yl]-1-thio-α-D-galactopyranoside,
3-Chloro-4-cyanophenyl 3-deoxy-3-[4-(3,4,5-trifluorophenyl)-1H-1,2,3-triazol-1-yl]-1-thio-α-D-galactopyranoside,
3-Chloro-6-fluoro-4-cyanophenyl 3-deoxy-3-[4-(3,4,5-trifluorophenyl)-1H-1,2,3-triazol-1-yl]-1-thio-α-D-galactopyranoside,
3-Bromo-4-cyanophenyl 3-deoxy-3-[4-(3,4,5-trifluorophenyl)-1H-1,2,3-triazol-1-yl]-1-thio-α-D-galactopyranoside,
5-Bromo-6-trifluoromethyl-pyridin-3-yl 3-deoxy-3-[4-(3,4,5-trifluorophenyl)-1H-1,2,3-triazol-1-yl]-1-thio-α-D-galactopyranoside, 5-Chloro-6-cyano-pyridin-3-yl 3-deoxy-3-[4-(3,4,5-trifluorophenyl)-1H-1,2,3-triazol-1-yl]-1-thio-α-D-galactopyranoside, 5-Chloro-6-cyano-pyridazin-3-yl 3-deoxy-3-[4-(3,4,5-trifluorophenyl)-1H-1,2,3-triazol-1-yl]-1-thio-α-D-galactopyranoside, 3,4-Dichlorophenyl 3-deoxy-3-[4-(2,3,4,5,6-pentafluorophenyl)-1H-1,2,3-triazol-1-yl]-1-thio-α-D-galactopyranoside, 3,4-Dichlorophenyl 3-deoxy-3-[4-(2,3,4,5,6-pentafluorophenyl)-1H-1,2,3-triazol-1-yl]-α-D-galactopyranosyl sulfone, 5-Methoxy-6-cyano-pyridazin-3-yl 3-deoxy-3-[4-(3,4,5-trifluorophenyl)-1H-1,2,3-triazol-1-yl]-1-thio-α-D-galactopyranoside, 5-Hydroxy-6-cyano-pyridazin-3-yl 3-deoxy-3-[4-(3,4,5-trifluorophenyl)-1H-1,2,3-triazol-1-yl]-1-thio-α-D-galactopyranoside, 3-Chloro-2,4-difluorophenyl 3-deoxy-1-thio-3-[4-(3,4,5-trifluorophenyl)-1H-1,2,3-triazol-1-yl]-α-D-galactopyranoside, 3,4-Dichlorophenyl 3-deoxy-3-[4-(phenyl)-1H-1,2,3-triazol-1-yl]-1-thio-α-D-galactopyranoside, 3,5-Dichloro-4-fluorophenyl 3-deoxy-3-[4-(3,4,5-trifluorophenyl)-1H-1,2,3-triazol-1-yl]-1-thio-α-D-galactopyranoside, 3,4-Dichloro-6-fluorophenyl 3-deoxy-3-[4-(3,4,5-trifluorophenyl)-1H-1,2,3-triazol-1-yl]-1-thio-α-D-galactopyranoside, 3-Bromo-4-fluorophenyl 3-deoxy-3-[4-(3,4,5-trifluorophenyl)-1H-1,2,3-triazol-1-yl]-1-thio-α-D-galactopyranoside, 3-Chloro-4-(trifluoromethyl)phenyl 3-deoxy-1-thio-3-[4-(3,4,5-trifluorophenyl)-1H-1,2,3-triazol-1-yl]-α-D-galactopyranoside, 3,4,5-Trichlorophenyl 3-deoxy-1-thio-3-[4-(3,4,5-trifluorophenyl)-1H-1,2,3-triazol-1-yl]-α-D-galactopyranoside, 5-Chloro-2-fluorophenyl 3-deoxy-1-thio-3-[4-(3,4,5-trifluorophenyl)-1H-1,2,3-triazol-1-yl]-α-D-galactopyranoside, 5-Bromo-2-fluorophenyl 3-deoxy-1-thio-3-[4-(3,4,5-trifluorophenyl)-1H-1,2,3-triazol-1-yl]-α-D-galactopyranoside, 5-Chloro-2-methoxyphenyl 3-deoxy-1-thio-3-[4-(3,4,5-trifluorophenyl)-1H-1,2,3-triazol-1-yl]-α-D-galactopyranoside, 3-Iodophenyl 3-deoxy-1-thio-3-[4-(3,4,5-trifluorophenyl)-1H-1,2,3-triazol-1-yl]-α-D-galactopyranoside, Picolinamide-5-yl 3-deoxy-3-[4-(3,4,5-trifluorophenyl)-1H-1,2,3-triazol-1-yl]-1-thio-α-D-galactopyranoside, 3-Cyanophenyl 3-deoxy-1-thio-3-[4-(3,4,5-trifluorophenyl)-1H-1,2,3-triazol-1-yl]-α-D-galactopyranoside, 2-Cyanopyridine-5-yl 3-deoxy-3-[4-(3,4,5-trifluorophenyl)-1H-1,2,3-triazol-1-yl]-1-thio-α-D-galactopyranoside, 4-Chloro-2-thienyl 3-deoxy-3-[4-(3,4,5-trifluorophenyl)-1H-1,2,3-triazol-1-yl]-1-thio-α-D-galactopyranoside, 3-Carboxyphenyl 3-deoxy-3-[4-(3,4,5-trifluorophenyl)-1H-1,2,3-triazol-1-yl]-1-thio-α-D-galactopyranoside, Benzamide-3-yl 3-deoxy-3-[4-(3,4,5-trifluorophenyl)-1H-1,2,3-triazol-1-yl]-1-thio-α-D-galactopyranoside, 3,4-Dichlorophenyl 3-deoxy-3-[4-(3,4-difluorophenyl)-1H-1,2,3-triazol-1-yl]-1-thio-α-D-galactopyranoside, 3,4-Dichlorophenyl 3-deoxy-3-[4-(3,4-difluorophenyl)-1H-1,2,3-triazol-1-yl]-1-thio-α-D-galactopyranoside, 3,4-Dichlorophenyl 3-deoxy-3-[4-(3-fluorophenyl)-1H-1,2,3-triazol-1-yl]-1-thio-α-D-galactopyranoside, 3,3'-difluoro-cyclohexyl 3-deoxy-3-[4-(3,4,5-trifluorophenyl)-1H-1,2,3-triazol-1-yl]-1-thio-α-D-galactopyranoside, n-Butyl 3-deoxy-3-[4-(3,4,5-trifluorophenyl)-1H-1,2,3-triazol-1-yl]-1-thio-α-D-galactopyranoside, 3,4-Dichlorophenyl 3-deoxy-3-[4-(3,5-difluoro-4-methoxyphenyl)-1H-1,2,3-triazol-1-yl]-1-thio-α-D-galactopyranoside, 2-Hydroxy-pyridin-4-yl 3-deoxy-3-[4-(3,4,5-trifluorophenyl)-1H-1,2,3-triazol-1-yl]-1-thio-α-D-galactopyranoside, 2-Chlorophenethyl 3-deoxy-3-[4-(3,4,5-trifluorophenyl)-1H-1,2,3-triazol-1-yl]-1-thio-α-D-galactopyranoside, 4-Chlorophenethyl 3-deoxy-3-[4-(3,4,5-trifluorophenyl)-1H-1,2,3-triazol-1-yl]-1-thio-α-D-galactopyranoside, 2-Chlorobenzyl 3-deoxy-1-thio-3-[4-(3,4,5-trifluorophenyl)-1H-1,2,3-triazol-1-yl]-α-D-galactopyranoside, 3,4-Dichlorobenzyl 3-deoxy-1-thio-3-[4-(3,4,5-trifluorophenyl)-1H-1,2,3-triazol-1-yl]-α-D-galactopyranoside, 3-Chlorophenethyl 3-deoxy-3-[4-(3,4,5-trifluorophenyl)-1H-1,2,3-triazol-1-yl]-1-thio-α-D-galactopyranoside, 4-Chlorobenzyl 3-deoxy-1-thio-3-[4-(3,4,5-trifluorophenyl)-1H-1,2,3-triazol-1-yl]-α-D-galactopyranoside, Propyl 3-deoxy-3-[4-(3,4,5-trifluorophenyl)-1H-1,2,3-triazol-1-yl]-1-thio-α-D-galactopyranoside, 2-Aminopyridin-4-yl 3-deoxy-3-[4-(3,4,5-trifluorophenyl)-1H-1,2,3-triazol-1-yl]-1-thio-α-D-galactopyranoside, 5-dimethylamino-naphatlen-2-yl 3-deoxy-3-[4-(3,4,5-trifluorophenyl)-1H-1,2,3-triazol-1-yl]-1-thio-α-D-galactopyranoside, Ethyl 3-deoxy-1-thio-3-[4-(3,4,5-trifluorophenyl)-1H-1,2,3-triazol-1-yl]-α-D-galactopyranoside, S-5-Bromopyridin-3-yl 3-deoxy-3-[4-(3,4,5-trifluorophenyl)-1H-1,2,3-triazol-1-yl]-α-D-galactopyranosyl sulfoxide, R-5-Bromopyridin-3-yl 3-deoxy-3-[4-(3,4,5-trifluorophenyl)-1H-1,2,3-triazol-1-yl]-α-D-galactopyranosyl sulfoxide, 5-Bromopyridin-3-yl 3-deoxy-3-[4-(3,4,5-trifluorophenyl)-1H-1,2,3-triazol-1-yl]-α-D-galactopyranosyl sulfone, S-5-Chloropyridin-3-yl 3-deoxy-3-[4-(3,4,5-trifluorophenyl)-1H-1,2,3-triazol-1-yl]-α-D-galactopyranosyl sulfoxide, R-5-Chloropyridin-3-yl 3-deoxy-3-[4-(3,4,5-trifluorophenyl)-1H-1,2,3-triazol-1-yl]-α-D-galactopyranosyl sulfoxide, 5-Dimethylamino-naphtalen-2-yl 3-deoxy-3-[4-(3,4,5-trifluorophenyl)-1H-1,2,3-triazol-1-yl]-a-D-galactopyranosyl sulfone, 3,4-dichlorophenyl-3-deoxy-3-(3,4,5-trifluorobenzamido)-1-thio-α-D-galactopyranoside, 3,4-Dichlorophenyl 3-deoxy-3-[4-(ethoxycarbonyl)-1H-1,2,3-triazol-1-yl]-1-thio-α-D-galactopyranoside, 3,4-Dichlorophenyl 3-deoxy-3-[4-(ethylaminocarbonyl)-1H-1,2,3-triazol-1-yl]-1-thio-α-D-galactopyranoside, 3,4-Dichlorophenyl 3-O-[(5,6-Difluoro-2-oxo-3-chromenyl)methyl]-1-thio-α-D-galactopyranoside, 5-Chloropyridin-3-yl 3-deoxy-3-[4-(3,4-difluorophenyl)-1H-1,2,3-triazol-1-yl]-1-thio-α-D-galactopyranoside, 5-Bromopyridin-3-yl 3-deoxy-3-[4-(3,4-difluorophenyl)-1H-1,2,3-triazol-1-yl]-1-thio-α-D-galactopyranoside, 3,4-Dichlorophenyl 3-deoxy-3-[4-(propyl-carbonyl)-1H-1,2,3-triazol-1-yl]-1-thio-α-D-galactopyranoside, 5-Chloro-6-trifluoromethyl-pyridine-3-yl 3-deoxy-3-[4-(3,4,5-trifluorophenyl)-1H-1,2,3-triazol-1-yl]-1-thio-α-D-galactopyranoside, 5-Chloro-2-trifluoromethyl-pyridine-3-yl 3-deoxy-3-[4-(3,4,5-trifluorophenyl)-1H-1,2,3-triazol-1-yl]-1-thio-α-D-galactopyranoside, 5-Chloro-6-cyano-pyridine-3-yl 3-deoxy-3-[4-(3,4-difluorophenyl)-1H-1,2,3-triazol-1-yl]-1-thio-α-D-galactopyranoside, and 3-Chloro-4-cyanophenyl 3-deoxy-3-[4-(3,4-difluorophenyl)-1H-1,2,3-triazol-1-yl]-1-thio-α-D-galactopyranoside.

26. A pharmaceutical composition comprising the compound of claim 1 and optionally a pharmaceutically acceptable additive.

27. A method for inhibiting expression of a galectin-3 in a mammal, comprising administering to a mammal in need thereof a therapeutically effective amount of at least one compound according to claim 1.

28. The method of claim 27, wherein the mammal suffers from a disorder selected from the group consisting of inflammation; fibrosis; scarring; keloid formation; aberrant scar formation; surgical adhesions; septic shock; cancer; metastasizing cancers; autoimmune diseases; metabolic disorders; heart disease; heart failure; pathological angiogenesis, ocular angiogenesis or a disease or condition associated with ocular angiogenesis; and eye diseases; atherosclerosis; metabolic diseases; asthma and other interstitial lung diseases, including Hermansky-Pudlak syndrome, mesothelioma; and liver disorders.

* * * * *